US011718829B2

(12) United States Patent
Zeigler

(10) Patent No.: US 11,718,829 B2
(45) Date of Patent: Aug. 8, 2023

(54) METHODS AND COMPOSITIONS FOR MANUFACTURING EXTRACELLULAR MATRIX

(71) Applicant: Breakthrough Tech LLC, Aliso Viejo, CA (US)

(72) Inventor: Francis Christopher Zeigler, Carlsbad, CA (US)

(73) Assignee: Breakthrough Tech LLC, Aliso Viejo, CA (US)

(*) Notice: Subject to any disclaimer, the term of this patent is extended or adjusted under 35 U.S.C. 154(b) by 73 days.

(21) Appl. No.: 15/662,901

(22) Filed: Jul. 28, 2017

(65) Prior Publication Data

US 2019/0032017 A1   Jan. 31, 2019

(51) Int. Cl.
*C12N 5/077* (2010.01)
*C12N 5/074* (2010.01)

(52) U.S. Cl.
CPC ......... *C12N 5/0656* (2013.01); *C12N 5/0696* (2013.01); *C12N 2501/10* (2013.01); *C12N 2506/1307* (2013.01); *C12N 2506/45* (2013.01)

(58) Field of Classification Search
CPC .................................................. C12N 5/0656
See application file for complete search history.

(56) References Cited

U.S. PATENT DOCUMENTS

| | | |
|---|---|---|
| 5,830,708 A | 11/1998 | Naughton |
| 6,372,494 B1 | 4/2002 | Naughton et al. |
| 6,378,527 B1 | 4/2002 | Hungerford et al. |
| 7,118,746 B1 | 10/2006 | Naughton et al. |
| 7,985,404 B1 | 7/2011 | Seiberg et al. |
| 8,128,924 B2 | 3/2012 | Naughton et al. |
| 8,138,147 B2 | 3/2012 | Naughton et al. |
| 8,257,947 B2 | 9/2012 | Naughton et al. |
| 8,361,485 B2 | 1/2013 | Naughton et al. |
| 8,476,231 B2 | 7/2013 | Naughton et al. |
| 8,530,415 B2 | 9/2013 | Naughton et al. |
| 8,535,913 B2 | 9/2013 | Naughton et al. |
| 8,852,637 B2 | 10/2014 | Naughton et al. |
| 9,034,312 B2 | 5/2015 | Naughton et al. |
| 9,213,999 B2 | 12/2015 | Sakurada et al. |
| 9,458,486 B2 | 10/2016 | Naughton et al. |
| 2010/0209404 A1 | 8/2010 | Hong |
| 2014/0349401 A1 | 11/2014 | Wang |

OTHER PUBLICATIONS

Zhang et al (Asian Pacific Journal of Tropical Medicine, 253-256, 2014. (Year: 2014).*
Shamis et al (In vitro Cell Dev Biol, Animal 48: 112-122, 2012). (Year: 2012).*
Devito et al (Stem Cells Transl Med, 3: 1116, 2014). (Year: 2014).*
Shamis (hESC-and iPSC-Derived Fibroblasts for Skin Engineering and Repair, Thesis p. ii-123, 2012. (Year: 2012).*
Bianchetti (Journal of Cellular and Molecular Medicine, 16(3): 483-495, 2012 (Year: 2012).*
Mak (Austin Biomark Diagn, 1(2): 1-9, 2014), (Year: 2014).*
Hayes (Animal Reproduction Science, 8: 181-192, 2005). (Year: 2005).*
Muiznieks (Biochimica et Biophysica Acta, 1832: 866-875, 2013). (Year: 2013).*
Bailey et al., "A Bacterial Dextranase", Biochem. J., vol. 72, No. 1, pp. 49-54, 1959.
General Electric Healthcare manual, "Microcarrier Cell Culture Principles and Methods", vol. 18, pp. 1140-1162, AC, www.gelifesciences.com, Nov. 2013.
Tour et al., "Cell-Derived Matrix Enhances Osteogenic Properties of Hydroxyapatite", Tissue Eng Part A, vol. 17, Nos. 1-2, pp. 127-137, Jan. 2011.
Tour et al., "Human fibroblast-derived extracellular matrix constructs for bone tissue engineering applications", J Biomed Mater Res A, vol. 101, No. 10, pp. 2826-2837, Oct. 2013.
Zhang et al., "Cell-Derived Extracellular Matrix: Basic Characteristics and Current Applications in Orthopedic Tissue Engineering", Tissue Engineering: Part B, vol. 22, No. 3, 2016.
Pinney et al, "Inhibition of metastasis of circulating human prostate cancer cells in the chick embryo by an extracellular matrix produced by foreskin fibroblasts in culture", Anticancer Res., vol. 32, No. 5, pp. 1573-1577, May 2012.
Pinney, et al, "Human Embryonic-like ECM (hECM) Stimulates Proliferation and Differentiation in Stem Cells While Killing Cancer Cells", International Journal of Stem, Cells, vol. 4, No. 1, 2011.
Itoh et al., "Generation of 3D Skin Equivalents Fully Reconstituted from Human Induced Pluripotent Stem Cells (IPSCs)", PLOS ONE, vol. 8, No. 10, e77673, pp. 1-9, Oct. 2013.
Batista et al., "Understanding telomere diseases through analysis of diseasespecific iPS cells", Curr Opin Genet Dev., vol. 23, No. 5, pp. 526-533, Oct. 2013.
Blakaj et al., "Fibrocytes in health and disease", Blakaj and Bucala Fibrogenesis & Tissue Repair, vol. 5 (Suppl 1), No. S6, 2012.
PCT International Search Report and Written Opinion of the International Searching Authority of PCT/US18/39362; dated Nov. 26, 2018; (21pgs.).
Franco-Barraza, J. et al., "Preparation of Extracellular Matrices Produced by Cultured and Primary Fibroblasts," Current Protocols in Cell Biology, 71(1):1934-2500 (2016).

* cited by examiner

*Primary Examiner* — Emily A Cordas
(74) *Attorney, Agent, or Firm* — Cooley LLP; Cynthia Kozakiewicz; Robert E. Powers

(57) ABSTRACT

Embodiments herein include methods, kits, and compositions for manufacturing extracellular matrix (ECM). In some embodiments, the methods comprise differentiating fibroblasts into induced pluripotent stem cells, expanding the induced pluripotent stem cells, and differentiating the induced pluripotent stem cells into fibroblasts. The fibroblasts can produced mature ECM, which can be isolated and used for medical and/or cosmetic products and procedures.

26 Claims, 3 Drawing Sheets
Specification includes a Sequence Listing.

METHODS AND COMPOSITIONS FOR MANUFACTURING EXTRACELLULAR MATRIX

REFERENCE TO SEQUENCE LISTING, TABLE, OR COMPUTER PROGRAM LISTING

The present application is being filed along with a Sequence Listing in electronic format. The Sequence Listing is provided as a file entitled SEQUENCEWYLD008A.TXT, created and last modified Jul. 18, 2017, which is 247,512 bytes in size. The information in the electronic format of the Sequence Listing is incorporated herein by reference in its entirety.

BACKGROUND

The extracellular matrix (ECM) is a versatile biomaterial with many cosmetic and therapeutic uses. The majority of connective tissues comprise collagens, and to a much lesser extent (based on relative abundance by weight) other glycoproteins such as laminins, fibronectin, and glycosaminoglycans (GAGs) including hyaluronic acid, and other sulfated GAGs such as aggrecan and perlecan. However, collagens are cross-linked and require enzymatic or chemical degradation to isolate for cosmetic or therapeutic uses and manufacture into useful products for human use. Examples including the use of bovine and porcine corium after pepsin digestion or chemical modification, porcine intestinal submucosa, and human cadaver-derived tissues such as skin and bone, are all widely known in the art.

Animal sources for ECM such as porcine and bovine tissues carry the risk of unwanted immune reactions, including known allergies to bovine and porcine antigens or allergens, mostly proteins, while human cells that use animal-derived components (including most often bovine serum, bovine albumin, or porcine trypsin), or non-human plant-derived proteins (including soybean trypsin inhibitor or recombinant human albumin produced in plants which can contain residual plant proteins or polypeptides) suffer from the same risks. Accordingly, the commercial usefulness of ECM from animal sources can be limited by safety concerns and/or regulatory hurdles for validating the animal components' removal to safer residual levels needed for approval to use commercially. The human immune system is sensitive enough to react to extremely low abundance antigens, and animal and plant proteins have been demonstrated to cause unwanted immune reactions, including potentially life-threatening allergic reactions which can cause anaphylactic shock and even death in some cases. Animal-derived and plant-derived protein components, and human cells grown in animal-derived or plant-derived protein components are collectively termed "xenogeneic." On the other hand, products manufactured without contact to these animal-derived and plant-derived protein components are known as "xeno-free." Conventional approaches for manufacturing ECM in xenogenic media can require removal of animal-derived and/or plant-derived protein components, limiting the commercial usefulness of these methods.

Human ECM can be derived from allogeneic tissues from cadavers. However, such cadaver-derived ECM presents risk of disease transmission, as well as limited commercial scalability, since each donor provides limited amounts of obtainable human ECM (e.g., a 70 kg human contains less than 20% by weight human collagens or no greater than a few kgs raw ECM materials). Additionally, cadaver-derived tissues involve expensive safety testing to mitigate some risk of disease transmission, and must be extensively tested for a number of disease-causing pathogens including viruses and bacteria for each single cadaverous donor.

Additionally, ECM can be used for animal feed. However, as a practical matter, conventional approaches for producing ECM using cell culture or harvest from cadavers can be cost-prohibitive on a commercial scale. Described in accordance with some embodiments herein are methods, compositions, and kits for efficiently producing ECM at a commercial scale, while minimizing risks of disease-transmission and immunogenicity.

Field

Some embodiments herein relate to methods and compositions for manufacturing extracellular matrix (ECM). In some embodiments, methods and compositions for cell culture are described.

SUMMARY

Some embodiments include a method of manufacturing extracellular matrix. The method can comprise differentiating induced Pluripotent Stem Cells (iPSCs) into a production fibroblast. The method can comprise culturing the production fibroblasts, and by way of the culturing, the production fibroblasts can produce extracellular matrix (ECM). The method can comprise isolating the ECM from the production fibroblasts, thus manufacturing the ECM. In some embodiments, the method further comprises de-differentiating a precursor fibroblast to form the iPSCs prior to differentiating the iPSCs into the production fibroblast. In some embodiments, the method further comprises expanding the iPSC's prior to the differentiating, for example at least about 2, 3, 4, 5, 6, 7, 8, 9, 10, 11, 12, 13, 14, 15, 16, 17, 18, 19, 20, 25, or 30 doublings, including ranges between any two of the listed values. In some embodiments, the method further comprises constructing a bank of the iPSC's prior to the differentiating. In some embodiments, only iPSCS are differentiated are from a single donor. In some embodiments, the culturing of the production fibroblasts is in normoxia. In some embodiments, culturing the production fibroblasts does not comprise culturing mesenchymal stem cells (MSCs). In some embodiments, the precursor fibroblast comprises an adult dermal (biopsy) fibroblast. In some embodiments, isolating the ECM comprises purifying the ECM, thereby manufacturing a composition that is at least about 80% w/w ECM. In some embodiments, purifying the ECM comprises washing the ECM in an acidic buffer, and contacting a solution comprising the production fibroblast and ECM with dextranase. In some embodiments, the ECM comprises collagen. In some embodiments, about 90% (w/w) of the ECM is COL1, and about 10% is selected from the group consisting of: COL3, COL4, COL5, COL6, and a combination of any of these. In some embodiments, the method further comprises contacting the precursor fibroblast with de-differentiation factors, thereby de-differentiating the precursor fibroblast into the iPSC. In some embodiments, the iPSCs are free of viral insertions encoding an Oct family member, a Sox family member, a Klf family member. In some embodiments, the iPSCs are footprint-free. In some embodiments, the method does not comprise any of: an embryonic stem (ES) cell, a bone marrow multipotent stem cell, an ES-derived MSC, or a non-multipotent neonatal foreskin fibroblast cell line. In some embodiments, the ECM comprises a c-terminal propeptide of COL1, or a triple-helical or non-reducible gamma-form fibrillar collagen, or both. In some embodiments, the method further comprises contacting the production fibroblasts with serum, until the production fibroblasts produce mature collagens, and then gradually reducing the amount of serum until there is a at least 95% reduction in the concentration of serum. In some embodiments, the gradual reducing is over a period of at least about 5 days.

Some embodiments include a kit for manufacturing ECM. The kit can comprise a composition comprising human fibroblasts. The kit can comprise de-differentiation factors. The kit can comprise fibroblast differentiation factors. In some embodiments, all of the fibroblasts of the composition are from a single donor. In some embodiments, the kit further comprises a substrate, such as dextran microcarriers. In some embodiments, the kit further comprises dextranase and DNAase.

Some embodiments include a composition comprising at least 80% (w/w) extracellular matrix, in which the extracellular matrix is manufactured according to any of he above methods.

Some embodiments include a cell culture comprising iPSC-derived fibroblasts, in which the iPSC-derived fibroblasts are producing mature extracellular matrix. The cell culture can further include de-differentiation factors. In some embodiments, at least 50% of the composition (w/w) comprises ECM.

Some embodiments include a method of manufacturing extracellular matrix (ECM). The method can comprise culturing fibroblasts and/or mesenchymal stem cells (MSCs) on a substrate. The substrate can comprise at least two surfaces. The culturing can be serum-free and xeno-free. The culturing can be performed until the fibroblasts and/or MSCs define a three-dimensional shape over the at least two-surfaces and at least 80% of fibroblasts and/or MSCs arrest their cell cycle. The method can then include contacting the fibroblasts and/or MSCs with serum for at least about two weeks, through which the fibroblasts and/or MSCs produce soluble mature ECM. Thus, a solution comprising soluble mature ECM and the fibroblasts or MSCs can be produced, in which the solution is xeno-free. The method can further include isolating the soluble mature ECM from the production fibroblast, thus manufacturing the ECM, wherein the ECM is mature xeno-free ECM. In some embodiments, the method further comprises expanding a human pluripotent cell culture, the expanding being serum-free and xeno-free, thereby producing human pluripotent cells; and contacting the human pluripotent cells with differentiation factors, though which the human pluripotent cells differentiate into the fibroblasts or MSCs. In some embodiments, the contacting of the fibroblasts and/or MSCs with serum is for about 2 weeks to about 8 weeks. In some embodiments, the contacting of the fibroblasts and/or MSCs with serum is for at least about 8 weeks. In some embodiments, the human pluripotent cells comprise induced pluripotent stem cells (iPSCSs). In some embodiments, the iPSCSs are footprint-free. In some embodiments, the iPSCSs are from a single donor. In some embodiments, the method further comprises manufacturing a cosmetic composition comprising the mature xeno-free ECM. In some embodiments, the method further comprises contacting the fibroblasts or MSCs with ascorbic acid during the at least two weeks of the contacting with the serum. In some embodiments, the fibroblasts or MSCs are not contacted with serum prior to said fibroblasts or MSCs over the at least two-surfaces defining a three-dimensional shape and at least 70% of the fibroblasts or MSCs arresting their cell cycle. In some embodiments, the amount of serum is about 0.1% to 10% (v/v). In some embodiments, the amount of serum is about 1-2% (v/v). In some embodiments, the serum comprises clinical-grade bovine calf serum, pooled human serum, or a combination thereof. In some embodiments, pluripotent cells are of a cell line that was previously grown using animal components. In some embodiments, the mature xeno-free ECM comprises fibrillar collagen. In some embodiments, the mature xeno-free ECM comprises a c-terminal propeptide of COL1, or a triple-helical or non-reducible gamma-form fibrillar collagen, or both. In some embodiments, the solution comprises at least 250 µg of collagen per $cm^2$ of the substrate. In some embodiments, the manufactured mature xeno-free ECM comprises at least 250 µg of collagen per $cm^2$ of the substrate. In some embodiments, the pluripotent cells are from a single donor. In some embodiments, the method further comprises detecting an amount of mature ECM in the solution. In some embodiments, the method further comprises collecting a quantity of spent culture medium from the solution and isolating soluble mature ECM from the spent culture medium.

Some embodiments include a solution comprising fibroblasts or MSCs and the soluble mature ECM produced according to any of the methods of the above paragraph. The solution can be xeno-free, and the soluble mature ECM can comprise cross-linked collagen.

Some embodiments include a method of manufacturing extracellular matrix (ECM). The method can comprise providing fibroblasts in a medium comprising a concentration of serum. The method can comprise gradually reducing the amount of serum in the medium comprising fibroblasts until the medium contains no more than 5% of the concentration of serum. The method can comprise, following the gradually reduction of serum, culturing the fibroblasts for at least about 2 weeks, through which the fibroblasts produce soluble ECM, thereby producing a solution comprising the fibroblasts and soluble ECM. The method can comprise isolating the soluble ECM from the fibroblasts, thereby manufacturing the ECM. In some embodiments, a quantity of fibroblasts in the medium at the start of gradually reducing the amount of serum is at least 0.7× of a quantity of fibroblasts in the medium when the medium contains no more than 5% of the concentration in serum. In some embodiments, the quantity of fibroblasts in the medium at the start of gradually reducing the amount of serum is at least 0.9× of the quantity of fibroblasts in the medium when the medium contains no more than 5% of the concentration in serum. In some embodiments, gradually reducing the amount of serum is done without cell expansion or cell subculture. In some embodiments, the serum is gradually reduced for at least about 5 days. In some embodiments, at least about 90% of the fibroblasts in the solution are in a $G_0$ cell cycle phase. In some embodiments, fewer than 1% of the fibroblasts in the solution are undergoing apoptosis. In some embodiments, the solution comprises nanostructures comprising the soluble ECM, said nanostructures having a greatest diameter of 200 nm to 10,000 nm. In some embodiments, manufacturing the ECM is performed without sterile-filtering. (so as not to exclude the nanostructures). In some embodiments, isolating the soluble ECM from the fibroblasts is performed without sterile-filtering.

Some embodiments include a solution comprising fibroblasts and soluble ECM. At least about 90% of the fibroblasts in the solution can be in a $G_0$ cell cycle phase. Fewer than 1% of the fibroblasts in the solution can be undergoing apoptosis. The solution can comprise nanostructures comprising the soluble ECM, said nanostructures having a greatest diameter of 200 nm to 10,000 nm. In some embodiments, the soluble ECM is manufactured according to a method of any one of claims 48-57.

DETAILED DESCRIPTION

Figure 1:
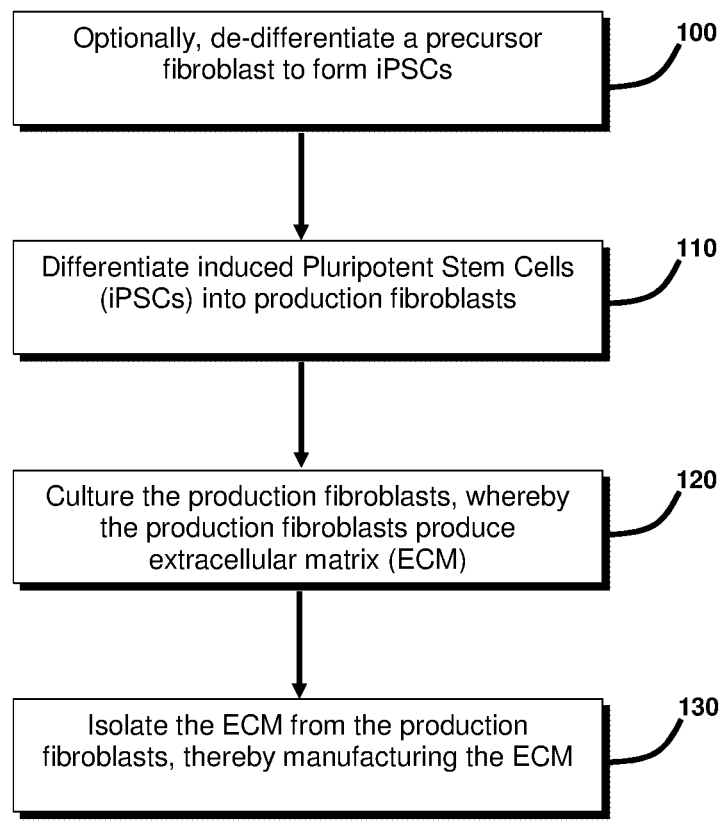
FIG. 1 is a flow diagram illustrating methods of manufacturing ECM using fibroblasts differentiated from iPSCs in accordance with some embodiments herein.

ECM can be useful for a number of cosmetic and therapeutic applications, but conventional methods of producing ECM can suffer from challenges related to scalability, ease of use, contamination (including immunogenicity in human hosts), disease transmission, and cost efficiency. Described herein are methods, compositions, and kits useful for efficiently manufacturing ECM, including at commercial scales. The ECM in accordance with methods, compositions, and kits of some embodiments herein can comprise a relatively high level of commercially-useful mature collagens (such as triple-helical or non-reducible gamma-form fibrillar collagen, or both), and can be relatively free of contaminants such as potentially harmful xeno substances.

Some embodiments include methods, compositions, and kits for making non-embryonic human fibroblasts for use as a bioreactor for manufacturing human extracellular matrix (ECM). In accordance with these embodiments, mature fibroblasts can be de-differentiated into induced pluripotent stem cells (iPSCs), expanded, and re-differentiated into mature non-embryonic production fibroblasts. These production fibroblasts can be used to manufacture collagen-rich ECM.

Some embodiments include methods, compositions, and/or kits for manufacturing mature xeno-free ECM. In accordance with these embodiments, cells can be cultured for an extended period of time (e.g., up to 8 weeks, such as over 2-3 weeks or more), which can yield ECM with desirable characteristics such as increased cross-linking of collagen and superior ECM solubility. In contrast, many conventional approaches for manufacturing ECM may perform cell culture for a much shorter time, for example 12-17 days. Surprisingly, the 2-3 week or more cell cultures in accordance with some embodiments herein produce ECM with increased cross-linking and solubility compared to cultures of shorter periods of time.

Some embodiments include methods of culturing fibroblasts to produce ECM in which the fibroblasts are gradually weaned off of serum. In accordance with these embodiments, fibroblasts can first be cultured in a serum-containing formulation, and the amount of serum can then gradually be reduced (for example, by removing and replacing culture medium so as to lower serum content and/or by moving the cells to different culture medium with lower serum content). The cells can produce mature soluble ECM for at least 2 weeks following the reduction of the serum, and the soluble ECM can be isolated from the cells. "Soluble" (for example in the context of soluble ECM), is used herein in accordance with its ordinary meaning in the field, and includes a type or fraction of ECM which is dissolved or can be dissolved in an aqueous phase. As such, soluble ECM can recovered in an aqueous phase and maintained in an aqueous phase. In some embodiments, the soluble ECM does not precipitate in an aqueous phase. In some embodiments, the soluble ECM can be maintained stably in an aqueous phase under the same conditions for at least 24 hours, with minimal precipitation, for example so that about or less than about 10%, 9%, 8%, 7%, 6%, 5%, 4%, 3%, 2%, or 1%, of the soluble ECM precipitates. This method can advantageously yield highly-soluble ECM, which can be useful for cosmetic and medical products. In some embodiments, ECM is produced efficiently without any cell expansion or subculturing. It is noted that in some embodiments, both soluble and non-soluble ECM can be recovered from the same culture, advantageously recovering ECM in both phases and obtaining higher yield than a method that only obtains ECM from one of the phases.

Extracellular Matrix (ECM)

"Extracellular Matrix" (ECM) is used herein in accordance with its ordinary meaning in the field, and includes molecules secreted by cells such as proteins and carbohydrates, which provide a structure to support the cells. The ECM can comprise fibrillar proteins such as collagen. Human ECM can include a number of collagen proteins, including, for example COL1, COL3, COL4, COL5, and COL6, as well as combinations of these proteins. Example polypeptide sequences of *Homo sapiens* COL1, COL3, COL4, COL5, and COL6 are shown in Table 1, below. In methods, compositions, and/or kits of some embodiments, cell cultures produce ECM, which can be isolated from the cell cultures. In some embodiments, the ECM comprises, consists essentially of, or consists of human ECM. In some embodiments, isolating the ECM from cell cultures comprises purifying the ECM. Human ECM products comprising, consisting essentially of, or consisting of the isolated ECM can thus be produced.

TABLE 1

Example *Homo sapiens* collagen polypeptide sequences

| Gene Name (Protein Name) | Uniprot ID | Polypeptide Sequence | SEQ ID NO: |
|---|---|---|---|
| COL1A1 (Collagen alpha-1(I) chain) | P02452 | MFSFVDLRLLLLLAATALLTHGQEEGQVEGQDEDIPPITCV QNGLRYHDRDVWKPEPCRICVCDNGKVLCDDVICDETKNCP GAEVPEGECCPVCPDGSESPTDQETTGVEGPKGDTGPRGPR GPAGPPGRDGIPGQPGLPGPPGPPGPPGPPGLGGNFAPQLS YGYDEKSTGGISVPGPMGPSGPRGLPGPPGAPGPQGFQGPP GEPGEPGASGPMGPRGPPGPPGKNGDDGEAGKPGRPGERGP PGPQGARGLPGTAGLPGMKGHRGFSGLDGAKGDAGPAGPKG EPGSPGENGAPGQMGPRGLPGERGRPGAPGPAGARGNDGAT | 1 |

TABLE 1-continued

Example Homo sapiens collagen polypeptide sequences

| Gene Name (Protein Name) | Uniprot ID | Polypeptide Sequence | SEQ ID NO: |
|---|---|---|---|
| | | GAAGPPGPTGPAGPPGFPGAVGAKGEAGPQGPRGSEGPQGV RGEPGPPGPAGAAGPAGNPGADGQPGAKGANGAPGIAGAPG FPGARGPSGPQGPGGPPGPKGNSGEPGAPGSKGDTGAKGEP GPVGVQGPPGPAGEEGKRGARGEPGPTGLPGPPGERGGPGS RGFPGADGVAGPKGPAGERGSPGPAGPKGSPGEAGRPGEAG LPGAKGLTGSPGSPGPDGKTGPPGPAGQDGRPGPPGPPGAR GQAGVMGFPGPKGAAGEPGKAGERGVPGPPGAVGPAGKDGE AGAQGPPGPAGPAGERGEQGPAGSPGFQGLPGPAGPPGEAG KPGEQGVPGDLGAPGPSGARGERGFPGERGVQGPPGPAGPR GANGAPGNDGAKGDAGAPGAPGSQGAPGLQGMPGERGAAGL PGPKGDRGDAGPKGADGSPGKDGVRGLTGPIGPPGPAGAPG DKGESGPSGPAGPTGARGAPGDRGEPGPPGPAGFAGPPGAD GQPGAKGEPGDAGAKGDAGPPGPAGPAGPPGPIGNVGAPGA KGARGSAGPPGATGFPGAAGRVGPPGPSGNAGPPGPPGPAG KEGGKGPRGETGPAGRPGEVGPPGPPGPAGEKGSPGADGPA GAPGTPGPQGIAGQRGVVGLPGQRGERGFPGLPGPSGEPGK QGPSGASGERGPPGPMGPPGLAGPPGESGREGAPGAEGSPG RDGSPGAKGDRGETGPAGPPGAPGAPGAPGPVGPAGKSGDR GETGPAGPTGPVGPVGARGPAGPQGPRGDKGETGEQGDRGI KGHRGFSGLQGPPGPPGSPGEQGPSGASGPAGPRGPPGSAG APGKDGLNGLPGPIGPPGPRGRTGDAGPVGPPGPPGPPGPP GPPSAGFDFSFLPQPPQEKAHDGGRYYRADDANVVRDRDLE VDTTLKSLSQQIENIRSPEGSRKNPARTCRDLKMCHSDWKS GEYWIDPNQGCNLDAIKVFCNMETGETCVYPTQPSVAQKNW YISKNPKDKRHVWFGESMTDGFQFEYGGQGSDPADVAIQLT FLRLMSTEASQNITYHCKNSVAYMDQQTGNLKKALLLQGSN EIEIRAEGNSRFTYSVTVDGCTSHTGAWGKTVIEYKTTKTS RLPIIDVAPLDVGAPDQEFGFDVGPVCFL | |
| COL1A2 Collagen alpha-2(I) chain | P08123 | MLSFVDTRTLLLLAVTLCLATCQSLQEETVRKGPAGDRGPR GERGPPGPPGRDGEDGPTGPPGPPGPPGPPGLGGNFAAQYD GKGVGLGPGPMGLMGPRGPPGAAGAPGPQGFQGPAGEPGEP GQTGPAGARGPAGPPGKAGEDGHPGKPGRPGERGVVGPQGA RGFPGTPGLPGFKGIRGHNGLDGLKGQPGAPGVKGEPGAPG ENGTPGQTGARGLPGERGRVGAPGPAGARGSDGSVGPVGPA GPIGSAGPPGFPGAPGPKGEIGAVGNAGPAGPAGPRGEVGL PGLSGPVGPPGNPGANGLTGAKGAAGLPGVAGAPGLPGPRG IPGPVGAAGATGARGLVGEPGPAGSKGESGNKGEPGSAGPQ GPPGPSGEEGKRGPNGEAGSAGPPGPPGLRGSPGSRGLPGA DGRAGVMGPPGSRGASGPAGVRGPNGDAGRPGEPGLMGPRG LPGSPGNIGPAGKEGPVGLPGIDGRPGPIGPAGARGEPGNI GFPGPKGPTGDPGKNGDKGHAGLAGARGAPGPDGNNGAQGP PGPQGVQGGKGEQGPPGPPGFQGLPGPSGPAGEVGKPGERG LHGEFGLPGPAGPRGERGPPGESGAAGPTGPIGSRGPSGPP GPDGNKGEPGVVGAVGTAGPSGPSGLPGERGAAGIPGGKGE KGEPGLRGEIGNPGRDGARGAPGAVGAPGPAGATGDRGEAG AAGPAGPAGPRGSPGERGEVGPAGPNGFAGPAGAAGQPGAK GERGAKGPKGENGVVGPTGPVGAAGPAGPNGPPGPAGSRGD GGPPGMTGFPGAAGRTGPPGPSGISGPPGPPGPAGKEGLRG PRGDQGPVGRTGEVGAVGPPGFAGEKGPSGEAGTAGPPGTP GPQGLLGAPGILGLPGSRGERGLPGVAGAVGEPGPLGIAGP PGARGPPGAVGSPGVNGAPGEAGRDGNPGNDGPPGRDGQPG HKGERGYPGNIGPVGAAGAPGPHGPVGPAGKHGNRGETGPS GPVGPAGAVGPRGPSGPQGIRGDKGEPGEKGPRGLPGLKGH NGLQGLPGIAGHHGDQGAPGSVGPAGPRGPAGPSGPAGKDG RTGHPGTVGPAGIRGPQGHQGPAGPPGPPGPPGPPGVSGGG YDFGYDGDFYRADQPRSAPSLRPKDYEVDATLKSLNNQIET LLTPEGSRKNPARTCRDLRLSHPEWSSGYYWIDPNQGCTMD AIKVYCDFSTGETCIRAQPENIPAKNWYRSSKDKKHVWLGE TINAGSQFEYNVEGVTSKEMATQLAFMRLLANYASQNITYH CKNSIAYMDEETGNLKKAVILQGSNDVELVAEGNSRFTYTV LVDGCSKKTNEWGKTIIEYKTNKPSRLPFLDIAPLDIGGAD QEFFVDIGPVCFK | 2 |
| COL2A1 Collagen alpha-1(II) chain | P02458 | MIRLGAPQTLVLLTLLVAAVLRCQGQDVQEAGSCVQDGQRY NDKDVWKPEPCRICVCDTGTVLCDDIICEDVKDCLSPEIPF GECCPICPTDLATASGQPGPKGQKGEPGDIKDIVGPKGPPG PQGPAGEQGPRGDRGDKGEKGAPGPRGRDGEPGTPGNPGPP GPPGPPGPPGLGGNFAAQMAGGFDEKAGGAQLGVMQGPMGP MGPRGPPGPAGAPGPQGFQGNPGEPGEPGVSGPMGPRGPPG PPGKPGDDGEAGKPGKAGERGPPGPQGARGFPGTPGLPGVK GHRGYPGLDGAKGEAGAPGVKGESGSPGENGSPGPMGPRGL PGERGRTGPAGAAGARGNDGQPGPAGPPGPVGPAGGPGFPG APGAKGEAGPTGARGPEGAQGPRGEPGTPGSPGPAGASGNP GTDGIPGAKGSAGAPGIAGAPGFPGPRGPPGPQGATGPLGP | 3 |

TABLE 1-continued

Example *Homo sapiens* collagen polypeptide sequences

| Gene Name (Protein Name) | Uniprot ID | Polypeptide Sequence | SEQ ID NO: |
|---|---|---|---|
| | | KGQTGEPGIAGFKGEQGPKGEPGPAGPQGAPGPAGEEGKRG ARGEPGGVGPIGPPGERGAPGNRGFPGQDGLAGPKGAPGER GPSGLAGPKGANGDPGRPGEPGLPGARGLTGRPGDAGPQGK VGPSGAPGEDGRPGPPGPQGARGQPGVMGFPGPKGANGEPG KAGEKGLPGAPGLRGLPGKDGETGAAGPPGPAGPAGERGEQ GAPGPSGFQGLPGPPGPPGEGGKPGDQGVPGEAGAPGLVGP RGERGFPGERGSPGAQGLQGPRGLPGTPGTDGPKGASGPAG PPGAQGPPGLQGMPGERGAAGIAGPKGDRGDVGEKGPEGAP GKDGGRGLTGPIGPPGPAGANGEKGEVGPPGPAGSAGARGA PGERGETGPPGPAGFAGPPGADGQPGAKGEQGEAGQKGDAG APGPQGPSGAPGPQGPTGVTGPKGARGAQGPPGATGFPGAA GRVGPPGSNGNPGPPGPPGPSGKDGPKGARGDSGPPGRAGE PGLQGPAGPPGEKGEPGDDGPSGAEGPPGPQGLAGQRGIVG LPGQRGERGFPGLPGPSGEPGKQGAPGASGDRGPPGPVGPP GLTGPAGEPGREGSPGADGPPGRDGAAGVKGDRGETGAVGA PGAPGPPGSPGPAGPTGKQGDRGEAGAQGPMGPSGPAGARG IQGPQGPRGDKGEAGEPGERGLKGHRGFTGLQGLPGPPGPS GDDQGASGPAGPSGPRGPPGPVGPSGKDGANGIPGPIGPPGP RGRSGETGPAGPPGNPGPPGPPGPPGPGIDMSAFAGLGPRE KGPDPLQYMRADQAAGGLRQHDAEVDATLKSLNNQIESIRS PEGSRKNPARTCRDLKLCHPEWKSGDYWIDPNQGCTLDAMK VFCNMETGETCVYPNPANVPKKNWWSSKSKEKKHIWFGETI NGGFHFSYGDDNLAPNTANVQMTFLRLLSTEGSQNITYHCK NSIAYLDEAAGNLKKALLIQGSNDVEIRAEGNSRFTYTALK DGCTKHTGKWGKTVIEYRSQKTSRLPIIDIAPMDIGGPEQE FGVDIGPVCFL | |
| COL3A1 Collagen alpha-1(III) chain | P02461 | MMSFVQKGSWLLLALLHPTIILAQQEAVEGGCSHLGQSYAD RDVWKPEPCQICVCDSGSVLCDDIICDDQELDCPNPEIPFG ECCAVCPQPPTAPTRPPNGQGPQGPKGDPGPPGIPGRNGDP GIPGQPGSPGSPGPPGICESCPTGPQNYSPQYDSYDVKSGV AVGGLAGYPGPAGPPGPPGPPGTSGHPGSPGSPGYQGPPGE PGQAGPSGPPGPPGAIGPSGPAGKDGESGRPGRPGERGLPG PPGIKGPAGIPGFPGMKGHRGFDGRNGEKGETGAPGLKGEN GLPGENGAPGPMGPRGAPGERGRPGLPGAAGARGNDGARGS DGQPGPPGPPGTAGFPGSPGAKGEVGPAGSPGSNGAPGQRG EPGPQGHAGAQGPPGPPGINGSPGGKGEMGPAGIPGAPGLM GARGPPGPAGANGAPGLRGGAGEPGKNGAKGEPGPRGERGE AGIPGVPGAKGEDGKDGSPGEPGANGLPGAAGERGAPGFRG PAGPNGIPGEKGPAGERGAPGPAGPRGAAGEPGRDGVPGGP GMRGMPGSPGGPGSDGKPGPPGSQGESGRPGPPGPSGPRGQ PGVMGFPGPKGNDGAPGKNGERGGPGGPGPQGPPGKNGETG PQGPPGPTGPGGDKGDTGPPGPQGLQGLPGTGGPPGENGKP GEPGPKGDAGAPGAPGGKGDAGAPGERGPPGLAGAPGLRGG AGPPGPEGGKGAAGPPGPPGAAGTPGLQGMPGERGGLGSPG PKGDKGEPGGPGADGVPGKDGPRGPTGPIGPPGPAGQPGDK GEGGAPGLPGIAGPRGSPGERGETGPPGPAGFPGAPGQNGE PGGKGERGAPGEKGEGGPPGVAGPPGGSGPAGPGPQGVKG ERGSPGGPGAAGFPGARGLPGPPGSNGNPGPPGPSGSPGKD GPPGPAGNTGAPGSPGVSGPKGDAGQPGEKGSPGAQGPPGA PGPLGIAGITGARGLAGPPGMPGPRGSPGPQGVKGESGKPG ANGLSGERGPPGPQGLPGLAGTAGEPGRDGNPGSDGLPGRD GSPGGKGDRGENGSPGAPGAPGHPGPPGPVGPAGKSGDRGE SGPAGPAGAPGPAGSRGAPGPQGPRGDKGETGERGAAGIKG HRGFPGNPGAPGSPGPAGQQGAIGSPGPAGPRGPVGPSGPP GKDGTSGHPGPIGPPGPRGNRGERGSEGSPGHPGQPGPPGP PGAPGPCCGGVGAAAIAGIGGEKAGGFAPYYGDEPMDFKIN TDEIMTSLKSVNGQIESLISPDGSRKNPARNCRDLKFCHPE LKSGEYWVDPNQGCKLDAIKVFCNMETGETCISANPLNVPR KHWWTDSSAEKKHVWFGESMDGGFQFSYGNPELPEDVLDVH LAFLRLLSSRASQNITYHCKNSIAYMDQASGNVKKALKLMG SNEGEFKAEGNSKFTYTVLEDGCTKHTGEWSKTVFEYRTRK AVRLRPIVDIAPYDIGGPDQEFGVDVGPVCFL | 4 |
| COL4A1 Collagen alpha-1(IV) chain | P02462 | MGPRLSVWLLLLPAALLLHEEHSRAAAKGGCAGSGCGKCDC HGVKGQKGERGLPGLQGVIGFPGMQGPEGPQGPPGQKGDTG EPGLPGTKGTRGPPGASGYPGNPGLPGIPGQDGPPGPPGPIP GCNGTKGERGPLGPPGLPGFAGNPGPPGLPGMKGDPGEILG HVPGMLLKGERGFPGIPGTPGPPGLPGLQGPVGPPGFTGPP GPPGPPGPPGEKGQMGLSFQGPKGDKGDQGVSGPPGVPGQA QVQEKGDFATKGEKGQKGEPGFQGMPGVGEKGEPGKPGPRG KPGKDGDKGEKGSPGFPGEPGYPGLIGRQGPQGEKGEAGPP GPPGIVGTGPLGEKGERGYPGTPGPRGEPGPKGFPGLPGQ PGPPGGLPVPGQAGAPGFPGERGEKGDRGFPGTSLPGPSGRD GLPGPPGSPGPPGQPGYTNGIVECQPGPPGDQGPPGIPGQP | 5 |

TABLE 1-continued

Example *Homo sapiens* collagen polypeptide sequences

| Gene Name (Protein Name) | Uniprot ID | Polypeptide Sequence | SEQ ID NO: |
|---|---|---|---|
| | | GFIGEIGEKGQKGESCLICDIDGYRGPPGPQGPPGEIGFPG QPGAKGDRGLPGRDGVAGVPGPQGTPGLIGQPGAKGEPGEF YFDLRLKGDKGDPGFPGQPGMTGRAGSPGRDGHPGLPGPKG SPGSVGLKGERGPPGGVGFPGSRGDTGPPGPPGYGPAGPIG DKGQAGFPGGPGSPGLPGPKGEPGKIVPLPGPPGAEGLPGS PGFPGPQGDRGFPGTPGRPGLPGEKGAVGQPGIGFPGPPGP KGVDGLPGDMGPPGTPGRPGFNGLPGNPGVQGQKGEPGVGL PGLKGLPGLPGIPGTPGEKGSIGVPGVPGEHGAIGPPGLQG IRGEPGPPGLPGSVGSPGVPGIGPPGARGPPGGQGPPGLSG PPGIKGEKGFPGFPGLDMPGPKGDKGAQGLPGITGQSGLPG LPGQQGAPGIPGFPGSKGEMGVMGTPGQPGSPGPVGAPGLP GEKGDHGFPGSSGPRGDPGLKGDKGDVGLPGKPGSMDKVDM GSMKGQKGDQGEKGQIGPIGEKGSRGDPGTPGVPGKDGQAG QPGQPGPKGDPGISGTPGAPGLPGPKGSVGGMGLPGTPGEK GVPGIPGPQGSPGLPGDKGAKGEKGQAGPPGIGIPGLRGEK GDQGIAGFPGSPGEKGEKGSIGIPGMPGSPGLKGSPGSVGY PGSPGLPGEKGDKGLPGLDGIPGVKGEAGLPGTPGPTGPAG QKGEPGSDGIPGSAGEKGEPGLPGRGFPGFPGAKGDKGSKG EVGFPGLAGSPGIPGSKGEQGFMGPPGPQGQPGLPGSPGHA TEGPKGDRGPQGQPGLPGLPGPMGPPGLPGIDGVKGDKGNP GWPGAPGVPGPKGDPGFQGMPGIGGSPGITGSKGDMGPPGV PGFQGPKGLPGLQGIKGDQGDQGVPGAKGLPGPGPPGPYD IIKGEPGLPGPEGPPGLKGLQGLPGPKGQQGVTGLVGIPGP PGIPGFDGAPGQKGEMGPAGPTGPRGFPGPPGPDGLPGSMG PPGTPSVDHGFLVTRHSQTIDDPQCPSGTKILYHGYSLLYV QGNERAHGQDLGTAGSCLRKFSTMPFLFCNINNVCNFASRN DYSYWLSTPEPMPMSMAPITGENIRPFISRCAVCEAPAMVM AVHSQTIQIPPCPSGWSSLWIGYSFVMHTSAGAEGSGQALA SPGSCLEEFRSAPFIECHGRGTCNYYANAYSFWLATIERSE MFKKKPTPSTLKAGELRTHVSRCQVCMRRT | |
| COL4A2 Collagen alpha-2(IV) chain | P08572 | MGRDQRAVAGPALRRWLLLGTVTVGFLAQSVLAGVKKFDVP CGGRDCSGGCQCYPEKGGRGQPGPVGPQGYNGPPGLQGFPG LQGRKGDKGERGAPGVTGPKGDVGARGVSGFPGADGIPGHP GQGGPRGRPGYDGCNGTQGDSGPQGPPGSEGFTGPPGPQGP KGQKGEPYALPKEERDRYRGEPGEPGLVGFQGPPGRPGHVG QMGPVGAPGRPGPPGPPGPKGQQGNRGLGFYGVKGEKGDVG QPGPNGIPSDTLHPIIAPTGVTFHPDQYKGEKGSEGEPGIR GISLKGEEGIMGFPGLRGYPGLSGEKGSPGQKGSRGLDGYQ GPDGPRGPKGEAGDPGPPGLPAYSPHPSLAKGARGDPGFPG AQGEPGSQGEPGDPGLPGPPGLSIGDGDQRRGLPGEMGPKG FIGDPGIPALYGGPPGPDGKRGPPGPPGLPGPPGPDGFLFG LKGAKGRAGFPGLPGSPGARGPKGWKGDAGECRCTEGDEAI KGLPGLPGPKGFAGINGEPGRKGDRGDPGQHGLPGFPGLKG VPGNIGAPGPKGAKGDSRTIITTKGERGQPGVPGVPGMKGDD GSPGRDGLDFPGLPGPPGDGIKGPPGDPGYPGIPGTKGTP GEMGPPGLGLPGLKGQRGFPGDAGLPGPGFLGPPGPAGTP GQIDCDTDVKRAVGGDRQEAIQPGCIGGPKGLPGLPGPPGP TGAKGLRGIPGFAGADGGPGPRGLPGDAGREGFPGPPGFIG PRGSKGAVGLPGPDGSPGPIGLPGPDGPPGERGLPGEVLGA QPGPRGDAGVPGQPGLKGLPGDRGPPGFRGSQGMPGMPGLK GQPGLPGPSGQPGLYGPPGLHGFPGAPGQEGPLGLPGIPGR EGLPGDRGDPGDTGAPGPVGMKGLSGDRGDAGFTGEQGHPG SPGFKGIDGMPGTPGLKGDRGSPGMDGFQGMPGLKGRPGFP GSKGEAGFFGIPGLKGLAGEPGFKGSRGDPGPPGPPPVILP GMKDIKGEKGDEGPMGLKGYLGAKGIQGMPGIPGLSGIPGL PGRPGHIKGVKGDIGVPGIPGLPGFPGVAGPPGITGFPGFI GSRGDKGAPGRAGLYGEIGATGDFGDIGDTINLPGRPGLKG ERGTTGIPGLKGFFGEKGTEGDIGFPGITGVTGVQGPPGLK GQTGFPGLTGPPGSQGELGRIGLPGGKGDDGWPGAPGLPGF PGLRGIRGLHGLPGTKGFPGSPGSDIHGDPGFPGPPGERGD PGEANTLPGPVGVPGQKGDQGAPGERGPPGSPGLQGFPGIT PPSNISGAPGDKGAPGIFGLKGYRGPPGPPGSAALPGSKGD TGNPGAPGTPGTKGWAGDSGPQGRPGVFGLPGEKGPRGEQG FMGNTGPTGAVGDRGPKGPKGDPGFPGAPGTVGAPGIAGIP QKIAVQPGTVGPQGRRGPPGAPGEMGPQGPPGEPGFRGAPG KAGPQGRGGVSAVPGFRGDEGPIGHQGPIGQEGAPGRPGSP GLPGMPGRSVSIGYLLVKHSQTDQEPMCPVGMNKLWSGYSL LYFEGQEKAHNQDLGLAGSCLARFSTMPFLYCNPDVCYYA SRNDKSYWLSTTAPLPMMPVAEDEIKPYISRCSVCEAPAIA IAVHSQDVSIPHCPAGWRSLWIGYSFLMHTAAGDEGGGQSL VSPGSCLEDFRATPFIECNGGRGTCHYYANKYSFWLTTIPE QSFQGSPSADTLKAGLIRTHISRCQVCMKNL | 6 |

TABLE 1-continued

Example Homo sapiens collagen polypeptide sequences

| Gene Name (Protein Name) | Uniprot ID | Polypeptide Sequence | SEQ ID NO: |
|---|---|---|---|
| COL4A3 Collagen alpha-3(IV) chain | Q01955 | MSARTAPRPQVLLLPLLLVLLAAAPAASKGCVCKDKGQCFC DGAKGEKGEKGFPGPPGSPGQKGFTGPEGLPGPQGPKGFPG LPGLTGSKGVRGISGLPGFSGSPGLPGTPGNTGPYGLVGVP GCSGSKGEQGFPGLPGTLGYPGIPGAAGLKGQKGAPAKEED IELDAKGDPGLPGAPGPQGLPGPPGFPGPVGPPGPPGFFGF PGAMGPRGPKGHMGERVIGHKGERGVKGLTGPPGPPGTVIV TLTGPDNRTDLKGEKGDKGAMGEPGPPGPSGLPGESYGSEK GAPGDPGLQGKPGKDGVPGFPGSEGVKGNRGFPGLMGEDGI KGQKGDIGPPGFRGPTEYYDTYQEKGDEGTPGPPGPRGARG PQGPSGPPGVPGSPGSSRPGLRGAPGWPGLKGSKGERGRPG KDAMGTPGSPGCAGSPGLPGSPGPPGPPGDIVFRKGPPGDH GLPGYLGSPGIPGVDGPKGEPGLLCTQCPYIPGPPGLPGLP GLHGVKGIPGRQGAAGLKGSPGSPGNTGLPGFPGFPGAQGD PGLKGEKGETLQPEGQVGVPGDPGLRGQPGRKGLDGIPGTP GVKGLPGPKGELALSGEKGDQGPPGDPGSPGSPGPAGPAGP PGYGPQGEPGLQGTQGVPGAPGPPGEAGPRGELSVSIPVPG PPGPPGPPGHPGPQGPPGIPGSLGKCGDPGLPGDGEPGIP GIGFPGPPGPKGDQGFPGTKGSLGCPGKMGEPGLPGKPGLP GAKGEPAVAMPGGPGTPGFPGERGNSGEHGEIGLPGLPGLP GTPGNEGLDGPRGDPGQPGPPGEQGPPGRCIEGPRGAQGLP GLNGLKGQQGRRGKTGPKGDPGIPGLDRSGFPGETGSPGIP GHQGEMGPLGQRGYPGNPGILGPPGEDGVIGMMGFPGAIGP PGPPGNPGTPGQRGSPGIPGVKGQRGTPGAKGEQGDKGNPG PSEISHVIGDKGEPGLKGFAGNPGEKGNRGVPGMPGLKGLK GLPGPAGPPGPRGDLGSTGNPGEPGLRGIPGSMGNMGMPGS KGKRGTLGFPGRAGRPGLPGIHGLQGDKGEPGYSEGTRPGP PGPTGDPGLPGDMGKKGEMGQPGPPGHLGPAGPEGAPGSPG SPGLPGKPGPHGDLGFKGIKGLLGPPGIRGPPGLPGFPGSP GPMGIRGDQGRDGIPGPAGEKGETGLLRAPPGPRGNPGAQG AKGDRGAPGFPGLPGRKGAMGDAGPRGPTGIEGFPGPPGLP GAIIPGQTGNRGPPGSRGSPGAPGPPGPPGSHVIGIKGDKG SMGHPGPKGPPGTAGDMGPPGRLGAPGTPGLPGPRGDPGFQ GFPGVKGEKGNPGFLGSIGPPGPIGPKGPPGVRGDPGTLKI ISLPGSPGPPGTPGEPGMQGEPGPPGPPGNLGPCGPRGKPG KDGKPGTPGPAGEKGNKGSKGEPGPAGSDGLPGLKGKRGDS GSPATWTTRGFVFTRHSQTTAIPSCPEGTVPLYSGFSFLFV QGNQRAHGQDLGTLGSCLQRFTTMPFLFCNVNDVCNFASRN DYSYWLSTPALMPMNMAPITGRALEPYISRCTVCEGPAIAI AVHSQTTDIPPCPHGWISLWKGFSFIMFTSAGSEGTGQALA SPGSCLEEFRASPFLECHGRGTCNYYSNSYSFWLASLNPER MFRKPIPSTVKAGELEKIISRCQVCMKKRH | 7 |
| COL4A4 Collagen alpha-4(IV) chain | P54320 | MWSLHIVLMRCSFRLTKSLATGPWSLILILFSVQYVYGSGK KYIGPCGGRDCSVCHCVPEKGSRGPPGPPGPQGPIGPLGAP GPIGLSGEKGMRGDRGPPGAAGDKGDKGPTGVPGFPGLDGI PGHPGPPGPRGKPGMSGHNGSRGDPGFPGGRGALGPGGPLG HPGEKGEKGNSVFILGAVKGIQGDRGDPGLPGLPGSWGAGG PAGPTGYPGEPGLVGPPGQPGRPGLKGNPGVGVKGQMGDPG EVGQQGSPGPTLLVEPPDFCLYKGEKGIKGIPGMVGLPGPP GRKGESGIGAKGEKGIPGFPGPRGDPGSYGSPGFPGLKGEL GLVGDPGLFGLIGPKGDPGNRGHPGPPGVLVTPPLPLKGPP GDPGFPGRYGETGDVGPPGPPGLLGRPGEACAGMIGPPGPQ GFPGLPGLPGEAGIPGRPDSAPGKPGKPGSPGLPGAPGLQG LPGSSVIYCSVGNPGPQGIKGKVGPPGGRGPKGEKGNEGLC ACEPGPMGPPGPPGLPGRQGSKGDLGLPGWLGTKGDPGPPG AEGPPGLPGKHGASGPPGNKGAKGDMVVSRVKGHKGERGPD GPPGFPGQPGSHGRDGHAGEKGDPGPPGDHEDATPGGKGFP GPLGPPPGKAGPVGPPGLGFPGPPGERGHPGVPGHPGVRGPD GLKGQKGDTISCNVTYPGRHGPPGFDGPPGPKGFPGPQGAP GLSGSDGHKGRPGTPGTAEIPGPPGFRGDMGDPGFGGEKGS SPVGPPGPPGSPGVNGQKGIPGDPAFGHLGPPGKRGLSGVP GIKGPRGDPGCPGAEGPAGIPGFLGLKGPKGREGHAGFPGV PGPPGHSCERGAPGIPGQPGLPGYPGSPGAPGGKGQPGDVG PPGPAGMKGLPGLPGRPGAHGPPGLPGIPGPFGDDGLPGPP GPKGPRGLPGFPGFPGERGKPGAEGCPGAKGEPGEKGMSGL PGDRGLRGAKGAIGPPGDEGEMAIISQKGTPGEPGPPGDDG FPGERGDKGTPGMQGRRGEPGRYGPPGFHRGEPGEKGQPGP PGPPGPPGSTGLRGFIGFPGLPGDQGEPGSPGPPGFSGIDG ARGPKGNKGDPASHFGPPGPKGEPGSPGCPGHFGASGEQGL PGIQGPRGSPGRPGPPGSSGPPGCPGDHGMPGLRGQPGEMG DPGPRGLQGDPGIPGPPGIKGPSGSPGLNGLHGLKGQKGTK GASGLHDVGPPGVGIPGLKGERGDPGSPGISPPGPRGKKG PPGPPGSSGPPGPAGATGRAPKDIPDPGPPGDQGPPGPDGP RGAPGPPGLPGSVDLLRGEPGDCGLPGPPGPPGPPGPPGYK GFPGCDGKDGQKGPVGFPGPQGPHGFPGPPPGEKGLPGPPGR | 8 |

TABLE 1-continued

Example *Homo sapiens* collagen polypeptide sequences

| Gene Name (Protein Name) | Uniprot ID | Polypeptide Sequence | SEQ ID NO: |
|---|---|---|---|
| | | KGPTGLPGPRGEPGPPADVDDCPRIPGLPGAPGMRGPEGAM GLPGMRGPSGPGCKGEPGLDGRRGVDGVPGSPGPPGRKGDT GEDGYPGGPGPPGPIGDPGPKGFGPGYLGGFLLVLHSQTDQ EPTCPLGMPRLWTGYSLLYLEGQEKAHNQDLGLAGSCLPVF STLPFAYCNIHQVCHYAQRNDRSYWLASAAPLPMMPLSEEA IRPYVSRCAVCEAPAQAVAVHSQDQSIPPCPQTWRSLWIGY SFLMHTGAGDQGGGQALMSPGSCLEDFRAAPFLECQGRQGT CHFFANKYSFWLTTVKADLQFSSAPAPDTLKESQAQRQKIS RCQVCVKYS | |
| COL4A5 Collagen alpha-5(IV) chain | P29400 | MKLRGVSLAAGLFLLALSLWGQPAEAAACYGCSPGSKCDCS GIKGEKGERGFPGLEGHPGLPGFPGPEGPPGPRGQKGDDGI PGPPGPKGIRGPPGLPGFPGTPGLPGMPGHDGAPGPQGIPG CNGTKGERGFPGSPGFPGLQGPPGPPGIPGMKGEPGSIIMS SLPGPKGNPGYPGPPGIQGLPGPTGIPGPIGPPGPPGLMGP PGPPGLPGPKGNMGLNFQGPKGEKGEQGLQGPPGPPGQISE QKRPIDVEFQKGDQGLPGDRGPPGPPGIRGPPGPPGGEKGE KGEQGEPGKRGKPGKDGENGQPGIPGLPGDPGYPGEPGRDG EKGQKGDTGPPGPPGLVIPRPGTGITIGEKGNIGLPGLPGE KGERGFPGIQGPPGLPGPPGAAVMGPPGPPGFPGERGQKGD EGPPGISIPGPPGLDGQPGAPGLPGPPGPAGPHIPPSDEIC EPGPPGPPGSPGDKGLQGEQGVKGDKGDTCFNCIGTGISGP PGQPGLPGLPGPPGSLGFPGQKGEKGQAGATGPKGLPGIPG APGAPGFPGSKGEPGDILTFPGMKGDKGELGSPGAPGLPGL PGTPGQDGLPGLPGPKGEPGGITFKGERGPPGNPGLPGLPG NIGPMGPPGFGPPGPVGEKGIQGVAGNPGQPGIPGPKGDPG QTITQPGKPGLPGNPGRDGDVGLPGDPGLPGQPGLPGIPGS KGEPGIPGIGLPGPPGPKGFPGIPGPPGAPGTPGRIGLEGP PGPPGFPGPKGEPGFALPGPPGPPGLPGFKGALGPKGDRGF PGPPGPPGRTGLDGLPGPKGDVGPNGQPGPMGPPGLPGIGV QGPPGPPGIPGPIGQPGLHGIPGEKGDPGPPGLDVPGPPGE RGSPGIPGAPGPIGPPGSPGLPGKAGASGFPGTKGEMGMMG PPGPPGPLGIPGRSGVPGLKGDDGLQGQPGLPGPTGEKGSK GEPGLPGPPGPMDPNLLGSKGEKGEPGLPGIPGVSGPKGYQ GLPGDPGQPGLSGQPGLPGPPGPKGNPGLPGQPGLIGPPGL KGTIGDMGFPGPQGVEGPPGPSGVPGQPGSPGLPGQKGDKG DPGISSIGLPGLPGPKGEPGLPGYPGNPGIKGSVGDPGLPG LPGTPGAKGQPGLPGFPGTGPPGPKGISGPPGNPGLPGEP GPVGGGHPGQPGPPGEKGKPGQDGIPGPAGQKGEPGQPGF GNPGPPGLPGLSGQKGDGGLPGIPGNPGLPGPKGEPGFHGF PGVQGPPGPPGSPGPALEGPKGNPGPQGPPGRPGLPGPEGP PGLPGNGGIKGEKGNPGQPGLPGLPGLKGDQGPPGLQGNPG RPGLNGMKGDPGLPGVPGFPGMKGPSGVPGSAGPEGEPGLI GPPGPPGLPGPSGQSIIIKGDAGPPGIPGQPGLKGLPGPQG PQGLPGPTGPPGDPGRNGLPGFDGAGGRKGDPGLPGQPGTR GLDGPPGPDGLQGPPGPPGTSSVAHGFLITRHSQTTDAPQC PQGTLQVYEGFSLLYVQGNKRAHGQDLGTAGSCLRRFSTMP FMFCNINNVCNFASRNDYSYWLSTPEPMPMSMQPLKGQSIQ PFISRCAVCEAPAVVIAVHSQTIQIPHCPQGWDSLWIGYSF MMHTSAGAEGSGQALASPGSCLEEFRSAPFIECHGRGTCNY YANSYSFWLATVDVSDMFSKPQSETLKAGDLRTRISRCQVC MKRT | 9 |
| COL4A6 Collagen alpha-6(IV) chain | Q14031 | MLINKLWLLLVTLCLTEELAAAGEKSYGKPCGGQDCSGSCQ CFPEKGARGRPGPIGIQGPTGPQGFTGSTGLSGLKGERGFP GLLGPYGPKGDKGPMGVPGFLGINGIPGHPGQPGPRGPPGL DGCNGTQGAVGFPGPDGYPGLLGPPGLPGQKGSKGDPVLAP GSFKGMKGDPGLPGLDGITGPQGAPGFPGAVGPAGPPGLQG PPGPPGPLGPDGNMGLGFQGEKGVKGDVGLPGPAGPPPSIG ELEFMGFPKGKKGSKGEPGKGFPGISGPPGFPGLGTTGEK GEKGEKGIPGLPGPRGPMGSEGVQGPPGQQGKKGTLGFPGL NGFQGIEGQKGDIGLPGPDVFIDIDGAVISGNPGDPGVPGL PGLKGDEGIQGLRGPSGVPGLPALSGVPGALGPQGFPGLKG DQGNPGRTTIGAAGLPGRDGLPGPPGPPGPPSPEFETETLH NKESGFPGLRGEQGPKGNLGLKGIKGDSGFCACDGGVPNTG PPGEPGPPGPWGLIGLPGLKGARGDRGSGGAQGPAGAPGLV GPLGPSGPKGKKGEPILSTIQGMPGDRGDSGSQGFRGVIGE PGKDGVPGLPGLPGLPGDGGQGFPGEKGLPGLPGEKGHPGP PGLPGNGLPGLPGPRGLPGDKGKDGLPGQQGLPGSKGITLP CIIPGSYGPSGFPGTPGFPGPKGSRGLPGTPGQPGSSGSKG EPGSPGLVHLPELPGFPGPRGEKGLPGFPGLPGKDGLPGMI GSPGLPGSKGATGDIFGAENGAPGEQGLQGLTGHKGFLGDS GLPGLKGVHGKPGLLGPKGERGSPGTPGQVGQPGTPGSSGP YGIKGKSGLPGAPGFPGISHPGKKGTRGKKGPPGSIVKKG LPGLKGLPGNPGLVGLKGSPGSPGVAGLPALSGPKGEKGSV | 10 |

TABLE 1-continued

Example *Homo sapiens* collagen polypeptide sequences

| Gene Name (Protein Name) | Uniprot ID | Polypeptide Sequence | SEQ ID NO: |
|---|---|---|---|
| | | GFVGFPGIPGLPGIPGTRGLKGIPGSTGKMGPSGRAGTPGE KGDRGNPGPVGIPSPRRPMSNLWLKGDKGSQGSAGSNGFPG PRGDKGEAGRPGPPGLPGAPGLPGIIKGVSGKPGPPGFMGI RGLPGLKGSSGITGFPGMPGESGSQGIRGSPGLPGASGLPG LKGDNGQTVEISGSPGPKGQPGESGFKGTKGRDGLIGNIGF PGNKGEDGKVGVSGDVGLPGAPGFPGVAGMRGEPGLPGSSG HQGAIGPLGSPGLIGPKGFPGFPGLHGLNGLPGTKGTHGTP GPSITGVPGPAGLPGPKGEKGYPGIGIGAPGKPGLRGQKGD RGFPGLQGPAGLPGAPGISLPSLIAGQPGDPGRPGLDGERG RPGPAGPPGPPGPSSNQGDTGDPGFPGIPGPKGPKGDQGIP GFSGLPGELGLKGMRGEPGFMGTPGKVGPPGDPGFPGMKGK AGPRGSSGLQGDPGQTPTAEAVQVPPGPLGLPGIDGIPGLT GDPGAQGPVGLQGSKGLPGIPGKDGPSGLPGPPGALGDPGL PGLQGPPGFEGAPGQQGPFGMPGMPGQSMRVGYTLVKHSQS EQVPPCPIGMSQLWVGYSLLFVEGQEKAHNQDLGFAGSCLP RFSTMPFIYCNINEVCHYARRNDKSYWLSTTAPIPMMPVSQ TQIPQYISRCSVCEAPSQAIAVHSQDITIPQCPLGWRSLWI GYSFLMHTAAGAEGGGQSLVSPGSCLEDFRATPFIECSGAR GTCHYFANKYSFWLTTVEERQQFGELPVSETLKAGQLHTRV SRCQVCMKSL | |
| COL5A1 Collagen alpha-1(V) chain | P20908 | MDVHTRWKARSALRPGAPLLPPLLLLLLWAPPPSRAAQPAD LLKVLDFHNLPDGITKTTGFCATRRSSKGPDVAYRVTKDAQ LSAPTKQLYPASAFPEDFSILTTVKAKKGSQAFLVSIYNEQ GIQQIGLELGRSPVFLYEDHTGKPGPEDYPLFRGINLSDGK WHRIALSVHKKNVTLILDCKKKTTKFLDRSDHPMIDINGII VFGTRILDEEVFEGDIQQLLFVSDHRAAYDYCEHYSPDCDT AVPDTPQSQDPNPDEYYTEGDGEGETYYYEYPYYEDPEDLG KEPTPSKKPVEAAKETTEVPEELTPTPTEAAPMPETSEGAG KEEDVGIGDYDYVPSEDYYTPSPYDDLTYGEGEENPDQPTD PGAGAEIPTSTADTSNSSNPAPPPGEGADDLEGEFTEETIR NLDENYYDPYYDPTSSPSEIGPGMPANQDTIYEGIGGPRGE KGGKGEPAIIEPGMLIEGPPGPEGPAGLPGPPGTMGPTGQV GDPGERGPPGRPGLPGADGLPGPPGTMLMLPFRFGGGGDAG SKGPMVSAQESQAQAILQQARLALRGPAGPMGLTGRPGPVG PPGSGGLKGEPGDVGPQGPRGVQGPPGPAGKPGRRGRAGSD GARGMPGQTGPKGDRGFDGLAGLPGEKGHRGDPGPSGPPGP PGDDGERGDDGEVGPRGLPGEPGPRGLLGPKGPPGPPGPPG VTGMDGQPGPKGNVGPQGEPGPPGQQGNPGAQGLPGPQGAI GPPGEKGPLGKPGLPGMPGADGPPGHPGKEGPPGEKGGQGP PGPQGPIGYPGPRGVKGADGIRGLKGTKGEKGEDGFPGFKG DMGIKGDRGEIGPPGPRGEDGPEGPKGRGGPNGDPGPLGPP GEKGKLGVPGLPGYPGRQGPKGSIGFPGPGANGEKGRGT PGKPGPGRGQRGPTGPRGERGPRGITGKPGPKGNSGGDGPAG PPGERGPNGPQGPTGFPGPKGPPGPPGKDGLPGHPGQRGET GFQGKTGPPGPPGVVGPQGPTGETGPMGERGHPGPPGPPGE QGLPGLAGKEGTKGDPGPAGLPGKDGPPGLRGFPGDRGLPG PVGALGLKGNEGPPGPPGPAGSPGERGPAGAAGPIGIPGRP GPQGPPGPAGEKGAPGEKGPQGPAGRDGLQGPVGLPGPAGP VGPPGEDGDKGEIGEPGQKGSKGDKGEQGPPGPTGPQGPIG QPGPSGADGEPGPRGQQGLFGQKGDEGPRGFPGPPGPVGLQ GLPGPPGEKGETGDVGQMGPPGPPGPRGPSGAPGADGPQGP PGGIGNPGAVGEKGEPGEAGEPGLPGEGGPPGPKGERGEKG ESGPSGAAGPPGPKGPPGDDGPKGSPGPVGFPGDPGPPGEP GPAGQDGPPGDKGDDGEPGQTGSPGPTGEPGPSGPPGKRGP PGPAGPEGRQGEKGAKGEAGLEGPPGKTGPIGPQGAPGKPG PDGLRGIPGPVGEQGLPGSPGPDGPPGPMGPPGLPGLKGDS GPKGEKGHPGLIGLIGPPGEQGEKGDRGLPGPQGSSGPKGE QGITGPSGPIGPPGPPGLPGPPGPKGAKGSSGPTGPKGEAG HPGPPGPPGPPGEVIQPLPIQASRTRRNIDASQLLDDGNGE NYVDYADGMEEIFGSLNSLKLEIEQMKRPLGTQQNPARTCK DLQLCHPDFPDGEYWVDPNQGCSRDSFKVYCNFTAGGSTCV FPDKKSEGARITSWPKENPGSWFSEFKRGKLLSYVDAEGNP VGVVQMTFLRLLSASAHQNVTYHCYQSVAWQDAATGSYDKA LRFLGSNDEEMSYDNNPYIRALVDGCATKKGYQKTVLEIDI PKVEQVPIVDIMFNDFGEASQKFGFEVGPACFMG | 11 |
| COL5A2 Collagen alpha-2(V) chain | P05997 | MMANWAEARPLLILIVLLGQFVSIKAQEEDEDEGYGEEIAC TQNGQMYLNRDIWKPAPCQICVCDNGAILCDKIECQDVLDC ADPVTPPGECCPVCSQTPGGGNTNFGRGRKGQKGEPGLVPV VTGIRGRPGPAGPPGSQGPRGERGPKGRPGPRGQGIDGEP GVPGQPGAPGPPGHPSHPGPDGLSRPFSAQMAGLDEKSGLG SQVGLMPGSVGPVGPRGPQGLQGQQGGAGPTGPPGEPGDPG PMGPIGSRGPEGPPGKPGEDGEPGRNGNPGEVGPAGSPGAR GFPGAPGLPGLKGHRGHKGLEGPKGEVGAPGSKGEAGPTGP | 12 |

TABLE 1-continued

Example Homo sapiens collagen polypeptide sequences

| Gene Name (Protein Name) | Uniprot ID | Polypeptide Sequence | SEQ ID NO: |
|---|---|---|---|
| | | MGAMGPLGPRGMPGERGRLGPQGAPGQRGAHGMPGKPGPMG PLGIPGSSGFPGNPGMKGEAGPTGARGPEGPQGQRGETGPP GPVGSPGLPGAIGTDGTPGAKGPTGSPGTSGPPGSAGPPGS PGPQGSTGPQGIRGQPGDPGVPGFKGEAGPKGEPGPHGIQG PIGPPGEEGKRGPRGDPGTVGPPGPVGERGAPGNRGFPGSD GLPGPKGAQGERGPVGSSGPKGSQGDPGRPGEPGLPGARGL TGNPGVQGPEGKLGPLGAPGEDGRPGPPGSIGIRGQPGSMG LPGPKGSSGDPGKPGEAGNAGVPGQRGAPGKDGEVGPSGPV GPPGLAGERGEQGPPGPTGFQGLPGPPGPPGEGGKPGDQGV PGDPGAVGPLGPRGERGNPGERGEPGITGLPGEKGMAGGHG PDGPKGSPGPSGTPGDTGPPGLQGMPGERGIAGTPGPKGDR GGIGEKGAEGTAGNDGARGLPGPLGPPGPAGPTGEKGEPGP RGLVGPPGSRGNPGSRGENGPTGAVGFAGPQGPDGQPGVKG EPGEPGQKGDAGSPGPQGLAGSPGPHGPNGVPGLKGGRGTQ GPPGATGFPGSAGRVGPPGPAGAPGPAGPLGEPGKEGPPGL RGDPGSHGRVGDRGPAGPPGGPGDKGDPGEDGQPGPDGPPG PAGTTGQRGIVGMPGQRGERGMPGLPGPAGTPGKVGPTGAT GDKGPPGPVGPPGSNGPVGEPGPEGPAGNDGTPGRDGAVGE RGDRGDPGPAGLPGSQGAPGTPGPVGAPGDAGQRGDPGSRG PIGPPGRAGKRGLPGPQGPRGDKGDHGDRGDRGQKGHRGFT GLQGLPGPPGPNGEQGSAGIPGPFGPRGPPGPVGPSGKEGN PGPLGPIGPPGVRGSVGEAGPEGPPGEPGPPGPPGPPGHLT AALGDIMGHYDESMPDPLPEFTEDQAAPDDKNKTDPGVHAT LKSLSSQIETMRSPDGSKKHPARTCDDLKLCHSAKQSGEYW IDPNQGSVEDAIKVYCNMETGETCISANPSSVPRKTWWASK SPDNKPVWYGLDMNRGSQFAYGDHQSPNTAITQMTFLRLLS KEASQNITYICKNSVGYMDDQAKNLKKAVVLKGANDLDIKA EGNIRFRYIVLQDTCSKRNGNVGKTVFEYRTQNVARLPIID LAPVDVGGTDQEFGVEIGPVCFV | |
| COL5A3 Collagen alpha-3(V) chain | P25940 | MGNRRDLGQPRAGLCLLLAALQLLPGTQADPVDVLKALGVQ GGQAGVPEGPGFCPQRTPEGDRAFRIGQASTLGIPTWELFP EGHFPENFSLLITLRGQPANQSVLLSIYDERGARQLGLALG PALGLLGDPFRPLPQQVNLTDGRWHRVAVSIDGEMVTLVAD CEAQPPVLGHGPRFISIAGLTVLGTQDLGEKTFEGDIQELL ISPDPQAAFQACERYLPDCDNLAPAATVAPQGEPETPRPRR KGKGKGRKKGRGRKGKGRKKNKEIWTSSPPPDSAENQTSTD IPKTETPAPNLPPTPTPLVVTSTVTTGLNATILERSLDPDS GTELGTLETKAAREDEEGDDSTMGPDFRAAEYPSRTQFQIF PGAGEKGAKGEPAVIEKGQQFEGPPGAPGPQGVVGPSGPPG PPGFPGDPGPPGPAGLPGIPGIDGIRGPPGTVIMMPFQFAG GSFKGPPVSFQQAQAQAVLQQTQLSMKGPPGPVGLTGRPGP VGLPGHPGLKGEEGAEGPQGPRGLQGPHGPPGRVGKMGRPG ADGARGLPGDTGPKGDRGFDGLPGLPGEKGQRGDFGHVGQP GPPGEDGERGAEGPPGPTGQAGEPGPRGLLGPRGSPGPTGR PGVTGIDGAPGAKGNVGPPGEPGPPGQQGNHGSQGLPGPQG LIGTPGEKGPPGNPGIPGLPGSDGPLGHPGHEGPTGEKGAQ GPPGSAGPPGYPGPRGVKGTSGNRGLQGEKGEKGEDGFPGF KGDVGLKGDQGKPGAPGPRGEDGPEGPKGQAGQAGEEGPPG SAGEKGKLGVPGLPGYPGRPGPKGSIGFPGPLGPIGEKGKS GKTGQPGLEGERGPPGSRGERGQPGATGQPGPKGDVGQDGA PGIPGEKGLPGLQGPPGFPGPKGPPGHQGKDGRPGHPGQRG ELGFQGQTGPPGPAGVLGPQGKTGEVGPLGERGPPGPPGPP GEQGLPGLEGREGAKGELGPPGPLGKEGPAGLRGFPGPKGG PGDPGPTGLKGDKGPPGPVGANGSPGERGPLGPAGGIGLPG QSGSEGPVGPAGKKGSRGERGPPGPTGKDGIPGPLGPLGPP GAAGPSGEEGDKGDVGAPGHKGSKGDKGDAGPPGQPGIRGP AGHPGPPGADGAQGRRGPPGLFGQKGDDGVRGFVGVIGPPG LQGLPGPPGEKGEVGDVGSMGPHGAPGPRGPQGPTGSEGTP GLPGGVGQPGAVGEKGERGDAGDPGPPGAPGIPGPKGDIGE KGDSGPSGAAGPPGKKGPPGEDGAKGSVGPTGLPGDLGPPG DPGVSGIDGSPGEKGDPGDVGGPGPPGASGEPGAPGPPGKR GPSGHMGREGREGEKGAKGEPGPDGPPGRTGPMGARGPPGR VGPEGLRGIPGPVGEPGLLGAPGQMGPPGPLGPSGLPGLKG DTGPKGEKGHIGLIGLIGPPGEAGEKGDQGLPGVQGPPGPK GDPGPPGPIGSLGHPGPPGVAGPLGQKGSKGSPGSMGPRGD TGPAGPPGPPGAPAELHGLRRRRRFVPVPLPVVEGGLEEVL ASLTSLSLELEQLRRPPGTAERPGLVCHELHRNHPHLPDGE YWIDPNQGCARDSFRVFCNFTAGGETCLYPDKKFEIVKLAS WSKEKPGGWYSTFRRGKKFSYVDADGSPVNVVQLNFLKLLS ATARQNFTYSCQNAAAWLDEATGDYSHSARFLGTNGEELSF NQTTAATVSVPQDGCRLRKGQTKTLFEFSSSRAGFLPLWDV AATDFGQTNQKFGFELGPVCFSS | 13 |

TABLE 1-continued

Example *Homo sapiens* collagen polypeptide sequences

| Gene Name (Protein Name) | Uniprot ID | Polypeptide Sequence | SEQ ID NO: |
|---|---|---|---|
| COL6A2 Collagen alpha-2(VI) chain | P12110 | MLQGTCSVLLLWGILGAIQAQQQEVISPDTTERNNNCPEKT DCPIHVYFVLDTSESVTMQSPTDILLEHMKQFVPQFISQLQ NEFYLDQVALSWRYGGLHFSDQVEVFSPPGSDRASFIKNLQ GISSERRGTFTDCALANMTEQIRQDRSKGTVHFAVVITDGH VTGSPCGGIKLQAERAREEGIRLFAVAPNQNLKEQGLRDIA STPHELYRNDYATMLPDSTEIDQDTINRIIKVMKHEAYGEC YKVSCLEIPGPSGPKGYRGQKGAKGNMGEPGEPGQKGRQGD PGIEGPIGFPGPKGVPGFKGEKGEFGADGRKGAPGLAGKNG TDGQKGKLGRIGPPGCKGDPGNRGPDGYPGEAGSPGERGDQ GGKGDPGRPGRRGPPGEIGAKGSKGYQGNSGAPGSPGVKGA KGGPGPGRGPKGEPGRRGDPGTKGSPGSDGPKGEKGDPGPEG PRGLAGEVGNKGAKGDRGLPGPRGPQGALGEPGKQGSRGDP GDAGPRGDSGQPGPKGDPGRPGFSYPGPRGAPGEKGEPGPR GPEGGRGDFGLKGEPGRKGEKGEPADPGPPGEPGPRGPRGV PGPEGEPGPPGDPGLTECDVMTYVRETCGCCDCEKRCGALD VVFVIDSSESIGYINFTLEKNEVINVVNRLGAIAKDPKSET GTRVGVVQYSHEGTFEAIQLDDERIDSLSSFKEAVKNLEWI AGGTWTPSALKFAYDRLIKESRRQKTRVFAVVITDGRHDPR DDDLNLRALCDRDVTVTAIGIGDMFHEKHESENLYSIACDK PQQVRNMTLFSDLVAEKFIDDMEDVLCPDPQIVCPDLPCQT ELSVAQCTQRPVDIVELLDGSERLGEQNFHKARREVEQVAR RLTLARRDDDPLNARVALLQFGGPGEQQVAFPLSHNLTAIH EALETTQYLNSFSHVGAGVVHAINAIVRSPRGGARRHAELS FVFLTDGVTGNDSLHESAHSMRKQNVVPTVLALGSDVDMDV LTTLSLGDRAAVFHEKDYDSLAQPGEFDREIRWIC | 14 |
| COL6A3 Collagen alpha-3(VI) chain | P12111 | MRKHRHLPLVAVFCLFLSGFPTTHAQQQQADVKNGAAADII FLVDSSWTIGEEHFQLVREFLYDVVKSLAVGENDFHFALVQ FNGNPHTEFLLNTYRTKQEVLSHISNMSYIGGINQTGKGLE YIMQSHLTKAAGSRAGDGVPQVIVVLTDGHSKDGLALPSAE LKSADVNVFAIGVEDADEGALKEIASEPLNMHMENLENFTS LHDIVGNLVSCVHSSVSPERAGDTETLKDITAQDSADIIFL IDGSNNTGSVNFAVILDFLVNLLEKLPIGTGQQIRVGVVQFS DEPRTMFSLDTYSTKAQVLGAVKALGFAGGELANIGLALDF VVENHFTRAGGSRVEEGVPQVLVLISAGPSSDEIRYGVVAL KQASVESEGLGAQAASRAELQHIATDDNLVETVPEFRSEGD LQEKLLPYIVGVAQRHIVLKPPTIVTQVIEVNKRDIVFLVD GSSALGLANFNAIRDFIAKVIQRLEIGQDLIQVAVAQYADT VRPEFYENTHPTKREVITAVRKMKPLDGSALYTGSALDFVR NNLFTSSAGYRAAEGIPKLLVLITGGKSLDEISQPAQELKR SSIMAFAIGNKGADQAELEEIAFDSSLVFIPAEFRAAPLQG MLPGLLAPLRTLSGTPEVHSNKRDIIFLLDGSANVGKINFP YVRDFVMNLVNSLDIGNDNIRVGLVQFSDTPVTEFSLNTYQ TKSDILGHLRQLQLQGGSGLNIGSALSYVYANHETEAGGSR IREHVPQLLLLLTAGQSEDSYLQAANALTRAGILTFCVGAS QANKAELEQIAFNPSLVYLMDDFSSLPALPQQLIQPLTTYV SGGVEEVPLAQPESKRDILFLEDGSANLVGQFPVVRDFLYK IIDELNVKPEGTRIAVAQYSDDVKVESRFDEHQSKPEILNL VKRMKIKTGKALNLGYALDYAQRYIFVKSAGSRIEDGVLQF LVLLLVAGRSSDRVDGPASNLKQSGVVPFIFQAKNADPAELE QIVLSPAFILAAESLPKIGDLHPQIVNLLKSVHNGAPAPVS GEKDVVFLLDGSEGVRSGFPLLKEFVQRVVESLDVGQDRVR VAVVQYSDRTRPEFYLNSYMNKQDVVNAVRQLTLLGGPTPN TGAALEFVLRNILVSSAGSRITEGVPQLLIVLTADRSGDDV RNPSVVVKRGGAVPIGIGIGNADITEMQTISFIPDFAVAIP TFRQLGTVQQVISERVTQLTREELSRLQPVLQPLPSPGVGG KRDVVFLIDGSQSAGPEFQYVRTLIERLVDYLDVGFDTTRV AVIQFSDDPKVEFLLNAHSSKDEVQNAVQRLRPKGGRQINV GNALEYVSRNIFKRPLGSRIEEGVPQFLVLISSGKSDDEVD DPAVELKQFGVAPFTIARNADQEELVKISLSPEYVFSVSTF RELPSLEQKLLTPITTLTSEQIQKLLASTRYPPPAVESDAA DIVFLIDSSEGVRPDGFAHIRDFVSRIVRRLNIGPSKVRVG VVQFSNDVFPEFYLKTYRSQAPVLDAIRRLRLRGGSPLNTG KALEFVARNLFVKSAGSRIEDGVPQHLVLVLGGKSQDDVSR FAQVIRSSGIVSLGVGDRNIDRTELQTITNDPRLVFTVREF RELPNIEERIMNSFGPSAATPAPPGVDTPPPSRPEKKKADI VFLLDGSINFRRDSFQEVLRFVSEIVDTVYEDGDSIQVGLV QYNSDPTDEFFLKDFSTKRQIIDAINKVVYKGGRHANTKVG LEHLRVNHFVPEAGSRLDQRVPQIAFVITGGKSVEDAQDVS LALTQRGVKVFAVGVRNIDSEEVGKIASNSATAFRVGNVQE LSELSEQVLETLHDAMHETLCPGVTDAAKACNLDVILGFDG SRDQNVFVAQKGFESKVDAILNRISQMHRVSCSGGRSPTVR VSVVANTPSGPVEAFDFDEYQPEMLEKFRNMRSQHPYVLTE DTLKVYLNKFRQSSPDSVKVVIHFTDGADGDLADLHRASEN LRQEGVRALILVGLERVVNLERLMHLEFGRGFMYDRPLRLN | 15 |

TABLE 1-continued

Example *Homo sapiens* collagen polypeptide sequences

| Gene Name (Protein Name) | Uniprot ID | Polypeptide Sequence | SEQ ID NO: |
|---|---|---|---|
| | | LLDLDYELAEQLDNIAEKACCGVPCKCSGQRGDRGPIGSIG PKGIPGEDGYRGYPGDEGGPGERGPPGVNGTQGFQGCPGQR GVKGSRGFPGEKGEVGEIGLDGLDGEDGDKGLPGSSGEKGN PGRRGDKGPRGEKGERGDVGIRGDPGNPGQDSQERGPKGET GDLGPMGVPGRDGVPGGPGETGKNGGFGRRGPPGAKGNKGG PGQPGFEGEQGTRGAQGPAGPAGPPGLIGEQGISGPRGSGG AAGAPGERGRTGPLGRKGEPGEPGPKGGIGNRGPRGETGDD GRDGVGSEGRRGKKGERGFPGYPGPKGNPGEPGLNGTTGPK GIRGRRGNSGPPGIVGQKGDPGYPGPAGPKGNRGDSIDQCA LIQSIKDKCPCCYGPLECPVFPTELAFALDTSEGVNQDTFG RMRDVVLSIVNDLTIAESNCPRGARVAVVTYNNEVTTEIRF ADSKRKSVLLDKIKNLQVALTSKQQSLETAMSFVARNTFKR VRNGFLMRKVAVFFSNTPTRASPQLREAVLKLSDAGITPLF LTRQEDRQLINALQINNTAVGHALVLPAGRDLTDFLENVLT CHVCLDICNIDPSCGFGSWRPSFRDRRAAGSDVDIDMAFIL DSAETTTLFQFNEMKKYIAYLVRQLDMSPDPKASQHFARVA VVQHAPSESVDNASMPPVKVEFSLTDYGSKEKLVDFLSRGM TQLQGTRALGSAIEYTIENVFESAPNPRDLKIVVLMLTGEV PEQQLEEAQRVILQAKCKGYFFVVLGIGRKVNIKEVYTFAS EPNDVFFKLVDKSTELNEEPLMRFGRLLPSFVSSENAFYLS PDIRKQCDWFQGDQPTKNLVKFGHKQVNVPNNVTSSPTSNP VTTTKPVTTTKPVTTTTKPVTTTTKPVTIINQPSVKPAAAK PAPAKAKPVAAKPVATKMATVRPPVAVKPATAAKPVAAKPAAV RPPAAAAAKPVATKPEVPRPQAAKPAATKPATTKPMVKMSR EVQVFEITENSAKLHWERAEPPGPYFYDLTVTSAHDQSLVL KQNLTVTDRVIGGLLAGQTYHVAVVCYLRSQVRATYHGSFS TKKSQPPPPQPARSASSSTINLMVSTEPLALTETDICKLPK DEGTCRDFILKWYYDPNTKSCARFWYGGCGGNENKFGSQKE CEKVCAPVLAKPGVISVMGT | |
| COL6A5 Collagen alpha-5(VI) chain | A8TX70 | MKILLIIFVLIIWTETLADQSPGPGPVYADVVFLVDSSDHL GPKSFPFVKTFINKMINSLPIEANKYRVALAQYSDEFHSEF HLSTFKGRSPMLNHLKKNFQFIGGSLQIGKALQEAHRTYFS APINGRDRKQFPPILVVLASAESEDEVEEASKALQKDGVKI ISVGVQKASEENLKAMATSHFHFNLRTIRDLSTFSQNMTQI IKDVTKYKEGAVDADMQVHFPISCQKDSLADLVFLVDESLG TGGNLRHLQTFLENIISSMDVKENCMRLGLMSYSNSAKTIS FLKSSTTQSEFQQQIKNLSIQVGKSNTGAAIDQMRRDGFSE SYGSRRAQGVPQIAVLVTHRPSDDEVHDAALNLRLEDVNVF ALSIQGANNTQLEEIVSYPPEQTISTLKSYADLETYSTKFL KKLQNEIWSQISTYAEQRNLDKTGCVDTKEADIHFLIDGSS SIQEKQFEQIKRFMLEVTEMFSIGPDKVRVGVVQYSDDTEV EFYITDYSNDIDLRKAIFNIKQLTGGTYTGKALDYILQIIK NGMKDRMSKVPCYLIVLTDGMSTDRVVEPAKRLRAEQITVH AVGIGAANKIELQEIAGKEERVSFGQNFDALKSIKNEVVRE ICAEKGCEDMKADIMFLVDSSWSIGNENFRKMKIFMKNLLT KIQIGADKTQIGVVQFSDKTKEEFQLNRYFTQQEISDAIDR MSLINEGTLTGKALNFVGQYFTHSKGARLGAKKFLILIIDG VAQDDVRDPARILRGKDVTIFSVGVYNANRSQLEEISGDSS LVFHVENFDHLKALERKLIFRVCALHDCKRITLLDVVFVLD HSGSIKKQYQDHMINLTIHLVKKADVGRDRVQFGALKYSDQ PNILFYLNTYSNRSAIIENLRKRRDTGGNTYTAKALKHANA LFTEEHGSRIKQNVKQMLIVITDGESHDHDQLNDTALELRN KGITIFAVGVGKANQKELEGMAGNKNNTIYVDNFDKLKDVF TLVQERMCTEAPEVCHLQEADVIFLCDGSDRVSNSDFVTMT TFLSDLIDNFDIQSQRMKIGMAQFGSNYQSIIELKNSLTKT QWKTQIQNVSKSGGFPRIDFALKKVSNMFNLHAGGRRNAGV PQTLVVITSGDPRYDVADAVKTLKDLGICVLVLGIGDVYKE HLLPITGNSEKIITFQDFDKLKNVDVKKRIIREICQSCGKT NCFMDIVVGFDISTHVQGQPLFQGHPQLESYLPGILEDISS IKGVSCGAGTEAQVSLAFKVNSDQGFPAKFQIYQKAVFDSL LQVNVSGPTHLNAQFLRSLWDTFKDKSASRGQVLLIFSDGL QSESNIMLENQSDRLREAGLDALLVVSLNTTAHHEFSSFEF GKRPFDYRTHLTIGMRELGKKLSQYLGNIAERTCCCTFCKCP GIPGPHGTRGLQAMKGSQGLKGSRGHRGEDGNPGVRGDTGP QGDKGIAGCPGAWGQKGLKGFSGPKGGHGDDGIDGLDEEG CHGFPGIKGEKGDPGSQGSPGSRGAPGQYGEKGFPGDPGNP GQNNNIKGQKGSKGEQGRQGRSGQKGVQGSPSSRGSRGREG QRGLRGVSGEPGNPGPTGTLGAEGLQGPQGSQGNPGRKGEK GSQGQKGPQGSPGLMGAKGSTGRPGLLGKKGEPGLPGDLGP VGQTGQRGRQGDSGIPGYGQMRKGVKGPRGFPGDAGQKGD IGNPGIPGGPGPKGFRGLALTVGLKGEEGSRGLPGPPGQRG IKGMAGQPVYSQCDLIRFLREHSPCWKEKCPAYPTELVFAL DNSYDVTEESFNKTRDIITSIVNDLNIRENNCPVGARVAMV SYNSGTSYLIRWSDYNRKKQLLQQLSQIKYQDTTEPRDVGN | 16 |

TABLE 1-continued

Example Homo sapiens collagen polypeptide sequences

| Gene Name (Protein Name) | Uniprot ID | Polypeptide Sequence | SEQ ID NO: |
|---|---|---|---|
| | | AMRFVTRNVFKRTYAGANVRRVAVFFSNGQTASRSSIITAT MEFSALDISPTVFAFDERVFLEAFGFDNTGTFQVIPVPPNG ENQTLERLRRCALCYDKCFPNACIREAFLPEDSYMDVVFLI DNSRNIAKDEFKAVKALVSSVIDNFNIASDPLISDSGDRIA LLSYSPWESSRRKMGTVKTEFDFITYDNQLLMKNHIQTSFQ QLNGEATIGRALLWTTENLFPETPYLRKHKVIFVVSAGENY ERKEFVKMMALRAKCQGYVIFVISLGSTRKDDMEELASYPL DQHLIQLGRIHKPDLNYIAKFLKPFLYSVRRGFNQYPPPML EDACRLINLGGENIQNDGFQFVTELQEDPLGGNGFIGQELN SGRESPFVKTEDNGSDYLVYLPSQMFEPQKLMINYEKDQKS AEIASLTSGHENYGRKEEPDHTYEPGDVSLQEYYMDVAFLI DASQRVGSDEFKEVKAFITSVLDYFHIAPTPLTSTLGDRVA VLSYSPPGYMPNTEECPVYLEFDLVTYNSIHQMKHHLQDSQ QLNGDVFIGHALQWTIDNVFVGTPNLRKNKVIFVISAGETN SLDKDVLRNVSLRAKCQGYSIFVFSFGPKHNDKELEELASH PLDHHLVQLGRTHKPDWNYIIKFVKPFVHLIRRAINKYPTE DMKATCVNMTSPNPENGGTENTVLLLPGIYEIKTENGDLFD EFDSQAQHLLVLGNNHSSGSETATDLMQKLYLLFSTEKLAM KDKEKAHLEEISALVVDKQQEKEDKEMEATDI | |
| COL6A6 Collagen alpha-6(VI) chain | A6NM27 | MMLLILFLVIICSHISVNQDSGPEYADVVFLVDSSDRLGSK SFPPVKMFITKMISSLPIEADKYRVALAQYSDKLHSEFHLS TFKGRSPMLNHLRKNFGFIGGSLQIGKALQEAHRTYFSAPA NGRDKKQFPPILVVLASSESEDNVEEASKALRKDGVKIISV GVQKASEENLKAMATSQFHFNLRTVRDLSMFSQNMTHIIKD VIKYKEGAVDDIFVEACQGPSMADVVFLLDMSINGSEENFD YLKGFLEESVSALDIKENCMRVGLVAYSNETKVINSLSMGI NKSEVLQHIQNLSPRTGKAYTGAAIKKLRKEVFSARNGSRK NQGVPQIAVLVTHRDSEDNVTKAAVNLRREGVTIFTLGIEG ASDTQLEKIASHPAEQYVSKLKTFADLAAHNQTFLKKLRNQ ITHTVSVFSERTETLKSGCVDTEEADIYLLIDGSGSTQATD FHEMKTFLSEVVGMFNIAPHKVRVGAVQYADSWDLEFEINK YSNKQDLGKAIENIRQMGGNTNTGAALNFTLSLLQKAKKQR GNKVPCHLVVLTNGMSKDSILEPANRLREEHIRVYAIGIKE ANQTQLREIAGEEKRVYYVHDFDALKDIRNQVVQEICTEEA CKEMKADIMFLVDSSGSIGPENFSKMKTFMKNLVSKSQIGP DRVQIGVVQFSDINKEEFQLNRFMSQSDISNAIDQMAHIGQ TTLTGSALSFVSQYFSPTKGARPNIRKFLILITDGEAQDIV KEPAVVLRQEGVIIYSVGVFGSNVTQLEEISGRPEMVFYVE NFDILQRIEDDLVFGICSPREECKRIEVLDVVFVIDSSGSI DYDEYNIMKDFMIGLVKKADVGKNQVRFGALKYADDPEVLF YLDDFGTKLEVISVLQNDQAMGGSTYTAEALGFSDHMFTEA RGSRLNKGVPQVLIVITDGESHDADKLNATAKALRDKGILV LAVGIDGANPVELLAMAGSSDKYFFVETFGGLKGIFSDVTA SVCNSSKVDCEIDKVDLVFLMDGSTSIQPNDFKKMKEFLAS VVQDFDVSLNRVRIGAAQFSDTYHPEFPLGTFIGEKEISFQ IENIKQIFGNTHIGAALREVEHYFRPDMGSRINTGTPQVLL VLTDGQSQDEVAQAEALRHRGIDIYSVGIGDVDDQQLIQI TGTAEKKLTVHNFDELKKVNKRIVRNICTTAGESNCFVDVV VGFDVSTQEKGQTLLEGQPWMETYLQDILRAISSLNGVSCE VGTETQVSVAFQVTNAMEKYSPKFEIYSENILNSLKDITVK GPSLLNANLLDSLWDTFQNKSAARGKVVLLFSDGLDDDVEK LEQKSDELRKEGLNALITVALDGPADSSDLADLPYIEFGKG FEYRTQLSIGMRELGSRLSKQLVNVAERTCCCLFCKCIGGD GTMGDPGPPGKRGPPGFKGSEGYLGEEGIAGERGAPGPVGE QGTKGCYGTKGPKGNRGLNGQEGEVGENGIDGLNGEQGDNG LPGRKGEKGDEGSQGSPGKRGTPGDRGAKGLRGDPGAPGVD SSIEGPTGLKGERGRQGRRGWPGPPGTPGSRRKTAAHGRRG HTGPQGTAGIPGPDGLEGSLGLKGPQGPRGEAGVKGEKGGV GSKGPQGPPGPGGEAGNQGRLGSQGNKGEPGDLGEKGAVGF PGPRGLQGNDGSPGYGSVGRKGAKGQEGFPGESGPKGEIGD PGGPGETGLKGARGKMISAGLPGEMGSPGEPGPPGRKGVKG AKGLASFSTCELIQYVRDRSPGRHGKPECPVHPTELVFALD HSRDVTEQEFERMKEMMAFLVRDIKVRENSCPVGAHIAILS YNSHARHLVRFSDAYKKSQLLREIETIPYERSSASREIGRA MRFISRNVFKRTLPGAHTRKIATFFSSGQSADAHSITTAAM EFGALEIIPVVITFSNVPSVRRAFAIDDTGTFQVIVVPSGA DYIPALERLQRCTFCYDVCKPDASCDQARPPPVQSYMDAAF LLDASRNMGSAEFEDIRAFLGALLDHFEITPEPETSVTGDR VALLSHAPPDFLPNTQKSPVRAEFNLTTYRSKRLMKRHVHE SVKQLNGDAFIGHALQWTLDNVFLSTPNLRRNKVIFVISAG ETSHLDGEILKKESLRAKCQGYALFVFSLGPIWDDKELEDL ASHPLDHHLVQLGRIHKPDHSYGVKFVKSFINSIRRAINKY | 17 |

TABLE 1-continued

Example Homo sapiens collagen polypeptide sequences

| Gene Name (Protein Name) | Uniprot ID | Polypeptide Sequence | SEQ ID NO: |
|---|---|---|---|
| | | PPINLKIKCNRLNSIDPKQPPRPFRSFVPGPLKATLKEDVL QKAKFFQDKKYLSRVARSGRDDAIQNFMRSTSHTFKNGRMI ESAPKQHD | |

Fibrillar collagenous ECM collagen, a kind of mature ECM in accordance with methods, compositions, and kits of some embodiments herein, can include COL1 a major component, and can also comprise COL3, COL4, COL5, and/or COL6, for example about 90% COL1 and about 10% COL3, COL4, COL5, and/or COL6, though other percentages of (i) COL1 and (ii) COL3, COL4, COL5 and/or COL6, are suitable, for example about 97% and 3% respectively, about 95% and 5% respectively, about 93% and 7% respectively, about 85% and 15% respectively, about 80% and 20% respectively, about 75% and 25% respectively, or about 70% and 30%, respectively.

ECM, and in particular, human ECM products as produced according to methods, compositions, and kits of some embodiments herein are useful for treating tissues in patients suffering from musculoskeletal disorders, orthopedic dysfunction and associated pain, cardiovascular disorders, cutaneous diseases, age-related cosmetic skin and hair conditions requiring improvement in appearance, surgical wounds, solid-tumors requiring treatment including surgical excision, chemotherapy and immunotherapy. Uses for the human ECM products produced by methods, kits, and compositions in accordance with some embodiments herein, by way of example, include medical devices and biologics for musculoskeletal applications including osteochondral defect repair, osteoarthritis, degenerative disc-disease, surgical wounds for orthopedics; surgical wounds associated with tumor resection cavities, cardiovascular regeneration devices and biologics, cutaneous wound devices and biologics, dermal fillers for treating wrinkles, topical cosmetics, therapeutic hair growth, and cell-delivery and drug-delivery vehicles for increased persistence and reduction of unwanted immune reactions when transferred to a patient. In some embodiments, ECM (e.g., a human ECM product) produced according to methods, compositions, and kits of some embodiments herein is used for at least one of a medical product, a cosmetic product, a drug, a medical device, a treatment, or a biologic. In some embodiments the ECM can be used for at least one of a medical product, a biologic, a medical device, a drug, or any other product or composition regulated by the FDA. In some embodiments, the ECM can be used for at least one of a medical or cosmetic procedure.

The use of human cell cultures for the production of human ECM in accordance with methods, compositions, and kits of some embodiments herein can offer advantages over animal and cadaver-derived ECMs. For example, in some embodiments, the cells in culture can be from a single donor, can be readily expanded, and/or can be xeno-free. On the other hand, conventional approaches for producing ECM in cell culture presented challenges, for example challenges related to commercial scale, cost-effectiveness, and the presence of non-human components. For example, fibroblast-derived human ECMs from cell culture and methods of manufacture have been described. For example, a group of patents by Naughton, et al (U.S. Pat. Nos. 6,378,527; 5,830,708; 7,118,746; 6,372,494; 8,257,947; 8,530,415; 8,535,913; 9,034,312; 8,852,637; 8,128,924; 8,138,147; 8,361,485; 8,476,231; and 9,458,486, referred to as the "Naughton patents," and hereby incorporated by reference in their entireties) disclose various compositions and methods of production for soluble and insoluble human ECM. For example, the Naughton patents disclose the use of animal proteins such as fetal bovine serum, calf serum, and porcine trypsin to support cell expansion and production of human ECM. These processes using animal components have also utilized porcine pepsin to collagens after the ECM is produced, for example in the manufacture of CosmoDerm™ and CosmoPlast™ dermal filler products. For example, porcine carbohydrates such as porcine heparin can cause deleterious immune reactions in humans.

The Naughton patents also disclose soybean trypsin inhibitor. Without being limited by theory, soybean trypsin inhibitor can be used when serum is not included to reduce deleterious protein degradation in cell cultures. However, some plant proteins, and soybean trypsin inhibitor in particular, can cause unwanted immune reactions in humans, even potentially allergies or anaphylactic shock or death in rare cases. As such, it is contemplated that replacement of enzyme inhibitors found in animal sera with plant components, such as soybean trypsin inhibitor can still cause unwanted immune reactions. Furthermore, it is contemplated that soybean trypsin inhibitor may possess enzymatic activity, which can affect compositions that contain soybean trypsin inhibitor, or skin tissue to which the soybean trypsin inhibitor is exposed, for example upon topical or transdermal application. Soybean trypsin inhibitor has also been shown to inhibit hair growth. While removing the soluble soybean trypsin inhibitor is formally possible, doing so is of limited commercial practicality as it would involve extensive and costly purification methods in an undefined mixture of cell-secreted products in spent culture medium, yielding products in which the exact active ingredients can be unknown. As such, some embodiments do not include animal-derived products, or soybean trypsin inhibitor. Some embodiments do not include animal-derived products or plant-derived products.

Advantageously, xeno-free methods of manufacturing ECM in accordance with some embodiments herein can obviate the need for clinical studies directed to removal of animal- (and/or plant-) derived components, as the xeno-free systems and methods can avoid the use of animal- and/or plant-derived components in the first place. For example, methods and compositions in accordance with some embodiments herein can produce soluble ECM compositions for cosmetic uses, and which do not necessarily contain known plant allergens such as soy proteins. Additionally, ECM compositions manufactured in accordance with some embodiments herein that do not contain animal- or plant-derived components will not require safety warnings for potential allergies to animal products or plant products such as soy proteins.

In some embodiments, cell-based in vitro culture methods can produce xeno-free human ECM at scales larger than a single human per batch. Furthermore, the xeno-free ECM can have a reduced risk of disease transmission since the cell lines can be extensively tested, and each set of tests can support many commercial-scale batches of manufactured products using human ECM, because the tested cell lines can be expanded.

Fibroblast spent medium can comprise soluble ECM, and thus can also be used for cosmetic purposes in some embodiments. Without being limited by theory, it is observed herein that fetal and embryonic ECM contains relatively lower degrees of abundance of mature and non-reducible crosslinks. However, soluble human ECM produced in accordance with some embodiments herein can comprise a greater amount of mature collagen type 1, for example a greater amount of mature triple-helical collagen type 1, as well as some less abundant fibrillar collagens, for example collagen types 3, 5, and 6.

A number of approaches can be used to assess the presence and/or levels of mature collagens in ECM in accordance with embodiments herein. For example, amounts of cross-linked mature collagens can be measured on reduced SDS-PAGE gels, using adult-tissue derived type I collagen for comparison.

Pluripotent Cells

"Pluripotent cell" is used herein in accordance with its ordinary meaning in the field, and includes a class of cells that are capable of differentiating according to multiple different fates. Examples of pluripotent cells include, but are not limited to, Induced Pluripotent Stem Cells (iPSCs) and embryonic stem (ES) cells. In some embodiments, pluripotent cells suitable for methods, compositions, and/or kits herein comprise, consist of, or consist essentially of iPSCs. In some embodiments, pluripotent cells suitable for methods, compositions, and kits herein comprise, consist of, or consist essentially of iPSCs or ES cells. In some embodiments, pluripotent cells suitable for methods, compositions, and kits herein comprise, consist of, or consist essentially of iPSCs, but not ES cells. In some embodiments, pluripotent cells suitable for methods, compositions, and/or kits herein are human cells. In some embodiments, pluripotent cells suitable for methods, compositions, and/or kits herein are from a single donor.

Without being limited by theory, pluripotent cells (induced or embryonic in origin) conventionally did not produce enough fibrillar collagenous ECM in cell cultures. However, in methods, compositions, and kits of some embodiments herein, pluripotent cells can provide an abundant supply (which can be thought of as nearly limitless) of cells from a single donor, and can be used when they are differentiated into fibroblastic cells that secrete and deposit ECM. Thus, de-differentiating fibroblasts into iPSCs, expanding the iPSCs, and then re-differentiating the iPSCs into fibroblasts in accordance with compositions, methods, and kits of some embodiments herein can produce commercial-scale quantities of single-donor fibroblasts for the production of ECM. As the cells are single-donor, there can be greater uniformity in the ECM product produced, and lower risk for contamination and/or transmission of diseases. The skilled artisan would appreciate that generically producing iPSC's from fibroblasts, and then differentiating the iPSC's back into fibroblasts would involve a considerable amount of effort, but that the practical advantages discussed herein for the practical uses discussed herein would make the effort worthwhile.

"Induced Pluripotent Stem Cell" (iPSC) is used herein in accordance with its ordinary meaning in the field, and includes a class of cells produced by de-differentiation of somatic cells into cells having similar characteristics as ES cells. A number of art-recognized approaches for making iPSCs are suitable for methods, kits, and compositions of embodiments herein. In some embodiments, an iPSC is made by contacting a somatic cell with de-differentiation factors. As noted in detail herein, de-differentiation factors can comprise nucleic acids, polypeptides, and/or small molecules that induce a somatic cell to de-differentiate into an iPSC.

As used herein "de-differentiation factors" (including variants of this root term) refers to a set of gene products, and/or nucleic acids encoding gene products, and/or small molecules, which are sufficient to de-differentiate a somatic cell (e.g., a fibroblast) into an iPSC. De-differentiation factors can be used to de-differentiate a somatic cell (e.g. a fibroblast) into an iPSC in accordance with methods of some embodiments herein. De-differentiation factors can also be included with compositions and kits in accordance with some embodiments herein, as they can be useful for de-differentiating a somatic cell (e.g., a fibroblast) into an iPSC. In some embodiments, the de-differentiation factors comprise two or more transcription factors. In some embodiments, the de-differentiation factors comprise, consist essentially of, or consist of an Oct family member (e.g., Oct3/4 or POU5F1), a Sox family member (e.g., Sox1, Sox2, Sox3, Sox4, Sox11, or Sox15), a Klf family member (e.g., Klf1, Klf2, Klf4, or Klf5), and least one of (i) a Myc family member (e.g., c-Myc, L-Myc, or N-Myc), (ii) Nanog, (iii) Lin28 or Lin28B, or (iv) Glis1, and/or (in the case of de-differentiated fibroblasts, an Oct family member (e.g., Oct 4) and Bmi1. In some embodiments, the de-differentiation factors comprise, consist essentially of, or consist of chemical de-differentiation factors (e.g., small molecules).

In some embodiments, the de-differentiation factors are provided as one or more nucleic acids that encode gene products sufficient to de-differentiate a somatic cell (e.g., a fibroblast) into an iPSC. Such de-differentiation factors can be provided on a single vector, or on a set of more than one vectors. Examples of suitable vectors in accordance with methods, compositions, and kits of some embodiments include, but are not limited to, retroviral vectors, adenoviral vectors, adeno-associated vectors, lentiviral vectors, and the like. In some embodiments, each of the nucleic acids encoding the de-differentiation factors is operably linked to a promoter (it is also contemplated that two or more nucleic acids can be under the control of the same promoter, for example, separated by an IRES or 2A element). In some embodiments, the de-differentiation factors are provided as one or more gene products (e.g. proteins) sufficient to de-differentiate a somatic cell (e.g., a fibroblast into an iPSC). In some embodiments, the de-differentiation factors are provided as a collection of proteins. In some embodiments, the de-differentiation factors are provided in a single polypeptide, which can be cleaved to yield individual de-differentiation factors. The polypeptide(s) can further include a tag, for example, a nuclear localization sequence, to facilitate entry and localization, into a suitable portion of a target cell. In some embodiments, the de-differentiation factors comprise chemical de-differentiation factors, as described herein. There can be additional advantages associated with "footprint free" de-differentiation factors (for example delivered by non-integrating vectors, removal of vectors, direct administration of mRNA or polypeptides, or chemical induction of pluripotency), since they do not use potentially harmful viruses to deliver factors that induce pluripotency, and do not insert foreign material into the host genome, which can raise a risk of insertional mutagenesis. Accordingly, in some embodiments, the de-differentiation factors are footprint-free. Examples of footprint-free generation of iPSCs from somatic cells by delivery of mRNAs encoding Klf4, c-Myc, Oct4, and Sox2 to the somatic cells can be found, for example, in Warren et al. (2010), Cell Stem Cell 7: 618-30, which is hereby incorporated by reference in its entirety such, in some embodiments, mRNAs encoding de-differentiation factors are used to make iPSCs. In some embodiments, chemical induction of pluripotency is as described herein.

It has been reported that a combination of an Oct family member (e.g., Oct3, Oct4, /or POU5F1) and a Sox family member (e.g., Sox1, Sox2, Sox3, Sox4, Sox11, or Sox15) are sufficient to de-differentiate a somatic cell into an iPSC. See U.S. Pat. No. 9,683,232, which is hereby incorporated by reference in its entirety. As such, in some embodiments, the de-differentiation factors comprise, consist essentially of, or consist of an Oct family member, and a Sox family member. See U.S. Pat. No. 9,683,232. Furthermore, without being limited by theory, it is contemplated that the inclusion of additional factors can increase the efficiency of de-differentiation. For example, in some embodiments, the de-differentiation factors comprise, consist essentially of, or consist of an Oct family member, a Klf family member (e.g., Klf1, Klf2, Klf4, or Klf5) and a Sox family member. For example, the combination of Oct 3/4, Klf4, c-Myc, and Sox2 is sufficient to de-differentiate somatic cells (and fibroblasts in particular) into iPSCs. See U.S. Pat. No. 8,058,065, which is hereby incorporated by reference in its entirety. Accordingly, in some embodiments, the de-differentiation factors comprise, consist essentially of, or consist of Oct 3/4 Klf4, c-Myc, and Sox2.

In some embodiments, the de-differentiation factors comprise, consist essentially of, or consist of an Oct family member (e.g., Oct3, Oct4, or POU5F1), a Klf family member (e.g., Klf1, Klf2, Klf4, or Klf5), a Myc family member (e.g., c-Myc, L-Myc, or N-Myc), and a Sox family member (e.g. Sox1, Sox2, Sox3, Sox4, Sox11, or Sox15). Furthermore, it has been reported that a combination of Oct3/4, Klf4, Sox2, and at least one of (i) a Myc family member, (ii) Nanog, (iii) Lin28 or Lin28B, or (iv) Glis1 is also sufficient to de-differentiate somatic cells, and fibroblasts in particular, into iPSCs. See U.S. Pat. No. 9,447,408, which is hereby incorporated by reference in its entirety. Accordingly, in some embodiments, the de-differentiation factors comprise, consist essentially of, or consist of Oct3/4, Klf4, Sox2, and at least one of (i) a Myc family member, (ii) Nanog, (iii) Lin28 or Lin28B, or (iv) Glis1.

It has also been reported that fibroblasts in particular can be reprogrammed into iPSCs using a combination of the factors Oct4 and Bmi1 (e.g., so that Bmi1 can be substituted for the combination of Sox2, Klf4, and/or c-Myc). Moon et al. (2011), Cell. Res. 21: 1305-15, which is hereby incorporated by reference in its entirety. Accordingly, in some embodiments, for example if a precursor fibroblast is de-differentiated into an iPSC, the de-differentiation factors comprise, consist essentially of, or consist of Oct4 and Bmi1.

It has been shown that a cocktail of small molecules, "VC6TF" (V, VPA; C, CHIR99021 or CHIR; 6, 616452; T, tranylcypromine; F, forskolin) can induce pluripotent stem cells from somatic cells. Hou et al. (2013), Science 341: 651-654, which is hereby incorporated by reference in its entirety. For example, the addition of EPZ 004777 (EPZ, E), an inhibitor of H3K79 histone methyltransferase DOT1L, and Ch 55, a retinoid acid receptor (RAR) agonist to VC6TF has been shown to boost de-differentiation of somatic cells. Ye et al. (2016), Cell Research 26: 34-35, which is hereby incorporated by reference in its entirety. Accordingly, in some embodiments, the de-differentiation factors comprise, consist of, or consist essentially of chemical de-differentiation factors, for example, VC6TF, or VC6TF along with EPZ 004777, DOT1L, and Ch 55.

In some embodiments, the iPSCs are derived from somatic cells of a single donor. Without being limited by theory, iPSCs (or other pluripotent cells) from a single donor can offer safety advantages, for example limiting the exposure of the cells to only a single donor's complement of viruses, microbial organisms, or other potential pathogens, and thus minimizing the risk for transmission of disease compared to collections of cells from multiple donors. It is also formally possible for the iPSCs, in some embodiments, to be derived from somatic cells of two or more donors. In some embodiments, the iPSCs are derived from adult dermal fibroblast biopsies.

Embryonic stem cells are another type of pluripotent stem cell. It is possible to use embryonic stem cells as pluripotent cells in the methods, compositions, and kits of some embodiments herein. Methods of isolating and preparing embryonic stem cells, including human embryonic stem cells are described, for example, in U.S. Pat. No. 6,200,806, which is hereby incorporated by reference in its entirety. However, it is also recognized that iPSC's in some embodiments can offer a number of advantages over embryonic stem cells. For example, ES cells may have limitations involving ethical and legal considerations around the destruction of a human embryo, which is one way to generate a pluripotent cell. Chemically-induced pluripotent cells are the preferred source.

Fibroblasts

"Fibroblast" is used herein in accordance with its ordinary meaning in the field, and includes a class of cells that provide structural framework (stroma) for a variety of animal tissues. Fibroblasts can also migrate at the site of a wound to mediate wound healing, and can be a component in a variety of connective tissues. Fibroblasts can be identified, for example, using fibroblast-specific antibodies, for example antibody TE-7, described in Goodpaster et al. (2008), J. Histochem Cyotchem. 56: 347-58, which is hereby incorporated by reference in its entirety.

Without being limited by theory, it is contemplated that any mesenchymal cell that can adhere to a substrate (e.g., a plastic), grow in the presence of serum, and synthesize and deposit fibrillar collagenous ECM collagen in cell culture can be used for making human ECM in culture. In some embodiments, fibroblasts, a type of mesenchymal cell, are used to produce ECM. Example types of cells that can produce ECM (which may be referred to as "ECM-producing cells") include, but are not limited to, a bone marrow mesenchymal stem cell (MSC), an iPSC-derived MSC, an ES-derived MSC, and a fibroblast, for example from a neonatal foreskin fibroblast cell line (which can be multipotent or non-multipotent), or from a skin or blood biopsy. Without being limited by theory, it is further contemplated that differences between mesenchymal cell types may be no greater than those between any cells of a single donor strain or cell line (from a common cell source). If the cells come from a human donor sample that contains connective tissues, these cells can be suitable for making ECM in cell culture in accordance with some embodiments herein.

Conventionally, fibroblasts have been obtained from neonatal foreskins, since these are easily obtained from discarded tissues. However, this approach generally requires cells from multiple donors in order to generate and screen production-scale cell banks. The use of more than one donor can also raise an increased risk for transmission of adventitious agents. The costs of developing and screening donor cell banks also can be large and disadvantageous. Adventitious agent testing requirements can represent another hurdle for banking and using cells from multiple donors. Furthermore, while primary cell lines can be limited theoretically by the Hayflick limit for non-transformed somatic cells, practically speaking, primary cell lines may be amenable to no more than about 8-20 passages after isolation from the tissue source. These limits on passages can limit the suitability of conventional fibroblasts for expansions in line with a cell banking process, for example that of a Master Cell Bank, Working Cell Bank, or Production Cell Bank schema for manufacturing commercial quantities. However, methods, kits, and compositions in accordance with some embodiments herein can offer advantages over conventional sources of fibroblast. For example, fibroblasts differentiated from iPSCs in accordance with some embodiments herein can be from a single donor (e.g., if iPSCs are expanded before they are differentiated into fibroblasts), reducing the risk for transmission of disease, and reducing testing requirements. Furthermore, in some embodiments, iPSCs can undergo many more cycles of expansion than primary cell lines, facilitating the commercial scaleability of fibroblasts or other ECM-producing cells derived from iPSCs. In some embodiments, the iPSCs are expanded in the absence of serum.

In some embodiments, fibroblasts can be obtained by differentiating iPSCs into fibroblasts. Without being limited by theory, it is contemplated that iPSCs can be differentiated into fibroblasts by contacting the iPSCs with one or more fibroblast differentiation factor, which can include, for example, one or more growth factors. As used herein "fibroblast differentiation factors" (including variants of this root term) refer to a set of gene products and/or nucleic acids encoding gene products, in which the gene products are sufficient to differentiate a pluripotent cell (e.g. an iPSC) into a fibroblast. For example, it has been reported that iPSCs can be differentiated into fibroblasts by contacting the iPSCs with connective tissue growth factor (CTGF). The iPSC's can be grown on a 3-D scaffold. Xu et al., Scientific Reports 5: 8480 DOI: 10.1038/srep08480, which is hereby incorporated by reference in its entirety. As such, in some embodiments, the fibroblast differentiation factors comprise, consist essentially of, or consist of CTGF. In some embodiments, the fibroblast differentiation factors comprise, consist essentially of, or consist of CTGF and fibrinogen. In some embodiments, the iPSCs are cultured on a 3-dimensional substrate (for example, a dextrin microcarriers; see, e.g., U.S. Pat. No. 6,378,527, which is hereby incorporated by reference in its entirety), and then contacted with the fibroblast differentiation factors.

As used herein "production fibroblasts" refer to fibroblasts that are being used, or can be used for the production of ECM in accordance with methods, compositions, and kits of some embodiments herein.

As used herein, "precursor fibroblasts" refer to fibroblasts that are being used, or can be used, a precursors to Pluripotent cells. For example, in accordance with methods and kits of some embodiments, a precursor fibroblast can be contacted with de-differentiation factors, so as to de-differentiate the precursor fibroblast into an iPSC.

Cell Culture and Substrates

A variety of approaches for cell culture can be used in accordance with methods, kits, and compositions of some embodiments herein. Detailed guidance on protocols and reagents for cell culture can be found, for example, in Sambrook et al., "Molecular Cloning: A Laboratory Manual (Third ed.), Cold Spring Harbor Laboratory Press, Cold Spring Harbor, N.Y., 2000, which is hereby incorporated by reference in its entirety. Generally, culturing fibroblasts for the manufacture of ECMs according to methods, compositions, and kits of some embodiments herein can be performed in culture medium.

In some embodiments, the cell culture medium comprises serum. The serum can be part of the cell culture medium initially, or can be added later in the culture process. Suitable types of serum for use with methods, compositions, and kits of some embodiments herein include tested clinical-grade bovine calf serum, pooled human serum from expired blood units, or combinations of these two substances. In some embodiments, the amount of serum in the culture medium (v/v) is about 0.1% to about 20%, for example about 0.1% to about 15%, about 0.1% to about 10%, about 0.1% to about 5%, about 0.1% to about 3%, about 0.1% to about 1%, about 1% to about 20%, about 1% to about 15%, about 1% to about 10%, about 1% to about 5%, about 1% to about 3%, about 3% to about 20%, about 3% to about 35%, about 3% to about 30%, about 3% to about 5%, about 5% to about 20%, about 5% to about 15%, about 5% to about 10%, about 10% to about 20%, or about 15% to about 20%, for example about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20%, including ranges between any two of the listed values. In some embodiments, the amount of serum in the culture medium (v/v) is about 0.1% to about 10%. In some embodiments, the amount of serum in the culture medium is an amount sufficient to increase bioproduction of ECM by cells in the culture. In some embodiments, the amount of serum in the culture medium is an amount sufficient to induce maturation and crosslinking of ECM produced by cells in the culture. As used herein, "crosslinked" ECM is used herein in accordance with its ordinary meaning in the field, and includes ECM for which polypeptides (e.g. collagen) are directly or indirectly bound one or more other polypeptides of the ECM by an ionic bond and/or covalent bond other than a peptide linkage. In some embodiments, each polypeptide of crosslinked ECM is covalently and/or ionically bound to at least one other polypeptide of the crosslinked ECM by a bond that is not a peptide bond. In some embodiments, a crosslinked peptide of the ECM is directly bound to another peptide of the ECM. In some embodiments, a crosslinked polypeptide of the ECM is indirectly bound to another polypeptide of the ECM, for example via an intervening small molecule, an ion, an amino acid, and/or a different polypeptide. In some embodiments, crosslinked ECM includes ECM in which a majority, substantially all, or all, of the polypeptides are bound by a non-peptide bond at least one other polypeptide of the ECM, for example about or at least about 50%, 60%, 65%, 70%, 75%, 80%, 85%, 90%, 95%, 97%, or 99% of the polypeptides, including ranges between any two of the listed values.

In some embodiments, pluripotent cells (e.g., iPSCs) or fibroblasts are cultured on or near a substrate. In some embodiments, the substrate comprises, consists of, or consists essentially of dextran, for example dextran microcarriers. Advantageously, dextran substrates can subsequently be digested using dextranase as described herein, which can facilitate isolation and purification of ECM produced by cell culture in accordance with some embodiments herein. In some embodiments, the substrate comprises, consists of, or consists essentially of a carbohydrate. In some embodiments, the substrate comprises, consists of, or consists essentially of a polymer. In some embodiments, the substrate comprises, consists of, or consists essentially of a plastic.

Dextran is a large, branched carbohydrate made out of many glucose molecules. Dextran chains can be of varying lengths, for example having molecular weights from as few as 3 kDa to more than 2000 kDa. It is contemplated that dextran structures such as dextran microcarriers can be used as a substrate for the culture of cells, such as pluripotent cells, or fibroblasts in methods, kits, and compositions of some embodiments herein. Advantageously, dextran can be non-toxic, and can readily be hydrolyzed by dextranase as described in more detail herein.

Dextranase is a bacterial enzyme widely used in industrial applications (EC 3.2.1.11, dextran hydrolase, endodextranase, dextranase DL 2, DL 2, endo-dextranase, alpha-D-1, 6-glucan-6-glucanohydrolase, 1,6-alpha-D-glucan 6-glucanohydrolase), and has the systematic name 6-alpha-D-glucan 6-glucanohydrolase. This enzyme catalyses the following chemical reaction: endohydrolysis of (1→6)-alpha-D-glucosidic linkages in dextran. Dextranase in cell culture can be used for a variety of applications, for example isolation of expanded mammalian cells, such as human chondrocytes, and mammalian cell lines for manufacturing cells and cell-derived virus or other biological products on dextran microcarriers (See, e.g., U.S. Pat. No. 6,378,527), or for waste-disposal of the massive volumes of beads used in commercial-scale cell cultures for biologics production. In methods, kits, and compositions of some embodiments, dextran can be used as a substrate or scaffold for pluripotent cells (for example iPSCs), or for fibroblasts derived from pluripotent cells (e.g., fibroblasts produced by de-differentiating a fibroblast into an iPSC, and then re-differentiating the iPSC into a fibroblast). In some embodiments, the dextran is not used for culture and/or expansion of chondrocytes. In some embodiments, the dextran is not used for culture of non-human cells, for example VERO (simian) and/or CHO (rodent) cells.

The use of dextranase enzyme on a variety of research-grade, small scale cultures, generally not applicable for commercial use, human ECM is disclosed by Pinney et al (See Pinney E, (2011) International Journal of Stem Cells 4: 70-75; and Menen et al., (2012) Anticancer Research 32: 1573-1578, each of which is hereby incorporated by reference in its entirety). It is noted that conventional approaches have involved the use of dextran for cell isolation after expansion, primarily in the context of waste disposal of dextran microcarriers. In some embodiments, dextran is used for the culture of pluripotent cells or fibroblasts that produce ECM. In some embodiments, the dextran is used in a culture of pluripotent cells or fibroblasts, but is not used for waste disposal. In some embodiments, the culture comprises human ECM produced by the pluripotent cells or fibroblasts.

In the methods, compositions, and/or kits of some embodiments, ECM is manufactured by cells in culture (e.g., fibroblasts, and/or iPSCs), and then the ECM is isolated from the cells in culture. In some embodiments, isolating the ECM comprises isolating a soluble fraction of ECM. Spent medium comprising soluble ECM can be isolated from cell cultures, and optionally, can be replaced by fresh medium so that the cell cultures can continue to produce. In some embodiments the ECM is isolated by an acidic wash, followed by dextranase digestion at a pH that facilitates the enzymatic activity of dextranase (e.g., pH 6.0 to 6.5). The dextranase can be at a relatively low concentration (less than 1000 U/ml, for example less than 1000 U/ml, 900 U/ml, 800 U/ml, 700 U/ml, 600 U/ml, 500 U/ml, 400 U/ml, 300 U/ml, 200 U/ml, 100 U/ml, 50 U/ml, 10 U/ml, 5 U/ml, 2 U/ml, or 1 U/ml, including ranges between any 2 of these values, for example 1-1000 U/ml; 500-1000 U/ml, 1-500 U/ml, 100-300 U/ml, or 600-800 U/ml). It is contemplated that the lower concentrations of dextranase are less likely to non-specifically degrade other non-dextran carbohydrates, a number of which can be components of the ECM. The ECM can further be contacted by DNase to remove cellular nucleic acids. The manufacture of the ECM in some embodiments can thus be without animal or plant proteins using xeno-free culture medium, and without Pinney's use for modulating cell expansion ex vivo.

Manufacturing ECM Using Fibroblasts Generated from Pluripotent Cells

In some embodiments, a method of manufacturing extracellular matrix is provided. The method can comprise differentiating a pluripotent cell (such as an induced Pluripotent Stem Cell (iPSC)) into a production fibroblast. The method can comprise culturing the production fibroblast, so that the production fibroblast produces ECM. The method can comprise isolating the ECM from the production fibroblast, thus manufacturing the ECM. In some embodiments, the method comprises de-differentiating a precursor fibroblast to form the pluripotent cell prior to differentiating the pluripotent cell into the production fibroblast. In some embodiments, the pluripotent cell is expanded before it is differentiated into fibroblasts. It is noted that by expanding the pluripotent cell first, a large population of pluripotent cells can be generated from a small number of initial pluripotent cells before re-differentiating the pluripotent cells into fibroblasts. In some embodiments, the pluripotent cell is expanded for at least about 10 doublings, for example about or at least about 10, 15, 20, 25, or 30 doublings, included ranges between any two of the listed values, for example about 10-30 doubles, about 10-25 doublings, about 10-20 doublings, about 15-30 doublings, about 15-25 doublings, about 15-20 doublings, or about 20-30 doublings. In some embodiments, the pluripotent cell is expanded for at least about 15 doublings. It is noted that the ability of pluripotent cells to undergo numerous doublings can offer an advantage over conventional sources of fibroblasts such as neonatal foreskin cells, which typically only undergo about 10-12 doublings before they exhaust and senesce.

FIG. 1 is a flow diagram illustrating methods of manufacturing ECM using fibroblasts differentiated from iPSCs in accordance with some embodiments herein. In the method, optionally, a precursor fibroblast can be de-differentiated to form iPSCs 100. In the method, induced Pluripotent Stem Cells (iPSCs) can be differentiated into production fibroblasts. 110. In the method, the production fibroblasts can be cultured, whereby the production fibroblasts produce extracellular matrix (ECM). 120. In the method, the production fibroblasts can be cultured, whereby the production fibroblasts produce extracellular matrix (ECM). 130.

In methods, kits, and compositions of some embodiments, precursor fibroblasts (or iPSCs) from a single donor are used to make the ECM. Advantageously, manufacturing ECM from a single donor can minimize the number of potential contaminants (such as viral contaminants). As such, in some embodiments, the only iPSCs that are differentiated into production fibroblasts are from a single donor. It is also noted that virus-free (for example retrovirus-fee) pluripotent cells can further minimize risk of contamination or immunogenicity. Accordingly, in some embodiments, the iPSCs are free of viral insertions encoding de-differentiation factors such as an Oct family member, a Sox family member, and a Klf family member as described herein. In some embodiments, the method does not comprise using any of: an embryonic stem (ES) cell, a bone marrow Pluripotent stem cell (MSC), an ES-derived MSC, or a non-multipotent neonatal foreskin fibroblast cell line. In some embodiments, the method does not comprise using any of: an embryonic stem (ES) cell, a bone marrow Pluripotent stem cell (MSC), an ES-derived MSC, or any neonatal foreskin fibroblast cell line. In some embodiments, iPSCs are footprint free, for example iPSCs that were de-differentiated using chemical de-differentiation factors or mRNA de-differentiation factors.

It is noted that the pluripotent cell can be differentiated into a production fibroblast using differentiation factors as described herein. In some embodiments, the pluripotent cells are expanded prior to differentiating them into production fibroblasts. In some embodiments, expanding the pluripotent cells prior to differentiation can provide a large quantity of cells from a single donor, which can be differentiated to yield a large quantity of production fibroblasts from a single donor. In some embodiments, following the expansion, but prior to differentiation into production fibroblasts, the pluripotent cells are banked. For example, the pluripotent cells can be banked by freezing in liquid nitrogen.

In some embodiments, the production fibroblasts are cultured in a medium comprising, consisting essentially of, or consisting of terminally-differentiated cells (for example, the production fibroblasts themselves). In some embodiments, the production fibroblasts are cultured in a medium that is substantially free or free of mesenchymal stem cells (MSCs). Without being limited by theory, it is contemplated that fibroblasts differentiated from fibroblast-derived iPSCs in accordance with methods, compositions, and kits of some embodiments herein can be effective for efficient, large-scale production of mature ECM. For example, de-differentiating, expanding, and re-differentiating single donor iPSC's into fibroblasts in accordance with some embodiments can yield commercial scales of ECM-producing fibroblast with minimum risk of contamination or disease transmission.

In some embodiments, the method is performed without any of: an embryonic stem (ES) cell, a bone marrow multipotent stem cell (MSC), an ES-derived MSC, a non-multipotent neonatal foreskin fibroblast cell line, or any neonatal foreskin fibroblast line, or two or more of these. In some embodiments, the method is performed without any of: an embryonic stem (ES) cell, a bone marrow multipotent stem cell (MSC), an ES-derived MSC, or a non-multipotent neonatal foreskin fibroblast cell line, or two or more of these. In some embodiments, the method is performed without any of these. In some embodiments, the method is performed at a commercial scale, thus achieving commercial-scale production of ECM. As noted above, commercial scaling of primary cells, for example primary bone marrow MSC's, or neonatal foreskin-derived cells can require cells from multiple donors, raising a risk of contamination or disease transmission. Also as noted above, ES cells can raise risks of disease transmission, as well as be subject to restricted availability and use, for example due to ethical considerations. Furthermore, MSCs such as bone marrow MSCs can remain multipotent, and thus be subject to further differentiation. On the other hand, methods, compositions, and kits in some embodiments can be performed with differentiated fibroblasts (but not MSCs), so that, advantageously, the fibroblasts are not subject to further differentiation.

In some embodiments, the method comprises de-differentiating a precursor fibroblast to form the iPSC. The precursor fibroblast can be contacted with de-differentiation factors, thereby de-differentiating the precursor fibroblast into an iPSC. In some embodiments, the precursor fibroblast comprises an adult dermal (biopsy) fibroblast. In some embodiments, the precursor fibroblast is from a single donor. In some embodiments, the iPSCs are free of viral insertions encoding an Oct family member, a Sox family member, or a Klf family member. In some embodiments, the iPSCs are footprint-free. The iPSCs can then be expanded and differentiated into the production fibroblasts.

The culturing of the production fibroblasts can be performed in the presence of oxygen. Without being limited by theory, it is contemplated that culturing in normoxia is advantageous because oxygen facilitates efficient and maximal conversion of carbon sources, which are involved in all or essentially all metabolic processes. At commercial scales, oxygen is a reactant in the reaction that converts glucose and glutamine into ATP, which supports synthesis of collagens, among other proteins. In low oxygen, cells are forced to rely much more on glycolysis, rather than aerobic respiration, leading to less efficient synthesis of proteins such as collagens. As such, in some embodiments, the culturing of the production fibroblasts is performed in normoxia. In some embodiments, the culturing of the production fibroblasts is not performed in hypoxia. Hypoxia generally refers to a lower oxygen concentration as compared to the oxygen concentration of ambient air (normoxia; approximately 15%-20% oxygen). In some embodiments, hypoxic conditions include an oxygen concentration less than about 10%. In some embodiments, hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%. Hypoxic conditions can be created and maintained by using a culture apparatus that allows one to control ambient gas concentrations, for example, an anaerobic chamber.

In some embodiments, the production fibroblasts are cultured in the presence of a substrate. In some embodiments, the substrate comprises a polymer, for example a plastic surface or dextran. In some embodiments, the substrate comprises a dextran microcarrier.

In some embodiments, for example in which the production fibroblasts are cultured in the presence of dextran microcarriers, isolating the ECM from the production fibroblast comprises washing the ECM in an acidic buffer, and contacting a solution comprising the production fibroblast and ECM with dextranase. The solution comprising the production fibroblast and ECM can also be contacted by a DNase. By way of example, the dextranase can comprise a bacterial dextranase. In some embodiments, the dextranase is provided at a concentration of between 1 to 1000 U/ml. It is contemplated that the dextranase and DNase can thus facilitate the purification of the ECM by removing other substances. In some embodiments, purifying the human ECM comprises washing with an acidic buffer at a pH of 6.0 to 6.5 to remove residual culture medium components. The acid-washed ECM can be contacted with a solution comprising between 1 and 1000 U/ml bacterial dextranase and between 1 and 1000 U/ml recombinant human DNse in an acidic solution at pH between 2.0 and 7.0, or preferably between pH 6.0 to 6.5, wherein enzymatic activity is sufficient for removing the dextran beads and cellular nucleic acids. Optionally, the purification can be performed after in-process testing of the ECM.

In some embodiments, upon isolation from production fibroblasts, the ECM is no longer in fluid communication with the production fibroblast. For example, the ECM can be in a separate container from the production fibroblast. In some embodiments, isolating the ECM from the production fibroblast comprises purifying the ECM, so as to manufacture a composition that is at least 20% (w/w) ECM, for example about or at least about 20%, 25%, 30%, 35%, 40%, 45%, 50%, 55%, 60%, 65%, 70%, 75%, 80%, 85%, 90%, 95%, 97%, or 99% ECM, including ranges between any two of the listed values. In some embodiments, the composition comprises at least about 80% ECM. In some embodiments, the composition comprises at least about 80%-95% ECM.

The ECM can comprise mature ECM components as described herein. "Mature ECM" is used herein in accordance with its ordinary meaning in the field, and include cross-linked ECM, ECM that comprises a c-terminal propeptide of COL1, a triple-helical or non-reducible gamma-form fibrillary collagen, or a combination of two or more of these features. In some embodiments, the mature ECM comprises collagen. In some embodiments, about 90% (w/w) of the ECM comprises COL1, and about 10% is selected from the group consisting of: COL3, COL4, COL5, COL6, or a combination of any of these or all of these. Example sequences of *Homo sapiens* COL1, COL3, COL4, COL5, and COL6 include, but are not limited to the sequences shown in Table 1 herein. In some embodiments, at least about 80% of the mature ECM comprises COL1, and at least about 10% is selected from the group consisting of: COL3, COL4, COL5, COL6, and a combination of any of these. In some embodiments, at least about 85% of the mature ECM comprises COL1 (for example, at least about 85%, 87%, 90%, or 95%), and at least about 5% (for example, at least about 5%, 10%, 13%, or 15%) is selected from the group consisting of: COL3, COL4, COL5, COL6, and a combination of any of these. In some embodiments, the mature ECM comprises a c-terminal propeptide of COL1, or a triple-helical or non-reducible gamma-form fibrillar collagen, or both. It is noted that different molecules of mature ECM, for example collagen molecules as described herein, can be readily detected using an ELISA, among other assays. In some embodiments, an antibody specific for a collagen protein (or C-terminal propeptide of COL1) is used in a quantitative ELISA to ascertain amounts of components of mature ECM.

In some embodiments, the method further comprises contacting the production fibroblasts with serum until the production fibroblasts produce mature collagens. Without being limited by theory, it is contemplated that contacting the production fibroblasts with serum can support ECM deposition, increase bioproduction, and induce the production of mature ECM, for example cross-linked ECM. Then the amount of serum can be gradually reduced until there is a at least 95% reduction in the concentration of serum. In some embodiments, the gradual reducing is over a period of at least about 5 days, for example about or at least about 5, 7, 10, 12, 15, 20, 25, 30, 35, 40, 45, or 50 days, including ranges between any two of the listed values.

In some embodiments, to initiate a production lot of fibroblasts, a vial of the pluripotent cells (e.g., iPSCs generated by contacting fibroblasts with de-differentiation factors) is expanded to suitable numbers, and pluripotent cells are then induced to de-differentiate into fibrillar collagenous ECM-producing cells such as MSCs or fibroblasts, and these cells are utilized to produce the mature ECM. As such, in some embodiments, a method for manufacturing ECM comprises (a) differentiating fibroblast skin biopsy or blood samples, (b) subsequently inducing pluripotency via a chemical, polypeptide, or nucleic acid-based vector-free/footprint-free induced pluripotency, (c) isolating clones and expand the cells in the pluripotent state, (d) generating cell banks (optionally including characterization of the cells and adventitious agent testing), (e) expanding pluripotent cells for initiating a production lot for ECM, and/or (f) de-differentiating the pluripotent cells back to a differentiated state that produces sufficient mature fibrillar collagenous ECM which is insoluble in culture.

In some embodiments, a kit for manufacturing ECM is provided. The kit can comprise a composition comprising human fibroblasts, de-differentiation factors; and fibroblast differentiation factors. In some embodiments, the composition comprising human fibroblasts comprises frozen human fibroblasts. In some embodiments, all of the fibroblasts of the composition are from a single donor. In some embodiments, the kit further comprises a substrate, for example dextran microcarriers. In some embodiments, the kit further comprises dextranase and DNAase, which can be useful, for example, in isolating ECM from cells and cell culture. In some embodiments, the kit comprises pluripotent cells such as iPSC's instead of the human fibroblasts and de-differentiation factors (but still comprise differentiation factors to differentiate the pluripotent cells into fibroblasts).

Some embodiments include a composition comprising at least about 80% (w/w) extracellular matrix, in which the extracellular matrix is manufactured according to any one of the methods described above. In some embodiments, the composition comprises about or at least about 60% (w/w) ECM, for example at least about 60%, 65%, 70%, 75%, 80%, 85%, 90%, 95%, 97%, or 99% ECM's, including ranges between any two of the listed values. In some embodiments, the ECM of the composition comprises, consists essentially of, or consists of mature ECM as described herein.

In some embodiments, a cell culture comprises a plurality of iPSC-derived fibroblasts in which the iPSC-derived fibroblasts are producing extracellular matrix. The cell culture can further comprise de-differentiation factors as described herein. In some embodiments, at least about 5% of the composition (w/w) is ECM, for example at least about 5%, 10%, 15%, 20%, 25%, 30%, 35%, 40%, 45%, 50%, 55%, 60%, 65%, 70%, or 75%, including ranges between any two of the listed values. In some embodiments, about 90% (w/w) of the ECM comprises COL1, and at least about 10% is selected from the group consisting of: COL3, COL4, COL5, COL6, and a combination of any of these. In some embodiments, at least about 80% of the ECM comprises COL1, and at least about 10% is selected from the group consisting of: COL3, COL4, COL5, COL6, and a combination of any of these. In some embodiments, at least about 85% of the ECM comprises COL1 (for example, at least about 85%, 87%, 90%, or 95%), and at least about 5% (for example, at least about 5%, 10%, 13%, or 15%) is selected from the group consisting of: COL3, COL4, COL5, COL6, and a combination of any of these. In some embodiments, the ECM comprises a c-terminal propeptide of COL1, or a triple-helical or non-reducible gamma-form fibrillar collagen, or both.

Production of Mature, Xeno-Free ECM

Some embodiments include a method of manufacturing extracellular matrix (ECM). The method can comprise culturing fibroblasts and/or mesenchymal stem cells (MSCs) on a substrate. The substrate can comprise at least two surfaces. The culturing can be performed serum-free and xeno-free, until the fibroblasts and/or MSCs define a three-dimensional shape over the at least two-surfaces and at least 80% of fibroblasts and/or MSCs arrest their cell cycle (for example, at least 80%, 85%, 90%, 93%, 95%, 97%, or 99%). The fibroblasts and/or MSCs can then be contacted with serum for about or at least about two weeks (for example, at least about two, three, four, five, six, seven, or eight weeks). As a result of contact with the serum, the fibroblasts and/or MSCs can produce soluble mature ECM, thus producing a solution comprising soluble mature ECM and the fibroblasts and/or MSCs. The solution can be xeno-free. The method can further include isolating the soluble mature ECM from the fibroblasts and/or MSCs, thus manufacturing the ECM, in which the ECM is mature xeno-free ECM. For example, isolating the soluble mature ECM can comprise collecting a soluble fraction of the solution, which comprises spent medium. It is also contemplated that in some embodiments, the method can be performed so that the fibroblasts and/or MSCs are in media that contains serum at the start of the culturing (rather than adding serum later on). It is noted that while fibroblasts and ECMs are mentioned above, it is expressly contemplated the method can also be performed with an ECM-producing cells described herein.

Figure 2:
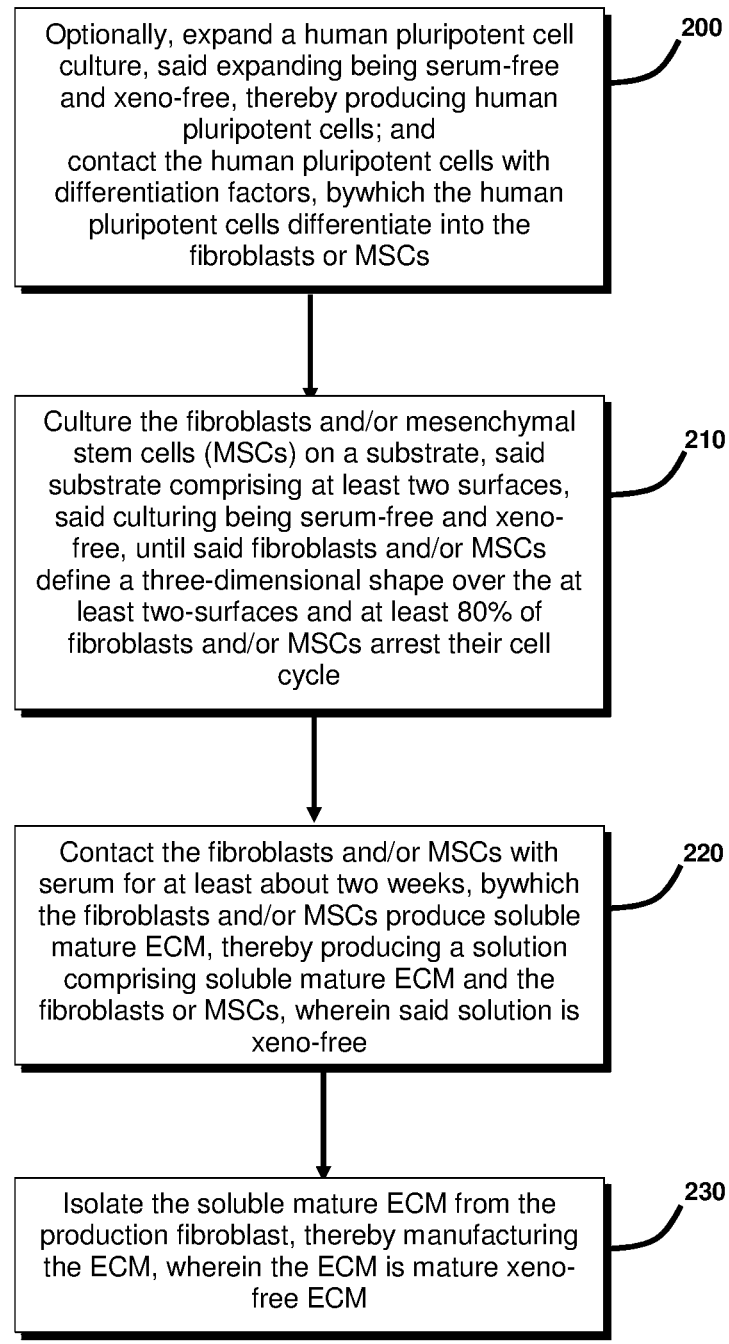
FIG. 2 is a flow diagram illustrating methods of manufacturing ECM comprising culturing fibroblasts or MSCs for at least two weeks in accordance with some embodiments herein.

FIG. 2 is a flow diagram illustrating methods of manufacturing ECM comprising culturing fibroblasts or MSCs for at least two weeks in accordance with some embodiments herein. In the method, optionally, a human pluripotent cell culture can be expanded. Said expanding can be serum-free and xeno-free, thereby producing human pluripotent cells. An the human pluripotent cells can be contacted with differentiation factors, by which the human pluripotent cells differentiate into the fibroblasts or MSCs. 200. In the method, the fibroblasts and/or mesenchymal stem cells (MSCs) can be cultured on a substrate. The substrate can comprise at least two surfaces. The culturing can be serum-free and xeno-free, and can be performed until the fibroblasts and/or MSCs define a three-dimensional shape over the at least two-surfaces and at least 80% of fibroblasts and/or MSCs arrest their cell cycle. 210. In the method, the fibroblasts and/or MSCs can be contacted with serum for at least about two weeks, by which the fibroblasts and/or MSCs produce soluble mature ECM, thereby producing a solution comprising soluble mature ECM and the fibroblasts or MSCs, wherein said solution is xeno-free. 220. In the method, the soluble mature ECM can be isolated from the production fibroblast, thereby manufacturing the ECM, wherein the ECM is mature xeno-free ECM. 230.

In some embodiments, the method further comprises expanding a human pluripotent cell culture (e.g., iPSCs, such as footprint-free iPSCs as described herein). The expanding can be performed in serum-free and xeno-free conditions, and can produce an expanded quantity of human pluripotent cells. The method can further comprise contacting the expanded human pluripotent cells with differentiation factors as described herein. The differentiation factors can be suitable for differentiating the human pluripotent cells into the fibroblasts or MSCs.

It has been observed herein that culturing fibroblasts and/or MSCs with serum for at least 2 weeks or more unexpectedly yielded production of mature ECM comprising collagen cross-linking, and with superior solubility. Accordingly, in some embodiments, contacting the fibroblasts and/or MSCs with serum is performed for at least about 2 weeks, for example, at least about 2 weeks, 3 weeks, 4 weeks, 5 weeks, 6 weeks, 7 weeks, 8 weeks, 9 weeks, 10 weeks, 11 weeks, or 12 weeks, including ranges between any two of the listed values. In some embodiments, contacting the fibroblasts and/or MSCs with serum is performed for at least about 8 weeks. In some embodiments, contacting fibroblasts and/or MSCs with serum is performed for about 2 weeks to about 12 weeks, for example about 2 weeks, 3 weeks, 4 weeks, 5 weeks, 6 weeks, 7 weeks, 8 weeks, 9 weeks, 10 weeks, 11 weeks, or 12 weeks, including ranges between any two of the listed values, for example about 2 weeks to about 11 weeks, about 2 weeks to about 10 weeks, about 2 weeks to about 8 weeks, about 2 weeks to about 6 weeks, about 2 weeks to about 4 weeks, about 3 weeks to about 12 weeks, about 3 weeks to about 10 weeks, about 3 weeks to about 8 weeks about 3 weeks to about 6 weeks, about 4 weeks to about 12 weeks, about 4 weeks to about 10 weeks, about 4 weeks to about 8 weeks, about 4 weeks to about 6 weeks, about 6 weeks to about 12 weeks, about 6 weeks to about 10 weeks, or about 6 weeks to about 8 weeks. In some embodiments the contacting is performed for about 2 weeks to about 8 weeks. In some embodiments the contacting is performed longer than 2 weeks. In some embodiments, the fibroblasts and/or MSCs are cultured with serum under normoxic conditions. In some embodiments, the fibroblasts and/or MSCs are not cultured with serum under hypoxic conditions.

In some embodiments, the human pluripotent cells comprise induced pluripotent stem cells (iPSCs). In some embodiments, the iPSCs are footprint-free. In some embodiments, the iPSCs are from a single donor. As discussed herein, the use of iPSCs can allow pluripotent cells to be expanded, and optionally banked, prior to being differentiated into ECM-producing cells such as fibroblasts in accordance with methods, compositions, and kits of some embodiments. Accordingly, as the iPSCs can come from a single donor and then be expanded, such uses of iPSCs can permit commercial-scale quantities of ECM-producing cells from a single donor.

In some embodiments, the method further comprises manufacturing a cosmetic composition comprising the mature xeno-free ECM. In some embodiments, spent medium can also be useful for the manufacture of some cosmetic compositions.

When serum is used in or added to a culture of ECM-producing cells, such as fibroblasts in accordance with methods, compositions, and kits described herein, ascorbic acid can also be useful, for example for maintenance of the health of cells in culture. Without being limited by theory, is noted that ascorbic acid can be required for certain post-translational modifications of collagen that stabilize the mature triple-helical collagens. By way of example, ascorbic acid can be a cofactor for some enzymes such as prolyl hydroxylase. Accordingly, in some embodiments, the method further comprises contacting the fibroblasts or MSCs with ascorbic acid during the time that the cells are contacted with the serum (e.g., at least two weeks).

Without being limited by theory, it is contemplated that cells such as fibroblasts and/or MSCs can support ECM deposition and maturation once they reach a sufficient density on a substrate (such as a scaffold or support, for example dextran microcarriers as described herein). Furthermore, as the cells start to reach a sufficient density, their cell cycles can arrest (i.e., the cells can enter the $G_0$ phase of the cell cycle). Accordingly, in some embodiments, the fibroblasts or MSCs are not contacted with serum until they have reached a suitable density to support ECM deposition and maturation. In some embodiments, the fibroblasts or MSCs are not contacted with serum until these fibroblasts or MSCs are disposed on at least two-surfaces of a substrate defining a three-dimensional shape, and at least about 70% of the fibroblasts or MSCs arrest their cell cycles. In some embodiments, the fibroblasts or MSC's are not contacted with serum until these fibroblasts or MSCs are disposed on at least two-surfaces of a substrate defining a three-dimensional shape and at least about 70%, 75%, 80%, 85%, 90%, 95%, 97%, or 99% of the fibroblasts or MSCs arrest their cell cycles, including ranges between any two of the listed values.

A number of suitable forms of serum can be contacted with the fibroblasts and/or MSCs, for example tested clinical-grade bovine calf serum or pooled human serum from expired blood units, or a combination of these. In some embodiments, contacting the serum with the fibroblasts comprises adding the serum to the solution that comprises the fibroblasts and/or MSCs. "Adding," is used broadly herein, and includes the addition of serum to solution containing the fibroblasts and/or MSCs, as well as the addition of solution containing fibroblasts and/or MSCs to serum. In some embodiments, serum is added to solution containing the fibroblasts and/or MSCs until the amount of serum (v/v) is about 0.1% to 10%, for example about 1-2%, 1-5%, 2-10%, 2-5%, 3-10%, 3-5%, or 5-10%.

Advantageously, producing xeno-free ECM in accordance with some embodiments herein can reduce the risk of adverse immune reactions in users of products that contain the ECM. Such products can further enjoy advantages such as streamlined regulatory review. In some embodiments, the fibroblasts and/or MSC's are derived from human pluripotent cells (e.g. iPSC's) of a cell line that was previously grown using animal components. In some embodiments, the pluripotent cells are from a single donor. The pluripotent cells can be expanded without the use of xenogenic components. Thus, a large quantity of xeno-free cells can be obtained. Xeno-free pluripotent cells, in accordance with some embodiments, can then be differentiated into ECM-producing cells, for example fibroblasts and/or MSC's. The differentiation can comprise contacting the xeno-free pluripotent cells with differentiation factors as described herein.

Moreover, the xeno-free ECM manufactured in accordance with methods, compositions, and kits of some embodiments can comprise mature ECM, as described herein. As such, the mature xeno-free ECM can be well-suited for a number of cosmetic and medical products. In some embodiments, the mature xeno-free ECM comprises fibrillar collagen. In some embodiments, the mature xeno-free ECM comprises a c-terminal propeptide of COL1, or a triple-helical or non-reducible gamma-form fibrillar collagen, or both.

In some embodiments, the solution comprises at least about 100 µg of collagen per cm$^2$ of the substrate, for example at least about 100 µg of collagen per cm$^2$, 150 µg of collagen per cm$^2$, 200 µg of collagen per cm$^2$, 250 µg of collagen per cm$^2$, 300 µg of collagen per cm$^2$, 350 µg of collagen per cm$^2$, 400 m of collagen per cm$^2$, 450 µg of collagen per cm$^2$, 500 µg of collagen per cm$^2$, 600 m of collagen per cm$^2$, 700 µg of collagen per cm$^2$, 800 µg of collagen per cm$^2$, 900 µg of collagen per cm$^2$, or 1000 µg of collagen per cm$^2$, including ranges between any two of the listed values. In some embodiments, the solution comprises at least 250 m of collagen per cm$^2$ of the substrate.

In some embodiments, the manufactured mature xeno-free ECM comprises at least about 100 µg of collagen per cm$^2$ of the substrate, for example at least about 100 µg of collagen per cm$^2$, 150 µg of collagen per cm$^2$, 200 µg of collagen per cm$^2$, 250 µg of collagen per cm$^2$, 300 µg of collagen per cm$^2$, 350 µg of collagen per cm$^2$, 400 µg of collagen per cm$^2$, 450 µg of collagen per cm$^2$, 500 µg of collagen per cm$^2$, 600 µg of collagen per cm$^2$, 700 µg of collagen per cm$^2$, 800 m of collagen per cm$^2$, 900 µg of collagen per cm$^2$, or 1000 µg of collagen per cm$^2$, including ranges between any two of the listed values. In some embodiments, the manufactured mature xeno-free ECM comprises comprises at least 250 m of collagen per cm$^2$ of the substrate.

In some embodiments, the method comprises detecting an amount of mature ECM in the solution. In some embodiments, the detecting is performed using an ELISA to detect the presence, absence, and or levels of one or more components of mature ECM as described herein.

Some embodiments include a solution comprising fibroblasts or MSCs and the soluble mature ECM produced according to any one the above methods. The solution can be xeno-free, and the soluble mature ECM can comprises cross-linked collagen. In some embodiments, the solution comprises fibroblasts, but not MSCs. In some embodiments, the fibroblasts or MSCs are over a substrate in the solution, and the solution comprises at least about 100 µg of collagen per cm$^2$ of the substrate, for example at least about 100 µg of collagen per cm$^2$, 150 µg of collagen per cm$^2$, 200 µg of collagen per cm$^2$, 250 µg of collagen per cm$^2$, 300 µg of collagen per cm$^2$, 350 µg of collagen per cm$^2$, 400 µg of collagen per cm$^2$, 450 µg of collagen per cm$^2$, 500 µg of collagen per cm$^2$, 600 µg of collagen per cm$^2$, 700 µg of collagen per cm$^2$, 800 m of collagen per cm$^2$, 900 µg of collagen per cm$^2$, or 1000 µg of collagen per cm$^2$, including ranges between any two of the listed values. In some embodiments, the solution comprises at least 250 µg of collagen per cm$^2$ of the substrate.

Producing ECM for periods of time as described in accordance with some embodiments herein, can produce higher abundances of mature ECM than conventional methods. For example, culturing the cells for about 8-12 weeks before collecting spent medium with soluble ECM, in accordance with some embodiments herein, can produce more ECM than conventional methods. On the other hand, production of embryonic-like ECM under hypoxic conditions according to some conventional methods can yield less ECM overall, and without necessarily producing any mature ECM. The amounts of ECM produced by a particular method can be measured, for example, by SDS-PAGE gel comparing adult-tissue derived type I collagen to ECM produced by the subject cell culture(s).

Manufacture of ECM Comprising Gradual Removal of Serum

Some embodiments include a method of manufacturing extracellular matrix (ECM). The method can include providing fibroblasts in a medium that comprises a non-zero concentration of serum. The method can include gradually reducing the amount of serum in the medium comprising fibroblasts until the medium contains no more than 5% of the concentration of serum, for example, no more than 5%, 4%, 3%, 2%, or 1%. This gradual reduction in serum may also be referred to herein as "serum weaning." After the gradual reduction in serum, the method can include culturing the fibroblasts for at least about 1 week (for example at least about 1, 2, 3, 4, 5, 6, 7, 8, 9, 10, 11, or 12, weeks, including ranges between any two of the listed values), by which the fibroblasts produce soluble ECM. Thus, the method can produce a solution comprising the fibroblasts and soluble ECM. The method can further include isolating the soluble ECM from the fibroblasts, thus manufacturing the ECM. In some embodiments, the method comprises little or no cell expansion once the serum weaning has begun. In some embodiments, a quantity of fibroblasts in the medium at the start of gradually reducing the amount of serum is at least about 0.7× of a quantity of fibroblasts in the medium when the medium contains no more than 5% of the concentration in serum. In some embodiments, a quantity of fibroblasts in the medium at the start of gradually reducing the amount of serum is at least about 0.6×, 0.7×, 0.8×, 0.9×, 1×, 1.1×, or 1.2× (including ranges between any two of the listed values) of a quantity of fibroblasts in the medium when the medium contains no more than 5% of the concentration in serum. In some embodiments, a the quantity of fibroblasts in the medium at the start of gradually reducing the amount of serum is at least 0.9× of the quantity of fibroblasts in the medium when the medium contains no more than 5% of the concentration in serum. In some embodiments, a the quantity of fibroblasts in the medium at the start of gradually reducing the amount of serum is about 0.8×-1.2× of the quantity of fibroblasts in the medium when the medium contains no more than 5% of the concentration in serum. In some embodiments, gradually reducing the amount of serum (i.e., the serum weaning) is done without cell expansion or cell subculture. In some embodiments, gradually reducing the amount of serum (i.e., the serum weaning) is done without cell subculture. In some embodiments, the serum is completely removed by the gradual reduction of serum (except for trace amounts that have no appreciable effect on the culture or ECM). It is noted that while fibroblasts are mentioned above, it is expressly contemplated the method can also be performed with an ECM-producing cells described herein.

Figure 3:
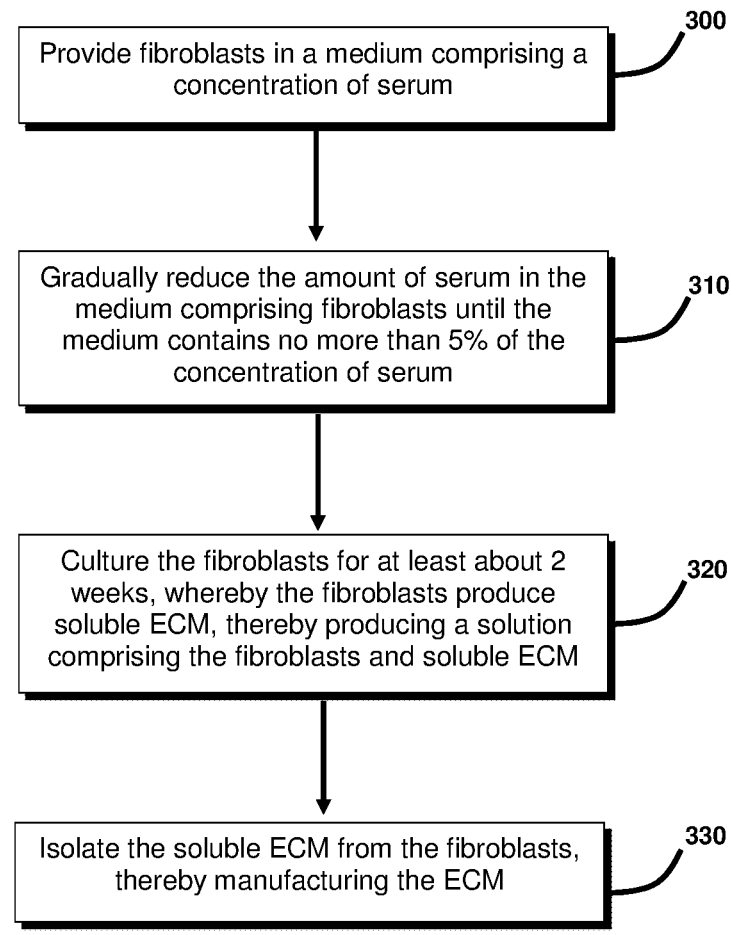
FIG. 3 is a flow diagram illustrating methods of manufacturing ECM comprising serum weaning in accordance with some embodiments herein. The ECM can be xeno-free.

FIG. 3 is a flow diagram illustrating methods of manufacturing ECM comprising serum weaning in accordance with some embodiments herein. The ECM can be xeno-free. In the method, fibroblasts in a medium comprising a concentration of serum can be provided. 300. In the method, the amount of serum in the medium can comprising fibroblasts can be gradually reduced until the medium contains no more than 5% of the concentration of serum. 310. In the method, the fibroblasts can be cultured for at least about 2 weeks (e.g., at least about 2, 3, 4, 5, 6, 7, or 8 weeks), whereby the fibroblasts produce soluble ECM, thereby producing a solution comprising the fibroblasts and soluble ECM. 320. In the method, the soluble ECM can be isolated from the fibroblasts, thereby manufacturing the ECM. 330.

As used herein, gradually reducing the amount of serum in the medium can take place over a period of days, for example at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, including ranges between any two of the listed valued, for example about 1-30 days, 1-20 days, 1-14 days, 1-10 days, 1-7 days, 1-5 days, 1-30 days, 2-20 days, 2-14 days, 2-10 days, 2-7 days, 2-5 days, 3-20 days, 3-14 days, 3-10 days, 3-7 days, 3-5 days, 5-20 days, 5-14 days, 5-10 days, 5-7 days, 7-20 days, 7-14 days, 7-10 days, 10-20 days, or 10-14 days. In some embodiments, the serum is gradually reduced for at least about 5 days. The gradual reduction of the serum can involve removal of serum-containing medium, and replacing in with serum-free medium. By performing multiple rounds of replacing a portion of serum-containing medium with serum-free medium, the serum can be gradually reduced, until it is effectively eliminated (i.e., so that no more than trace amounts of serum remain, which have no appreciable effect on the cell culture or ECM).

Surprisingly, gradually removing the serum, until the serum is completely, (or nearly completely) removed as described in accordance with some embodiments herein can induce a majority of the ECM-producing cells to arrest the cell cycle (i.e., enter a $G_0$ phase), and produce soluble mature ECM without substantially degrading the ECM or inducing apoptosis. Accordingly, in some embodiments, following the gradual reducing of the serum, soluble, intact, and mature ECM is produced.

In some embodiments, following the gradual reducing of the serum, at least about 70% of the fibroblasts in the solution are in a $G_0$ cell cycle phase, for example at least about 70%, 75%, 80%, 85%, 90%, 95%, 97%, or 99%, including ranges between any two of the listed values, for example 70-99%, 70-95%, 70-90%, 80-99%, 80-95%, 80-90%, 85-99%, 85-95%, or 85-90%. In some embodiments, at least about 90% of the fibroblasts in the solution are in a $G_0$ cell cycle phase.

In some embodiments, following the gradual reducing of the serum, fewer than about 5% of the fibroblasts in the solution are undergoing apoptosis. As used herein, a percentage of cells "undergoing" apoptosis refers to cells that exhibit detectable markers indicative of apoptosis, and thus may include cells that are in the process of apoptosis, as well as cells that have recently completed a program of apoptosis. A percentage of cells undergoing apoptosis can be measured, for example by detection of caspase cleavage, or TUNEL staining. In some embodiments, fewer than 5%, for example fewer than about 4%, 3%, 2%, 1%, 0.5%, or 0.1% of the fibroblasts in the solution are undergoing apoptosis, including ranges between any two of the listed values, for example, 0.1% to 5%, 0.1% to 3%, 0.1% to 1%, 0.5% to 5%, 0.5% to 3%, 0.5% to 1%, 1% to 5%, 1% to 3%, or 3% to 5%. In some embodiments, fewer than about 1% of the fibroblasts in the solution are undergoing apoptosis.

It is noted that methods, compositions, and kits in accordance with some embodiments herein can produce large quantities of mature ECM. In some embodiments, large structures comprising ECM are manufactured, to the extent that some of the structures are visible under a microscope. In some embodiments, the solution comprises nanostructures comprising the soluble ECM, in which the nanostructures have a greatest diameter of at least 200 nm, and up to 10,000 nm, for example at least 200 nm, 300 nm, 400 nm 500 nm, 1000 nm, 2000 nm, 5000 nm, or more. In some embodiments, the nanostructures have a greatest diameter of 200 nm to 10,000 nm. It is noted that in view of these large diameters, filtration thorough certain filters may not be feasible, as the structures comprising ECM may readily clog the filter, causing substantial loss of recovered ECM. As such, in some embodiments, manufacturing, purifying, and/or isolating the ECM comprises purification that does not comprise filtering. In some embodiments, manufacturing the ECM comprises purification that does not comprise sterile filtering. In some embodiments, manufacturing the ECM comprises purification that does not comprise 0.1 μM filtering. In some embodiments, avoiding filtering (or sterile filtering) such as 0.1 μM filtering can substantially increase the yield of mature ECM that is recovered. In some embodiments, isolating the ECM from the fibroblasts is performed without sterile filtering solution comprising the ECM. In some embodiments, manufacturing the ECM is performed without sterile filtering solution.

Some embodiments include a solution comprising fibroblasts and soluble ECM, in which at least about 90% of the fibroblasts in the solution are in a $G_0$ cell cycle phase, and fewer than 1% of the fibroblasts in the solution are undergoing apoptosis. The solution can comprises nanostructures comprising the soluble ECM. The nanostructures can have a greatest diameter of 200 nm to 10,000 nm. In some embodiments, the content of serum in the solution (v/v) is less than 0.1%, for example, less than 0.1%, 0.05%, 0.01%, 0.005%, or 0.001%, including ranges between any two of the listed values, for example, a serum content of 0.1% to 0.001%. In some embodiments the solution is free of serum (as used herein, a solution that is "free" of serum may optionally contain insignificant amounts of serum that have no appreciable effects on the cell culture of production of ECM). In some embodiments the solution is manufactured according to any of the above methods.

Additional Embodiments

Some embodiments also include systems and methods for manufacture and distribution of human ECM and products that contain ECM for cosmetic and therapeutic uses. In some embodiments, the methods and systems provide efficiencies in the manufacture and distribution of: 1) low-cost and efficient removal of majority of dextran microcarriers, sufficient for collecting and further processing of the human ECM without interference from the microcarriers, 2) desirable features for marketing and commercial implementation of xeno-free products, including methods and systems for communicating such desirable features to manufacturers and users, and 3) efficiencies in making products from both soluble and non-soluble fractions from a single manufacturing lot, which can be more resource-efficient than only using one of these fractions to manufacture a product. As such, methods and systems in accordance with some embodiments herein can provide efficiencies in the manufacture of ECM and ECM-containing products.

Additional options are set forth below:

1. A method of manufacturing extracellular matrix, the method comprising:
    differentiating induced Pluripotent Stem Cells (iPSCs) into a production fibroblast;
    culturing the production fibroblasts, whereby the production fibroblasts produce extracellular matrix (ECM); and
    isolating the ECM from the production fibroblasts, thereby manufacturing the ECM.

2. The method of option 1, further comprising de-differentiating a precursor fibroblast to form the iPSCs prior to differentiating the iPSCs into the production fibroblast.

3. The method of any one of options 1-2, further comprising expanding the iPSC's prior to said differentiating.

4. The method of any one of options 2-3, further comprising constructing a bank of the iPSC's prior to said differentiating.

5. The method of option 1, wherein the only iPSCS that are differentiated are from a single donor.

6. The method of any one of options 1-5, wherein the culturing of the production fibroblasts is in normoxia.

7. The method of any one of options 1-6, wherein culturing the production fibroblasts does not comprise culturing mesenchymal stem cells (MSCs).

8. The method of any one of options 1-7, wherein the precursor fibroblast comprises an adult dermal (biopsy) fibroblast.

9. The method of any of options 1-8, wherein isolating the ECM comprises purifying the ECM, thereby manufacturing a composition that is at least about 80% w/w ECM 10. The method of option 9, wherein purifying the ECM comprises:
    washing the ECM in an acidic buffer; and
    contacting a solution comprising the production fibroblast and ECM with dextranase.

11. The method of any one of options 1-10, wherein the ECM comprises collagen.

12. The method of option 11, wherein about 90% (w/w/) of the ECM is COL1, and about 10% is selected from the group consisting of: COL3, COL4, COL5, COL6, and a combination of any of these.

13. The method of any one of options 2-12, further contacting the precursor fibroblast with de-differentiation factors, thereby de-differentiating the precursor fibroblast into the iPSC.

14. The method of any one of options 1-13, wherein the iPSCs are free of viral insertions encoding an Oct family member, a Sox family member, a Klf family member.

15. The method of any one of options 1-13, wherein the iPSCs are footprint-free.

16. The method of any one of options 1-15, wherein the method does not comprise any of: an embryonic stem (ES) cell, a bone marrow multipotent stem cell, an ES-derived MSC, or a non-multipotent neonatal foreskin fibroblast cell line.

17. The method of any one of options 1-16, wherein the ECM comprises a c-terminal propeptide of COL1, or a triple-helical or non-reducible gamma-form fibrillar collagen, or both.

18. The method of any one of options 1-17, further comprising contacting the production fibroblasts with serum, until the production fibroblasts produce mature collagens, and then gradually reducing the amount of serum until there is a at least 95% reduction in the concentration of serum.

19. The method of option 18, wherein the gradual reducing is over a period of at least about 5 days.

20. A kit for manufacturing ECM, the kit comprising:
    a composition comprising human fibroblasts;
    de-differentiation factors; and
    fibroblast differentiation factors.

21. The kit of option 20, wherein all of the fibroblasts of the composition are from a single donor.

22. The kit of any one of options 20-21, further comprising a substrate, such as dextran microcarriers.

23. The kit of option 22, further comprising dextranase and DNAase.

24. A composition comprising at least 80% (w/w) extracellular matrix, wherein the extracellular matrix is manufactured according to the method of any one of options 1-14.

25. A cell culture comprising:
    iPSC-derived fibroblasts, wherein the iPSC-derived fibroblasts are producing mature extracellular matrix; and
    de-differentiation factors,
    wherein at least 50% of the composition (w/w) comprises ECM.

26. A method of manufacturing extracellular matrix (ECM), the method comprising:
    culturing fibroblasts and/or mesenchymal stem cells (MSCs) on a substrate, said substrate comprising at least two surfaces, said culturing being serum-free and xeno-free, until said fibroblasts and/or MSCs define a three-dimensional shape over the at least two-surfaces and at least 80% of fibroblasts and/or MSCs arrest their cell cycle;
    thereafter contacting the fibroblasts and/or MSCs with serum for at least about two weeks, by which the fibroblasts and/or MSCs produce soluble mature ECM, thereby producing a solution comprising soluble mature ECM and the fibroblasts or MSCs, wherein said solution is xeno-free; and
    isolating the soluble mature ECM from the production fibroblast, thereby manufacturing the ECM, wherein the ECM is mature xeno-free ECM.

27. The method of option 26, further comprising:
   expanding a human pluripotent cell culture, said expanding being serum-free and xeno-free, thereby producing human pluripotent cells; and
   contacting the human pluripotent cells with differentiation factors, by which the human pluripotent cells differentiate into the fibroblasts or MSCs.

28. The method of any one of options 26-27, wherein said contacting of the fibroblasts and/or MSCs with serum is for about 2 weeks to about 8 weeks 29. The method of any one of options 26-27, wherein said contacting of the fibroblasts and/or MSCs with serum is for at least about 8 weeks 30. The method of any one of options 27-29, wherein said human pluripotent cells comprise induced pluripotent stem cells (iPSCSs).

31. The method of option 30, wherein said iPSCSs are footprint-free.

32. The method of any one of options 30-31, wherein said iPSCSs are from a single donor.

33. The method of any one of options 26-32, further comprising manufacturing a cosmetic composition comprising the mature xeno-free ECM.

34. The method of any one of options 26-33, further comprises contacting the fibroblasts or MSCs with ascorbic acid during the at least two weeks of the contacting with the serum.

35. The method of any one of options 26-34, wherein the fibroblasts or MSCs are not contacted with serum prior to said fibroblasts or MSCs over the at least two-surfaces defining a three-dimensional shape and at least 70% of the fibroblasts or MSCs arresting their cell cycle 36. The method of any one of options 26-35, wherein the amount of serum is about 0.1% to 10% (v/v)

37. The method of any one of options 26-36, wherein the amount of serum is about 1-2% (v/v).

38. The method of any one of options 26-37, wherein the serum comprises clinical-grade bovine calf serum, pooled human serum, or a combination thereof.

39. The method of any one of options 26-38, wherein human pluripotent cells are of a cell line that was previously grown using animal components.

40. The method of any one of options 26-39, wherein the mature xeno-free ECM comprises fibrillar collagen.

41. The method of option 40, wherein the mature xeno-free ECM comprises a c-terminal propeptide of COL1, or a triple-helical or non-reducible gamma-form fibrillar collagen, or both.

42. The method of any one of options 26-41, wherein the solution comprises at least 250 m of collagen per cm$^2$ of the substrate.

43. The method of any one of option 26-42, wherein the manufactured mature xeno-free ECM comprises at least 250m of collagen per cm$^2$ of the substrate 44. The method of any one of options 27-43, wherein the pluripotent cells are from a single donor.

45. The method of any one of option 26-44, further comprising detecting an amount of mature ECM in the solution.

46. The method of any one of option 26-45, further comprising collecting a quantity of spent culture medium from the solution and isolating soluble mature ECM from the spent culture medium.

47. A solution comprising fibroblasts or MSCs and the soluble mature ECM produced according to any one of options 26-45, wherein said solution is xeno-free, and wherein the soluble mature ECM comprises cross-linked collagen.

48. A method of manufacturing extracellular matrix (ECM), the method comprising:
   providing fibroblasts in a medium comprising a concentration of serum;
   gradually reducing the amount of serum in the medium comprising fibroblasts until the medium contains no more than 5% of the concentration of serum;
   following said gradually reducing, culturing the fibroblasts for at least about 2 weeks, whereby the fibroblasts produce soluble ECM, thereby producing a solution comprising the fibroblasts and soluble ECM; and
   isolating the soluble ECM from the fibroblasts, thereby manufacturing the ECM.

49. The method of option 48, wherein a quantity of fibroblasts in the medium at the start of gradually reducing the amount of serum is at least 0.7× of a quantity of fibroblasts in the medium when the medium contains no more than 5% of the concentration in serum.

50. The method of option 49, wherein the quantity of fibroblasts in the medium at the start of gradually reducing the amount of serum is at least 0.9× of the quantity of fibroblasts in the medium when the medium contains no more than 5% of the concentration in serum.

51. The method of any one of options 48-50, wherein gradually reducing the amount of serum is done without cell expansion or cell subculture.

52. The method of any one of options 48-51, wherein the serum is gradually reduced for at least about 5 days.

53. The method of any one of options 48-52, wherein at least about 90% of the fibroblasts in the solution are in a $G_0$ cell cycle phase.

54. The method of any one of options 48-53, wherein fewer than 1% of the fibroblasts in the solution are undergoing apoptosis.

55. The method of any one of options 48-54, wherein the solution comprises nanostructures comprising the soluble ECM, said nanostructures having a greatest diameter of 200 nm to 10,000 nm.

56. The method of any one of options 48-55, wherein manufacturing the ECM is performed without sterile-filtering. (so as not to exclude the nanostructures).

57. The method of any one of options 48-56 wherein isolating the soluble ECM from the fibroblasts is performed without sterile-filtering.

58. A solution comprising fibroblasts and soluble ECM, wherein at least about 90% of the fibroblasts in the solution are in a $G_0$ cell cycle phase, wherein fewer than 1% of the fibroblasts in the solution are undergoing apoptosis, and wherein the solution comprises nanostructures comprising the soluble ECM, said nanostructures having a greatest diameter of 200 nm to 10,000 nm.

59. The solution of option 58, wherein the soluble ECM is manufactured according to a method of any one of options 48-57.

EXAMPLES

Example 1

Human fibroblasts are derived from a skin biopsy of a single donor. The fibroblasts are contacted with Oct4, Sox2, and c-Myc mRNA, so as to induced them into footprint-free iPSC's. The footprint-free iPSC's are expanded from 30 doublings, and the iPSC's are banked. A commercial-scale quantity of the iPSC's are contacted with connective tissue growth factor (CTGF) so as to induce them to differentiate into fibroblasts. The fibroblasts are cultured in medium comprising dextran microcarrier substrates, and proceed to produce mature ECM. The ECM is insoluble in culture. The dextran microcarriers are digested using dextranase. A remaining insoluble fraction, comprising mature ECM, is recovered. As such, an insoluble fraction of the culture comprising the mature ECM is isolated from the fibroblasts and soluble components. Thus, mature ECM is manufactured, and is suitable for use in medical and cosmetic products.

Example 2

Human fibroblasts are chemically de-differentiated into footprint-free iPSC's using the small molecule cocktail "VC6TF" (V, VPA; C, CHIR99021 or CHIR; 6, 616452; T, tranylcypromine; F, forskolin). The iPSC's are expanded to a commercial production scale, and banked in a liquid-nitrogen deep-freeze. A commercial quantity of iPSC's is recovered, and differentiated into fibroblasts using CTGF. The fibroblasts are cultured in serum-free, xeno-free media comprising dextran microcarrier substrates. When the fibroblasts reach a sufficient density over two or more surfaces of the substrates, about 90% the fibroblasts enter the $G_0$ phase of the cell cycle. At this, point pooled human serum from expired blood is added to the fibroblast culture up to a concentration (v/v) of 2% serum. Ascorbic acid is added to the culture along with the serum. The cells are cultured for an additional 8 weeks in serum, and produce mature ECM. The mature ECM is isolated from the cell culture, and subsequently used to manufacture cosmetic products.

Example 3

Human fibroblasts are derived from single donor human iPSC's as described in Example 1. The fibroblasts are cultured in 2% fetal bovine serum, and produce mature ECM. Every day for 10 days, one-half of the serum-containing medium is replaced with serum-free medium. As such, it is estimated that after 10 days of replacement, the 2% serum has been reduced by a factor of $2^{10}$, so that the culture contains less than 0.002% serum. After the gradual serum replacement is completed, the fibroblasts are cultured in the medium (containing an estimate of less than 0.002% serum) for six weeks. Soluble ECM is recovered from spent media. Additionally, large structures (200 nm to 10,000 nm in diameter) comprising ECM are present in the media, so the isolation of ECM is performed without sterile filtering.

In some embodiments, the method, use, or composition comprises various steps or features that are present as single steps or features (as opposed to multiple steps or features). For example, in one embodiment, the method includes a single administration of a flow modulator, or the composition comprises or consists essentially of a flow modulator for single use. The flow modulator may be present in a single dosage unit effective for increasing flow (or decreasing immune cell migration). A composition or use may comprise a single dosage unit of a flow modulator effective for increasing flow (or inhibiting migration of immune cells) as described herein. Multiple features or components are provided in alternate embodiments. In some embodiments, the method, composition, or use comprises one or more means for flow modulation. In some embodiments, the means comprises a flow modulator.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. For each method of described herein, relevant compositions for use in the method are expressly contemplated, uses of compositions in the method, and, as applicable, methods of making a medicament for use in the method are also expressly contemplated. For example, for methods of increasing flow that comprise a flow modulator, flow modulators for use in the corresponding method are also contemplated, as are uses of a flow modulator in increasing flow according to the method, as are methods of making a medicament comprising the flow modulator for use in increasing flow.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc.

As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. For example, "about 5", shall include the number 5. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of manufacturing extracellular matrix (ECM), the method comprising:
   (a) culturing first fibroblasts with one or more de-differentiation factors, thereby de-differentiating the first fibroblasts into induced Pluripotent Stem Cells (iPSCs);
   (b) culturing the iPSCs with one or more fibroblast differentiation factors, thereby differentiating the iPSCs into second fibroblasts;
   (c) culturing the second fibroblasts in a solution comprising serum at an initial concentration of 0.1% to 20% (v/v), until the second fibroblasts produce mature collagens;
   (d) gradually reducing the concentration of serum in the fibroblast culture of step (c) by performing multiple rounds of replacing a portion of the serum-containing solution of step (c) with a serum-free solution over a period of at least 5 days such that there is an at least 95% reduction in the concentration of serum (v/v), wherein gradually reducing the concentration of serum results in the second fibroblasts producing soluble mature ECM without substantially degrading the ECM; and (e) isolating the soluble mature ECM from the second fibroblasts, wherein isolating the soluble mature ECM comprises contacting the second fibroblasts with dextranase, thereby manufacturing the ECM.

2. The method of claim 1, further comprising expanding the iPSCs prior to (b).

3. The method of claim 1, wherein the culturing of the second fibroblasts is in normoxia.

4. The method of claim 1, wherein culturing the second fibroblasts does not comprise culturing mesenchymal stem cells (MSCs).

5. The method of claim 1, wherein the method does not comprise differentiating any of: an embryonic stem (ES) cell, a bone marrow multipotent stem cell, an ES-derived MSC, or a non-multipotent neonatal foreskin fibroblast cell line.

6. The method of claim 1, wherein the ECM comprises a triple-helical or non-reducible gamma-form fibrillary collagen, or both.

7. The method of claim 1, wherein the first fibroblasts comprise adult dermal fibroblasts.

8. The method of claim 1, wherein isolating the ECM comprises purifying the ECM, thereby manufacturing a composition that is at least about 80% w/w ECM.

9. The method of claim 8, wherein purifying the ECM comprises contacting the ECM with an acidic buffer.

10. The method of claim 1, wherein the production of ECM by the production fibroblasts comprises production of nanostructures comprising soluble ECM, the nanostructures having a greatest diameter of at least 200 nm.

11. The method of claim 1, further comprising manufacturing a cosmetic product comprising the ECM.

12. The method of claim 7, wherein the first fibroblasts comprise an adult dermal biopsy fibroblast.

13. The method of claim 1, wherein the second fibroblasts are cultured in the second solution for at least two weeks prior to gradually reducing the concentration of serum.

14. A method of manufacturing extracellular matrix (ECM), the method comprising:

(a) providing fibroblasts in a medium comprising serum at a concentration of 0.1% to 20% (v/v);

(b) gradually reducing the concentration of serum in the medium comprising fibroblasts by performing multiple rounds of replacing a portion of the serum-containing medium of step (a) with a serum-free medium until the medium contains no more than 5% of the concentration of serum in step (a), wherein the gradual reducing of the concentration of serum is performed over a period of at least 5 days, wherein gradually reducing the concentration of serum results in the fibroblasts producing soluble mature ECM without substantially degrading the ECM;

(c) following (b), culturing the fibroblasts for at least about 2 weeks, whereby the fibroblasts produce soluble mature ECM comprising triple-helical or non-reducible gamma-form fibrillary collagen, or both, thereby producing a solution comprising the fibroblasts and the soluble mature ECM; and (d) isolating the soluble mature ECM comprising triple-helical or non-reducible gamma-form fibrillary collagen from the fibroblasts, wherein isolating the soluble mature ECM comprises contacting the soluble mature ECM and fibroblasts with dextranase, thereby manufacturing the ECM.

15. The method of claim 14, wherein i) a quantity of fibroblasts in the medium at the start of (b) is at least 0.7× of ii) a quantity of fibroblasts in the medium when the medium contains no more than 5% of the concentration in the serum.

16. The method of claim 14, wherein gradually reducing the amount of serum is done without cell expansion or cell subculture.

17. The method of claim 14, wherein at least about 90% of the fibroblasts in the solution are in a $G_0$ cell cycle phase.

18. The method of claim 14, wherein fewer than 1% of the fibroblasts in the solution are undergoing apoptosis.

19. The method of claim 14, wherein the solution comprises nanostructures comprising the soluble ECM, said nanostructures having a greatest diameter of 200 nm to 10,000 nm.

20. The method of claim 14, further comprising manufacturing a cosmetic product compromising the ECM.

21. The method of claim 14, wherein the solution comprising the fibroblasts and the ECM comprises nanostructures comprising the ECM, the nanostructures having a greatest diameter of at least 200 nm.

22. The method of claim 14, wherein the fibroblasts are cultured in the medium comprising serum at a concentration of 0.1% to 20% (v/v) for at least two weeks prior to gradually reducing the concentration of serum.

23. A method of manufacturing extracellular matrix, the method comprising:

(a) culturing a first fibroblast with one or more de-differentiation factors, thereby de-differentiating the first fibroblast into an induced Pluripotent Stem Cell (iPSC);

(b) expanding the iPSC into iPSCs;

(c) culturing the expanded iPSCs with one or more fibroblast differentiation factors, thereby differentiating the expanded iPSCs into second fibroblasts;

(d) culturing the second fibroblasts in a solution comprising serum at an initial concentration of 0.1% to 20% (v/v), until the second fibroblasts produce mature collagens;

(e) gradually reducing the concentration of serum in the fibroblast culture of step (d) by performing multiple rounds of replacing a portion of the serum-containing solution of step (d) with a serum-free solution over a period of at least five days such that there is at least a 95% reduction in the concentration of serum, wherein gradually reducing the concentration of serum results in the second fibroblasts producing soluble mature ECM without substantially degrading the ECM, whereby the second fibroblasts produce soluble mature extracellular matrix (ECM) comprising a triple-helical or non-reducible gamma-form fibrillar collagen, or both; and (f) isolating the soluble mature ECM from the second fibroblasts, thereby manufacturing the ECM.

24. The method of claim 23, wherein the production of ECM by the second fibroblasts comprises production of nanostructures comprising the soluble ECM, the nanostructures having a greatest diameter of at least 200 nm.

25. The method of claim 23, further comprising manufacturing a cosmetic product comprising the ECM.

26. The method of claim 23, wherein the second fibroblasts are cultured in the second solution for at least two weeks prior to gradually reducing the concentration of serum.

* * * * *

SEQUENCE LISTING

<160> NUMBER OF SEQ ID NOS: 17

<210> SEQ ID NO 1
<211> LENGTH: 1464
<212> TYPE: PRT
<213> ORGANISM: Homo sapiens

<400> SEQUENCE: 1

Met Phe Ser Phe Val Asp Leu Arg Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His
            35                  40                  45

Asp Arg Asp Val Trp Lys Pro Glu Pro Cys Arg Ile Cys Val Cys Asp
        50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

-continued

```
Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590
```

-continued

```
Gly Lys Ala Gly Glu Arg Gly Val Pro Gly Pro Gly Ala Val Gly
            595                 600                 605
Pro Ala Gly Lys Asp Gly Glu Ala Gly Ala Gln Gly Pro Pro Gly Pro
        610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
            645                 650                 655
Lys Pro Gly Glu Gln Gly Val Pro Gly Asp Leu Gly Ala Pro Gly Pro
            660                 665                 670
Ser Gly Ala Arg Gly Glu Arg Gly Phe Pro Gly Glu Arg Gly Val Gln
            675                 680                 685
Gly Pro Pro Gly Pro Ala Gly Pro Arg Gly Ala Asn Gly Ala Pro Gly
        690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
            725                 730                 735
Gly Leu Pro Gly Pro Lys Gly Asp Arg Gly Asp Ala Gly Pro Lys Gly
            740                 745                 750
Ala Asp Gly Ser Pro Gly Lys Asp Gly Val Arg Gly Leu Thr Gly Pro
        755                 760                 765
Ile Gly Pro Pro Gly Pro Ala Gly Ala Pro Gly Asp Lys Gly Glu Ser
        770                 775                 780
Gly Pro Ser Gly Pro Ala Gly Pro Thr Gly Ala Arg Gly Ala Pro Gly
785                 790                 795                 800
Asp Arg Gly Glu Pro Gly Pro Pro Gly Pro Ala Gly Phe Ala Gly Pro
            805                 810                 815
Pro Gly Ala Asp Gly Gln Pro Gly Ala Lys Gly Glu Pro Gly Asp Ala
            820                 825                 830
Gly Ala Lys Gly Asp Ala Gly Pro Pro Gly Pro Ala Gly Pro Ala Gly
            835                 840                 845
Pro Pro Gly Pro Ile Gly Asn Val Gly Ala Pro Gly Ala Lys Gly Ala
        850                 855                 860
Arg Gly Ser Ala Gly Pro Pro Gly Ala Thr Gly Phe Pro Gly Ala Ala
865                 870                 875                 880
Gly Arg Val Gly Pro Pro Gly Pro Ser Gly Asn Ala Gly Pro Pro Gly
                885                 890                 895
Pro Pro Gly Pro Ala Gly Lys Glu Gly Gly Lys Gly Pro Arg Gly Glu
            900                 905                 910
Thr Gly Pro Ala Gly Arg Pro Gly Glu Val Gly Pro Pro Gly Pro Pro
            915                 920                 925
Gly Pro Ala Gly Glu Lys Gly Ser Pro Gly Ala Asp Gly Pro Ala Gly
        930                 935                 940
Ala Pro Gly Thr Pro Gly Pro Gln Gly Ile Ala Gly Gln Arg Gly Val
945                 950                 955                 960
Val Gly Leu Pro Gly Gln Arg Gly Glu Arg Gly Phe Pro Gly Leu Pro
            965                 970                 975
Gly Pro Ser Gly Glu Pro Gly Lys Gln Gly Pro Ser Gly Ala Ser Gly
            980                 985                 990
Glu Arg Gly Pro Pro Gly Pro Met Gly Pro Pro Gly Leu Ala Gly Pro
        995                 1000                1005
Pro Gly Glu Ser Gly Arg Glu Gly Ala Pro Gly Ala Glu Gly Ser Pro
```

```
                    1010              1015              1020
Gly Arg Asp Gly Ser Pro Gly Ala Lys Gly Asp Arg Gly Glu Thr Gly
1025              1030              1035              1040

Pro Ala Gly Pro Pro Gly Ala Pro Gly Ala Pro Gly Ala Pro Gly Pro
            1045              1050              1055

Val Gly Pro Ala Gly Lys Ser Gly Asp Arg Gly Glu Thr Gly Pro Ala
        1060              1065              1070

Gly Pro Thr Gly Pro Val Gly Pro Val Gly Ala Arg Gly Pro Ala Gly
            1075              1080              1085

Pro Gln Gly Pro Arg Gly Asp Lys Gly Glu Thr Gly Glu Gln Gly Asp
        1090              1095              1100

Arg Gly Ile Lys Gly His Arg Gly Phe Ser Gly Leu Gln Gly Pro Pro
1105              1110              1115              1120

Gly Pro Pro Gly Ser Pro Gly Glu Gln Gly Pro Ser Gly Ala Ser Gly
            1125              1130              1135

Pro Ala Gly Pro Arg Gly Pro Pro Gly Ser Ala Gly Ala Pro Gly Lys
        1140              1145              1150

Asp Gly Leu Asn Gly Leu Pro Gly Pro Ile Gly Pro Pro Gly Pro Arg
        1155              1160              1165

Gly Arg Thr Gly Asp Ala Gly Pro Val Gly Pro Pro Gly Pro Pro Gly
        1170              1175              1180

Pro Pro Gly Pro Pro Gly Pro Pro Ser Ala Gly Phe Asp Phe Ser Phe
1185              1190              1195              1200

Leu Pro Gln Pro Pro Gln Glu Lys Ala His Asp Gly Gly Arg Tyr Tyr
                1205              1210              1215

Arg Ala Asp Asp Ala Asn Val Val Arg Asp Arg Asp Leu Glu Val Asp
            1220              1225              1230

Thr Thr Leu Lys Ser Leu Ser Gln Gln Ile Glu Asn Ile Arg Ser Pro
        1235              1240              1245

Glu Gly Ser Arg Lys Asn Pro Ala Arg Thr Cys Arg Asp Leu Lys Met
        1250              1255              1260

Cys His Ser Asp Trp Lys Ser Gly Glu Tyr Trp Ile Asp Pro Asn Gln
1265              1270              1275              1280

Gly Cys Asn Leu Asp Ala Ile Lys Val Phe Cys Asn Met Glu Thr Gly
            1285              1290              1295

Glu Thr Cys Val Tyr Pro Thr Gln Pro Ser Val Ala Gln Lys Asn Trp
        1300              1305              1310

Tyr Ile Ser Lys Asn Pro Lys Asp Lys Arg His Val Trp Phe Gly Glu
        1315              1320              1325

Ser Met Thr Asp Gly Phe Gln Phe Glu Tyr Gly Gly Gln Gly Ser Asp
        1330              1335              1340

Pro Ala Asp Val Ala Ile Gln Leu Thr Phe Leu Arg Leu Met Ser Thr
1345              1350              1355              1360

Glu Ala Ser Gln Asn Ile Thr Tyr His Cys Lys Asn Ser Val Ala Tyr
            1365              1370              1375

Met Asp Gln Gln Thr Gly Asn Leu Lys Lys Ala Leu Leu Leu Gln Gly
        1380              1385              1390

Ser Asn Glu Ile Glu Ile Arg Ala Glu Gly Asn Ser Arg Phe Thr Tyr
        1395              1400              1405

Ser Val Thr Val Asp Gly Cys Thr Ser His Thr Gly Ala Trp Gly Lys
        1410              1415              1420

Thr Val Ile Glu Tyr Lys Thr Thr Lys Thr Ser Arg Leu Pro Ile Ile
1425              1430              1435              1440
```

```
Asp Val Ala Pro Leu Asp Val Gly Ala Pro Asp Gln Glu Phe Gly Phe
                1445                1450                1455

Asp Val Gly Pro Val Cys Phe Leu
            1460

<210> SEQ ID NO 2
<211> LENGTH: 1366
<212> TYPE: PRT
<213> ORGANISM: Homo sapiens

<400> SEQUENCE: 2

Met Leu Ser Phe Val Asp Thr Arg Thr Leu Leu Leu Ala Val Thr
1               5                   10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
        50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
            260                 265                 270

Ala Gly Pro Ala Gly Pro Ala Gly Pro Arg Gly Glu Val Gly Leu Pro
        275                 280                 285

Gly Leu Ser Gly Pro Val Gly Pro Pro Gly Asn Pro Gly Ala Asn Gly
    290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
```

-continued

```
                340             345             350
Ser Lys Gly Glu Ser Gly Asn Lys Gly Glu Pro Gly Ser Ala Gly Pro
            355                 360                 365
Gln Gly Pro Pro Gly Pro Ser Gly Glu Glu Gly Lys Arg Gly Pro Asn
        370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
                405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
        435                 440                 445
Pro Arg Gly Leu Pro Gly Ser Pro Gly Asn Ile Gly Pro Ala Gly Lys
        450                 455                 460
Glu Gly Pro Val Gly Leu Pro Gly Ile Asp Gly Arg Pro Gly Pro Ile
465                 470                 475                 480
Gly Pro Ala Gly Ala Arg Gly Glu Pro Gly Asn Ile Gly Phe Pro Gly
                485                 490                 495
Pro Lys Gly Pro Thr Gly Asp Pro Gly Lys Asn Gly Asp Lys Gly His
            500                 505                 510
Ala Gly Leu Ala Gly Ala Arg Gly Ala Pro Gly Pro Asp Gly Asn Asn
        515                 520                 525
Gly Ala Gln Gly Pro Pro Gly Pro Gln Gly Val Gln Gly Gly Lys Gly
        530                 535                 540
Glu Gln Gly Pro Pro Gly Pro Pro Gly Phe Gln Gly Leu Pro Gly Pro
545                 550                 555                 560
Ser Gly Pro Ala Gly Glu Val Gly Lys Pro Gly Glu Arg Gly Leu His
                565                 570                 575
Gly Glu Phe Gly Leu Pro Gly Pro Ala Gly Pro Arg Gly Glu Arg Gly
            580                 585                 590
Pro Pro Gly Glu Ser Gly Ala Ala Gly Pro Thr Gly Pro Ile Gly Ser
        595                 600                 605
Arg Gly Pro Ser Gly Pro Pro Gly Pro Asp Gly Asn Lys Gly Glu Pro
        610                 615                 620
Gly Val Val Gly Ala Val Gly Thr Ala Gly Pro Ser Gly Pro Ser Gly
625                 630                 635                 640
Leu Pro Gly Glu Arg Gly Ala Ala Gly Ile Pro Gly Gly Lys Gly Glu
                645                 650                 655
Lys Gly Glu Pro Gly Leu Arg Gly Glu Ile Gly Asn Pro Gly Arg Asp
            660                 665                 670
Gly Ala Arg Gly Ala Pro Gly Ala Val Gly Ala Pro Gly Pro Ala Gly
        675                 680                 685
Ala Thr Gly Asp Arg Gly Glu Ala Gly Ala Ala Gly Pro Ala Gly Pro
        690                 695                 700
Ala Gly Pro Arg Gly Ser Pro Gly Glu Arg Gly Glu Val Gly Pro Ala
705                 710                 715                 720
Gly Pro Asn Gly Phe Ala Gly Pro Ala Gly Ala Ala Gly Gln Pro Gly
                725                 730                 735
Ala Lys Gly Glu Arg Gly Ala Lys Gly Pro Lys Gly Glu Asn Gly Val
            740                 745                 750
Val Gly Pro Thr Gly Pro Val Gly Ala Ala Gly Pro Ala Gly Pro Asn
        755                 760                 765
```

-continued

Gly Pro Pro Gly Pro Ala Gly Ser Arg Gly Asp Gly Pro Gly
    770                 775             780

Met Thr Gly Phe Pro Gly Ala Ala Gly Arg Thr Gly Pro Pro Gly Pro
785             790             795             800

Ser Gly Ile Ser Gly Pro Pro Gly Pro Pro Gly Ala Gly Lys Glu
            805             810             815

Gly Leu Arg Gly Pro Arg Gly Asp Gln Gly Pro Val Gly Arg Thr Gly
            820             825             830

Glu Val Gly Ala Val Gly Pro Pro Gly Phe Ala Gly Glu Lys Gly Pro
        835             840             845

Ser Gly Glu Ala Gly Thr Ala Gly Pro Pro Gly Thr Pro Gly Pro Gln
    850             855             860

Gly Leu Leu Gly Ala Pro Gly Ile Leu Gly Leu Pro Gly Ser Arg Gly
865             870             875             880

Glu Arg Gly Leu Pro Gly Val Ala Gly Ala Val Gly Glu Pro Gly Pro
                885             890             895

Leu Gly Ile Ala Gly Pro Pro Gly Ala Arg Gly Pro Pro Gly Ala Val
            900             905             910

Gly Ser Pro Gly Val Asn Gly Ala Pro Gly Glu Ala Gly Arg Asp Gly
        915             920             925

Asn Pro Gly Asn Asp Gly Pro Pro Gly Arg Asp Gly Gln Pro Gly His
    930             935             940

Lys Gly Glu Arg Gly Tyr Pro Gly Asn Ile Gly Pro Val Gly Ala Ala
945             950             955             960

Gly Ala Pro Gly Pro His Gly Pro Val Gly Pro Ala Gly Lys His Gly
                965             970             975

Asn Arg Gly Glu Thr Gly Pro Ser Gly Pro Val Gly Pro Ala Gly Ala
            980             985             990

Val Gly Pro Arg Gly Pro Ser Gly Pro Gln Gly Ile Arg Gly Asp Lys
        995             1000            1005

Gly Glu Pro Gly Glu Lys Gly Pro Arg Gly Leu Pro Gly Leu Lys Gly
    1010            1015            1020

His Asn Gly Leu Gln Gly Leu Pro Gly Ile Ala Gly His His Gly Asp
1025            1030            1035            1040

Gln Gly Ala Pro Gly Ser Val Gly Pro Ala Gly Pro Arg Gly Pro Ala
                1045            1050            1055

Gly Pro Ser Gly Pro Ala Gly Lys Asp Gly Arg Thr Gly His Pro Gly
            1060            1065            1070

Thr Val Gly Pro Ala Gly Ile Arg Gly Pro Gln Gly His Gln Gly Pro
        1075            1080            1085

Ala Gly Pro Pro Gly Pro Pro Gly Pro Pro Gly Pro Pro Gly Val Ser
    1090            1095            1100

Gly Gly Gly Tyr Asp Phe Gly Tyr Asp Gly Asp Phe Tyr Arg Ala Asp
1105            1110            1115            1120

Gln Pro Arg Ser Ala Pro Ser Leu Arg Pro Lys Asp Tyr Glu Val Asp
                1125            1130            1135

Ala Thr Leu Lys Ser Leu Asn Asn Gln Ile Glu Thr Leu Leu Thr Pro
            1140            1145            1150

Glu Gly Ser Arg Lys Asn Pro Ala Arg Thr Cys Arg Asp Leu Arg Leu
        1155            1160            1165

Ser His Pro Glu Trp Ser Ser Gly Tyr Tyr Trp Ile Asp Pro Asn Gln
    1170            1175            1180

```
Gly Cys Thr Met Asp Ala Ile Lys Val Tyr Cys Asp Phe Ser Thr Gly
            1185                1190                1195                1200

Glu Thr Cys Ile Arg Ala Gln Pro Glu Asn Ile Pro Ala Lys Asn Trp
            1205                1210                1215

Tyr Arg Ser Ser Lys Asp Lys Lys His Val Trp Leu Gly Glu Thr Ile
            1220                1225                1230

Asn Ala Gly Ser Gln Phe Glu Tyr Asn Val Glu Gly Val Thr Ser Lys
            1235                1240                1245

Glu Met Ala Thr Gln Leu Ala Phe Met Arg Leu Leu Ala Asn Tyr Ala
            1250                1255                1260

Ser Gln Asn Ile Thr Tyr His Cys Lys Asn Ser Ile Ala Tyr Met Asp
1265                1270                1275                1280

Glu Glu Thr Gly Asn Leu Lys Lys Ala Val Ile Leu Gln Gly Ser Asn
            1285                1290                1295

Asp Val Glu Leu Val Ala Glu Gly Asn Ser Arg Phe Thr Tyr Thr Val
            1300                1305                1310

Leu Val Asp Gly Cys Ser Lys Lys Thr Asn Glu Trp Gly Lys Thr Ile
            1315                1320                1325

Ile Glu Tyr Lys Thr Asn Lys Pro Ser Arg Leu Pro Phe Leu Asp Ile
            1330                1335                1340

Ala Pro Leu Asp Ile Gly Gly Ala Asp Gln Glu Phe Val Asp Ile
1345                1350                1355                1360

Gly Pro Val Cys Phe Lys
            1365

<210> SEQ ID NO 3
<211> LENGTH: 1487
<212> TYPE: PRT
<213> ORGANISM: Homo sapiens

<400> SEQUENCE: 3

Met Ile Arg Leu Gly Ala Pro Gln Thr Leu Val Leu Leu Thr Leu Leu
1               5                   10                  15

Val Ala Ala Val Leu Arg Cys Gln Gly Gln Asp Val Gln Glu Ala Gly
            20                  25                  30

Ser Cys Val Gln Asp Gly Gln Arg Tyr Asn Asp Lys Asp Val Trp Lys
        35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190
```

```
Gly Ala Gln Leu Gly Val Met Gln Gly Pro Met Gly Pro Met Gly Pro
            195                 200                 205

Arg Gly Pro Pro Gly Pro Ala Gly Ala Pro Gly Pro Gln Gly Phe Gln
            210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
                260                 265                 270

Gly Ala Arg Gly Phe Pro Gly Thr Pro Gly Leu Pro Gly Val Lys Gly
            275                 280                 285

His Arg Gly Tyr Pro Gly Leu Asp Gly Ala Lys Gly Glu Ala Gly Ala
            290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
            355                 360                 365

Gly Ala Pro Gly Ala Lys Gly Glu Ala Gly Pro Thr Gly Ala Arg Gly
            370                 375                 380

Pro Glu Gly Ala Gln Gly Pro Arg Gly Glu Pro Gly Thr Pro Gly Ser
385                 390                 395                 400

Pro Gly Pro Ala Gly Ala Ser Gly Asn Pro Gly Thr Asp Gly Ile Pro
                405                 410                 415

Gly Ala Lys Gly Ser Ala Gly Ala Pro Gly Ile Ala Gly Ala Pro Gly
                420                 425                 430

Phe Pro Gly Pro Arg Gly Pro Pro Gly Pro Gln Gly Ala Thr Gly Pro
            435                 440                 445

Leu Gly Pro Lys Gly Gln Thr Gly Glu Pro Gly Ile Ala Gly Phe Lys
            450                 455                 460

Gly Glu Gln Gly Pro Lys Gly Glu Pro Gly Pro Ala Gly Pro Gln Gly
465                 470                 475                 480

Ala Pro Gly Pro Ala Gly Glu Glu Gly Lys Arg Gly Ala Arg Gly Glu
                485                 490                 495

Pro Gly Gly Val Gly Pro Ile Gly Pro Pro Gly Glu Arg Gly Ala Pro
            500                 505                 510

Gly Asn Arg Gly Phe Pro Gly Gln Asp Gly Leu Ala Gly Pro Lys Gly
            515                 520                 525

Ala Pro Gly Glu Arg Gly Pro Ser Gly Leu Ala Gly Pro Lys Gly Ala
            530                 535                 540

Asn Gly Asp Pro Gly Arg Pro Gly Glu Pro Gly Leu Pro Gly Ala Arg
545                 550                 555                 560

Gly Leu Thr Gly Arg Pro Gly Asp Ala Gly Pro Gln Gly Lys Val Gly
                565                 570                 575

Pro Ser Gly Ala Pro Gly Glu Asp Gly Arg Pro Gly Pro Pro Gly Pro
            580                 585                 590

Gln Gly Ala Arg Gly Gln Pro Gly Val Met Gly Phe Pro Gly Pro Lys
            595                 600                 605
```

```
Gly Ala Asn Gly Glu Pro Gly Lys Ala Gly Glu Lys Gly Leu Pro Gly
            610                 615                 620

Ala Pro Gly Leu Arg Gly Leu Pro Gly Lys Asp Gly Glu Thr Gly Ala
625                 630                 635                 640

Ala Gly Pro Pro Gly Pro Ala Gly Pro Ala Gly Glu Arg Gly Glu Gln
                645                 650                 655

Gly Ala Pro Gly Pro Ser Gly Phe Gln Gly Leu Pro Gly Pro Pro Gly
                660                 665                 670

Pro Pro Gly Glu Gly Lys Pro Gly Asp Gln Gly Val Pro Gly Glu
                675                 680                 685

Ala Gly Ala Pro Gly Leu Val Gly Pro Arg Gly Glu Arg Gly Phe Pro
690                 695                 700

Gly Glu Arg Gly Ser Pro Gly Ala Gln Gly Leu Gln Gly Pro Arg Gly
705                 710                 715                 720

Leu Pro Gly Thr Pro Gly Thr Asp Gly Pro Lys Gly Ala Ser Gly Pro
                725                 730                 735

Ala Gly Pro Pro Gly Ala Gln Gly Pro Pro Gly Leu Gln Gly Met Pro
                740                 745                 750

Gly Glu Arg Gly Ala Ala Gly Ile Ala Gly Pro Lys Gly Asp Arg Gly
                755                 760                 765

Asp Val Gly Glu Lys Gly Pro Glu Gly Ala Pro Gly Lys Asp Gly Gly
                770                 775                 780

Arg Gly Leu Thr Gly Pro Ile Gly Pro Pro Gly Pro Ala Gly Ala Asn
785                 790                 795                 800

Gly Glu Lys Gly Glu Val Gly Pro Pro Gly Pro Ala Gly Ser Ala Gly
                805                 810                 815

Ala Arg Gly Ala Pro Gly Glu Arg Gly Glu Thr Gly Pro Pro Gly Pro
                820                 825                 830

Ala Gly Phe Ala Gly Pro Pro Gly Ala Asp Gly Gln Pro Gly Ala Lys
                835                 840                 845

Gly Glu Gln Gly Glu Ala Gly Gln Lys Gly Asp Ala Gly Ala Pro Gly
                850                 855                 860

Pro Gln Gly Pro Ser Gly Ala Pro Gly Pro Gln Gly Pro Thr Gly Val
865                 870                 875                 880

Thr Gly Pro Lys Gly Ala Arg Gly Ala Gln Gly Pro Pro Gly Ala Thr
                885                 890                 895

Gly Phe Pro Gly Ala Ala Gly Arg Val Gly Pro Pro Gly Ser Asn Gly
                900                 905                 910

Asn Pro Gly Pro Pro Gly Pro Pro Gly Pro Ser Gly Lys Asp Gly Pro
                915                 920                 925

Lys Gly Ala Arg Gly Asp Ser Gly Pro Pro Gly Arg Ala Gly Glu Pro
930                 935                 940

Gly Leu Gln Gly Pro Ala Gly Pro Pro Gly Glu Lys Gly Glu Pro Gly
945                 950                 955                 960

Asp Asp Gly Pro Ser Gly Ala Glu Gly Pro Pro Gly Pro Gln Gly Leu
                965                 970                 975

Ala Gly Gln Arg Gly Ile Val Gly Leu Pro Gly Gln Arg Gly Glu Arg
                980                 985                 990

Gly Phe Pro Gly Leu Pro Gly Pro Ser Gly Glu Pro Gly Lys Gln Gly
                995                 1000                1005

Ala Pro Gly Ala Ser Gly Asp Arg Gly Pro Pro Gly Pro Val Gly Pro
                1010                1015                1020

Pro Gly Leu Thr Gly Pro Ala Gly Glu Pro Gly Arg Glu Gly Ser Pro
```

```
                1025                1030                1035                1040
        Gly Ala Asp Gly Pro Pro Gly Arg Asp Gly Ala Ala Gly Val Lys Gly
                        1045                1050                1055

Asp Arg Gly Glu Thr Gly Ala Val Gly Ala Pro Gly Ala Pro Gly Pro
                        1060                1065                1070

Pro Gly Ser Pro Gly Pro Ala Gly Pro Thr Gly Lys Gln Gly Asp Arg
                        1075                1080                1085

Gly Glu Ala Gly Ala Gln Gly Pro Met Gly Pro Ser Gly Pro Ala Gly
                        1090                1095                1100

Ala Arg Gly Ile Gln Gly Pro Gln Gly Pro Arg Gly Asp Lys Gly Glu
                        1105                1110                1115                1120

Ala Gly Glu Pro Gly Glu Arg Gly Leu Lys Gly His Arg Gly Phe Thr
                                1125                1130                1135

Gly Leu Gln Gly Leu Pro Gly Pro Pro Gly Pro Ser Gly Asp Gln Gly
                        1140                1145                1150

Ala Ser Gly Pro Ala Gly Pro Ser Gly Pro Arg Gly Pro Pro Gly Pro
                        1155                1160                1165

Val Gly Pro Ser Gly Lys Asp Gly Ala Asn Gly Ile Pro Gly Pro Ile
                        1170                1175                1180

Gly Pro Pro Gly Pro Arg Gly Arg Ser Gly Glu Thr Gly Pro Ala Gly
        1185                1190                1195                1200

Pro Pro Gly Asn Pro Gly Pro Pro Gly Pro Pro Gly Pro Pro Gly Pro
                        1205                1210                1215

Gly Ile Asp Met Ser Ala Phe Ala Gly Leu Gly Pro Arg Glu Lys Gly
                        1220                1225                1230

Pro Asp Pro Leu Gln Tyr Met Arg Ala Asp Gln Ala Ala Gly Gly Leu
                        1235                1240                1245

Arg Gln His Asp Ala Glu Val Asp Ala Thr Leu Lys Ser Leu Asn Asn
                        1250                1255                1260

Gln Ile Glu Ser Ile Arg Ser Pro Glu Gly Ser Arg Lys Asn Pro Ala
        1265                1270                1275                1280

Arg Thr Cys Arg Asp Leu Lys Leu Cys His Pro Glu Trp Lys Ser Gly
                        1285                1290                1295

Asp Tyr Trp Ile Asp Pro Asn Gln Gly Cys Thr Leu Asp Ala Met Lys
                        1300                1305                1310

Val Phe Cys Asn Met Glu Thr Gly Glu Thr Cys Val Tyr Pro Asn Pro
                        1315                1320                1325

Ala Asn Val Pro Lys Lys Asn Trp Trp Ser Ser Lys Ser Lys Glu Lys
                        1330                1335                1340

Lys His Ile Trp Phe Gly Glu Thr Ile Asn Gly Gly Phe His Phe Ser
        1345                1350                1355                1360

Tyr Gly Asp Asp Asn Leu Ala Pro Asn Thr Ala Asn Val Gln Met Thr
                        1365                1370                1375

Phe Leu Arg Leu Leu Ser Thr Glu Gly Ser Gln Asn Ile Thr Tyr His
                        1380                1385                1390

Cys Lys Asn Ser Ile Ala Tyr Leu Asp Glu Ala Ala Gly Asn Leu Lys
                        1395                1400                1405

Lys Ala Leu Leu Ile Gln Gly Ser Asn Asp Val Glu Ile Arg Ala Glu
                        1410                1415                1420

Gly Asn Ser Arg Phe Thr Tyr Thr Ala Leu Lys Asp Gly Cys Thr Lys
        1425                1430                1435                1440

His Thr Gly Lys Trp Gly Lys Thr Val Ile Glu Tyr Arg Ser Gln Lys
                        1445                1450                1455
```

-continued

Thr Ser Arg Leu Pro Ile Ile Asp Ile Ala Pro Met Asp Ile Gly Gly
              1460                1465                1470

Pro Glu Gln Glu Phe Gly Val Asp Ile Gly Pro Val Cys Phe Leu
    1475                1480                1485

<210> SEQ ID NO 4
<211> LENGTH: 1466
<212> TYPE: PRT
<213> ORGANISM: Homo sapiens

<400> SEQUENCE: 4

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu

-continued

```
                340             345             350
Val Gly Pro Ala Gly Ser Pro Gly Ser Asn Gly Ala Pro Gly Gln Arg
            355             360             365
Gly Glu Pro Gly Pro Gln Gly His Ala Gly Ala Gln Gly Pro Pro Gly
        370             375             380
Pro Pro Gly Ile Asn Gly Ser Pro Gly Gly Lys Gly Glu Met Gly Pro
385             390             395             400
Ala Gly Ile Pro Gly Ala Pro Gly Leu Met Gly Ala Arg Gly Pro Pro
                405             410             415
Gly Pro Ala Gly Ala Asn Gly Ala Pro Gly Leu Arg Gly Gly Ala Gly
            420             425             430
Glu Pro Gly Lys Asn Gly Ala Lys Gly Glu Pro Gly Pro Arg Gly Glu
        435             440             445
Arg Gly Glu Ala Gly Ile Pro Gly Val Pro Gly Ala Lys Gly Glu Asp
                450             455             460
Gly Lys Asp Gly Ser Pro Gly Glu Pro Gly Ala Asn Gly Leu Pro Gly
465             470             475             480
Ala Ala Gly Glu Arg Gly Ala Pro Gly Phe Arg Gly Pro Ala Gly Pro
                485             490             495
Asn Gly Ile Pro Gly Glu Lys Gly Pro Ala Gly Glu Arg Gly Ala Pro
            500             505             510
Gly Pro Ala Gly Pro Arg Gly Ala Ala Gly Glu Pro Gly Arg Asp Gly
        515             520             525
Val Pro Gly Pro Gly Met Arg Gly Met Pro Gly Ser Pro Gly Gly
        530             535             540
Pro Gly Ser Asp Gly Lys Pro Gly Pro Pro Gly Ser Gln Gly Glu Ser
545             550             555             560
Gly Arg Pro Gly Pro Pro Gly Pro Ser Gly Pro Arg Gly Gln Pro Gly
                565             570             575
Val Met Gly Phe Pro Gly Pro Lys Gly Asn Asp Gly Ala Pro Gly Lys
            580             585             590
Asn Gly Glu Arg Gly Gly Pro Gly Gly Pro Gly Pro Gln Gly Pro Pro
                595             600             605
Gly Lys Asn Gly Glu Thr Gly Pro Gln Gly Pro Pro Gly Pro Thr Gly
            610             615             620
Pro Gly Gly Asp Lys Gly Asp Thr Gly Pro Pro Gly Pro Gln Gly Leu
625             630             635             640
Gln Gly Leu Pro Gly Thr Gly Gly Pro Pro Gly Glu Asn Gly Lys Pro
                645             650             655
Gly Glu Pro Gly Pro Lys Gly Asp Ala Gly Ala Pro Gly Ala Pro Gly
            660             665             670
Gly Lys Gly Asp Ala Gly Ala Pro Gly Glu Arg Gly Pro Pro Gly Leu
        675             680             685
Ala Gly Ala Pro Gly Leu Arg Gly Gly Ala Gly Pro Pro Gly Pro Glu
        690             695             700
Gly Gly Lys Gly Ala Ala Gly Pro Pro Gly Pro Pro Gly Ala Ala Gly
705             710             715             720
Thr Pro Gly Leu Gln Gly Met Pro Gly Glu Arg Gly Gly Leu Gly Ser
                725             730             735
Pro Gly Pro Lys Gly Asp Lys Gly Glu Pro Gly Gly Pro Gly Ala Asp
            740             745             750
Gly Val Pro Gly Lys Asp Gly Pro Arg Gly Pro Thr Gly Pro Ile Gly
        755             760             765
```

```
Pro Pro Gly Pro Ala Gly Gln Pro Gly Asp Lys Gly Glu Gly Gly Ala
    770                 775                 780
Pro Gly Leu Pro Gly Ile Ala Gly Pro Arg Gly Ser Pro Gly Glu Arg
785                 790                 795                 800
Gly Glu Thr Gly Pro Pro Gly Pro Ala Gly Phe Pro Gly Ala Pro Gly
                805                 810                 815
Gln Asn Gly Glu Pro Gly Gly Lys Gly Glu Arg Gly Ala Pro Gly Glu
            820                 825                 830
Lys Gly Glu Gly Gly Pro Pro Gly Val Ala Gly Pro Pro Gly Gly Ser
        835                 840                 845
Gly Pro Ala Gly Pro Pro Gly Pro Gln Gly Val Lys Gly Glu Arg Gly
    850                 855                 860
Ser Pro Gly Gly Pro Gly Ala Ala Gly Phe Pro Gly Ala Arg Gly Leu
865                 870                 875                 880
Pro Gly Pro Pro Gly Ser Asn Gly Asn Pro Gly Pro Pro Gly Pro Ser
                885                 890                 895
Gly Ser Pro Gly Lys Asp Gly Pro Pro Gly Pro Ala Gly Asn Thr Gly
            900                 905                 910
Ala Pro Gly Ser Pro Gly Val Ser Gly Pro Lys Gly Asp Ala Gly Gln
        915                 920                 925
Pro Gly Glu Lys Gly Ser Pro Gly Ala Gln Gly Pro Pro Gly Ala Pro
    930                 935                 940
Gly Pro Leu Gly Ile Ala Gly Ile Thr Gly Ala Arg Gly Leu Ala Gly
945                 950                 955                 960
Pro Pro Gly Met Pro Gly Pro Arg Gly Ser Pro Gly Pro Gln Gly Val
                965                 970                 975
Lys Gly Glu Ser Gly Lys Pro Gly Ala Asn Gly Leu Ser Gly Glu Arg
            980                 985                 990
Gly Pro Pro Gly Pro Gln Gly Leu Pro Gly Leu Ala Gly Thr Ala Gly
        995                 1000                1005
Glu Pro Gly Arg Asp Gly Asn Pro Gly Ser Asp Gly Leu Pro Gly Arg
    1010                1015                1020
Asp Gly Ser Pro Gly Gly Lys Gly Asp Arg Gly Glu Asn Gly Ser Pro
1025                1030                1035                1040
Gly Ala Pro Gly Ala Pro Gly His Pro Gly Pro Pro Gly Pro Val Gly
                1045                1050                1055
Pro Ala Gly Lys Ser Gly Asp Arg Gly Glu Ser Gly Pro Ala Gly Pro
            1060                1065                1070
Ala Gly Ala Pro Gly Pro Ala Gly Ser Arg Gly Ala Pro Gly Pro Gln
        1075                1080                1085
Gly Pro Arg Gly Asp Lys Gly Glu Thr Gly Glu Arg Gly Ala Ala Gly
    1090                1095                1100
Ile Lys Gly His Arg Gly Phe Pro Gly Asn Pro Gly Ala Pro Gly Ser
1105                1110                1115                1120
Pro Gly Pro Ala Gly Gln Gln Gly Ala Ile Gly Ser Pro Gly Pro Ala
                1125                1130                1135
Gly Pro Arg Gly Pro Val Gly Pro Ser Gly Pro Pro Gly Lys Asp Gly
            1140                1145                1150
Thr Ser Gly His Pro Gly Pro Ile Gly Pro Pro Gly Pro Arg Gly Asn
        1155                1160                1165
Arg Gly Glu Arg Gly Ser Glu Gly Ser Pro Gly His Pro Gly Gln Pro
    1170                1175                1180
```

-continued

```
Gly Pro Pro Gly Pro Pro Gly Ala Gly Pro Cys Cys Gly Gly Val
        1185                1190                1195                1200

Gly Ala Ala Ala Ile Ala Gly Ile Gly Gly Glu Lys Ala Gly Phe
                1205                1210                1215

Ala Pro Tyr Tyr Gly Asp Glu Pro Met Asp Phe Lys Ile Asn Thr Asp
                1220                1225                1230

Glu Ile Met Thr Ser Leu Lys Ser Val Asn Gly Gln Ile Glu Ser Leu
                1235                1240                1245

Ile Ser Pro Asp Gly Ser Arg Lys Asn Pro Ala Arg Asn Cys Arg Asp
                1250                1255                1260

Leu Lys Phe Cys His Pro Glu Leu Lys Ser Gly Glu Tyr Trp Val Asp
1265                1270                1275                1280

Pro Asn Gln Gly Cys Lys Leu Asp Ala Ile Lys Val Phe Cys Asn Met
                1285                1290                1295

Glu Thr Gly Glu Thr Cys Ile Ser Ala Asn Pro Leu Asn Val Pro Arg
                1300                1305                1310

Lys His Trp Trp Thr Asp Ser Ser Ala Glu Lys Lys His Val Trp Phe
                1315                1320                1325

Gly Glu Ser Met Asp Gly Gly Phe Gln Phe Ser Tyr Gly Asn Pro Glu
                1330                1335                1340

Leu Pro Glu Asp Val Leu Asp Val His Leu Ala Phe Leu Arg Leu Leu
1345                1350                1355                1360

Ser Ser Arg Ala Ser Gln Asn Ile Thr Tyr His Cys Lys Asn Ser Ile
                1365                1370                1375

Ala Tyr Met Asp Gln Ala Ser Gly Asn Val Lys Lys Ala Leu Lys Leu
                1380                1385                1390

Met Gly Ser Asn Glu Gly Glu Phe Lys Ala Glu Gly Asn Ser Lys Phe
                1395                1400                1405

Thr Tyr Thr Val Leu Glu Asp Gly Cys Thr Lys His Thr Gly Glu Trp
                1410                1415                1420

Ser Lys Thr Val Phe Glu Tyr Arg Thr Arg Lys Ala Val Arg Leu Pro
1425                1430                1435                1440

Ile Val Asp Ile Ala Pro Tyr Asp Ile Gly Gly Pro Asp Gln Glu Phe
                1445                1450                1455

Gly Val Asp Val Gly Pro Val Cys Phe Leu
                1460                1465

<210> SEQ ID NO 5
<211> LENGTH: 1669
<212> TYPE: PRT
<213> ORGANISM: Homo sapiens

<400> SEQUENCE: 5

Met Gly Pro Arg Leu Ser Val Trp Leu Leu Leu Leu Pro Ala Ala Leu
1               5                   10                  15

Leu Leu His Glu Glu His Ser Arg Ala Ala Ala Lys Gly Gly Cys Ala
                20                  25                  30

Gly Ser Gly Cys Gly Lys Cys Asp Cys His Gly Val Lys Gly Gln Lys
            35                  40                  45

Gly Glu Arg Gly Leu Pro Gly Leu Gln Gly Val Ile Gly Phe Pro Gly
        50                  55                  60

Met Gln Gly Pro Glu Gly Pro Gln Gly Pro Gly Gln Lys Gly Asp
65                  70                  75                  80

Thr Gly Glu Pro Gly Leu Pro Gly Thr Lys Gly Thr Arg Gly Pro Pro
                85                  90                  95
```

Gly Ala Ser Gly Tyr Pro Gly Asn Pro Gly Leu Pro Gly Ile Pro Gly
            100                 105                 110

Gln Asp Gly Pro Pro Gly Pro Pro Gly Ile Pro Gly Cys Asn Gly Thr
            115                 120                 125

Lys Gly Glu Arg Gly Pro Leu Gly Pro Pro Gly Leu Pro Gly Phe Ala
130                 135                 140

Gly Asn Pro Gly Pro Pro Gly Leu Pro Gly Met Lys Gly Asp Pro Gly
145                 150                 155                 160

Glu Ile Leu Gly His Val Pro Gly Met Leu Leu Lys Gly Glu Arg Gly
                165                 170                 175

Phe Pro Gly Ile Pro Gly Thr Pro Gly Pro Pro Gly Leu Pro Gly Leu
            180                 185                 190

Gln Gly Pro Val Gly Pro Pro Gly Phe Thr Gly Pro Pro Gly Pro Pro
            195                 200                 205

Gly Pro Pro Gly Pro Pro Gly Glu Lys Gly Gln Met Gly Leu Ser Phe
            210                 215                 220

Gln Gly Pro Lys Gly Asp Lys Gly Asp Gln Gly Val Ser Gly Pro Pro
225                 230                 235                 240

Gly Val Pro Gly Gln Ala Gln Val Gln Glu Lys Gly Asp Phe Ala Thr
                245                 250                 255

Lys Gly Glu Lys Gly Gln Lys Gly Glu Pro Gly Phe Gln Gly Met Pro
            260                 265                 270

Gly Val Gly Glu Lys Gly Glu Pro Gly Lys Pro Gly Pro Arg Gly Lys
            275                 280                 285

Pro Gly Lys Asp Gly Asp Lys Gly Glu Lys Gly Ser Pro Gly Phe Pro
            290                 295                 300

Gly Glu Pro Gly Tyr Pro Gly Leu Ile Gly Arg Gln Gly Pro Gln Gly
305                 310                 315                 320

Glu Lys Gly Glu Ala Gly Pro Pro Gly Pro Pro Gly Ile Val Ile Gly
                325                 330                 335

Thr Gly Pro Leu Gly Glu Lys Gly Glu Arg Gly Tyr Pro Gly Thr Pro
            340                 345                 350

Gly Pro Arg Gly Glu Pro Gly Pro Lys Gly Phe Pro Gly Leu Pro Gly
            355                 360                 365

Gln Pro Gly Pro Pro Gly Leu Pro Val Pro Gly Gln Ala Gly Ala Pro
            370                 375                 380

Gly Phe Pro Gly Glu Arg Gly Glu Lys Gly Asp Arg Gly Phe Pro Gly
385                 390                 395                 400

Thr Ser Leu Pro Gly Pro Ser Gly Arg Asp Gly Leu Pro Gly Pro Pro
                405                 410                 415

Gly Ser Pro Gly Pro Pro Gly Gln Pro Gly Tyr Thr Asn Gly Ile Val
            420                 425                 430

Glu Cys Gln Pro Gly Pro Pro Gly Asp Gln Gly Pro Pro Gly Ile Pro
            435                 440                 445

Gly Gln Pro Gly Phe Ile Gly Glu Ile Gly Glu Lys Gly Gln Lys Gly
            450                 455                 460

Glu Ser Cys Leu Ile Cys Asp Ile Asp Gly Tyr Arg Gly Pro Pro Gly
465                 470                 475                 480

Pro Gln Gly Pro Pro Gly Glu Ile Gly Phe Pro Gly Gln Pro Gly Ala
                485                 490                 495

Lys Gly Asp Arg Gly Leu Pro Gly Arg Asp Gly Val Ala Gly Val Pro
            500                 505                 510

Gly Pro Gln Gly Thr Pro Gly Leu Ile Gly Gln Pro Gly Ala Lys Gly
        515                 520                 525

Glu Pro Gly Glu Phe Tyr Phe Asp Leu Arg Leu Lys Gly Asp Lys Gly
        530                 535                 540

Asp Pro Gly Phe Pro Gly Gln Pro Gly Met Thr Gly Arg Ala Gly Ser
545                 550                 555                 560

Pro Gly Arg Asp Gly His Pro Gly Leu Pro Gly Pro Lys Gly Ser Pro
                565                 570                 575

Gly Ser Val Gly Leu Lys Gly Glu Arg Gly Pro Pro Gly Gly Val Gly
            580                 585                 590

Phe Pro Gly Ser Arg Gly Asp Thr Gly Pro Pro Gly Pro Pro Gly Tyr
        595                 600                 605

Gly Pro Ala Gly Pro Ile Gly Asp Lys Gly Gln Ala Gly Phe Pro Gly
        610                 615                 620

Gly Pro Gly Ser Pro Gly Leu Pro Gly Pro Lys Gly Glu Pro Gly Lys
625                 630                 635                 640

Ile Val Pro Leu Pro Gly Pro Pro Gly Ala Glu Gly Leu Pro Gly Ser
                645                 650                 655

Pro Gly Phe Pro Gly Pro Gln Gly Asp Arg Gly Phe Pro Gly Thr Pro
            660                 665                 670

Gly Arg Pro Gly Leu Pro Gly Glu Lys Gly Ala Val Gly Gln Pro Gly
        675                 680                 685

Ile Gly Phe Pro Gly Pro Pro Gly Pro Lys Gly Val Asp Gly Leu Pro
        690                 695                 700

Gly Asp Met Gly Pro Pro Gly Thr Pro Gly Arg Pro Gly Phe Asn Gly
705                 710                 715                 720

Leu Pro Gly Asn Pro Gly Val Gln Gly Gln Lys Gly Glu Pro Gly Val
                725                 730                 735

Gly Leu Pro Gly Leu Lys Gly Leu Pro Gly Leu Pro Gly Ile Pro Gly
            740                 745                 750

Thr Pro Gly Glu Lys Gly Ser Ile Gly Val Pro Gly Val Pro Gly Glu
        755                 760                 765

His Gly Ala Ile Gly Pro Pro Gly Leu Gln Gly Ile Arg Gly Glu Pro
        770                 775                 780

Gly Pro Pro Gly Leu Pro Gly Ser Val Gly Ser Pro Gly Val Pro Gly
785                 790                 795                 800

Ile Gly Pro Pro Gly Ala Arg Gly Pro Pro Gly Gly Gln Gly Pro Pro
                805                 810                 815

Gly Leu Ser Gly Pro Gly Ile Lys Gly Glu Lys Gly Phe Pro Gly
            820                 825                 830

Phe Pro Gly Leu Asp Met Pro Gly Pro Lys Gly Asp Lys Gly Ala Gln
        835                 840                 845

Gly Leu Pro Gly Ile Thr Gly Gln Ser Gly Leu Pro Gly Leu Pro Gly
        850                 855                 860

Gln Gln Gly Ala Pro Gly Ile Pro Gly Phe Pro Gly Ser Lys Gly Glu
865                 870                 875                 880

Met Gly Val Met Gly Thr Pro Gly Gln Pro Gly Ser Pro Gly Pro Val
                885                 890                 895

Gly Ala Pro Gly Leu Pro Gly Glu Lys Gly Asp His Gly Phe Pro Gly
            900                 905                 910

Ser Ser Gly Pro Arg Gly Asp Pro Gly Leu Lys Gly Asp Lys Gly Asp
        915                 920                 925

Val Gly Leu Pro Gly Lys Pro Gly Ser Met Asp Lys Val Asp Met Gly

```
                930            935              940
Ser Met Lys Gly Gln Lys Gly Asp Gln Gly Glu Lys Gly Gln Ile Gly
945                950              955                  960
Pro Ile Gly Glu Lys Gly Ser Arg Gly Asp Pro Gly Thr Pro Gly Val
                965              970                  975
Pro Gly Lys Asp Gly Gln Ala Gly Gln Pro Gly Gln Pro Gly Pro Lys
            980              985                  990
Gly Asp Pro Gly Ile Ser Gly Thr Pro Gly Ala Pro Gly Leu Pro Gly
            995              1000                  1005
Pro Lys Gly Ser Val Gly Gly Met Gly Leu Pro Gly Thr Pro Gly Glu
            1010              1015                  1020
Lys Gly Val Pro Gly Ile Pro Gly Pro Gln Gly Ser Pro Gly Leu Pro
1025              1030              1035                  1040
Gly Asp Lys Gly Ala Lys Gly Glu Lys Gly Gln Ala Gly Pro Pro Gly
            1045              1050                  1055
Ile Gly Ile Pro Gly Leu Arg Gly Glu Lys Gly Asp Gln Gly Ile Ala
            1060              1065                  1070
Gly Phe Pro Gly Ser Pro Gly Glu Lys Gly Glu Lys Gly Ser Ile Gly
            1075              1080                  1085
Ile Pro Gly Met Pro Gly Ser Pro Gly Leu Lys Gly Ser Pro Gly Ser
            1090              1095                  1100
Val Gly Tyr Pro Gly Ser Pro Gly Leu Pro Gly Glu Lys Gly Asp Lys
1105              1110              1115                  1120
Gly Leu Pro Gly Leu Asp Gly Ile Pro Gly Val Lys Gly Glu Ala Gly
            1125              1130                  1135
Leu Pro Gly Thr Pro Gly Pro Thr Gly Pro Ala Gly Gln Lys Gly Glu
            1140              1145                  1150
Pro Gly Ser Asp Gly Ile Pro Gly Ser Ala Gly Glu Lys Gly Glu Pro
            1155              1160                  1165
Gly Leu Pro Gly Arg Gly Phe Pro Gly Phe Pro Gly Ala Lys Gly Asp
            1170              1175                  1180
Lys Gly Ser Lys Gly Glu Val Gly Phe Pro Gly Leu Ala Gly Ser Pro
1185              1190              1195                  1200
Gly Ile Pro Gly Ser Lys Gly Glu Gln Gly Phe Met Gly Pro Pro Gly
            1205              1210                  1215
Pro Gln Gly Gln Pro Gly Leu Pro Gly Ser Pro Gly His Ala Thr Glu
            1220              1225                  1230
Gly Pro Lys Gly Asp Arg Gly Pro Gln Gly Gln Pro Gly Leu Pro Gly
            1235              1240                  1245
Leu Pro Gly Pro Met Gly Pro Pro Gly Leu Pro Gly Ile Asp Gly Val
            1250              1255                  1260
Lys Gly Asp Lys Gly Asn Pro Gly Trp Pro Gly Ala Pro Gly Val Pro
1265              1270              1275                  1280
Gly Pro Lys Gly Asp Pro Gly Phe Gln Gly Met Pro Gly Ile Gly Gly
            1285              1290                  1295
Ser Pro Gly Ile Thr Gly Ser Lys Gly Asp Met Gly Pro Pro Gly Val
            1300              1305                  1310
Pro Gly Phe Gln Gly Pro Lys Gly Leu Pro Gly Leu Gln Gly Ile Lys
            1315              1320                  1325
Gly Asp Gln Gly Asp Gln Gly Val Pro Gly Ala Lys Gly Leu Pro Gly
            1330              1335                  1340
Pro Pro Gly Pro Pro Gly Pro Tyr Asp Ile Ile Lys Gly Glu Pro Gly
1345              1350              1355                  1360
```

```
Leu Pro Gly Pro Glu Gly Pro Pro Gly Leu Lys Gly Leu Gln Gly Leu
                1365                1370                1375

Pro Gly Pro Lys Gly Gln Gln Gly Val Thr Gly Leu Val Gly Ile Pro
            1380                1385                1390

Gly Pro Pro Gly Ile Pro Gly Phe Asp Gly Ala Pro Gly Gln Lys Gly
        1395                1400                1405

Glu Met Gly Pro Ala Gly Pro Thr Gly Arg Gly Phe Pro Gly Pro
    1410                1415                1420

Pro Gly Pro Asp Gly Leu Pro Gly Ser Met Gly Pro Pro Gly Thr Pro
1425                1430                1435                1440

Ser Val Asp His Gly Phe Leu Val Thr Arg His Ser Gln Thr Ile Asp
                1445                1450                1455

Asp Pro Gln Cys Pro Ser Gly Thr Lys Ile Leu Tyr His Gly Tyr Ser
                1460                1465                1470

Leu Leu Tyr Val Gln Gly Asn Glu Arg Ala His Gly Gln Asp Leu Gly
            1475                1480                1485

Thr Ala Gly Ser Cys Leu Arg Lys Phe Ser Thr Met Pro Phe Leu Phe
        1490                1495                1500

Cys Asn Ile Asn Asn Val Cys Asn Phe Ala Ser Arg Asn Asp Tyr Ser
1505                1510                1515                1520

Tyr Trp Leu Ser Thr Pro Glu Pro Met Pro Met Ser Met Ala Pro Ile
                1525                1530                1535

Thr Gly Glu Asn Ile Arg Pro Phe Ile Ser Arg Cys Ala Val Cys Glu
                1540                1545                1550

Ala Pro Ala Met Val Met Ala Val His Ser Gln Thr Ile Gln Ile Pro
            1555                1560                1565

Pro Cys Pro Ser Gly Trp Ser Ser Leu Trp Ile Gly Tyr Ser Phe Val
        1570                1575                1580

Met His Thr Ser Ala Gly Ala Glu Gly Ser Gly Gln Ala Leu Ala Ser
1585                1590                1595                1600

Pro Gly Ser Cys Leu Glu Glu Phe Arg Ser Ala Pro Phe Ile Glu Cys
                1605                1610                1615

His Gly Arg Gly Thr Cys Asn Tyr Tyr Ala Asn Ala Tyr Ser Phe Trp
                1620                1625                1630

Leu Ala Thr Ile Glu Arg Ser Glu Met Phe Lys Lys Pro Thr Pro Ser
            1635                1640                1645

Thr Leu Lys Ala Gly Glu Leu Arg Thr His Val Ser Arg Cys Gln Val
        1650                1655                1660

Cys Met Arg Arg Thr
1665

<210> SEQ ID NO 6
<211> LENGTH: 1712
<212> TYPE: PRT
<213> ORGANISM: Homo sapiens

<400> SEQUENCE: 6

Met Gly Arg Asp Gln Arg Ala Val Ala Gly Pro Ala Leu Arg Arg Trp
1               5                   10                  15

Leu Leu Leu Gly Thr Val Thr Val Gly Phe Leu Ala Gln Ser Val Leu
                20                  25                  30

Ala Gly Val Lys Lys Phe Asp Val Pro Cys Gly Gly Arg Asp Cys Ser
            35                  40                  45

Gly Gly Cys Gln Cys Tyr Pro Glu Lys Gly Gly Arg Gly Gln Pro Gly
```

```
                50             55              60
Pro Val Gly Pro Gln Gly Tyr Asn Gly Pro Pro Gly Leu Gln Gly Phe
65                  70                  75                  80

Pro Gly Leu Gln Gly Arg Lys Gly Asp Lys Gly Glu Arg Gly Ala Pro
                85                  90                  95

Gly Val Thr Gly Pro Lys Gly Asp Val Gly Ala Arg Gly Val Ser Gly
            100                 105                 110

Phe Pro Gly Ala Asp Gly Ile Pro Gly His Pro Gly Gln Gly Gly Pro
            115                 120                 125

Arg Gly Arg Pro Gly Tyr Asp Gly Cys Asn Gly Thr Gln Gly Asp Ser
        130                 135                 140

Gly Pro Gln Gly Pro Pro Gly Ser Glu Gly Phe Thr Gly Pro Pro Gly
145                 150                 155                 160

Pro Gln Gly Pro Lys Gly Gln Lys Gly Glu Pro Tyr Ala Leu Pro Lys
                165                 170                 175

Glu Glu Arg Asp Arg Tyr Arg Gly Glu Pro Gly Glu Pro Gly Leu Val
            180                 185                 190

Gly Phe Gln Gly Pro Pro Gly Arg Pro Gly His Val Gly Gln Met Gly
        195                 200                 205

Pro Val Gly Ala Pro Gly Arg Pro Gly Pro Pro Gly Pro Pro Gly Pro
210                 215                 220

Lys Gly Gln Gln Gly Asn Arg Gly Leu Gly Phe Tyr Gly Val Lys Gly
225                 230                 235                 240

Glu Lys Gly Asp Val Gly Gln Pro Gly Pro Asn Gly Ile Pro Ser Asp
            245                 250                 255

Thr Leu His Pro Ile Ile Ala Pro Thr Gly Val Thr Phe His Pro Asp
            260                 265                 270

Gln Tyr Lys Gly Glu Lys Gly Ser Glu Gly Glu Pro Gly Ile Arg Gly
        275                 280                 285

Ile Ser Leu Lys Gly Glu Glu Gly Ile Met Gly Phe Pro Gly Leu Arg
290                 295                 300

Gly Tyr Pro Gly Leu Ser Gly Glu Lys Gly Ser Pro Gly Gln Lys Gly
305                 310                 315                 320

Ser Arg Gly Leu Asp Gly Tyr Gln Gly Pro Asp Gly Pro Arg Gly Pro
            325                 330                 335

Lys Gly Glu Ala Gly Asp Pro Gly Pro Pro Gly Leu Pro Ala Tyr Ser
            340                 345                 350

Pro His Pro Ser Leu Ala Lys Gly Ala Arg Gly Asp Pro Gly Phe Pro
        355                 360                 365

Gly Ala Gln Gly Glu Pro Gly Ser Gln Gly Glu Pro Gly Asp Pro Gly
        370                 375                 380

Leu Pro Gly Pro Pro Gly Leu Ser Ile Gly Asp Gly Asp Gln Arg Arg
385                 390                 395                 400

Gly Leu Pro Gly Glu Met Gly Pro Lys Gly Phe Ile Gly Asp Pro Gly
            405                 410                 415

Ile Pro Ala Leu Tyr Gly Gly Pro Pro Gly Pro Asp Gly Lys Arg Gly
            420                 425                 430

Pro Pro Gly Pro Pro Gly Leu Pro Gly Pro Pro Gly Pro Asp Gly Phe
            435                 440                 445

Leu Phe Gly Leu Lys Gly Ala Lys Gly Arg Ala Gly Phe Pro Gly Leu
        450                 455                 460

Pro Gly Ser Pro Gly Ala Arg Gly Pro Lys Gly Trp Lys Gly Asp Ala
465                 470                 475                 480
```

-continued

Gly Glu Cys Arg Cys Thr Gly Asp Glu Ala Ile Lys Gly Leu Pro
                485                 490                 495
Gly Leu Pro Gly Pro Lys Gly Phe Ala Gly Ile Asn Gly Glu Pro Gly
            500                 505                 510
Arg Lys Gly Asp Arg Gly Asp Pro Gly Gln His Gly Leu Pro Gly Phe
            515                 520                 525
Pro Gly Leu Lys Gly Val Pro Gly Asn Ile Gly Ala Pro Gly Pro Lys
            530                 535                 540
Gly Ala Lys Gly Asp Ser Arg Thr Ile Thr Thr Lys Gly Glu Arg Gly
545                 550                 555                 560
Gln Pro Gly Val Pro Gly Val Pro Gly Met Lys Gly Asp Asp Gly Ser
                565                 570                 575
Pro Gly Arg Asp Gly Leu Asp Gly Phe Pro Gly Leu Pro Gly Pro Pro
            580                 585                 590
Gly Asp Gly Ile Lys Gly Pro Pro Gly Asp Pro Gly Tyr Pro Gly Ile
            595                 600                 605
Pro Gly Thr Lys Gly Thr Pro Gly Glu Met Gly Pro Pro Gly Leu Gly
            610                 615                 620
Leu Pro Gly Leu Lys Gly Gln Arg Gly Phe Pro Gly Asp Ala Gly Leu
625                 630                 635                 640
Pro Gly Pro Pro Gly Phe Leu Gly Pro Pro Gly Pro Ala Gly Thr Pro
                645                 650                 655
Gly Gln Ile Asp Cys Asp Thr Asp Val Lys Arg Ala Val Gly Gly Asp
            660                 665                 670
Arg Gln Glu Ala Ile Gln Pro Gly Cys Ile Gly Pro Lys Gly Leu
            675                 680                 685
Pro Gly Leu Pro Gly Pro Pro Gly Pro Thr Gly Ala Lys Gly Leu Arg
            690                 695                 700
Gly Ile Pro Gly Phe Ala Gly Ala Asp Gly Gly Pro Gly Pro Arg Gly
705                 710                 715                 720
Leu Pro Gly Asp Ala Gly Arg Glu Gly Phe Pro Gly Pro Pro Gly Phe
                725                 730                 735
Ile Gly Pro Arg Gly Ser Lys Gly Ala Val Gly Leu Pro Gly Pro Asp
            740                 745                 750
Gly Ser Pro Gly Pro Ile Gly Leu Pro Gly Pro Asp Gly Pro Pro Gly
            755                 760                 765
Glu Arg Gly Leu Pro Gly Glu Val Leu Gly Ala Gln Pro Gly Pro Arg
            770                 775                 780
Gly Asp Ala Gly Val Pro Gly Gln Pro Gly Leu Lys Gly Leu Pro Gly
785                 790                 795                 800
Asp Arg Gly Pro Pro Gly Phe Arg Gly Ser Gln Gly Met Pro Gly Met
                805                 810                 815
Pro Gly Leu Lys Gly Gln Pro Gly Leu Pro Gly Pro Ser Gly Gln Pro
            820                 825                 830
Gly Leu Tyr Gly Pro Pro Gly Leu His Gly Phe Pro Gly Ala Pro Gly
            835                 840                 845
Gln Glu Gly Pro Leu Gly Leu Pro Gly Ile Pro Gly Arg Glu Gly Leu
            850                 855                 860
Pro Gly Asp Arg Gly Asp Pro Gly Asp Thr Gly Ala Pro Gly Pro Val
865                 870                 875                 880
Gly Met Lys Gly Leu Ser Gly Asp Arg Gly Asp Ala Gly Phe Thr Gly
                885                 890                 895

```
Glu Gln Gly His Pro Gly Ser Pro Gly Phe Lys Gly Ile Asp Gly Met
            900                 905                 910

Pro Gly Thr Pro Gly Leu Lys Gly Asp Arg Gly Ser Pro Gly Met Asp
        915                 920                 925

Gly Phe Gln Gly Met Pro Gly Leu Lys Gly Arg Pro Gly Phe Pro Gly
        930                 935                 940

Ser Lys Gly Glu Ala Gly Phe Phe Gly Ile Pro Gly Leu Lys Gly Leu
945                 950                 955                 960

Ala Gly Glu Pro Gly Phe Lys Gly Ser Arg Gly Asp Pro Gly Pro Pro
            965                 970                 975

Gly Pro Pro Pro Val Ile Leu Pro Gly Met Lys Asp Ile Lys Gly Glu
        980                 985                 990

Lys Gly Asp Glu Gly Pro Met Gly Leu Lys Gly Tyr Leu Gly Ala Lys
        995                 1000                1005

Gly Ile Gln Gly Met Pro Gly Ile Pro Gly Leu Ser Gly Ile Pro Gly
        1010                1015                1020

Leu Pro Gly Arg Pro Gly His Ile Lys Gly Val Lys Gly Asp Ile Gly
1025                1030                1035                1040

Val Pro Gly Ile Pro Gly Leu Pro Gly Phe Pro Gly Val Ala Gly Pro
            1045                1050                1055

Pro Gly Ile Thr Gly Phe Pro Gly Phe Ile Gly Ser Arg Gly Asp Lys
        1060                1065                1070

Gly Ala Pro Gly Arg Ala Gly Leu Tyr Gly Glu Ile Gly Ala Thr Gly
        1075                1080                1085

Asp Phe Gly Asp Ile Gly Asp Thr Ile Asn Leu Pro Gly Arg Pro Gly
        1090                1095                1100

Leu Lys Gly Glu Arg Gly Thr Thr Gly Ile Pro Gly Leu Lys Gly Phe
1105                1110                1115                1120

Phe Gly Glu Lys Gly Thr Glu Gly Asp Ile Gly Phe Pro Gly Ile Thr
            1125                1130                1135

Gly Val Thr Gly Val Gln Gly Pro Pro Gly Leu Lys Gly Gln Thr Gly
        1140                1145                1150

Phe Pro Gly Leu Thr Gly Pro Pro Gly Ser Gln Gly Glu Leu Gly Arg
        1155                1160                1165

Ile Gly Leu Pro Gly Gly Lys Gly Asp Asp Gly Trp Pro Gly Ala Pro
        1170                1175                1180

Gly Leu Pro Gly Phe Pro Gly Leu Arg Gly Ile Arg Gly Leu His Gly
1185                1190                1195                1200

Leu Pro Gly Thr Lys Gly Phe Pro Gly Ser Pro Gly Ser Asp Ile His
            1205                1210                1215

Gly Asp Pro Gly Phe Pro Gly Pro Gly Glu Arg Gly Asp Pro Gly
        1220                1225                1230

Glu Ala Asn Thr Leu Pro Gly Pro Val Gly Val Pro Gly Gln Lys Gly
        1235                1240                1245

Asp Gln Gly Ala Pro Gly Glu Arg Gly Pro Pro Gly Ser Pro Gly Leu
        1250                1255                1260

Gln Gly Phe Pro Gly Ile Thr Pro Pro Ser Asn Ile Ser Gly Ala Pro
1265                1270                1275                1280

Gly Asp Lys Gly Ala Pro Gly Ile Phe Gly Leu Lys Gly Tyr Arg Gly
            1285                1290                1295

Pro Pro Gly Pro Pro Gly Ser Ala Ala Leu Pro Gly Ser Lys Gly Asp
        1300                1305                1310

Thr Gly Asn Pro Gly Ala Pro Gly Thr Pro Gly Thr Lys Gly Trp Ala
```

```
                   1315                1320                1325

Gly Asp Ser Gly Pro Gln Gly Arg Pro Gly Val Phe Gly Leu Pro Gly
            1330                1335                1340

Glu Lys Gly Pro Arg Gly Glu Gln Gly Phe Met Gly Asn Thr Gly Pro
1345                1350                1355                1360

Thr Gly Ala Val Gly Asp Arg Gly Pro Lys Gly Pro Lys Gly Asp Pro
                1365                1370                1375

Gly Phe Pro Gly Ala Pro Gly Thr Val Gly Ala Pro Gly Ile Ala Gly
            1380                1385                1390

Ile Pro Gln Lys Ile Ala Val Gln Pro Gly Thr Val Gly Pro Gln Gly
                1395                1400                1405

Arg Arg Gly Pro Pro Gly Ala Pro Gly Glu Met Gly Pro Gln Gly Pro
            1410                1415                1420

Pro Gly Glu Pro Gly Phe Arg Gly Ala Pro Gly Lys Ala Gly Pro Gln
1425                1430                1435                1440

Gly Arg Gly Gly Val Ser Ala Val Pro Gly Phe Arg Gly Asp Glu Gly
                1445                1450                1455

Pro Ile Gly His Gln Gly Pro Ile Gly Gln Glu Gly Ala Pro Gly Arg
            1460                1465                1470

Pro Gly Ser Pro Gly Leu Pro Gly Met Pro Gly Arg Ser Val Ser Ile
                1475                1480                1485

Gly Tyr Leu Leu Val Lys His Ser Gln Thr Asp Gln Glu Pro Met Cys
            1490                1495                1500

Pro Val Gly Met Asn Lys Leu Trp Ser Gly Tyr Ser Leu Leu Tyr Phe
1505                1510                1515                1520

Glu Gly Gln Glu Lys Ala His Asn Gln Asp Leu Gly Leu Ala Gly Ser
                1525                1530                1535

Cys Leu Ala Arg Phe Ser Thr Met Pro Phe Leu Tyr Cys Asn Pro Gly
            1540                1545                1550

Asp Val Cys Tyr Tyr Ala Ser Arg Asn Asp Lys Ser Tyr Trp Leu Ser
                1555                1560                1565

Thr Thr Ala Pro Leu Pro Met Met Pro Val Ala Glu Asp Glu Ile Lys
            1570                1575                1580

Pro Tyr Ile Ser Arg Cys Ser Val Cys Glu Ala Pro Ala Ile Ala Ile
1585                1590                1595                1600

Ala Val His Ser Gln Asp Val Ser Ile Pro His Cys Pro Ala Gly Trp
                1605                1610                1615

Arg Ser Leu Trp Ile Gly Tyr Ser Phe Leu Met His Thr Ala Ala Gly
            1620                1625                1630

Asp Glu Gly Gly Gly Gln Ser Leu Val Ser Pro Gly Ser Cys Leu Glu
            1635                1640                1645

Asp Phe Arg Ala Thr Pro Phe Ile Glu Cys Asn Gly Gly Arg Gly Thr
            1650                1655                1660

Cys His Tyr Tyr Ala Asn Lys Tyr Ser Phe Trp Leu Thr Thr Ile Pro
1665                1670                1675                1680

Glu Gln Ser Phe Gln Gly Ser Pro Ser Ala Asp Thr Leu Lys Ala Gly
                1685                1690                1695

Leu Ile Arg Thr His Ile Ser Arg Cys Gln Val Cys Met Lys Asn Leu
            1700                1705                1710

<210> SEQ ID NO 7
<211> LENGTH: 1670
<212> TYPE: PRT
<213> ORGANISM: Homo sapiens
```

```
<400> SEQUENCE: 7

Met Ser Ala Arg Thr Ala Pro Arg Pro Gln Val Leu Leu Pro Leu
1               5                   10                  15

Leu Leu Val Leu Leu Ala Ala Pro Ala Ala Ser Lys Gly Cys Val
                20                  25                  30

Cys Lys Asp Lys Gly Gln Cys Phe Cys Asp Gly Ala Lys Gly Glu Lys
            35                  40                  45

Gly Glu Lys Gly Phe Pro Pro Gly Ser Pro Gly Gln Lys Gly
    50                  55                  60

Phe Thr Gly Pro Glu Gly Leu Pro Gly Pro Gln Gly Pro Lys Gly Phe
65                  70                  75                  80

Pro Gly Leu Pro Gly Leu Thr Gly Ser Lys Gly Val Arg Gly Ile Ser
                85                  90                  95

Gly Leu Pro Gly Phe Ser Gly Ser Pro Gly Leu Pro Gly Thr Pro Gly
                100                 105                 110

Asn Thr Gly Pro Tyr Gly Leu Val Gly Val Pro Gly Cys Ser Gly Ser
                115                 120                 125

Lys Gly Glu Gln Gly Phe Pro Gly Leu Pro Gly Thr Leu Gly Tyr Pro
    130                 135                 140

Gly Ile Pro Gly Ala Ala Gly Leu Lys Gly Gln Lys Gly Ala Pro Ala
145                 150                 155                 160

Lys Glu Glu Asp Ile Glu Leu Asp Ala Lys Gly Asp Pro Gly Leu Pro
                165                 170                 175

Gly Ala Pro Gly Pro Gln Gly Leu Pro Gly Pro Gly Phe Pro Gly
                180                 185                 190

Pro Val Gly Pro Pro Gly Pro Pro Gly Phe Phe Gly Phe Pro Gly Ala
                195                 200                 205

Met Gly Pro Arg Gly Pro Lys Gly His Met Gly Glu Arg Val Ile Gly
                210                 215                 220

His Lys Gly Glu Arg Gly Val Lys Gly Leu Thr Gly Pro Pro Gly Pro
225                 230                 235                 240

Pro Gly Thr Val Ile Val Thr Leu Thr Gly Pro Asp Asn Arg Thr Asp
                245                 250                 255

Leu Lys Gly Glu Lys Gly Asp Lys Gly Ala Met Gly Glu Pro Gly Pro
                260                 265                 270

Pro Gly Pro Ser Gly Leu Pro Gly Glu Ser Tyr Gly Ser Glu Lys Gly
                275                 280                 285

Ala Pro Gly Asp Pro Gly Leu Gln Gly Lys Pro Gly Lys Asp Gly Val
                290                 295                 300

Pro Gly Phe Pro Gly Ser Glu Gly Val Lys Gly Asn Arg Gly Phe Pro
305                 310                 315                 320

Gly Leu Met Gly Glu Asp Gly Ile Lys Gly Gln Lys Gly Asp Ile Gly
                325                 330                 335

Pro Pro Gly Phe Arg Gly Pro Thr Glu Tyr Tyr Asp Thr Tyr Gln Glu
                340                 345                 350

Lys Gly Asp Glu Gly Thr Pro Gly Pro Pro Gly Pro Arg Gly Ala Arg
                355                 360                 365

Gly Pro Gln Gly Pro Ser Gly Pro Pro Gly Val Pro Gly Ser Pro Gly
                370                 375                 380

Ser Ser Arg Pro Gly Leu Arg Gly Ala Pro Gly Trp Pro Gly Leu Lys
385                 390                 395                 400

Gly Ser Lys Gly Glu Arg Gly Arg Pro Gly Lys Asp Ala Met Gly Thr
```

```
                    405                 410                 415
Pro Gly Ser Pro Gly Cys Ala Gly Ser Pro Gly Leu Pro Gly Ser Pro
                420                 425                 430

Gly Pro Pro Gly Pro Pro Gly Asp Ile Val Phe Arg Lys Gly Pro Pro
            435                 440                 445

Gly Asp His Gly Leu Pro Gly Tyr Leu Gly Ser Pro Gly Ile Pro Gly
        450                 455                 460

Val Asp Gly Pro Lys Gly Glu Pro Gly Leu Leu Cys Thr Gln Cys Pro
465                 470                 475                 480

Tyr Ile Pro Gly Pro Pro Gly Leu Pro Gly Leu Pro Gly Leu His Gly
                485                 490                 495

Val Lys Gly Ile Pro Gly Arg Gln Gly Ala Ala Gly Leu Lys Gly Ser
            500                 505                 510

Pro Gly Ser Pro Gly Asn Thr Gly Leu Pro Gly Phe Pro Gly Phe Pro
        515                 520                 525

Gly Ala Gln Gly Asp Pro Gly Leu Lys Gly Glu Lys Gly Glu Thr Leu
    530                 535                 540

Gln Pro Glu Gly Gln Val Gly Val Pro Gly Asp Pro Gly Leu Arg Gly
545                 550                 555                 560

Gln Pro Gly Arg Lys Gly Leu Asp Gly Ile Pro Gly Thr Pro Gly Val
                565                 570                 575

Lys Gly Leu Pro Gly Pro Lys Gly Glu Leu Ala Leu Ser Gly Glu Lys
            580                 585                 590

Gly Asp Gln Gly Pro Pro Gly Asp Pro Gly Ser Pro Gly Ser Pro Gly
        595                 600                 605

Pro Ala Gly Pro Ala Gly Pro Pro Gly Tyr Gly Pro Gln Gly Glu Pro
    610                 615                 620

Gly Leu Gln Gly Thr Gln Gly Val Pro Gly Ala Pro Gly Pro Pro Gly
625                 630                 635                 640

Glu Ala Gly Pro Arg Gly Glu Leu Ser Val Ser Thr Pro Val Pro Gly
                645                 650                 655

Pro Pro Gly Pro Pro Gly Pro Gly His Pro Gly Pro Gln Gly Pro
            660                 665                 670

Pro Gly Ile Pro Gly Ser Leu Gly Lys Cys Gly Asp Pro Gly Leu Pro
        675                 680                 685

Gly Pro Asp Gly Glu Pro Gly Ile Pro Gly Ile Gly Phe Pro Gly Pro
    690                 695                 700

Pro Gly Pro Lys Gly Asp Gln Gly Phe Pro Gly Thr Lys Gly Ser Leu
705                 710                 715                 720

Gly Cys Pro Gly Lys Met Gly Glu Pro Gly Leu Pro Gly Lys Pro Gly
                725                 730                 735

Leu Pro Gly Ala Lys Gly Glu Pro Ala Val Ala Met Pro Gly Gly Pro
            740                 745                 750

Gly Thr Pro Gly Phe Pro Gly Glu Arg Gly Asn Ser Gly Glu His Gly
        755                 760                 765

Glu Ile Gly Leu Pro Gly Leu Pro Gly Leu Pro Gly Thr Pro Gly Asn
    770                 775                 780

Glu Gly Leu Asp Gly Pro Arg Gly Asp Pro Gly Gln Pro Gly Pro Pro
785                 790                 795                 800

Gly Glu Gln Gly Pro Pro Gly Arg Cys Ile Glu Gly Pro Arg Gly Ala
                805                 810                 815

Gln Gly Leu Pro Gly Leu Asn Gly Leu Lys Gly Gln Gln Gly Arg Arg
            820                 825                 830
```

```
Gly Lys Thr Gly Pro Lys Gly Asp Pro Gly Ile Pro Gly Leu Asp Arg
            835                 840                 845

Ser Gly Phe Pro Gly Glu Thr Gly Ser Pro Gly Ile Pro Gly His Gln
    850                 855                 860

Gly Glu Met Gly Pro Leu Gly Gln Arg Gly Tyr Pro Gly Asn Pro Gly
865                 870                 875                 880

Ile Leu Gly Pro Pro Gly Glu Asp Gly Val Ile Gly Met Met Gly Phe
                885                 890                 895

Pro Gly Ala Ile Gly Pro Gly Pro Pro Gly Asn Pro Gly Thr Pro
            900                 905                 910

Gly Gln Arg Gly Ser Pro Gly Ile Pro Gly Val Lys Gly Gln Arg Gly
            915                 920                 925

Thr Pro Gly Ala Lys Gly Glu Gln Gly Asp Lys Gly Asn Pro Gly Pro
            930                 935                 940

Ser Glu Ile Ser His Val Ile Gly Asp Lys Gly Glu Pro Gly Leu Lys
945                 950                 955                 960

Gly Phe Ala Gly Asn Pro Gly Glu Lys Gly Asn Arg Gly Val Pro Gly
                965                 970                 975

Met Pro Gly Leu Lys Gly Leu Lys Gly Leu Pro Gly Pro Ala Gly Pro
            980                 985                 990

Pro Gly Pro Arg Gly Asp Leu Gly Ser Thr Gly Asn Pro Gly Glu Pro
            995                 1000                1005

Gly Leu Arg Gly Ile Pro Gly Ser Met Gly Asn Met Gly Met Pro Gly
            1010                1015                1020

Ser Lys Gly Lys Arg Gly Thr Leu Gly Phe Pro Gly Arg Ala Gly Arg
1025                1030                1035                1040

Pro Gly Leu Pro Gly Ile His Gly Leu Gln Gly Asp Lys Gly Glu Pro
            1045                1050                1055

Gly Tyr Ser Glu Gly Thr Arg Pro Gly Pro Pro Gly Pro Thr Gly Asp
            1060                1065                1070

Pro Gly Leu Pro Gly Asp Met Gly Lys Lys Gly Glu Met Gly Gln Pro
            1075                1080                1085

Gly Pro Pro Gly His Leu Gly Pro Ala Gly Pro Glu Gly Ala Pro Gly
            1090                1095                1100

Ser Pro Gly Ser Pro Gly Leu Pro Gly Lys Pro Gly Pro His Gly Asp
1105                1110                1115                1120

Leu Gly Phe Lys Gly Ile Lys Gly Leu Leu Gly Pro Pro Gly Ile Arg
            1125                1130                1135

Gly Pro Pro Gly Leu Pro Gly Phe Pro Gly Ser Pro Gly Pro Met Gly
            1140                1145                1150

Ile Arg Gly Asp Gln Gly Arg Asp Gly Ile Pro Gly Pro Ala Gly Glu
            1155                1160                1165

Lys Gly Glu Thr Gly Leu Leu Arg Ala Pro Gly Pro Arg Gly Asn
1170                1175                1180

Pro Gly Ala Gln Gly Ala Lys Gly Asp Arg Gly Ala Pro Gly Phe Pro
1185                1190                1195                1200

Gly Leu Pro Gly Arg Lys Gly Ala Met Gly Asp Ala Gly Pro Arg Gly
            1205                1210                1215

Pro Thr Gly Ile Glu Gly Phe Pro Gly Pro Pro Gly Leu Pro Gly Ala
            1220                1225                1230

Ile Ile Pro Gly Gln Thr Gly Asn Arg Gly Pro Pro Gly Ser Arg Gly
            1235                1240                1245
```

```
Ser Pro Gly Ala Pro Gly Pro Pro Gly Pro Pro Gly Ser His Val Ile
    1250                1255                1260

Gly Ile Lys Gly Asp Lys Gly Ser Met Gly His Pro Gly Pro Lys Gly
1265                1270                1275                1280

Pro Pro Gly Thr Ala Gly Asp Met Gly Pro Pro Gly Arg Leu Gly Ala
                1285                1290                1295

Pro Gly Thr Pro Gly Leu Pro Gly Pro Arg Gly Asp Pro Gly Phe Gln
            1300                1305                1310

Gly Phe Pro Gly Val Lys Gly Glu Lys Gly Asn Pro Gly Phe Leu Gly
        1315                1320                1325

Ser Ile Gly Pro Pro Gly Pro Ile Gly Lys Gly Pro Pro Gly Pro Val
    1330                1335                1340

Arg Gly Asp Pro Gly Thr Leu Lys Ile Ile Ser Leu Pro Gly Ser Pro
1345                1350                1355                1360

Gly Pro Pro Gly Thr Pro Gly Glu Pro Gly Met Gln Gly Glu Pro Gly
                1365                1370                1375

Pro Pro Gly Pro Pro Gly Asn Leu Gly Pro Cys Gly Pro Arg Gly Lys
            1380                1385                1390

Pro Gly Lys Asp Gly Lys Pro Gly Thr Pro Gly Pro Ala Gly Glu Lys
        1395                1400                1405

Gly Asn Lys Gly Ser Lys Gly Glu Pro Gly Pro Ala Gly Ser Asp Gly
    1410                1415                1420

Leu Pro Gly Leu Lys Gly Lys Arg Gly Asp Ser Gly Ser Pro Ala Thr
1425                1430                1435                1440

Trp Thr Thr Arg Gly Phe Val Phe Thr Arg His Ser Gln Thr Thr Ala
                1445                1450                1455

Ile Pro Ser Cys Pro Glu Gly Thr Val Pro Leu Tyr Ser Gly Phe Ser
            1460                1465                1470

Phe Leu Phe Val Gln Gly Asn Gln Arg Ala His Gly Gln Asp Leu Gly
        1475                1480                1485

Thr Leu Gly Ser Cys Leu Gln Arg Phe Thr Thr Met Pro Phe Leu Phe
    1490                1495                1500

Cys Asn Val Asn Asp Val Cys Asn Phe Ala Ser Arg Asn Asp Tyr Ser
1505                1510                1515                1520

Tyr Trp Leu Ser Thr Pro Ala Leu Met Pro Met Asn Met Ala Pro Ile
                1525                1530                1535

Thr Gly Arg Ala Leu Glu Pro Tyr Ile Ser Arg Cys Thr Val Cys Glu
            1540                1545                1550

Gly Pro Ala Ile Ala Ile Ala Val His Ser Gln Thr Thr Asp Ile Pro
        1555                1560                1565

Pro Cys Pro His Gly Trp Ile Ser Leu Trp Lys Gly Phe Ser Phe Ile
    1570                1575                1580

Met Phe Thr Ser Ala Gly Ser Glu Gly Thr Gly Gln Ala Leu Ala Ser
1585                1590                1595                1600

Pro Gly Ser Cys Leu Glu Glu Phe Arg Ala Ser Pro Phe Leu Glu Cys
                1605                1610                1615

His Gly Arg Gly Thr Cys Asn Tyr Tyr Ser Asn Ser Tyr Ser Phe Trp
            1620                1625                1630

Leu Ala Ser Leu Asn Pro Glu Arg Met Phe Arg Lys Pro Ile Pro Ser
        1635                1640                1645

Thr Val Lys Ala Gly Glu Leu Glu Lys Ile Ile Ser Arg Cys Gln Val
    1650                1655                1660

Cys Met Lys Lys Arg His
```

1665                    1670

<210> SEQ ID NO 8
<211> LENGTH: 1690
<212> TYPE: PRT
<213> ORGANISM: Homo sapiens

<400> SEQUENCE: 8

Met Trp Ser Leu His Ile Val Leu Met Arg Cys Ser Phe Arg Leu Thr
1               5                   10                  15

Lys Ser Leu Ala Thr Gly Pro Trp Ser Leu Ile Leu Ile Leu Phe Ser
            20                  25                  30

Val Gln Tyr Val Tyr Gly Ser Gly Lys Lys Tyr Ile Gly Pro Cys Gly
        35                  40                  45

Gly Arg Asp Cys Ser Val Cys His Cys Val Pro Glu Lys Gly Ser Arg
    50                  55                  60

Gly Pro Pro Gly Pro Pro Gly Pro Gln Gly Pro Ile Gly Pro Leu Gly
65                  70                  75                  80

Ala Pro Gly Pro Ile Gly Leu Ser Gly Glu Lys Gly Met Arg Gly Asp
                85                  90                  95

Arg Gly Pro Pro Gly Ala Ala Gly Asp Lys Gly Asp Lys Gly Pro Thr
            100                 105                 110

Gly Val Pro Gly Phe Pro Gly Leu Asp Gly Ile Pro Gly His Pro Gly
        115                 120                 125

Pro Pro Gly Pro Arg Gly Lys Pro Gly Met Ser Gly His Asn Gly Ser
    130                 135                 140

Arg Gly Asp Pro Gly Phe Pro Gly Gly Arg Gly Ala Leu Gly Pro Gly
145                 150                 155                 160

Gly Pro Leu Gly His Pro Gly Glu Lys Gly Glu Lys Gly Asn Ser Val
                165                 170                 175

Phe Ile Leu Gly Ala Val Lys Gly Ile Gln Gly Asp Arg Gly Asp Pro
            180                 185                 190

Gly Leu Pro Gly Leu Pro Gly Ser Trp Gly Ala Gly Gly Pro Ala Gly
        195                 200                 205

Pro Thr Gly Tyr Pro Gly Glu Pro Gly Leu Val Gly Pro Pro Gly Gln
    210                 215                 220

Pro Gly Arg Pro Gly Leu Lys Gly Asn Pro Gly Val Gly Val Lys Gly
225                 230                 235                 240

Gln Met Gly Asp Pro Gly Glu Val Gly Gln Gln Gly Ser Pro Gly Pro
                245                 250                 255

Thr Leu Leu Val Glu Pro Pro Asp Phe Cys Leu Tyr Lys Gly Glu Lys
            260                 265                 270

Gly Ile Lys Gly Ile Pro Gly Met Val Gly Leu Pro Gly Pro Pro Gly
            275                 280                 285

Arg Lys Gly Glu Ser Gly Ile Gly Ala Lys Gly Glu Lys Gly Ile Pro
    290                 295                 300

Gly Phe Pro Gly Pro Arg Gly Asp Pro Gly Ser Tyr Gly Ser Pro Gly
305                 310                 315                 320

Phe Pro Gly Leu Lys Gly Glu Leu Gly Leu Val Gly Asp Pro Gly Leu
                325                 330                 335

Phe Gly Leu Ile Gly Pro Lys Gly Asp Pro Gly Asn Arg Gly His Pro
            340                 345                 350

Gly Pro Pro Gly Val Leu Val Thr Pro Pro Leu Pro Leu Lys Gly Pro
        355                 360                 365

-continued

```
Pro Gly Asp Pro Gly Phe Pro Gly Arg Tyr Gly Glu Thr Gly Asp Val
    370                 375                 380
Gly Pro Gly Pro Pro Gly Leu Leu Gly Arg Pro Gly Glu Ala Cys
385                 390                 395                 400
Ala Gly Met Ile Gly Pro Gly Pro Gln Gly Phe Pro Gly Leu Pro
                405                 410                 415
Gly Leu Pro Gly Glu Ala Gly Ile Pro Gly Arg Pro Asp Ser Ala Pro
            420                 425                 430
Gly Lys Pro Gly Lys Pro Gly Ser Pro Gly Leu Pro Gly Ala Pro Gly
            435                 440                 445
Leu Gln Gly Leu Pro Gly Ser Ser Val Ile Tyr Cys Ser Val Gly Asn
    450                 455                 460
Pro Gly Pro Gln Gly Ile Lys Gly Lys Val Gly Pro Gly Gly Arg
465                 470                 475                 480
Gly Pro Lys Gly Glu Lys Gly Asn Glu Gly Leu Cys Ala Cys Glu Pro
            485                 490                 495
Gly Pro Met Gly Pro Gly Pro Gly Leu Pro Gly Arg Gln Gly
            500                 505                 510
Ser Lys Gly Asp Leu Gly Leu Pro Gly Trp Leu Gly Thr Lys Gly Asp
            515                 520                 525
Pro Gly Pro Pro Gly Ala Glu Gly Pro Pro Gly Leu Pro Gly Lys His
    530                 535                 540
Gly Ala Ser Gly Pro Pro Gly Asn Lys Gly Ala Lys Gly Asp Met Val
545                 550                 555                 560
Val Ser Arg Val Lys Gly His Lys Gly Glu Arg Gly Pro Asp Gly Pro
                565                 570                 575
Pro Gly Phe Pro Gly Gln Pro Gly Ser His Gly Arg Asp Gly His Ala
            580                 585                 590
Gly Glu Lys Gly Asp Pro Gly Pro Pro Gly Asp His Glu Asp Ala Thr
            595                 600                 605
Pro Gly Gly Lys Gly Phe Pro Gly Pro Leu Gly Pro Pro Gly Lys Ala
    610                 615                 620
Gly Pro Val Gly Pro Pro Gly Leu Gly Phe Pro Gly Pro Pro Gly Glu
625                 630                 635                 640
Arg Gly His Pro Gly Val Pro Gly His Pro Gly Val Arg Gly Pro Asp
                645                 650                 655
Gly Leu Lys Gly Gln Lys Gly Asp Thr Ile Ser Cys Asn Val Thr Tyr
            660                 665                 670
Pro Gly Arg His Gly Pro Pro Gly Phe Asp Gly Pro Pro Gly Pro Lys
            675                 680                 685
Gly Phe Pro Gly Pro Gln Gly Ala Pro Gly Leu Ser Gly Ser Asp Gly
    690                 695                 700
His Lys Gly Arg Pro Gly Thr Pro Gly Thr Ala Glu Ile Pro Gly Pro
705                 710                 715                 720
Pro Gly Phe Arg Gly Asp Met Gly Asp Pro Gly Phe Gly Gly Glu Lys
                725                 730                 735
Gly Ser Ser Pro Val Gly Pro Pro Gly Pro Gly Ser Pro Gly Val
            740                 745                 750
Asn Gly Gln Lys Gly Ile Pro Gly Asp Pro Ala Phe Gly His Leu Gly
            755                 760                 765
Pro Pro Gly Lys Arg Gly Leu Ser Gly Val Pro Gly Ile Lys Gly Pro
    770                 775                 780
Arg Gly Asp Pro Gly Cys Pro Gly Ala Glu Gly Pro Ala Gly Ile Pro
```

```
                785                 790                 795                 800
        Gly Phe Leu Gly Leu Lys Gly Pro Lys Gly Arg Glu Gly His Ala Gly
                        805                 810                 815
        Phe Pro Gly Val Pro Gly Pro Pro Gly His Ser Cys Glu Arg Gly Ala
                        820                 825                 830
        Pro Gly Ile Pro Gly Gln Pro Gly Leu Pro Gly Tyr Pro Gly Ser Pro
                        835                 840                 845
        Gly Ala Pro Gly Gly Lys Gly Gln Pro Gly Asp Val Gly Pro Pro Gly
                        850                 855                 860
        Pro Ala Gly Met Lys Gly Leu Pro Gly Leu Pro Gly Arg Pro Gly Ala
        865                 870                 875                 880
        His Gly Pro Pro Gly Leu Pro Gly Ile Pro Gly Pro Phe Gly Asp Asp
                        885                 890                 895
        Gly Leu Pro Gly Pro Gly Pro Lys Gly Pro Arg Gly Leu Pro Gly
                        900                 905                 910
        Phe Pro Gly Phe Pro Gly Glu Arg Gly Lys Pro Gly Ala Glu Gly Cys
                        915                 920                 925
        Pro Gly Ala Lys Gly Glu Pro Gly Glu Lys Gly Met Ser Gly Leu Pro
                930                 935                 940
        Gly Asp Arg Gly Leu Arg Gly Ala Lys Gly Ala Ile Gly Pro Pro Gly
        945                 950                 955                 960
        Asp Glu Gly Glu Met Ala Ile Ile Ser Gln Lys Gly Thr Pro Gly Glu
                        965                 970                 975
        Pro Gly Pro Pro Gly Asp Asp Gly Phe Pro Gly Glu Arg Gly Asp Lys
                        980                 985                 990
        Gly Thr Pro Gly Met Gln Gly Arg Arg Gly Glu Pro Gly Arg Tyr Gly
                        995                 1000                1005
        Pro Pro Gly Phe His Arg Gly Glu Pro Gly Glu Lys Gly Gln Pro Gly
                        1010                1015                1020
        Pro Pro Gly Pro Pro Gly Pro Pro Gly Ser Thr Gly Leu Arg Gly Phe
        1025                1030                1035                1040
        Ile Gly Phe Pro Gly Leu Pro Gly Asp Gln Gly Glu Pro Gly Ser Pro
                        1045                1050                1055
        Gly Pro Pro Gly Phe Ser Gly Ile Asp Gly Ala Arg Gly Pro Lys Gly
                        1060                1065                1070
        Asn Lys Gly Asp Pro Ala Ser His Phe Gly Pro Pro Gly Pro Lys Gly
                        1075                1080                1085
        Glu Pro Gly Ser Pro Gly Cys Pro Gly His Phe Gly Ala Ser Gly Glu
                        1090                1095                1100
        Gln Gly Leu Pro Gly Ile Gln Gly Pro Arg Gly Ser Pro Gly Arg Pro
        1105                1110                1115                1120
        Gly Pro Pro Gly Ser Ser Gly Pro Pro Gly Cys Pro Gly Asp His Gly
                        1125                1130                1135
        Met Pro Gly Leu Arg Gly Gln Pro Gly Glu Met Gly Asp Pro Gly Pro
                        1140                1145                1150
        Arg Gly Leu Gln Gly Asp Pro Gly Ile Pro Gly Pro Gly Ile Lys
                        1155                1160                1165
        Gly Pro Ser Gly Ser Pro Gly Leu Asn Gly Leu His Gly Leu Lys Gly
                        1170                1175                1180
        Gln Lys Gly Thr Lys Gly Ala Ser Gly Leu His Asp Val Gly Pro Pro
        1185                1190                1195                1200
        Gly Pro Val Gly Ile Pro Gly Leu Lys Gly Glu Arg Gly Asp Pro Gly
                        1205                1210                1215
```

```
Ser Pro Gly Ile Ser Pro Pro Gly Pro Arg Gly Lys Lys Gly Pro Pro
            1220                1225                1230

Gly Pro Pro Gly Ser Ser Gly Pro Pro Gly Pro Ala Gly Ala Thr Gly
            1235                1240                1245

Arg Ala Pro Lys Asp Ile Pro Asp Pro Gly Pro Pro Gly Asp Gln Gly
            1250                1255                1260

Pro Pro Gly Pro Asp Gly Pro Arg Gly Ala Pro Gly Pro Pro Gly Leu
1265                1270                1275                1280

Pro Gly Ser Val Asp Leu Leu Arg Gly Glu Pro Gly Asp Cys Gly Leu
                1285                1290                1295

Pro Gly Pro Pro Gly Pro Pro Gly Pro Pro Gly Pro Pro Gly Tyr Lys
            1300                1305                1310

Gly Phe Pro Gly Cys Asp Gly Lys Asp Gly Gln Lys Gly Pro Val Gly
            1315                1320                1325

Phe Pro Gly Pro Gln Gly Pro His Gly Phe Pro Gly Pro Pro Gly Glu
            1330                1335                1340

Lys Gly Leu Pro Gly Pro Pro Gly Arg Lys Gly Pro Thr Gly Leu Pro
1345                1350                1355                1360

Gly Pro Arg Gly Glu Pro Gly Pro Pro Ala Asp Val Asp Asp Cys Pro
                1365                1370                1375

Arg Ile Pro Gly Leu Pro Gly Ala Pro Gly Met Arg Gly Pro Glu Gly
            1380                1385                1390

Ala Met Gly Leu Pro Gly Met Arg Gly Pro Ser Gly Pro Gly Cys Lys
            1395                1400                1405

Gly Glu Pro Gly Leu Asp Gly Arg Arg Gly Val Asp Gly Val Pro Gly
            1410                1415                1420

Ser Pro Gly Pro Pro Gly Arg Lys Gly Asp Thr Gly Glu Asp Gly Tyr
1425                1430                1435                1440

Pro Gly Gly Pro Gly Pro Pro Gly Pro Ile Gly Asp Pro Gly Pro Lys
                1445                1450                1455

Gly Phe Gly Pro Gly Tyr Leu Gly Gly Phe Leu Leu Val Leu His Ser
            1460                1465                1470

Gln Thr Asp Gln Glu Pro Thr Cys Pro Leu Gly Met Pro Arg Leu Trp
            1475                1480                1485

Thr Gly Tyr Ser Leu Leu Tyr Leu Glu Gly Gln Glu Lys Ala His Asn
            1490                1495                1500

Gln Asp Leu Gly Leu Ala Gly Ser Cys Leu Pro Val Phe Ser Thr Leu
1505                1510                1515                1520

Pro Phe Ala Tyr Cys Asn Ile His Gln Val Cys His Tyr Ala Gln Arg
                1525                1530                1535

Asn Asp Arg Ser Tyr Trp Leu Ala Ser Ala Ala Pro Leu Pro Met Met
            1540                1545                1550

Pro Leu Ser Glu Glu Ala Ile Arg Pro Tyr Val Ser Arg Cys Ala Val
            1555                1560                1565

Cys Glu Ala Pro Ala Gln Ala Val Ala Val His Ser Gln Asp Gln Ser
            1570                1575                1580

Ile Pro Pro Cys Pro Gln Thr Trp Arg Ser Leu Trp Ile Gly Tyr Ser
1585                1590                1595                1600

Phe Leu Met His Thr Gly Ala Gly Asp Gln Gly Gly Gly Gln Ala Leu
                1605                1610                1615

Met Ser Pro Gly Ser Cys Leu Glu Asp Phe Arg Ala Ala Pro Phe Leu
            1620                1625                1630
```

-continued

```
Glu Cys Gln Gly Arg Gln Gly Thr Cys His Phe Phe Ala Asn Lys Tyr
            1635                1640                1645

Ser Phe Trp Leu Thr Thr Val Lys Ala Asp Leu Gln Phe Ser Ser Ala
        1650                1655                1660

Pro Ala Pro Asp Thr Leu Lys Glu Ser Gln Ala Gln Arg Gln Lys Ile
1665                1670                1675                1680

Ser Arg Cys Gln Val Cys Val Lys Tyr Ser
        1685                1690

<210> SEQ ID NO 9
<211> LENGTH: 1685
<212> TYPE: PRT
<213> ORGANISM: Homo sapiens

<400> SEQUENCE: 9

Met Lys Leu Arg Gly Val Ser Leu Ala Ala Gly Leu Phe Leu Leu Ala
1               5                   10                  15

Leu Ser Leu Trp Gly Gln Pro Ala Glu Ala Ala Ala Cys Tyr Gly Cys
            20                  25                  30

Ser Pro Gly Ser Lys Cys Asp Cys Ser Gly Ile Lys Gly Glu Lys Gly
        35                  40                  45

Glu Arg Gly Phe Pro Gly Leu Glu Gly His Pro Gly Leu Pro Gly Phe
    50                  55                  60

Pro Gly Pro Glu Gly Pro Pro Gly Pro Arg Gly Gln Lys Gly Asp Asp
65                  70                  75                  80

Gly Ile Pro Gly Pro Pro Gly Pro Lys Gly Ile Arg Gly Pro Pro Gly
                85                  90                  95

Leu Pro Gly Phe Pro Gly Thr Pro Gly Leu Pro Gly Met Pro Gly His
            100                 105                 110

Asp Gly Ala Pro Gly Pro Gln Gly Ile Pro Gly Cys Asn Gly Thr Lys
        115                 120                 125

Gly Glu Arg Gly Phe Pro Gly Ser Pro Gly Phe Pro Gly Leu Gln Gly
    130                 135                 140

Pro Pro Gly Pro Pro Gly Ile Pro Gly Met Lys Gly Glu Pro Gly Ser
145                 150                 155                 160

Ile Ile Met Ser Ser Leu Pro Gly Pro Lys Gly Asn Pro Gly Tyr Pro
                165                 170                 175

Gly Pro Pro Gly Ile Gln Gly Leu Pro Gly Pro Thr Gly Ile Pro Gly
            180                 185                 190

Pro Ile Gly Pro Pro Gly Pro Pro Gly Leu Met Gly Pro Pro Gly Pro
        195                 200                 205

Pro Gly Leu Pro Gly Pro Lys Gly Asn Met Gly Leu Asn Phe Gln Gly
    210                 215                 220

Pro Lys Gly Glu Lys Gly Glu Gln Gly Leu Gln Gly Pro Pro Gly Pro
225                 230                 235                 240

Pro Gly Gln Ile Ser Glu Gln Lys Arg Pro Ile Asp Val Glu Phe Gln
                245                 250                 255

Lys Gly Asp Gln Gly Leu Pro Gly Asp Arg Gly Pro Pro Gly Pro Pro
            260                 265                 270

Gly Ile Arg Gly Pro Pro Gly Pro Pro Gly Glu Lys Gly Glu Lys Gly
        275                 280                 285

Gly Glu Gln Gly Glu Pro Gly Lys Arg Gly Lys Pro Gly Lys Asp Gly
    290                 295                 300

Glu Asn Gly Gln Pro Gly Ile Pro Gly Leu Pro Gly Asp Pro Gly Tyr
305                 310                 315                 320
```

```
Pro Gly Glu Pro Gly Arg Asp Gly Glu Lys Gly Gln Lys Gly Asp Thr
            325                 330                 335
Gly Pro Pro Gly Pro Gly Leu Val Ile Pro Arg Pro Gly Thr Gly
        340                 345                 350
Ile Thr Ile Gly Glu Lys Gly Asn Ile Gly Leu Pro Gly Leu Pro Gly
            355                 360                 365
Glu Lys Gly Glu Arg Gly Phe Pro Gly Ile Gln Gly Pro Pro Gly Leu
    370                 375                 380
Pro Gly Pro Pro Gly Ala Ala Val Met Gly Pro Pro Gly Pro Pro Gly
385                 390                 395                 400
Phe Pro Gly Glu Arg Gly Gln Lys Gly Asp Glu Gly Pro Pro Gly Ile
            405                 410                 415
Ser Ile Pro Gly Pro Pro Gly Leu Asp Gly Gln Pro Gly Ala Pro Gly
            420                 425                 430
Leu Pro Gly Pro Pro Gly Pro Ala Gly Pro His Ile Pro Pro Ser Asp
        435                 440                 445
Glu Ile Cys Glu Pro Gly Pro Pro Gly Pro Pro Gly Ser Pro Gly Asp
    450                 455                 460
Lys Gly Leu Gln Gly Glu Gln Gly Val Lys Gly Asp Lys Gly Asp Thr
465                 470                 475                 480
Cys Phe Asn Cys Ile Gly Thr Gly Ile Ser Gly Pro Pro Gly Gln Pro
                485                 490                 495
Gly Leu Pro Gly Leu Pro Gly Pro Gly Ser Leu Gly Phe Pro Gly
            500                 505                 510
Gln Lys Gly Glu Lys Gly Gln Ala Gly Ala Thr Gly Pro Lys Gly Leu
        515                 520                 525
Pro Gly Ile Pro Gly Ala Pro Gly Ala Pro Gly Phe Pro Gly Ser Lys
        530                 535                 540
Gly Glu Pro Gly Asp Ile Leu Thr Phe Pro Gly Met Lys Gly Asp Lys
545                 550                 555                 560
Gly Glu Leu Gly Ser Pro Gly Ala Pro Gly Leu Pro Gly Leu Pro Gly
                565                 570                 575
Thr Pro Gly Gln Asp Gly Leu Pro Gly Leu Pro Gly Pro Lys Gly Glu
            580                 585                 590
Pro Gly Gly Ile Thr Phe Lys Gly Glu Arg Gly Pro Pro Gly Asn Pro
        595                 600                 605
Gly Leu Pro Gly Leu Pro Gly Asn Ile Gly Pro Met Gly Pro Pro Gly
    610                 615                 620
Phe Gly Pro Pro Gly Pro Val Gly Glu Lys Gly Ile Gln Gly Val Ala
625                 630                 635                 640
Gly Asn Pro Gly Gln Pro Gly Ile Pro Gly Pro Lys Gly Asp Pro Gly
            645                 650                 655
Gln Thr Ile Thr Gln Pro Gly Lys Pro Gly Leu Pro Gly Asn Pro Gly
            660                 665                 670
Arg Asp Gly Asp Val Gly Leu Pro Gly Asp Pro Gly Leu Pro Gly Gln
        675                 680                 685
Pro Gly Leu Pro Gly Ile Pro Gly Ser Lys Gly Glu Pro Gly Ile Pro
    690                 695                 700
Gly Ile Gly Leu Pro Gly Pro Pro Gly Pro Lys Gly Phe Pro Gly Ile
705                 710                 715                 720
Pro Gly Pro Pro Gly Ala Pro Gly Thr Pro Gly Arg Ile Gly Leu Glu
            725                 730                 735
```

```
Gly Pro Pro Gly Pro Pro Gly Phe Pro Gly Pro Lys Gly Glu Pro Gly
            740                 745                 750

Phe Ala Leu Pro Gly Pro Gly Pro Gly Leu Pro Gly Phe Lys
        755                 760                 765

Gly Ala Leu Gly Pro Lys Gly Asp Arg Gly Phe Pro Gly Pro Pro Gly
        770                 775                 780

Pro Pro Gly Arg Thr Gly Leu Asp Gly Leu Pro Gly Pro Lys Gly Asp
785                 790                 795                 800

Val Gly Pro Asn Gly Gln Pro Gly Met Gly Pro Gly Leu Pro
                805                 810                 815

Gly Ile Gly Val Gln Gly Pro Pro Gly Pro Gly Ile Pro Gly Pro
            820                 825                 830

Ile Gly Gln Pro Gly Leu His Gly Ile Pro Gly Glu Lys Gly Asp Pro
            835                 840                 845

Gly Pro Pro Gly Leu Asp Val Pro Gly Pro Gly Glu Arg Gly Ser
            850                 855                 860

Pro Gly Ile Pro Gly Ala Pro Gly Pro Ile Gly Pro Gly Ser Pro
865                 870                 875                 880

Gly Leu Pro Gly Lys Ala Gly Ala Ser Gly Phe Pro Gly Thr Lys Gly
                885                 890                 895

Glu Met Gly Met Met Gly Pro Pro Gly Pro Pro Gly Pro Leu Gly Ile
                900                 905                 910

Pro Gly Arg Ser Gly Val Pro Gly Leu Lys Gly Asp Asp Gly Leu Gln
            915                 920                 925

Gly Gln Pro Gly Leu Pro Gly Pro Thr Gly Glu Lys Gly Ser Lys Gly
            930                 935                 940

Glu Pro Gly Leu Pro Gly Pro Pro Gly Pro Met Asp Pro Asn Leu Leu
945                 950                 955                 960

Gly Ser Lys Gly Glu Lys Gly Glu Pro Gly Leu Pro Gly Ile Pro Gly
                965                 970                 975

Val Ser Gly Pro Lys Gly Tyr Gln Gly Leu Pro Gly Asp Pro Gly Gln
            980                 985                 990

Pro Gly Leu Ser Gly Gln Pro Gly Leu Pro Gly Pro Pro Gly Pro Lys
            995                 1000                1005

Gly Asn Pro Gly Leu Pro Gly Gln Pro Gly Leu Ile Gly Pro Pro Gly
        1010                1015                1020

Leu Lys Gly Thr Ile Gly Asp Met Gly Phe Pro Gly Pro Gln Gly Val
1025                1030                1035                1040

Glu Gly Pro Pro Gly Pro Ser Gly Val Pro Gly Gln Pro Gly Ser Pro
                1045                1050                1055

Gly Leu Pro Gly Gln Lys Gly Asp Lys Gly Asp Pro Gly Ile Ser Ser
            1060                1065                1070

Ile Gly Leu Pro Gly Leu Pro Gly Pro Lys Gly Glu Pro Gly Leu Pro
        1075                1080                1085

Gly Tyr Pro Gly Asn Pro Gly Ile Lys Gly Ser Val Gly Asp Pro Gly
            1090                1095                1100

Leu Pro Gly Leu Pro Gly Thr Pro Gly Ala Lys Gly Gln Pro Gly Leu
1105                1110                1115                1120

Pro Gly Phe Pro Gly Thr Pro Gly Pro Pro Gly Pro Lys Gly Ile Ser
                1125                1130                1135

Gly Pro Pro Gly Asn Pro Gly Leu Pro Gly Glu Pro Gly Pro Val Gly
            1140                1145                1150

Gly Gly Gly His Pro Gly Gln Pro Gly Pro Pro Gly Glu Lys Gly Lys
```

```
            1155                1160                1165
Pro Gly Gln Asp Gly Ile Pro Gly Pro Ala Gly Gln Lys Gly Glu Pro
            1170                1175                1180
Gly Gln Pro Gly Phe Gly Asn Pro Gly Pro Pro Gly Leu Pro Gly Leu
1185                1190                1195                1200
Ser Gly Gln Lys Gly Asp Gly Gly Leu Pro Gly Ile Pro Gly Asn Pro
            1205                1210                1215
Gly Leu Pro Gly Pro Lys Gly Glu Pro Gly Phe His Gly Phe Pro Gly
            1220                1225                1230
Val Gln Gly Pro Pro Gly Pro Pro Gly Ser Pro Gly Pro Ala Leu Glu
            1235                1240                1245
Gly Pro Lys Gly Asn Pro Gly Pro Gln Gly Pro Pro Gly Arg Pro Gly
            1250                1255                1260
Leu Pro Gly Pro Glu Gly Pro Pro Gly Leu Pro Gly Asn Gly Gly Ile
1265                1270                1275                1280
Lys Gly Glu Lys Gly Asn Pro Gly Gln Pro Gly Leu Pro Gly Leu Pro
            1285                1290                1295
Gly Leu Lys Gly Asp Gln Gly Pro Pro Gly Leu Gln Gly Asn Pro Gly
            1300                1305                1310
Arg Pro Gly Leu Asn Gly Met Lys Gly Asp Pro Gly Leu Pro Gly Val
            1315                1320                1325
Pro Gly Phe Pro Gly Met Lys Gly Pro Ser Gly Val Pro Gly Ser Ala
            1330                1335                1340
Gly Pro Glu Gly Glu Pro Gly Leu Ile Gly Pro Pro Gly Pro Pro Gly
1345                1350                1355                1360
Leu Pro Gly Pro Ser Gly Gln Ser Ile Ile Ile Lys Gly Asp Ala Gly
            1365                1370                1375
Pro Pro Gly Ile Pro Gly Gln Pro Gly Leu Lys Gly Leu Pro Gly Pro
            1380                1385                1390
Gln Gly Pro Gln Gly Leu Pro Gly Pro Thr Gly Pro Pro Gly Asp Pro
            1395                1400                1405
Gly Arg Asn Gly Leu Pro Gly Phe Asp Gly Ala Gly Gly Arg Lys Gly
            1410                1415                1420
Asp Pro Gly Leu Pro Gly Gln Pro Gly Thr Arg Gly Leu Asp Gly Pro
1425                1430                1435                1440
Pro Gly Pro Asp Gly Leu Gln Gly Pro Pro Gly Pro Pro Gly Thr Ser
            1445                1450                1455
Ser Val Ala His Gly Phe Leu Ile Thr Arg His Ser Gln Thr Thr Asp
            1460                1465                1470
Ala Pro Gln Cys Pro Gln Gly Thr Leu Gln Val Tyr Glu Gly Phe Ser
            1475                1480                1485
Leu Leu Tyr Val Gln Gly Asn Lys Arg Ala His Gly Gln Asp Leu Gly
            1490                1495                1500
Thr Ala Gly Ser Cys Leu Arg Arg Phe Ser Thr Met Pro Phe Met Phe
1505                1510                1515                1520
Cys Asn Ile Asn Asn Val Cys Asn Phe Ala Ser Arg Asn Asp Tyr Ser
            1525                1530                1535
Tyr Trp Leu Ser Thr Pro Glu Pro Met Pro Met Ser Met Gln Pro Leu
            1540                1545                1550
Lys Gly Gln Ser Ile Gln Pro Phe Ile Ser Arg Cys Ala Val Cys Glu
            1555                1560                1565
Ala Pro Ala Val Val Ile Ala Val His Ser Gln Thr Ile Gln Ile Pro
            1570                1575                1580
```

-continued

```
His Cys Pro Gln Gly Trp Asp Ser Leu Trp Ile Gly Tyr Ser Phe Met
1585                1590                1595                1600

Met His Thr Ser Ala Gly Ala Glu Gly Ser Gly Gln Ala Leu Ala Ser
            1605                1610                1615

Pro Gly Ser Cys Leu Glu Glu Phe Arg Ser Ala Pro Phe Ile Glu Cys
        1620                1625                1630

His Gly Arg Gly Thr Cys Asn Tyr Tyr Ala Asn Ser Tyr Ser Phe Trp
    1635                1640                1645

Leu Ala Thr Val Asp Val Ser Asp Met Phe Ser Lys Pro Gln Ser Glu
1650                1655                1660

Thr Leu Lys Ala Gly Asp Leu Arg Thr Arg Ile Ser Arg Cys Gln Val
1665                1670                1675                1680

Cys Met Lys Arg Thr
            1685

<210> SEQ ID NO 10
<211> LENGTH: 1691
<212> TYPE: PRT
<213> ORGANISM: Homo sapiens

<400> SEQUENCE: 10

Met Leu Ile Asn Lys Leu Trp Leu Leu Leu Val Thr Leu Cys Leu Thr
1               5                   10                  15

Glu Glu Leu Ala Ala Gly Glu Lys Ser Tyr Gly Lys Pro Cys Gly Gly
            20                  25                  30

Gly Gln Asp Cys Ser Ser Cys Gln Cys Phe Pro Glu Lys Gly Ala
        35                  40                  45

Arg Gly Arg Pro Gly Pro Ile Gly Ile Gln Gly Pro Thr Gly Pro Gln
    50                  55                  60

Gly Phe Thr Gly Ser Thr Gly Leu Ser Gly Leu Lys Gly Glu Arg Gly
65                  70                  75                  80

Phe Pro Gly Leu Leu Gly Pro Tyr Gly Pro Lys Gly Asp Lys Gly Pro
                85                  90                  95

Met Gly Val Pro Gly Phe Leu Gly Ile Asn Gly Ile Pro Gly His Pro
            100                 105                 110

Gly Gln Pro Gly Pro Arg Gly Pro Gly Leu Asp Gly Cys Asn Gly
        115                 120                 125

Thr Gln Gly Ala Val Gly Phe Pro Gly Pro Asp Gly Tyr Pro Gly Leu
    130                 135                 140

Leu Gly Pro Pro Gly Leu Pro Gly Gln Lys Gly Ser Lys Gly Asp Pro
145                 150                 155                 160

Val Leu Ala Pro Gly Ser Phe Lys Gly Met Lys Gly Asp Pro Gly Leu
                165                 170                 175

Pro Gly Leu Asp Gly Ile Thr Gly Pro Gln Gly Ala Pro Gly Phe Pro
            180                 185                 190

Gly Ala Val Gly Pro Ala Gly Pro Pro Gly Leu Gln Gly Pro Pro Gly
        195                 200                 205

Pro Pro Gly Pro Leu Gly Pro Asp Gly Asn Met Gly Leu Gly Phe Gln
    210                 215                 220

Gly Glu Lys Gly Val Lys Gly Asp Val Gly Leu Pro Gly Pro Ala Gly
225                 230                 235                 240

Pro Pro Pro Ser Thr Gly Glu Leu Glu Phe Met Gly Phe Pro Lys Gly
                245                 250                 255

Lys Lys Gly Ser Lys Gly Glu Pro Gly Pro Lys Gly Phe Pro Gly Ile
```

-continued

```
                260                 265                 270
Ser Gly Pro Pro Gly Phe Pro Gly Leu Gly Thr Thr Gly Glu Lys Gly
                275                 280                 285

Glu Lys Gly Glu Lys Gly Ile Pro Gly Leu Pro Gly Pro Arg Gly Pro
            290                 295                 300

Met Gly Ser Glu Gly Val Gln Gly Pro Pro Gly Gln Gln Gly Lys Lys
305                 310                 315                 320

Gly Thr Leu Gly Phe Pro Gly Leu Asn Gly Phe Gln Gly Ile Glu Gly
                325                 330                 335

Gln Lys Gly Asp Ile Gly Leu Pro Gly Pro Asp Val Phe Ile Asp Ile
                340                 345                 350

Asp Gly Ala Val Ile Ser Gly Asn Pro Gly Asp Pro Gly Val Pro Gly
                355                 360                 365

Leu Pro Gly Leu Lys Gly Asp Glu Gly Ile Gln Gly Leu Arg Gly Pro
                370                 375                 380

Ser Gly Val Pro Gly Leu Pro Ala Leu Ser Gly Val Pro Gly Ala Leu
385                 390                 395                 400

Gly Pro Gln Gly Phe Pro Gly Leu Lys Gly Asp Gln Gly Asn Pro Gly
                405                 410                 415

Arg Thr Thr Ile Gly Ala Ala Gly Leu Pro Gly Arg Asp Gly Leu Pro
                420                 425                 430

Gly Pro Pro Gly Pro Gly Pro Pro Ser Pro Glu Phe Glu Thr Glu
                435                 440                 445

Thr Leu His Asn Lys Glu Ser Gly Phe Pro Gly Leu Arg Gly Glu Gln
                450                 455                 460

Gly Pro Lys Gly Asn Leu Gly Leu Lys Gly Ile Lys Gly Asp Ser Gly
465                 470                 475                 480

Phe Cys Ala Cys Asp Gly Val Pro Asn Thr Gly Pro Pro Gly Glu
                485                 490                 495

Pro Gly Pro Pro Gly Pro Trp Gly Leu Ile Gly Leu Pro Gly Leu Lys
                500                 505                 510

Gly Ala Arg Gly Asp Arg Gly Ser Gly Gly Ala Gln Gly Pro Ala Gly
                515                 520                 525

Ala Pro Gly Leu Val Gly Pro Leu Gly Pro Ser Gly Pro Lys Gly Lys
                530                 535                 540

Lys Gly Glu Pro Ile Leu Ser Thr Ile Gln Gly Met Pro Gly Asp Arg
545                 550                 555                 560

Gly Asp Ser Gly Ser Gln Gly Phe Arg Gly Val Ile Gly Glu Pro Gly
                565                 570                 575

Lys Asp Gly Val Pro Gly Leu Pro Gly Leu Pro Gly Leu Pro Gly Asp
                580                 585                 590

Gly Gly Gln Gly Phe Pro Gly Glu Lys Gly Leu Pro Gly Leu Pro Gly
                595                 600                 605

Glu Lys Gly His Pro Gly Pro Pro Gly Leu Pro Gly Asn Gly Leu Pro
                610                 615                 620

Gly Leu Pro Gly Pro Arg Gly Leu Pro Gly Asp Lys Gly Lys Asp Gly
625                 630                 635                 640

Leu Pro Gly Gln Gln Gly Leu Pro Gly Ser Lys Gly Ile Thr Leu Pro
                645                 650                 655

Cys Ile Ile Pro Gly Ser Tyr Gly Pro Ser Gly Phe Pro Gly Thr Pro
                660                 665                 670

Gly Phe Pro Gly Pro Lys Gly Ser Arg Gly Leu Pro Gly Thr Pro Gly
                675                 680                 685
```

```
Gln Pro Gly Ser Ser Gly Ser Lys Gly Glu Pro Gly Ser Pro Gly Leu
        690                 695                 700
Val His Leu Pro Glu Leu Pro Gly Phe Pro Gly Pro Arg Gly Glu Lys
705                 710                 715                 720
Gly Leu Pro Gly Phe Pro Gly Leu Pro Gly Lys Asp Gly Leu Pro Gly
                    725                 730                 735
Met Ile Gly Ser Pro Gly Leu Pro Gly Ser Lys Gly Ala Thr Gly Asp
                740                 745                 750
Ile Phe Gly Ala Glu Asn Gly Ala Pro Gly Glu Gln Gly Leu Gln Gly
            755                 760                 765
Leu Thr Gly His Lys Gly Phe Leu Gly Asp Ser Gly Leu Pro Gly Leu
        770                 775                 780
Lys Gly Val His Gly Lys Pro Gly Leu Leu Gly Pro Lys Gly Glu Arg
785                 790                 795                 800
Gly Ser Pro Gly Thr Pro Gly Gln Val Gly Gln Pro Gly Thr Pro Gly
                    805                 810                 815
Ser Ser Gly Pro Tyr Gly Ile Lys Gly Lys Ser Gly Leu Pro Gly Ala
                820                 825                 830
Pro Gly Phe Pro Gly Ile Ser Gly His Pro Gly Lys Lys Gly Thr Arg
            835                 840                 845
Gly Lys Lys Gly Pro Pro Gly Ser Ile Val Lys Lys Gly Leu Pro Gly
        850                 855                 860
Leu Lys Gly Leu Pro Gly Asn Pro Gly Leu Val Gly Leu Lys Gly Ser
865                 870                 875                 880
Pro Gly Ser Pro Gly Val Ala Gly Leu Pro Ala Leu Ser Gly Pro Lys
                    885                 890                 895
Gly Glu Lys Gly Ser Val Gly Phe Val Gly Phe Pro Gly Ile Pro Gly
                900                 905                 910
Leu Pro Gly Ile Pro Gly Thr Arg Gly Leu Lys Gly Ile Pro Gly Ser
            915                 920                 925
Thr Gly Lys Met Gly Pro Ser Gly Arg Ala Gly Thr Pro Gly Glu Lys
        930                 935                 940
Gly Asp Arg Gly Asn Pro Gly Pro Val Gly Ile Pro Ser Pro Arg Arg
945                 950                 955                 960
Pro Met Ser Asn Leu Trp Leu Lys Gly Asp Lys Gly Ser Gln Gly Ser
                    965                 970                 975
Ala Gly Ser Asn Gly Phe Pro Gly Pro Arg Gly Asp Lys Gly Glu Ala
                980                 985                 990
Gly Arg Pro Gly Pro Pro Gly Leu Pro Gly Ala Pro Gly Leu Pro Gly
            995                1000                1005
Ile Ile Lys Gly Val Ser Gly Lys Pro Gly Pro Pro Gly Phe Met Gly
       1010                1015                1020
Ile Arg Gly Leu Pro Gly Leu Lys Gly Ser Ser Gly Ile Thr Gly Phe
1025                1030                1035                1040
Pro Gly Met Pro Gly Glu Ser Gly Ser Gln Gly Ile Arg Gly Ser Pro
                   1045                1050                1055
Gly Leu Pro Gly Ala Ser Gly Leu Pro Gly Leu Lys Gly Asp Asn Gly
               1060                1065                1070
Gln Thr Val Glu Ile Ser Gly Ser Pro Gly Pro Lys Gly Gln Pro Gly
           1075                1080                1085
Glu Ser Gly Phe Lys Gly Thr Lys Gly Arg Asp Gly Leu Ile Gly Asn
       1090                1095                1100
```

```
Ile Gly Phe Pro Gly Asn Lys Gly Glu Asp Gly Lys Val Gly Val Ser
1105                1110                1115                1120

Gly Asp Val Gly Leu Pro Gly Ala Pro Gly Phe Pro Gly Val Ala Gly
            1125                1130                1135

Met Arg Gly Glu Pro Gly Leu Pro Gly Ser Ser Gly His Gln Gly Ala
        1140                1145                1150

Ile Gly Pro Leu Gly Ser Pro Gly Leu Ile Gly Pro Lys Gly Phe Pro
        1155                1160                1165

Gly Phe Pro Gly Leu His Gly Leu Asn Gly Leu Pro Gly Thr Lys Gly
    1170                1175                1180

Thr His Gly Thr Pro Gly Pro Ser Ile Thr Gly Val Pro Gly Pro Ala
1185                1190                1195                1200

Gly Leu Pro Gly Pro Lys Gly Glu Lys Gly Tyr Pro Gly Ile Gly Ile
            1205                1210                1215

Gly Ala Pro Gly Lys Pro Gly Leu Arg Gly Gln Lys Gly Asp Arg Gly
            1220                1225                1230

Phe Pro Gly Leu Gln Gly Pro Ala Gly Leu Pro Gly Ala Pro Gly Ile
        1235                1240                1245

Ser Leu Pro Ser Leu Ile Ala Gly Gln Pro Gly Asp Pro Gly Arg Pro
1250                1255                1260

Gly Leu Asp Gly Glu Arg Gly Arg Pro Gly Pro Ala Gly Pro Pro Gly
1265                1270                1275                1280

Pro Pro Gly Pro Ser Ser Asn Gln Gly Asp Thr Gly Asp Pro Gly Phe
            1285                1290                1295

Pro Gly Ile Pro Gly Pro Lys Gly Pro Lys Gly Asp Gln Gly Ile Pro
            1300                1305                1310

Gly Phe Ser Gly Leu Pro Gly Glu Leu Gly Leu Lys Gly Met Arg Gly
        1315                1320                1325

Glu Pro Gly Phe Met Gly Thr Pro Gly Lys Val Gly Pro Pro Gly Asp
        1330                1335                1340

Pro Gly Phe Pro Gly Met Lys Gly Lys Ala Gly Pro Arg Gly Ser Ser
1345                1350                1355                1360

Gly Leu Gln Gly Asp Pro Gly Gln Thr Pro Thr Ala Glu Ala Val Gln
            1365                1370                1375

Val Pro Pro Gly Pro Leu Gly Leu Pro Gly Ile Asp Gly Ile Pro Gly
            1380                1385                1390

Leu Thr Gly Asp Pro Gly Ala Gln Gly Pro Val Gly Leu Gln Gly Ser
            1395                1400                1405

Lys Gly Leu Pro Gly Ile Pro Gly Lys Asp Gly Pro Ser Gly Leu Pro
            1410                1415                1420

Gly Pro Pro Gly Ala Leu Gly Asp Pro Gly Leu Pro Gly Leu Gln Gly
1425                1430                1435                1440

Pro Pro Gly Phe Glu Gly Ala Pro Gly Gln Gln Gly Pro Phe Gly Met
            1445                1450                1455

Pro Gly Met Pro Gly Gln Ser Met Arg Val Gly Tyr Thr Leu Val Lys
            1460                1465                1470

His Ser Gln Ser Glu Gln Val Pro Pro Cys Pro Ile Gly Met Ser Gln
        1475                1480                1485

Leu Trp Val Gly Tyr Ser Leu Leu Phe Val Glu Gly Gln Glu Lys Ala
        1490                1495                1500

His Asn Gln Asp Leu Gly Phe Ala Gly Ser Cys Leu Pro Arg Phe Ser
1505                1510                1515                1520

Thr Met Pro Phe Ile Tyr Cys Asn Ile Asn Glu Val Cys His Tyr Ala
```

```
                    1525              1530              1535
Arg Arg Asn Asp Lys Ser Tyr Trp Leu Ser Thr Thr Ala Pro Ile Pro
            1540              1545              1550

Met Met Pro Val Ser Gln Thr Gln Ile Pro Gln Tyr Ile Ser Arg Cys
            1555              1560              1565

Ser Val Cys Glu Ala Pro Ser Gln Ala Ile Ala Val His Ser Gln Asp
            1570              1575              1580

Ile Thr Ile Pro Gln Cys Pro Leu Gly Trp Arg Ser Leu Trp Ile Gly
1585              1590              1595              1600

Tyr Ser Phe Leu Met His Thr Ala Ala Gly Glu Gly Gly Gly Gln
                1605              1610              1615

Ser Leu Val Ser Pro Gly Ser Cys Leu Glu Asp Phe Arg Ala Thr Pro
            1620              1625              1630

Phe Ile Glu Cys Ser Gly Ala Arg Gly Thr Cys His Tyr Phe Ala Asn
            1635              1640              1645

Lys Tyr Ser Phe Trp Leu Thr Thr Val Glu Glu Arg Gln Gln Phe Gly
            1650              1655              1660

Glu Leu Pro Val Ser Glu Thr Leu Lys Ala Gly Gln Leu His Thr Arg
1665              1670              1675              1680

Val Ser Arg Cys Gln Val Cys Met Lys Ser Leu
                1685              1690

<210> SEQ ID NO 11
<211> LENGTH: 1838
<212> TYPE: PRT
<213> ORGANISM: Homo sapiens

<400> SEQUENCE: 11

Met Asp Val His Thr Arg Trp Lys Ala Arg Ser Ala Leu Arg Pro Gly
1               5                   10                  15

Ala Pro Leu Leu Pro Pro Leu Leu Leu Leu Leu Trp Ala Pro Pro
                20                  25                  30

Pro Ser Arg Ala Ala Gln Pro Ala Asp Leu Leu Lys Val Leu Asp Phe
            35                  40                  45

His Asn Leu Pro Asp Gly Ile Thr Lys Thr Thr Gly Phe Cys Ala Thr
        50                  55                  60

Arg Arg Ser Ser Lys Gly Pro Asp Val Ala Tyr Arg Val Thr Lys Asp
65                  70                  75                  80

Ala Gln Leu Ser Ala Pro Thr Lys Gln Leu Tyr Pro Ala Ser Ala Phe
                85                  90                  95

Pro Glu Asp Phe Ser Ile Leu Thr Thr Val Lys Ala Lys Lys Gly Ser
            100                 105                 110

Gln Ala Phe Leu Val Ser Ile Tyr Asn Glu Gln Gly Ile Gln Gln Ile
        115                 120                 125

Gly Leu Glu Leu Gly Arg Ser Pro Val Phe Leu Tyr Glu Asp His Thr
    130                 135                 140

Gly Lys Pro Gly Pro Glu Asp Tyr Pro Leu Phe Arg Gly Ile Asn Leu
145                 150                 155                 160

Ser Asp Gly Lys Trp His Arg Ile Ala Leu Ser Val His Lys Lys Asn
                165                 170                 175

Val Thr Leu Ile Leu Asp Cys Lys Lys Lys Thr Thr Lys Phe Leu Asp
            180                 185                 190

Arg Ser Asp His Pro Met Ile Asp Ile Asn Gly Ile Ile Val Phe Gly
        195                 200                 205
```

-continued

```
Thr Arg Ile Leu Asp Glu Glu Val Phe Glu Gly Asp Ile Gln Gln Leu
    210                 215                 220

Leu Phe Val Ser Asp His Arg Ala Ala Tyr Asp Tyr Cys Glu His Tyr
225                 230                 235                 240

Ser Pro Asp Cys Asp Thr Ala Val Pro Asp Thr Pro Gln Ser Gln Asp
                245                 250                 255

Pro Asn Pro Asp Glu Tyr Tyr Thr Glu Gly Asp Gly Glu Gly Glu Thr
            260                 265                 270

Tyr Tyr Tyr Glu Tyr Pro Tyr Tyr Glu Asp Pro Glu Asp Leu Gly Lys
        275                 280                 285

Glu Pro Thr Pro Ser Lys Lys Pro Val Glu Ala Ala Lys Glu Thr Thr
    290                 295                 300

Glu Val Pro Glu Glu Leu Thr Pro Thr Pro Thr Glu Ala Ala Pro Met
305                 310                 315                 320

Pro Glu Thr Ser Glu Gly Ala Gly Lys Glu Glu Asp Val Gly Ile Gly
                325                 330                 335

Asp Tyr Asp Tyr Val Pro Ser Glu Asp Tyr Tyr Thr Pro Ser Pro Tyr
            340                 345                 350

Asp Asp Leu Thr Tyr Gly Glu Gly Glu Glu Asn Pro Asp Gln Pro Thr
        355                 360                 365

Asp Pro Gly Ala Gly Ala Glu Ile Pro Thr Ser Thr Ala Asp Thr Ser
    370                 375                 380

Asn Ser Ser Asn Pro Ala Pro Pro Gly Glu Gly Ala Asp Asp Leu
385                 390                 395                 400

Glu Gly Glu Phe Thr Glu Glu Thr Ile Arg Asn Leu Asp Glu Asn Tyr
                405                 410                 415

Tyr Asp Pro Tyr Tyr Asp Pro Thr Ser Ser Pro Ser Glu Ile Gly Pro
            420                 425                 430

Gly Met Pro Ala Asn Gln Asp Thr Ile Tyr Glu Gly Ile Gly Gly Pro
        435                 440                 445

Arg Gly Glu Lys Gly Gln Lys Gly Glu Pro Ala Ile Ile Glu Pro Gly
    450                 455                 460

Met Leu Ile Glu Gly Pro Pro Gly Pro Glu Gly Pro Ala Gly Leu Pro
465                 470                 475                 480

Gly Pro Pro Gly Thr Met Gly Pro Thr Gly Gln Val Gly Asp Pro Gly
                485                 490                 495

Glu Arg Gly Pro Pro Gly Arg Pro Gly Leu Pro Gly Ala Asp Gly Leu
            500                 505                 510

Pro Gly Pro Pro Gly Thr Met Leu Met Leu Pro Phe Arg Phe Gly Gly
        515                 520                 525

Gly Gly Asp Ala Gly Ser Lys Gly Pro Met Val Ser Ala Gln Glu Ser
    530                 535                 540

Gln Ala Gln Ala Ile Leu Gln Gln Ala Arg Leu Ala Leu Arg Gly Pro
545                 550                 555                 560

Ala Gly Pro Met Gly Leu Thr Gly Arg Pro Gly Pro Val Gly Pro Pro
                565                 570                 575

Gly Ser Gly Gly Leu Lys Gly Glu Pro Gly Asp Val Gly Pro Gln Gly
            580                 585                 590

Pro Arg Gly Val Gln Gly Pro Pro Gly Pro Ala Gly Lys Pro Gly Arg
        595                 600                 605

Arg Gly Arg Ala Gly Ser Asp Gly Ala Arg Gly Met Pro Gly Gln Thr
    610                 615                 620

Gly Pro Lys Gly Asp Arg Gly Phe Asp Gly Leu Ala Gly Leu Pro Gly
```

```
                625                 630                 635                 640
Glu Lys Gly His Arg Gly Asp Pro Gly Pro Ser Gly Pro Pro Gly Pro
                    645                 650                 655

Pro Gly Asp Asp Gly Glu Arg Gly Asp Asp Gly Glu Val Gly Pro Arg
                660                 665                 670

Gly Leu Pro Gly Glu Pro Gly Pro Arg Gly Leu Leu Gly Pro Lys Gly
                675                 680                 685

Pro Pro Gly Pro Pro Gly Pro Pro Gly Val Thr Gly Met Asp Gly Gln
            690                 695                 700

Pro Gly Pro Lys Gly Asn Val Gly Pro Gln Gly Glu Pro Gly Pro Pro
705                 710                 715                 720

Gly Gln Gln Gly Asn Pro Gly Ala Gln Gly Leu Pro Gly Pro Gln Gly
                        725                 730                 735

Ala Ile Gly Pro Pro Gly Glu Lys Gly Pro Leu Gly Lys Pro Gly Leu
                    740                 745                 750

Pro Gly Met Pro Gly Ala Asp Gly Pro Pro Gly His Pro Gly Lys Glu
                755                 760                 765

Gly Pro Pro Gly Glu Lys Gly Gly Gln Gly Pro Pro Gly Pro Gln Gly
            770                 775                 780

Pro Ile Gly Tyr Pro Gly Pro Arg Gly Val Lys Gly Ala Asp Gly Ile
785                 790                 795                 800

Arg Gly Leu Lys Gly Thr Lys Gly Glu Lys Gly Glu Asp Gly Phe Pro
                        805                 810                 815

Gly Phe Lys Gly Asp Met Gly Ile Lys Gly Asp Arg Gly Glu Ile Gly
                    820                 825                 830

Pro Pro Gly Pro Arg Gly Glu Asp Gly Pro Glu Gly Pro Lys Gly Arg
                835                 840                 845

Gly Gly Pro Asn Gly Asp Pro Gly Pro Leu Gly Pro Pro Gly Glu Lys
            850                 855                 860

Gly Lys Leu Gly Val Pro Gly Leu Pro Gly Tyr Pro Gly Arg Gln Gly
865                 870                 875                 880

Pro Lys Gly Ser Ile Gly Phe Pro Gly Phe Pro Gly Ala Asn Gly Glu
                        885                 890                 895

Lys Gly Gly Arg Gly Thr Pro Gly Lys Pro Gly Pro Arg Gly Gln Arg
                    900                 905                 910

Gly Pro Thr Gly Pro Arg Gly Glu Arg Gly Pro Arg Gly Ile Thr Gly
                915                 920                 925

Lys Pro Gly Pro Lys Gly Asn Ser Gly Gly Asp Gly Pro Ala Gly Pro
930                 935                 940

Pro Gly Glu Arg Gly Pro Asn Gly Pro Gln Gly Pro Thr Gly Phe Pro
945                 950                 955                 960

Gly Pro Lys Gly Pro Pro Gly Pro Pro Gly Lys Asp Gly Leu Pro Gly
                        965                 970                 975

His Pro Gly Gln Arg Gly Glu Thr Gly Phe Gln Gly Lys Thr Gly Pro
                    980                 985                 990

Pro Gly Pro Pro Gly Val Val Gly Pro Gln Gly Pro Thr Gly Glu Thr
                995                 1000                1005

Gly Pro Met Gly Glu Arg Gly His Pro Gly Pro Pro Gly Pro Pro Gly
            1010                1015                1020

Glu Gln Gly Leu Pro Gly Leu Ala Gly Lys Glu Gly Thr Lys Gly Asp
1025                1030                1035                1040

Pro Gly Pro Ala Gly Leu Pro Gly Lys Asp Gly Pro Pro Gly Leu Arg
                        1045                1050                1055
```

```
Gly Phe Pro Gly Asp Arg Gly Leu Pro Gly Pro Val Gly Ala Leu Gly
            1060                1065                1070
Leu Lys Gly Asn Glu Gly Pro Pro Gly Pro Pro Gly Pro Ala Gly Ser
        1075                1080                1085
Pro Gly Glu Arg Gly Pro Ala Gly Ala Ala Gly Pro Ile Gly Ile Pro
    1090                1095                1100
Gly Arg Pro Gly Pro Gln Gly Pro Gly Pro Ala Gly Glu Lys Gly
1105                1110                1115                1120
Ala Pro Gly Glu Lys Gly Pro Gln Pro Ala Gly Arg Asp Gly Leu
            1125                1130                1135
Gln Gly Pro Val Gly Leu Pro Gly Pro Ala Gly Pro Val Gly Pro Pro
        1140                1145                1150
Gly Glu Asp Gly Asp Lys Gly Glu Ile Gly Glu Pro Gly Gln Lys Gly
    1155                1160                1165
Ser Lys Gly Asp Lys Gly Glu Gln Gly Pro Pro Gly Pro Thr Gly Pro
1170                1175                1180
Gln Gly Pro Ile Gly Gln Pro Gly Pro Ser Gly Ala Asp Gly Glu Pro
1185                1190                1195                1200
Gly Pro Arg Gly Gln Gln Gly Leu Phe Gly Gln Lys Gly Asp Glu Gly
            1205                1210                1215
Pro Arg Gly Phe Pro Gly Pro Pro Gly Pro Val Gly Leu Gln Gly Leu
        1220                1225                1230
Pro Gly Pro Pro Gly Glu Lys Gly Glu Thr Gly Asp Val Gly Gln Met
    1235                1240                1245
Gly Pro Pro Gly Pro Pro Gly Pro Arg Gly Pro Ser Gly Ala Pro Gly
    1250                1255                1260
Ala Asp Gly Pro Gln Gly Pro Pro Gly Gly Ile Gly Asn Pro Gly Ala
1265                1270                1275                1280
Val Gly Glu Lys Gly Glu Pro Gly Glu Ala Gly Glu Pro Gly Leu Pro
            1285                1290                1295
Gly Glu Gly Gly Pro Pro Gly Pro Lys Gly Glu Arg Gly Glu Lys Gly
        1300                1305                1310
Glu Ser Gly Pro Ser Gly Ala Ala Gly Pro Pro Gly Pro Lys Gly Pro
        1315                1320                1325
Pro Gly Asp Asp Gly Pro Lys Gly Ser Pro Gly Pro Val Gly Phe Pro
    1330                1335                1340
Gly Asp Pro Gly Pro Pro Gly Glu Pro Gly Pro Ala Gly Gln Asp Gly
1345                1350                1355                1360
Pro Pro Gly Asp Lys Gly Asp Asp Gly Glu Pro Gly Gln Thr Gly Ser
            1365                1370                1375
Pro Gly Pro Thr Gly Glu Pro Gly Pro Ser Gly Pro Pro Gly Lys Arg
        1380                1385                1390
Gly Pro Pro Gly Pro Ala Gly Pro Glu Gly Arg Gln Gly Glu Lys Gly
        1395                1400                1405
Ala Lys Gly Glu Ala Gly Leu Glu Gly Pro Pro Gly Lys Thr Gly Pro
        1410                1415                1420
Ile Gly Pro Gln Gly Ala Pro Gly Lys Pro Gly Pro Asp Gly Leu Arg
1425                1430                1435                1440
Gly Ile Pro Gly Pro Val Gly Glu Gln Gly Leu Pro Gly Ser Pro Gly
            1445                1450                1455
Pro Asp Gly Pro Pro Gly Pro Met Gly Pro Pro Gly Leu Pro Gly Leu
        1460                1465                1470
```

-continued

Lys Gly Asp Ser Gly Pro Lys Gly Glu Lys Gly His Pro Gly Leu Ile
            1475                1480                1485

Gly Leu Ile Gly Pro Pro Gly Glu Gln Gly Lys Gly Asp Arg Gly
        1490                1495                1500

Leu Pro Gly Pro Gln Gly Ser Ser Gly Pro Lys Gly Glu Gln Gly Ile
1505                1510                1515                1520

Thr Gly Pro Ser Gly Pro Ile Gly Pro Pro Gly Pro Pro Gly Leu Pro
            1525                1530                1535

Gly Pro Pro Gly Pro Lys Gly Ala Lys Gly Ser Ser Gly Pro Thr Gly
        1540                1545                1550

Pro Lys Gly Glu Ala Gly His Pro Gly Pro Pro Gly Pro Pro Gly Pro
        1555                1560                1565

Pro Gly Glu Val Ile Gln Pro Leu Pro Ile Gln Ala Ser Arg Thr Arg
        1570                1575                1580

Arg Asn Ile Asp Ala Ser Gln Leu Leu Asp Asp Gly Asn Gly Glu Asn
1585                1590                1595                1600

Tyr Val Asp Tyr Ala Asp Gly Met Glu Glu Ile Phe Gly Ser Leu Asn
            1605                1610                1615

Ser Leu Lys Leu Glu Ile Glu Gln Met Lys Arg Pro Leu Gly Thr Gln
        1620                1625                1630

Gln Asn Pro Ala Arg Thr Cys Lys Asp Leu Gln Leu Cys His Pro Asp
        1635                1640                1645

Phe Pro Asp Gly Glu Tyr Trp Val Asp Pro Asn Gln Gly Cys Ser Arg
        1650                1655                1660

Asp Ser Phe Lys Val Tyr Cys Asn Phe Thr Ala Gly Gly Ser Thr Cys
1665                1670                1675                1680

Val Phe Pro Asp Lys Lys Ser Glu Gly Ala Arg Ile Thr Ser Trp Pro
            1685                1690                1695

Lys Glu Asn Pro Gly Ser Trp Phe Ser Glu Phe Lys Arg Gly Lys Leu
        1700                1705                1710

Leu Ser Tyr Val Asp Ala Glu Gly Asn Pro Val Gly Val Val Gln Met
        1715                1720                1725

Thr Phe Leu Arg Leu Leu Ser Ala Ser Ala His Gln Asn Val Thr Tyr
        1730                1735                1740

His Cys Tyr Gln Ser Val Ala Trp Gln Asp Ala Ala Thr Gly Ser Tyr
1745                1750                1755                1760

Asp Lys Ala Leu Arg Phe Leu Gly Ser Asn Asp Glu Glu Met Ser Tyr
            1765                1770                1775

Asp Asn Asn Pro Tyr Ile Arg Ala Leu Val Asp Gly Cys Ala Thr Lys
        1780                1785                1790

Lys Gly Tyr Gln Lys Thr Val Leu Glu Ile Asp Thr Pro Lys Val Glu
        1795                1800                1805

Gln Val Pro Ile Val Asp Ile Met Phe Asn Asp Phe Gly Glu Ala Ser
        1810                1815                1820

Gln Lys Phe Gly Phe Glu Val Gly Pro Ala Cys Phe Met Gly
1825                1830                1835

<210> SEQ ID NO 12
<211> LENGTH: 1499
<212> TYPE: PRT
<213> ORGANISM: Homo sapiens

<400> SEQUENCE: 12

Met Met Ala Asn Trp Ala Glu Ala Arg Pro Leu Leu Ile Leu Ile Val
1               5                   10                  15

```
Leu Leu Gly Gln Phe Val Ser Ile Lys Ala Gln Glu Glu Asp Glu Asp
            20                  25                  30

Glu Gly Tyr Gly Glu Glu Ile Ala Cys Thr Gln Asn Gly Gln Met Tyr
            35                  40                  45

Leu Asn Arg Asp Ile Trp Lys Pro Ala Pro Cys Gln Ile Cys Val Cys
 50                  55                  60

Asp Asn Gly Ala Ile Leu Cys Asp Lys Ile Glu Cys Gln Asp Val Leu
 65                  70                  75                  80

Asp Cys Ala Asp Pro Val Thr Pro Pro Gly Glu Cys Cys Pro Val Cys
                 85                  90                  95

Ser Gln Thr Pro Gly Gly Asn Thr Asn Phe Gly Arg Gly Arg Lys
                100                 105                 110

Gly Gln Lys Gly Glu Pro Gly Leu Val Pro Val Val Thr Gly Ile Arg
            115                 120                 125

Gly Arg Pro Gly Pro Ala Gly Pro Pro Gly Ser Gln Gly Pro Arg Gly
130                 135                 140

Glu Arg Gly Pro Lys Gly Arg Pro Gly Pro Arg Gly Pro Gln Gly Ile
145                 150                 155                 160

Asp Gly Glu Pro Gly Val Pro Gly Gln Pro Gly Ala Pro Gly Pro Pro
                165                 170                 175

Gly His Pro Ser His Pro Gly Pro Asp Gly Leu Ser Arg Pro Phe Ser
                180                 185                 190

Ala Gln Met Ala Gly Leu Asp Glu Lys Ser Gly Leu Gly Ser Gln Val
            195                 200                 205

Gly Leu Met Pro Gly Ser Val Gly Pro Val Gly Pro Arg Gly Pro Gln
            210                 215                 220

Gly Leu Gln Gly Gln Gln Gly Ala Gly Pro Thr Gly Pro Pro Gly
225                 230                 235                 240

Glu Pro Gly Asp Pro Gly Pro Met Gly Pro Ile Gly Ser Arg Gly Pro
                245                 250                 255

Glu Gly Pro Pro Gly Lys Pro Gly Glu Asp Gly Glu Pro Gly Arg Asn
                260                 265                 270

Gly Asn Pro Gly Glu Val Gly Phe Ala Gly Ser Pro Gly Ala Arg Gly
            275                 280                 285

Phe Pro Gly Ala Pro Gly Leu Pro Gly Leu Lys Gly His Arg Gly His
            290                 295                 300

Lys Gly Leu Glu Gly Pro Lys Gly Glu Val Gly Ala Pro Gly Ser Lys
305                 310                 315                 320

Gly Glu Ala Gly Pro Thr Gly Pro Met Gly Ala Met Gly Pro Leu Gly
                325                 330                 335

Pro Arg Gly Met Pro Gly Glu Arg Gly Arg Leu Gly Pro Gln Gly Ala
                340                 345                 350

Pro Gly Gln Arg Gly Ala His Gly Met Pro Gly Lys Pro Gly Pro Met
            355                 360                 365

Gly Pro Leu Gly Ile Pro Gly Ser Ser Gly Phe Pro Gly Asn Pro Gly
            370                 375                 380

Met Lys Gly Glu Ala Gly Pro Thr Gly Ala Arg Gly Pro Glu Gly Pro
385                 390                 395                 400

Gln Gly Gln Arg Gly Glu Thr Gly Pro Pro Gly Pro Val Gly Ser Pro
                405                 410                 415

Gly Leu Pro Gly Ala Ile Gly Thr Asp Gly Thr Pro Gly Ala Lys Gly
                420                 425                 430
```

-continued

Pro Thr Gly Ser Pro Gly Thr Ser Gly Pro Pro Gly Ser Ala Gly Pro
           435                 440                 445

Pro Gly Ser Pro Gly Pro Gln Gly Ser Thr Gly Pro Gln Gly Ile Arg
       450                 455                 460

Gly Gln Pro Gly Asp Pro Gly Val Pro Gly Phe Lys Gly Glu Ala Gly
465                 470                 475                 480

Pro Lys Gly Glu Pro Gly Pro His Gly Ile Gln Gly Pro Ile Gly Pro
               485                 490                 495

Pro Gly Glu Glu Gly Lys Arg Gly Pro Arg Gly Asp Pro Gly Thr Val
           500                 505                 510

Gly Pro Pro Gly Pro Val Gly Glu Arg Gly Ala Pro Gly Asn Arg Gly
       515                 520                 525

Phe Pro Gly Ser Asp Gly Leu Pro Gly Pro Lys Gly Ala Gln Gly Glu
   530                 535                 540

Arg Gly Pro Val Gly Ser Ser Gly Pro Lys Gly Ser Gln Gly Asp Pro
545                 550                 555                 560

Gly Arg Pro Gly Glu Pro Gly Leu Pro Gly Ala Arg Gly Leu Thr Gly
               565                 570                 575

Asn Pro Gly Val Gln Gly Pro Glu Gly Lys Leu Gly Pro Leu Gly Ala
           580                 585                 590

Pro Gly Glu Asp Gly Arg Pro Gly Pro Pro Gly Ser Ile Gly Ile Arg
       595                 600                 605

Gly Gln Pro Gly Ser Met Gly Leu Pro Gly Pro Lys Gly Ser Ser Gly
   610                 615                 620

Asp Pro Gly Lys Pro Gly Glu Ala Gly Asn Ala Gly Val Pro Gly Gln
625                 630                 635                 640

Arg Gly Ala Pro Gly Lys Asp Gly Glu Val Gly Pro Ser Gly Pro Val
               645                 650                 655

Gly Pro Pro Gly Leu Ala Gly Glu Arg Gly Glu Gln Gly Pro Pro Gly
           660                 665                 670

Pro Thr Gly Phe Gln Gly Leu Pro Gly Pro Gly Pro Pro Gly Glu
       675                 680                 685

Gly Gly Lys Pro Gly Asp Gln Gly Val Pro Gly Asp Pro Gly Ala Val
   690                 695                 700

Gly Pro Leu Gly Pro Arg Gly Glu Arg Gly Asn Pro Gly Glu Arg Gly
705                 710                 715                 720

Glu Pro Gly Ile Thr Gly Leu Pro Gly Glu Lys Gly Met Ala Gly Gly
               725                 730                 735

His Gly Pro Asp Gly Pro Lys Gly Ser Pro Gly Pro Ser Gly Thr Pro
           740                 745                 750

Gly Asp Thr Gly Pro Pro Gly Leu Gln Gly Met Pro Gly Glu Arg Gly
       755                 760                 765

Ile Ala Gly Thr Pro Gly Pro Lys Gly Asp Arg Gly Gly Ile Gly Glu
   770                 775                 780

Lys Gly Ala Glu Gly Thr Ala Gly Asn Asp Gly Ala Arg Gly Leu Pro
785                 790                 795                 800

Gly Pro Leu Gly Pro Pro Gly Pro Ala Gly Pro Thr Gly Glu Lys Gly
               805                 810                 815

Glu Pro Gly Pro Arg Gly Leu Val Gly Pro Pro Gly Ser Arg Gly Asn
           820                 825                 830

Pro Gly Ser Arg Gly Glu Asn Gly Pro Thr Gly Ala Val Gly Phe Ala
       835                 840                 845

Gly Pro Gln Gly Pro Asp Gly Gln Pro Gly Val Lys Gly Glu Pro Gly

```
            850                 855                 860
Glu Pro Gly Gln Lys Gly Asp Ala Gly Ser Pro Gly Pro Gln Gly Leu
865                 870                 875                 880

Ala Gly Ser Pro Gly Pro His Gly Pro Asn Gly Val Pro Gly Leu Lys
                885                 890                 895

Gly Gly Arg Gly Thr Gln Gly Pro Pro Gly Ala Thr Gly Phe Pro Gly
            900                 905                 910

Ser Ala Gly Arg Val Gly Pro Pro Gly Pro Ala Gly Ala Pro Gly Pro
            915                 920                 925

Ala Gly Pro Leu Gly Glu Pro Gly Lys Glu Gly Pro Pro Gly Leu Arg
            930                 935                 940

Gly Asp Pro Gly Ser His Gly Arg Val Gly Asp Arg Gly Pro Ala Gly
945                 950                 955                 960

Pro Pro Gly Gly Pro Gly Asp Lys Gly Asp Pro Gly Glu Asp Gly Gln
                965                 970                 975

Pro Gly Pro Asp Gly Pro Pro Gly Pro Ala Gly Thr Thr Gly Gln Arg
            980                 985                 990

Gly Ile Val Gly Met Pro Gly Gln Arg Gly Glu Arg Gly Met Pro Gly
            995                1000                1005

Leu Pro Gly Pro Ala Gly Thr Pro Gly Lys Val Gly Pro Thr Gly Ala
           1010                1015                1020

Thr Gly Asp Lys Gly Pro Pro Gly Pro Val Gly Pro Pro Gly Ser Asn
1025                1030                1035                1040

Gly Pro Val Gly Glu Pro Gly Pro Glu Gly Pro Ala Gly Asn Asp Gly
                1045                1050                1055

Thr Pro Gly Arg Asp Gly Ala Val Gly Glu Arg Gly Asp Arg Gly Asp
           1060                1065                1070

Pro Gly Pro Ala Gly Leu Pro Gly Ser Gln Gly Ala Pro Gly Thr Pro
           1075                1080                1085

Gly Pro Val Gly Ala Pro Gly Asp Ala Gly Gln Arg Gly Asp Pro Gly
           1090                1095                1100

Ser Arg Gly Pro Ile Gly Pro Pro Gly Arg Ala Gly Lys Arg Gly Leu
1105                1110                1115                1120

Pro Gly Pro Gln Gly Pro Arg Gly Asp Lys Gly Asp His Gly Asp Arg
                1125                1130                1135

Gly Asp Arg Gly Gln Lys Gly His Arg Gly Phe Thr Gly Leu Gln Gly
           1140                1145                1150

Leu Pro Gly Pro Pro Gly Pro Asn Gly Glu Gln Gly Ser Ala Gly Ile
           1155                1160                1165

Pro Gly Pro Phe Gly Pro Arg Gly Pro Pro Gly Pro Val Gly Pro Ser
           1170                1175                1180

Gly Lys Glu Gly Asn Pro Gly Pro Leu Gly Pro Ile Gly Pro Pro Gly
1185                1190                1195                1200

Val Arg Gly Ser Val Gly Glu Ala Gly Pro Glu Gly Pro Pro Gly Glu
                1205                1210                1215

Pro Gly Pro Pro Gly Pro Pro Gly Pro Pro Gly His Leu Thr Ala Ala
           1220                1225                1230

Leu Gly Asp Ile Met Gly His Tyr Asp Glu Ser Met Pro Asp Pro Leu
           1235                1240                1245

Pro Glu Phe Thr Glu Asp Gln Ala Ala Pro Asp Asp Lys Asn Lys Thr
           1250                1255                1260

Asp Pro Gly Val His Ala Thr Leu Lys Ser Leu Ser Ser Gln Ile Glu
1265                1270                1275                1280
```

```
Thr Met Arg Ser Pro Asp Gly Ser Lys Lys His Pro Ala Arg Thr Cys
            1285                1290                1295

Asp Asp Leu Lys Leu Cys His Ser Ala Lys Gln Ser Gly Glu Tyr Trp
        1300                1305                1310

Ile Asp Pro Asn Gln Gly Ser Val Glu Asp Ala Ile Lys Val Tyr Cys
    1315                1320                1325

Asn Met Glu Thr Gly Glu Thr Cys Ile Ser Ala Asn Pro Ser Ser Val
1330                1335                1340

Pro Arg Lys Thr Trp Trp Ala Ser Lys Ser Pro Asp Asn Lys Pro Val
1345                1350                1355                1360

Trp Tyr Gly Leu Asp Met Asn Arg Gly Ser Gln Phe Ala Tyr Gly Asp
            1365                1370                1375

His Gln Ser Pro Asn Thr Ala Ile Thr Gln Met Thr Phe Leu Arg Leu
        1380                1385                1390

Leu Ser Lys Glu Ala Ser Gln Asn Ile Thr Tyr Ile Cys Lys Asn Ser
    1395                1400                1405

Val Gly Tyr Met Asp Asp Gln Ala Lys Asn Leu Lys Lys Ala Val Val
        1410                1415                1420

Leu Lys Gly Ala Asn Asp Leu Asp Ile Lys Ala Glu Gly Asn Ile Arg
1425                1430                1435                1440

Phe Arg Tyr Ile Val Leu Gln Asp Thr Cys Ser Lys Arg Asn Gly Asn
            1445                1450                1455

Val Gly Lys Thr Val Phe Glu Tyr Arg Thr Gln Asn Val Ala Arg Leu
        1460                1465                1470

Pro Ile Ile Asp Leu Ala Pro Val Asp Val Gly Thr Asp Gln Glu
    1475                1480                1485

Phe Gly Val Glu Ile Gly Pro Val Cys Phe Val
    1490                1495

<210> SEQ ID NO 13
<211> LENGTH: 1745
<212> TYPE: PRT
<213> ORGANISM: Homo sapiens

<400> SEQUENCE: 13

Met Gly Asn Arg Arg Asp Leu Gly Gln Pro Arg Ala Gly Leu Cys Leu
1               5                   10                  15

Leu Leu Ala Ala Leu Gln Leu Pro Gly Thr Gln Ala Asp Pro Val
            20                  25                  30

Asp Val Leu Lys Ala Leu Gly Val Gln Gly Gln Ala Gly Val Pro
        35                  40                  45

Glu Gly Pro Gly Phe Cys Pro Gln Arg Thr Pro Glu Gly Asp Arg Ala
    50                  55                  60

Phe Arg Ile Gly Gln Ala Ser Thr Leu Gly Ile Pro Thr Trp Glu Leu
65                  70                  75                  80

Phe Pro Glu Gly His Phe Pro Glu Asn Phe Ser Leu Leu Ile Thr Leu
            85                  90                  95

Arg Gly Gln Pro Ala Asn Gln Ser Val Leu Leu Ser Ile Tyr Asp Glu
        100                 105                 110

Arg Gly Ala Arg Gln Leu Gly Leu Ala Leu Gly Pro Ala Leu Gly Leu
    115                 120                 125

Leu Gly Asp Pro Phe Arg Pro Leu Pro Gln Gln Val Asn Leu Thr Asp
130                 135                 140

Gly Arg Trp His Arg Val Ala Val Ser Ile Asp Gly Glu Met Val Thr
```

```
                145                 150                 155                 160
        Leu Val Ala Asp Cys Glu Ala Gln Pro Pro Val Leu Gly His Gly Pro
                        165                 170                 175
        Arg Phe Ile Ser Ile Ala Gly Leu Thr Val Leu Gly Thr Gln Asp Leu
                        180                 185                 190
        Gly Glu Lys Thr Phe Glu Gly Asp Ile Gln Glu Leu Leu Ile Ser Pro
                        195                 200                 205
        Asp Pro Gln Ala Ala Phe Gln Ala Cys Glu Arg Tyr Leu Pro Asp Cys
                        210                 215                 220
        Asp Asn Leu Ala Pro Ala Ala Thr Val Ala Pro Gln Gly Glu Pro Glu
        225                 230                 235                 240
        Thr Pro Arg Pro Arg Arg Lys Gly Lys Gly Lys Gly Arg Lys Lys Gly
                        245                 250                 255
        Arg Gly Arg Lys Gly Lys Gly Arg Lys Lys Asn Lys Glu Ile Trp Thr
                        260                 265                 270
        Ser Ser Pro Pro Pro Asp Ser Ala Glu Asn Gln Thr Ser Thr Asp Ile
                        275                 280                 285
        Pro Lys Thr Glu Thr Pro Ala Pro Asn Leu Pro Pro Thr Pro Thr Pro
                        290                 295                 300
        Leu Val Val Thr Ser Thr Val Thr Thr Gly Leu Asn Ala Thr Ile Leu
        305                 310                 315                 320
        Glu Arg Ser Leu Asp Pro Asp Ser Gly Thr Glu Leu Gly Thr Leu Glu
                        325                 330                 335
        Thr Lys Ala Ala Arg Glu Asp Glu Gly Asp Asp Ser Thr Met Gly
                        340                 345                 350
        Pro Asp Phe Arg Ala Ala Glu Tyr Pro Ser Arg Thr Gln Phe Gln Ile
                        355                 360                 365
        Phe Pro Gly Ala Gly Glu Lys Gly Ala Lys Gly Glu Pro Ala Val Ile
                        370                 375                 380
        Glu Lys Gly Gln Gln Phe Glu Gly Pro Pro Gly Ala Pro Gly Pro Gln
        385                 390                 395                 400
        Gly Val Val Gly Pro Ser Gly Pro Pro Gly Pro Gly Phe Pro Gly
                        405                 410                 415
        Asp Pro Gly Pro Gly Pro Ala Gly Leu Pro Gly Ile Pro Gly Ile
                        420                 425                 430
        Asp Gly Ile Arg Gly Pro Pro Gly Thr Val Ile Met Met Pro Phe Gln
                        435                 440                 445
        Phe Ala Gly Gly Ser Phe Lys Gly Pro Pro Val Ser Phe Gln Gln Ala
        450                 455                 460
        Gln Ala Gln Ala Val Leu Gln Gln Thr Gln Leu Ser Met Lys Gly Pro
        465                 470                 475                 480
        Pro Gly Pro Val Gly Leu Thr Gly Arg Pro Gly Pro Val Gly Leu Pro
                        485                 490                 495
        Gly His Pro Gly Leu Lys Gly Glu Glu Gly Ala Glu Gly Pro Gln Gly
                        500                 505                 510
        Pro Arg Gly Leu Gln Gly Pro His Gly Pro Pro Gly Arg Val Gly Lys
                        515                 520                 525
        Met Gly Arg Pro Gly Ala Asp Gly Ala Arg Gly Leu Pro Gly Asp Thr
                        530                 535                 540
        Gly Pro Lys Gly Asp Arg Gly Phe Asp Gly Leu Pro Gly Leu Pro Gly
        545                 550                 555                 560
        Glu Lys Gly Gln Arg Gly Asp Phe Gly His Val Gly Gln Pro Gly Pro
                        565                 570                 575
```

-continued

```
Pro Gly Glu Asp Gly Glu Arg Gly Ala Glu Gly Pro Pro Gly Pro Thr
            580                 585                 590
Gly Gln Ala Gly Glu Pro Gly Pro Arg Gly Leu Leu Gly Pro Arg Gly
        595                 600                 605
Ser Pro Gly Pro Thr Gly Arg Pro Gly Val Thr Gly Ile Asp Gly Ala
    610                 615                 620
Pro Gly Ala Lys Gly Asn Val Gly Pro Pro Gly Glu Pro Gly Pro Pro
625                 630                 635                 640
Gly Gln Gln Gly Asn His Gly Ser Gln Gly Leu Pro Gly Pro Gln Gly
                645                 650                 655
Leu Ile Gly Thr Pro Gly Glu Lys Gly Pro Gly Asn Pro Gly Ile
            660                 665                 670
Pro Gly Leu Pro Gly Ser Asp Gly Pro Leu Gly His Pro Gly His Glu
        675                 680                 685
Gly Pro Thr Gly Glu Lys Gly Ala Gln Gly Pro Pro Gly Ser Ala Gly
    690                 695                 700
Pro Pro Gly Tyr Pro Gly Pro Arg Gly Val Lys Gly Thr Ser Gly Asn
705                 710                 715                 720
Arg Gly Leu Gln Gly Glu Lys Gly Glu Lys Gly Glu Asp Gly Phe Pro
                725                 730                 735
Gly Phe Lys Gly Asp Val Gly Leu Lys Gly Asp Gln Gly Lys Pro Gly
            740                 745                 750
Ala Pro Gly Pro Arg Gly Glu Asp Gly Pro Glu Gly Pro Lys Gly Gln
        755                 760                 765
Ala Gly Gln Ala Gly Glu Gly Pro Pro Gly Ser Ala Gly Glu Lys
    770                 775                 780
Gly Lys Leu Gly Val Pro Gly Leu Pro Gly Tyr Pro Gly Arg Pro Gly
785                 790                 795                 800
Pro Lys Gly Ser Ile Gly Phe Pro Gly Pro Leu Gly Pro Ile Gly Glu
                805                 810                 815
Lys Gly Lys Ser Gly Lys Thr Gly Gln Pro Gly Leu Glu Gly Glu Arg
            820                 825                 830
Gly Pro Pro Gly Ser Arg Gly Glu Arg Gly Gln Pro Gly Ala Thr Gly
        835                 840                 845
Gln Pro Gly Pro Lys Gly Asp Val Gly Gln Asp Gly Ala Pro Gly Ile
    850                 855                 860
Pro Gly Glu Lys Gly Leu Pro Gly Leu Gln Gly Pro Pro Gly Phe Pro
865                 870                 875                 880
Gly Pro Lys Gly Pro Gly His Gln Gly Lys Asp Gly Arg Pro Gly
                885                 890                 895
His Pro Gly Gln Arg Gly Glu Leu Gly Phe Gln Gly Gln Thr Gly Pro
            900                 905                 910
Pro Gly Pro Ala Gly Val Leu Gly Pro Gln Lys Thr Gly Glu Val
        915                 920                 925
Gly Pro Leu Gly Glu Arg Gly Pro Pro Gly Pro Gly Pro Pro Gly
    930                 935                 940
Glu Gln Gly Leu Pro Gly Leu Glu Gly Arg Glu Gly Ala Lys Gly Glu
945                 950                 955                 960
Leu Gly Pro Pro Gly Pro Leu Gly Lys Glu Gly Pro Ala Gly Leu Arg
                965                 970                 975
Gly Phe Pro Gly Pro Lys Gly Gly Pro Gly Asp Pro Gly Pro Thr Gly
            980                 985                 990
```

```
Leu Lys Gly Asp Lys Gly Pro Pro Gly Pro Val Gly Ala Asn Gly Ser
            995                 1000                1005

Pro Gly Glu Arg Gly Pro Leu Gly Pro Ala Gly Gly Ile Gly Leu Pro
    1010                1015                1020

Gly Gln Ser Gly Ser Glu Gly Pro Val Gly Pro Ala Gly Lys Lys Gly
1025                1030                1035                1040

Ser Arg Gly Glu Arg Gly Pro Pro Gly Pro Thr Gly Lys Asp Gly Ile
            1045                1050                1055

Pro Gly Pro Leu Gly Pro Leu Gly Pro Pro Gly Ala Ala Gly Pro Ser
            1060                1065                1070

Gly Glu Glu Gly Asp Lys Gly Asp Val Gly Ala Pro Gly His Lys Gly
            1075                1080                1085

Ser Lys Gly Asp Lys Gly Asp Ala Gly Pro Pro Gly Gln Pro Gly Ile
            1090                1095                1100

Arg Gly Pro Ala Gly His Pro Gly Pro Pro Gly Ala Asp Gly Ala Gln
1105                1110                1115                1120

Gly Arg Arg Gly Pro Pro Gly Leu Phe Gly Gln Lys Gly Asp Asp Gly
            1125                1130                1135

Val Arg Gly Phe Val Gly Val Ile Gly Pro Pro Gly Leu Gln Gly Leu
            1140                1145                1150

Pro Gly Pro Pro Gly Glu Lys Gly Glu Val Gly Asp Val Gly Ser Met
            1155                1160                1165

Gly Pro His Gly Ala Pro Gly Pro Arg Gly Pro Gln Gly Pro Thr Gly
            1170                1175                1180

Ser Glu Gly Thr Pro Gly Leu Pro Gly Gly Val Gly Gln Pro Gly Ala
1185                1190                1195                1200

Val Gly Glu Lys Gly Glu Arg Gly Asp Ala Gly Asp Pro Gly Pro Pro
            1205                1210                1215

Gly Ala Pro Gly Ile Pro Gly Pro Lys Gly Asp Ile Gly Glu Lys Gly
            1220                1225                1230

Asp Ser Gly Pro Ser Gly Ala Ala Gly Pro Pro Gly Lys Lys Gly Pro
            1235                1240                1245

Pro Gly Glu Asp Gly Ala Lys Gly Ser Val Gly Pro Thr Gly Leu Pro
    1250                1255                1260

Gly Asp Leu Gly Pro Pro Gly Asp Pro Gly Val Ser Gly Ile Asp Gly
1265                1270                1275                1280

Ser Pro Gly Glu Lys Gly Asp Pro Gly Asp Val Gly Pro Gly Pro
            1285                1290                1295

Pro Gly Ala Ser Gly Glu Pro Gly Ala Pro Gly Pro Pro Gly Lys Arg
            1300                1305                1310

Gly Pro Ser Gly His Met Gly Arg Glu Gly Arg Glu Gly Glu Lys Gly
            1315                1320                1325

Ala Lys Gly Glu Pro Gly Pro Asp Gly Pro Pro Gly Arg Thr Gly Pro
            1330                1335                1340

Met Gly Ala Arg Gly Pro Pro Gly Arg Val Gly Pro Glu Gly Leu Arg
1345                1350                1355                1360

Gly Ile Pro Gly Pro Val Gly Glu Pro Gly Leu Leu Gly Ala Pro Gly
            1365                1370                1375

Gln Met Gly Pro Pro Gly Pro Leu Gly Pro Ser Gly Leu Pro Gly Leu
            1380                1385                1390

Lys Gly Asp Thr Gly Pro Lys Gly Glu Lys Gly His Ile Gly Leu Ile
            1395                1400                1405

Gly Leu Ile Gly Pro Pro Gly Glu Ala Gly Glu Lys Gly Asp Gln Gly
```

```
                    1410                1415                1420

Leu Pro Gly Val Gln Gly Pro Gly Pro Lys Gly Asp Pro Gly Pro
1425                1430                1435                1440

Pro Gly Pro Ile Gly Ser Leu Gly His Pro Gly Pro Gly Val Ala
            1445                1450                1455

Gly Pro Leu Gly Gln Lys Gly Ser Lys Gly Ser Pro Gly Ser Met Gly
        1460                1465                1470

Pro Arg Gly Asp Thr Gly Pro Ala Gly Pro Gly Pro Gly Ala
        1475                1480                1485

Pro Ala Glu Leu His Gly Leu Arg Arg Arg Arg Phe Val Pro Val
    1490                1495                1500

Pro Leu Pro Val Val Glu Gly Leu Glu Glu Val Leu Ala Ser Leu
1505                1510                1515                1520

Thr Ser Leu Ser Leu Glu Leu Glu Gln Leu Arg Arg Pro Gly Thr
            1525                1530                1535

Ala Glu Arg Pro Gly Leu Val Cys His Glu Leu His Arg Asn His Pro
        1540                1545                1550

His Leu Pro Asp Gly Glu Tyr Trp Ile Asp Pro Asn Gln Gly Cys Ala
        1555                1560                1565

Arg Asp Ser Phe Arg Val Phe Cys Asn Phe Thr Ala Gly Gly Glu Thr
        1570                1575                1580

Cys Leu Tyr Pro Asp Lys Lys Phe Glu Ile Val Lys Leu Ala Ser Trp
1585                1590                1595                1600

Ser Lys Glu Lys Pro Gly Gly Trp Tyr Ser Thr Phe Arg Arg Gly Lys
            1605                1610                1615

Lys Phe Ser Tyr Val Asp Ala Asp Gly Ser Pro Val Asn Val Val Gln
        1620                1625                1630

Leu Asn Phe Leu Lys Leu Leu Ser Ala Thr Ala Arg Gln Asn Phe Thr
        1635                1640                1645

Tyr Ser Cys Gln Asn Ala Ala Ala Trp Leu Asp Glu Ala Thr Gly Asp
    1650                1655                1660

Tyr Ser His Ser Ala Arg Phe Leu Gly Thr Asn Gly Glu Glu Leu Ser
1665                1670                1675                1680

Phe Asn Gln Thr Thr Ala Ala Thr Val Ser Val Pro Gln Asp Gly Cys
            1685                1690                1695

Arg Leu Arg Lys Gly Gln Thr Lys Thr Leu Phe Glu Phe Ser Ser Ser
        1700                1705                1710

Arg Ala Gly Phe Leu Pro Leu Trp Asp Val Ala Ala Thr Asp Phe Gly
        1715                1720                1725

Gln Thr Asn Gln Lys Phe Gly Phe Glu Leu Gly Pro Val Cys Phe Ser
    1730                1735                1740

Ser
1745

<210> SEQ ID NO 14
<211> LENGTH: 1019
<212> TYPE: PRT
<213> ORGANISM: Homo sapiens

<400> SEQUENCE: 14

Met Leu Gln Gly Thr Cys Ser Val Leu Leu Leu Trp Gly Ile Leu Gly
1               5                   10                  15

Ala Ile Gln Ala Gln Gln Gln Glu Val Ile Ser Pro Asp Thr Thr Glu
            20                  25                  30
```

-continued

```
Arg Asn Asn Asn Cys Pro Glu Lys Thr Asp Cys Pro Ile His Val Tyr
        35                  40                  45
Phe Val Leu Asp Thr Ser Glu Ser Val Thr Met Gln Ser Pro Thr Asp
 50                  55                  60
Ile Leu Leu Phe His Met Lys Gln Phe Val Pro Gln Phe Ile Ser Gln
65                  70                  75                  80
Leu Gln Asn Glu Phe Tyr Leu Asp Gln Val Ala Leu Ser Trp Arg Tyr
                85                  90                  95
Gly Gly Leu His Phe Ser Asp Gln Val Glu Val Phe Ser Pro Pro Gly
               100                 105                 110
Ser Asp Arg Ala Ser Phe Ile Lys Asn Leu Gln Gly Ile Ser Ser Phe
            115                 120                 125
Arg Arg Gly Thr Phe Thr Asp Cys Ala Leu Ala Asn Met Thr Glu Gln
130                 135                 140
Ile Arg Gln Asp Arg Ser Lys Gly Thr Val His Phe Ala Val Val Ile
145                 150                 155                 160
Thr Asp Gly His Val Thr Gly Ser Pro Cys Gly Gly Ile Lys Leu Gln
                165                 170                 175
Ala Glu Arg Ala Arg Glu Gly Ile Arg Leu Phe Ala Val Ala Pro
            180                 185                 190
Asn Gln Asn Leu Lys Glu Gln Gly Leu Arg Asp Ile Ala Ser Thr Pro
            195                 200                 205
His Glu Leu Tyr Arg Asn Asp Tyr Ala Thr Met Leu Pro Asp Ser Thr
210                 215                 220
Glu Ile Asp Gln Asp Thr Ile Asn Arg Ile Ile Lys Val Met Lys His
225                 230                 235                 240
Glu Ala Tyr Gly Glu Cys Tyr Lys Val Ser Cys Leu Glu Ile Pro Gly
                245                 250                 255
Pro Ser Gly Pro Lys Gly Tyr Arg Gly Gln Lys Gly Ala Lys Gly Asn
            260                 265                 270
Met Gly Glu Pro Gly Glu Pro Gly Gln Lys Gly Arg Gln Gly Asp Pro
            275                 280                 285
Gly Ile Glu Gly Pro Ile Gly Phe Pro Gly Pro Lys Gly Val Pro Gly
290                 295                 300
Phe Lys Gly Glu Lys Gly Glu Phe Gly Ala Asp Gly Arg Lys Gly Ala
305                 310                 315                 320
Pro Gly Leu Ala Gly Lys Asn Gly Thr Asp Gly Gln Lys Gly Lys Leu
                325                 330                 335
Gly Arg Ile Gly Pro Pro Gly Cys Lys Gly Asp Pro Gly Asn Arg Gly
            340                 345                 350
Pro Asp Gly Tyr Pro Gly Glu Ala Gly Ser Pro Gly Glu Arg Gly Asp
            355                 360                 365
Gln Gly Gly Lys Gly Asp Pro Gly Arg Pro Gly Arg Arg Gly Pro Pro
370                 375                 380
Gly Glu Ile Gly Ala Lys Gly Ser Lys Gly Tyr Gln Gly Asn Ser Gly
385                 390                 395                 400
Ala Pro Gly Ser Pro Gly Val Lys Gly Ala Lys Gly Pro Gly Pro
                405                 410                 415
Arg Gly Pro Lys Gly Glu Pro Gly Arg Arg Gly Asp Pro Gly Thr Lys
            420                 425                 430
Gly Ser Pro Gly Ser Asp Gly Pro Lys Gly Glu Lys Gly Asp Pro Gly
            435                 440                 445
Pro Glu Gly Pro Arg Gly Leu Ala Gly Glu Val Gly Asn Lys Gly Ala
```

```
            450                 455                 460
Lys Gly Asp Arg Gly Leu Pro Gly Pro Arg Gly Pro Gln Gly Ala Leu
465                 470                 475                 480

Gly Glu Pro Gly Lys Gln Gly Ser Arg Gly Asp Pro Gly Asp Ala Gly
                    485                 490                 495

Pro Arg Gly Asp Ser Gly Gln Pro Gly Pro Lys Gly Asp Pro Gly Arg
                500                 505                 510

Pro Gly Phe Ser Tyr Pro Gly Pro Arg Gly Ala Pro Gly Glu Lys Gly
            515                 520                 525

Glu Pro Gly Pro Arg Gly Pro Glu Gly Arg Gly Asp Phe Gly Leu
        530                 535                 540

Lys Gly Glu Pro Gly Arg Lys Gly Glu Lys Gly Glu Pro Ala Asp Pro
545                 550                 555                 560

Gly Pro Pro Gly Glu Pro Gly Pro Arg Gly Pro Arg Gly Val Pro Gly
                    565                 570                 575

Pro Glu Gly Glu Pro Gly Pro Pro Gly Asp Pro Gly Leu Thr Glu Cys
                580                 585                 590

Asp Val Met Thr Tyr Val Arg Glu Thr Cys Gly Cys Asp Cys Glu
                595                 600                 605

Lys Arg Cys Gly Ala Leu Asp Val Val Phe Val Ile Asp Ser Ser Glu
        610                 615                 620

Ser Ile Gly Tyr Thr Asn Phe Thr Leu Glu Lys Asn Phe Val Ile Asn
625                 630                 635                 640

Val Val Asn Arg Leu Gly Ala Ile Ala Lys Asp Pro Lys Ser Glu Thr
                645                 650                 655

Gly Thr Arg Val Gly Val Val Gln Tyr Ser His Glu Gly Thr Phe Glu
                660                 665                 670

Ala Ile Gln Leu Asp Asp Glu Arg Ile Asp Ser Leu Ser Ser Phe Lys
            675                 680                 685

Glu Ala Val Lys Asn Leu Glu Trp Ile Ala Gly Gly Thr Trp Thr Pro
        690                 695                 700

Ser Ala Leu Lys Phe Ala Tyr Asp Arg Leu Ile Lys Glu Ser Arg Arg
705                 710                 715                 720

Gln Lys Thr Arg Val Phe Ala Val Val Ile Thr Asp Gly Arg His Asp
                    725                 730                 735

Pro Arg Asp Asp Asp Leu Asn Leu Arg Ala Leu Cys Asp Arg Asp Val
                740                 745                 750

Thr Val Thr Ala Ile Gly Ile Gly Asp Met Phe His Glu Lys His Glu
            755                 760                 765

Ser Glu Asn Leu Tyr Ser Ile Ala Cys Asp Lys Pro Gln Gln Val Arg
        770                 775                 780

Asn Met Thr Leu Phe Ser Asp Leu Val Ala Lys Phe Ile Asp Asp
785                 790                 795                 800

Met Glu Asp Val Leu Cys Pro Asp Pro Gln Ile Val Cys Pro Asp Leu
                    805                 810                 815

Pro Cys Gln Thr Glu Leu Ser Val Ala Gln Cys Thr Gln Arg Pro Val
                820                 825                 830

Asp Ile Val Phe Leu Leu Asp Gly Ser Glu Arg Leu Gly Glu Gln Asn
            835                 840                 845

Phe His Lys Ala Arg Arg Phe Val Glu Gln Val Ala Arg Arg Leu Thr
        850                 855                 860

Leu Ala Arg Arg Asp Asp Asp Pro Leu Asn Ala Arg Val Ala Leu Leu
865                 870                 875                 880
```

```
Gln Phe Gly Gly Pro Gly Glu Gln Gln Val Ala Phe Pro Leu Ser His
                885                 890                 895
Asn Leu Thr Ala Ile His Glu Ala Leu Glu Thr Thr Gln Tyr Leu Asn
            900                 905                 910
Ser Phe Ser His Val Gly Ala Gly Val Val His Ala Ile Asn Ala Ile
        915                 920                 925
Val Arg Ser Pro Arg Gly Gly Ala Arg Arg His Ala Glu Leu Ser Phe
    930                 935                 940
Val Phe Leu Thr Asp Gly Val Thr Gly Asn Asp Ser Leu His Glu Ser
945                 950                 955                 960
Ala His Ser Met Arg Lys Gln Asn Val Val Pro Thr Val Leu Ala Leu
                965                 970                 975
Gly Ser Asp Val Asp Met Asp Val Leu Thr Thr Leu Ser Leu Gly Asp
            980                 985                 990
Arg Ala Ala Val Phe His Glu Lys Asp Tyr Asp Ser Leu Ala Gln Pro
        995                1000                1005
Gly Phe Phe Asp Arg Phe Ile Arg Trp Ile Cys
    1010                1015
```

<210> SEQ ID NO 15
<211> LENGTH: 3177
<212> TYPE: PRT
<213> ORGANISM: Homo sapiens

<400> SEQUENCE: 15

```
Met Arg Lys His Arg His Leu Pro Leu Val Ala Val Phe Cys Leu Phe
1               5                   10                  15
Leu Ser Gly Phe Pro Thr Thr His Ala Gln Gln Gln Gln Ala Asp Val
            20                  25                  30
Lys Asn Gly Ala Ala Ala Asp Ile Ile Phe Leu Val Asp Ser Ser Trp
        35                  40                  45
Thr Ile Gly Glu Glu His Phe Gln Leu Val Arg Glu Phe Leu Tyr Asp
    50                  55                  60
Val Val Lys Ser Leu Ala Val Gly Glu Asn Asp Phe His Phe Ala Leu
65                  70                  75                  80
Val Gln Phe Asn Gly Asn Pro His Thr Glu Phe Leu Leu Asn Thr Tyr
                85                  90                  95
Arg Thr Lys Gln Glu Val Leu Ser His Ile Ser Asn Met Ser Tyr Ile
            100                 105                 110
Gly Gly Thr Asn Gln Thr Gly Lys Gly Leu Glu Tyr Ile Met Gln Ser
        115                 120                 125
His Leu Thr Lys Ala Ala Gly Ser Arg Ala Gly Asp Gly Val Pro Gln
    130                 135                 140
Val Ile Val Val Leu Thr Asp Gly His Ser Lys Asp Gly Leu Ala Leu
145                 150                 155                 160
Pro Ser Ala Glu Leu Lys Ser Asp Val Asn Val Phe Ala Ile Gly
                165                 170                 175
Val Glu Asp Ala Asp Glu Gly Ala Leu Lys Glu Ile Ala Ser Glu Pro
            180                 185                 190
Leu Asn Met His Met Phe Asn Leu Glu Asn Phe Thr Ser Leu His Asp
        195                 200                 205
Ile Val Gly Asn Leu Val Ser Cys Val His Ser Ser Val Ser Pro Glu
    210                 215                 220
Arg Ala Gly Asp Thr Glu Thr Leu Lys Asp Ile Thr Ala Gln Asp Ser
```

-continued

```
        225                 230                 235                 240
Ala Asp Ile Ile Phe Leu Ile Asp Gly Ser Asn Asn Thr Gly Ser Val
                    245                 250                 255

Asn Phe Ala Val Ile Leu Asp Phe Leu Val Asn Leu Leu Glu Lys Leu
                260                 265                 270

Pro Ile Gly Thr Gln Gln Ile Arg Val Gly Val Val Gln Phe Ser Asp
            275                 280                 285

Glu Pro Arg Thr Met Phe Ser Leu Asp Thr Tyr Ser Thr Lys Ala Gln
            290                 295                 300

Val Leu Gly Ala Val Lys Ala Leu Gly Phe Ala Gly Gly Glu Leu Ala
305                 310                 315                 320

Asn Ile Gly Leu Ala Leu Asp Phe Val Glu Asn His Phe Thr Arg
                325                 330                 335

Ala Gly Gly Ser Arg Val Glu Glu Gly Val Pro Gln Val Leu Val Leu
                340                 345                 350

Ile Ser Ala Gly Pro Ser Ser Asp Glu Ile Arg Tyr Gly Val Val Ala
            355                 360                 365

Leu Lys Gln Ala Ser Val Phe Ser Phe Gly Leu Gly Ala Gln Ala Ala
    370                 375                 380

Ser Arg Ala Glu Leu Gln His Ile Ala Thr Asp Asp Asn Leu Val Phe
385                 390                 395                 400

Thr Val Pro Glu Phe Arg Ser Phe Gly Asp Leu Gln Glu Lys Leu Leu
                405                 410                 415

Pro Tyr Ile Val Gly Val Ala Gln Arg His Ile Val Leu Lys Pro Pro
            420                 425                 430

Thr Ile Val Thr Gln Val Ile Glu Val Asn Lys Arg Asp Ile Val Phe
        435                 440                 445

Leu Val Asp Gly Ser Ser Ala Leu Gly Leu Ala Asn Phe Asn Ala Ile
    450                 455                 460

Arg Asp Phe Ile Ala Lys Val Ile Gln Arg Leu Glu Ile Gly Gln Asp
465                 470                 475                 480

Leu Ile Gln Val Ala Val Ala Gln Tyr Ala Asp Thr Val Arg Pro Glu
                485                 490                 495

Phe Tyr Phe Asn Thr His Pro Thr Lys Arg Glu Val Ile Thr Ala Val
                500                 505                 510

Arg Lys Met Lys Pro Leu Asp Gly Ser Ala Leu Tyr Thr Gly Ser Ala
            515                 520                 525

Leu Asp Phe Val Arg Asn Asn Leu Phe Thr Ser Ser Ala Gly Tyr Arg
        530                 535                 540

Ala Ala Glu Gly Ile Pro Lys Leu Leu Val Leu Ile Thr Gly Gly Lys
545                 550                 555                 560

Ser Leu Asp Glu Ile Ser Gln Pro Ala Gln Glu Leu Lys Arg Ser Ser
                565                 570                 575

Ile Met Ala Phe Ala Ile Gly Asn Lys Gly Ala Asp Gln Ala Glu Leu
                580                 585                 590

Glu Glu Ile Ala Phe Asp Ser Ser Leu Val Phe Ile Pro Ala Glu Phe
            595                 600                 605

Arg Ala Ala Pro Leu Gln Gly Met Leu Pro Gly Leu Leu Ala Pro Leu
610                 615                 620

Arg Thr Leu Ser Gly Thr Pro Glu Val His Ser Asn Lys Arg Asp Ile
625                 630                 635                 640

Ile Phe Leu Leu Asp Gly Ser Ala Asn Val Gly Lys Thr Asn Phe Pro
                645                 650                 655
```

```
Tyr Val Arg Asp Phe Val Met Asn Leu Val Asn Ser Leu Asp Ile Gly
            660                 665                 670

Asn Asp Asn Ile Arg Val Gly Leu Val Gln Phe Ser Asp Thr Pro Val
            675                 680                 685

Thr Glu Phe Ser Leu Asn Thr Tyr Gln Thr Lys Ser Asp Ile Leu Gly
            690                 695                 700

His Leu Arg Gln Leu Gln Leu Gln Gly Gly Ser Gly Leu Asn Thr Gly
705                 710                 715                 720

Ser Ala Leu Ser Tyr Val Tyr Ala Asn His Phe Thr Glu Ala Gly Gly
                725                 730                 735

Ser Arg Ile Arg Glu His Val Pro Gln Leu Leu Leu Leu Leu Thr Ala
            740                 745                 750

Gly Gln Ser Glu Asp Ser Tyr Leu Gln Ala Ala Asn Ala Leu Thr Arg
            755                 760                 765

Ala Gly Ile Leu Thr Phe Cys Val Gly Ala Ser Gln Ala Asn Lys Ala
            770                 775                 780

Glu Leu Glu Gln Ile Ala Phe Asn Pro Ser Leu Val Tyr Leu Met Asp
785                 790                 795                 800

Asp Phe Ser Ser Leu Pro Ala Leu Pro Gln Gln Leu Ile Gln Pro Leu
                805                 810                 815

Thr Thr Tyr Val Ser Gly Gly Val Glu Glu Val Pro Leu Ala Gln Pro
            820                 825                 830

Glu Ser Lys Arg Asp Ile Leu Phe Leu Phe Asp Gly Ser Ala Asn Leu
            835                 840                 845

Val Gly Gln Phe Pro Val Val Arg Asp Phe Leu Tyr Lys Ile Ile Asp
850                 855                 860

Glu Leu Asn Val Lys Pro Glu Gly Thr Arg Ile Ala Val Ala Gln Tyr
865                 870                 875                 880

Ser Asp Asp Val Lys Val Glu Ser Arg Phe Asp Glu His Gln Ser Lys
                885                 890                 895

Pro Glu Ile Leu Asn Leu Val Lys Arg Met Lys Ile Lys Thr Gly Lys
            900                 905                 910

Ala Leu Asn Leu Gly Tyr Ala Leu Asp Tyr Ala Gln Arg Tyr Ile Phe
            915                 920                 925

Val Lys Ser Ala Gly Ser Arg Ile Glu Asp Gly Val Leu Gln Phe Leu
            930                 935                 940

Val Leu Leu Val Ala Gly Arg Ser Ser Asp Arg Val Asp Gly Pro Ala
945                 950                 955                 960

Ser Asn Leu Lys Gln Ser Gly Val Val Pro Phe Ile Phe Gln Ala Lys
                965                 970                 975

Asn Ala Asp Pro Ala Glu Leu Glu Gln Ile Val Leu Ser Pro Ala Phe
            980                 985                 990

Ile Leu Ala Ala Glu Ser Leu Pro Lys Ile Gly Asp Leu His Pro Gln
            995                 1000                1005

Ile Val Asn Leu Leu Lys Ser Val His Asn Gly Ala Pro Ala Pro Val
            1010                1015                1020

Ser Gly Glu Lys Asp Val Val Phe Leu Leu Asp Gly Ser Glu Gly Val
1025                1030                1035                1040

Arg Ser Gly Phe Pro Leu Leu Lys Glu Phe Val Gln Arg Val Val Glu
                1045                1050                1055

Ser Leu Asp Val Gly Gln Asp Arg Val Arg Val Ala Val Val Gln Tyr
            1060                1065                1070
```

```
Ser Asp Arg Thr Arg Pro Glu Phe Tyr Leu Asn Ser Tyr Met Asn Lys
        1075                1080                1085

Gln Asp Val Val Asn Ala Val Arg Gln Leu Thr Leu Leu Gly Gly Pro
        1090                1095                1100

Thr Pro Asn Thr Gly Ala Ala Leu Glu Phe Val Leu Arg Asn Ile Leu
1105                1110                1115                1120

Val Ser Ser Ala Gly Ser Arg Ile Thr Glu Gly Val Pro Gln Leu Leu
                1125                1130                1135

Ile Val Leu Thr Ala Asp Arg Ser Gly Asp Asp Val Arg Asn Pro Ser
            1140                1145                1150

Val Val Val Lys Arg Gly Gly Ala Val Pro Ile Gly Ile Gly Ile Gly
            1155                1160                1165

Asn Ala Asp Ile Thr Glu Met Gln Thr Ile Ser Phe Ile Pro Asp Phe
        1170                1175                1180

Ala Val Ala Ile Pro Thr Phe Arg Gln Leu Gly Thr Val Gln Gln Val
1185                1190                1195                1200

Ile Ser Glu Arg Val Thr Gln Leu Thr Arg Glu Glu Leu Ser Arg Leu
            1205                1210                1215

Gln Pro Val Leu Gln Pro Leu Pro Ser Pro Gly Val Gly Gly Lys Arg
        1220                1225                1230

Asp Val Val Phe Leu Ile Asp Gly Ser Gln Ser Ala Gly Pro Glu Phe
        1235                1240                1245

Gln Tyr Val Arg Thr Leu Ile Glu Arg Leu Val Asp Tyr Leu Asp Val
        1250                1255                1260

Gly Phe Asp Thr Thr Arg Val Ala Val Ile Gln Phe Ser Asp Asp Pro
1265                1270                1275                1280

Lys Val Glu Phe Leu Leu Asn Ala His Ser Ser Lys Asp Glu Val Gln
            1285                1290                1295

Asn Ala Val Gln Arg Leu Arg Pro Lys Gly Gly Arg Gln Ile Asn Val
            1300                1305                1310

Gly Asn Ala Leu Glu Tyr Val Ser Arg Asn Ile Phe Lys Arg Pro Leu
            1315                1320                1325

Gly Ser Arg Ile Glu Glu Gly Val Pro Gln Phe Leu Val Leu Ile Ser
        1330                1335                1340

Ser Gly Lys Ser Asp Asp Glu Val Asp Asp Pro Ala Val Glu Leu Lys
1345                1350                1355                1360

Gln Phe Gly Val Ala Pro Phe Thr Ile Ala Arg Asn Ala Asp Gln Glu
                1365                1370                1375

Glu Leu Val Lys Ile Ser Leu Ser Pro Glu Tyr Val Phe Ser Val Ser
                1380                1385                1390

Thr Phe Arg Glu Leu Pro Ser Leu Glu Gln Lys Leu Leu Thr Pro Ile
        1395                1400                1405

Thr Thr Leu Thr Ser Glu Gln Ile Gln Lys Leu Leu Ala Ser Thr Arg
        1410                1415                1420

Tyr Pro Pro Pro Ala Val Glu Ser Asp Ala Ala Asp Ile Val Phe Leu
1425                1430                1435                1440

Ile Asp Ser Ser Glu Gly Val Arg Pro Asp Gly Phe Ala His Ile Arg
            1445                1450                1455

Asp Phe Val Ser Arg Ile Val Arg Arg Leu Asn Ile Gly Pro Ser Lys
                1460                1465                1470

Val Arg Val Gly Val Val Gln Phe Ser Asn Asp Val Phe Pro Glu Phe
            1475                1480                1485

Tyr Leu Lys Thr Tyr Arg Ser Gln Ala Pro Val Leu Asp Ala Ile Arg
```

```
            1490                1495                1500
Arg Leu Arg Leu Arg Gly Gly Ser Pro Leu Asn Thr Gly Lys Ala Leu
1505                1510                1515                1520
Glu Phe Val Ala Arg Asn Leu Phe Val Lys Ser Ala Gly Ser Arg Ile
                1525                1530                1535
Glu Asp Gly Val Pro Gln His Leu Val Leu Val Leu Gly Gly Lys Ser
            1540                1545                1550
Gln Asp Asp Val Ser Arg Phe Ala Gln Val Ile Arg Ser Ser Gly Ile
            1555                1560                1565
Val Ser Leu Gly Val Gly Asp Arg Asn Ile Asp Arg Thr Glu Leu Gln
            1570                1575                1580
Thr Ile Thr Asn Asp Pro Arg Leu Val Phe Thr Val Arg Glu Phe Arg
1585                1590                1595                1600
Glu Leu Pro Asn Ile Glu Glu Arg Ile Met Asn Ser Phe Gly Pro Ser
                1605                1610                1615
Ala Ala Thr Pro Ala Pro Pro Gly Val Asp Thr Pro Pro Ser Arg
            1620                1625                1630
Pro Glu Lys Lys Lys Ala Asp Ile Val Phe Leu Leu Asp Gly Ser Ile
            1635                1640                1645
Asn Phe Arg Arg Asp Ser Phe Gln Glu Val Leu Arg Phe Val Ser Glu
            1650                1655                1660
Ile Val Asp Thr Val Tyr Glu Asp Gly Asp Ser Ile Gln Val Gly Leu
1665                1670                1675                1680
Val Gln Tyr Asn Ser Asp Pro Thr Asp Glu Phe Phe Leu Lys Asp Phe
                1685                1690                1695
Ser Thr Lys Arg Gln Ile Ile Asp Ala Ile Asn Lys Val Val Tyr Lys
            1700                1705                1710
Gly Gly Arg His Ala Asn Thr Lys Val Gly Leu Glu His Leu Arg Val
            1715                1720                1725
Asn His Phe Val Pro Glu Ala Gly Ser Arg Leu Asp Gln Arg Val Pro
            1730                1735                1740
Gln Ile Ala Phe Val Ile Thr Gly Gly Lys Ser Val Glu Asp Ala Gln
1745                1750                1755                1760
Asp Val Ser Leu Ala Leu Thr Gln Arg Gly Val Lys Val Phe Ala Val
                1765                1770                1775
Gly Val Arg Asn Ile Asp Ser Glu Glu Val Gly Lys Ile Ala Ser Asn
            1780                1785                1790
Ser Ala Thr Ala Phe Arg Val Gly Asn Val Gln Glu Leu Ser Glu Leu
            1795                1800                1805
Ser Glu Gln Val Leu Glu Thr Leu His Asp Ala Met His Glu Thr Leu
            1810                1815                1820
Cys Pro Gly Val Thr Asp Ala Ala Lys Ala Cys Asn Leu Asp Val Ile
1825                1830                1835                1840
Leu Gly Phe Asp Gly Ser Arg Asp Gln Asn Val Phe Val Ala Gln Lys
                1845                1850                1855
Gly Phe Glu Ser Lys Val Asp Ala Ile Leu Asn Arg Ile Ser Gln Met
            1860                1865                1870
His Arg Val Ser Cys Ser Gly Gly Arg Ser Pro Thr Val Arg Val Ser
            1875                1880                1885
Val Val Ala Asn Thr Pro Ser Gly Pro Val Glu Ala Phe Asp Phe Asp
            1890                1895                1900
Glu Tyr Gln Pro Glu Met Leu Glu Lys Phe Arg Asn Met Arg Ser Gln
1905                1910                1915                1920
```

-continued

```
His Pro Tyr Val Leu Thr Glu Asp Thr Leu Lys Val Tyr Leu Asn Lys
            1925                1930                1935

Phe Arg Gln Ser Ser Pro Asp Ser Val Lys Val Val Ile His Phe Thr
        1940                1945                1950

Asp Gly Ala Asp Gly Asp Leu Ala Asp Leu His Arg Ala Ser Glu Asn
    1955                1960                1965

Leu Arg Gln Glu Gly Val Arg Ala Leu Ile Leu Val Gly Leu Glu Arg
    1970                1975                1980

Val Val Asn Leu Glu Arg Leu Met His Leu Glu Phe Gly Arg Gly Phe
1985                1990                1995                2000

Met Tyr Asp Arg Pro Leu Arg Leu Asn Leu Leu Asp Leu Asp Tyr Glu
            2005                2010                2015

Leu Ala Glu Gln Leu Asp Asn Ile Ala Glu Lys Ala Cys Cys Gly Val
            2020                2025                2030

Pro Cys Lys Cys Ser Gly Gln Arg Gly Asp Arg Gly Pro Ile Gly Ser
            2035                2040                2045

Ile Gly Pro Lys Gly Ile Pro Gly Glu Asp Gly Tyr Arg Gly Tyr Pro
        2050                2055                2060

Gly Asp Glu Gly Gly Pro Gly Glu Arg Gly Pro Pro Gly Val Asn Gly
2065                2070                2075                2080

Thr Gln Gly Phe Gln Gly Cys Pro Gly Gln Arg Gly Val Lys Gly Ser
            2085                2090                2095

Arg Gly Phe Pro Gly Glu Lys Gly Glu Val Gly Glu Ile Gly Leu Asp
            2100                2105                2110

Gly Leu Asp Gly Glu Asp Gly Asp Lys Gly Leu Pro Gly Ser Ser Gly
            2115                2120                2125

Glu Lys Gly Asn Pro Gly Arg Arg Gly Asp Lys Gly Pro Arg Gly Glu
            2130                2135                2140

Lys Gly Glu Arg Gly Asp Val Gly Ile Arg Gly Asp Pro Gly Asn Pro
2145                2150                2155                2160

Gly Gln Asp Ser Gln Glu Arg Gly Pro Lys Gly Glu Thr Gly Asp Leu
            2165                2170                2175

Gly Pro Met Gly Val Pro Gly Arg Asp Gly Val Pro Gly Gly Pro Gly
            2180                2185                2190

Glu Thr Gly Lys Asn Gly Gly Phe Gly Arg Arg Gly Pro Pro Gly Ala
            2195                2200                2205

Lys Gly Asn Lys Gly Gly Pro Gly Gln Pro Gly Phe Glu Gly Glu Gln
            2210                2215                2220

Gly Thr Arg Gly Ala Gln Gly Pro Ala Gly Pro Ala Gly Pro Pro Gly
2225                2230                2235                2240

Leu Ile Gly Glu Gln Gly Ile Ser Gly Pro Arg Gly Ser Gly Gly Ala
            2245                2250                2255

Ala Gly Ala Pro Gly Glu Arg Gly Arg Thr Gly Pro Leu Gly Arg Lys
            2260                2265                2270

Gly Glu Pro Gly Glu Pro Gly Pro Lys Gly Gly Ile Gly Asn Arg Gly
            2275                2280                2285

Pro Arg Gly Glu Thr Gly Asp Asp Gly Arg Asp Gly Val Gly Ser Glu
        2290                2295                2300

Gly Arg Arg Gly Lys Lys Gly Glu Arg Gly Phe Pro Gly Tyr Pro Gly
2305                2310                2315                2320

Pro Lys Gly Asn Pro Gly Glu Pro Gly Leu Asn Gly Thr Thr Gly Pro
            2325                2330                2335
```

```
Lys Gly Ile Arg Gly Arg Gly Asn Ser Gly Pro Pro Gly Ile Val
            2340                2345                2350

Gly Gln Lys Gly Asp Pro Gly Tyr Pro Gly Pro Ala Gly Pro Lys Gly
        2355                2360                2365

Asn Arg Gly Asp Ser Ile Asp Gln Cys Ala Leu Ile Gln Ser Ile Lys
        2370                2375                2380

Asp Lys Cys Pro Cys Cys Tyr Gly Pro Leu Glu Cys Pro Val Phe Pro
2385                2390                2395                2400

Thr Glu Leu Ala Phe Ala Leu Asp Thr Ser Glu Gly Val Asn Gln Asp
                2405                2410                2415

Thr Phe Gly Arg Met Arg Asp Val Val Leu Ser Ile Val Asn Asp Leu
                2420                2425                2430

Thr Ile Ala Glu Ser Asn Cys Pro Arg Gly Ala Arg Val Ala Val Val
                2435                2440                2445

Thr Tyr Asn Asn Glu Val Thr Thr Glu Ile Arg Phe Ala Asp Ser Lys
                2450                2455                2460

Arg Lys Ser Val Leu Leu Asp Lys Ile Lys Asn Leu Gln Val Ala Leu
2465                2470                2475                2480

Thr Ser Lys Gln Gln Ser Leu Glu Thr Ala Met Ser Phe Val Ala Arg
                2485                2490                2495

Asn Thr Phe Lys Arg Val Arg Asn Gly Phe Leu Met Arg Lys Val Ala
                2500                2505                2510

Val Phe Phe Ser Asn Thr Pro Thr Arg Ala Ser Pro Gln Leu Arg Glu
                2515                2520                2525

Ala Val Leu Lys Leu Ser Asp Ala Gly Ile Thr Pro Leu Phe Leu Thr
                2530                2535                2540

Arg Gln Glu Asp Arg Gln Leu Ile Asn Ala Leu Gln Ile Asn Asn Thr
2545                2550                2555                2560

Ala Val Gly His Ala Leu Val Leu Pro Ala Gly Arg Asp Leu Thr Asp
                2565                2570                2575

Phe Leu Glu Asn Val Leu Thr Cys His Val Cys Leu Asp Ile Cys Asn
                2580                2585                2590

Ile Asp Pro Ser Cys Gly Phe Gly Ser Trp Arg Pro Ser Phe Arg Asp
                2595                2600                2605

Arg Arg Ala Ala Gly Ser Asp Val Asp Ile Asp Met Ala Phe Ile Leu
2610                2615                2620

Asp Ser Ala Glu Thr Thr Thr Leu Phe Gln Phe Asn Glu Met Lys Lys
2625                2630                2635                2640

Tyr Ile Ala Tyr Leu Val Arg Gln Leu Asp Met Ser Pro Asp Pro Lys
                2645                2650                2655

Ala Ser Gln His Phe Ala Arg Val Ala Val Val Gln His Ala Pro Ser
                2660                2665                2670

Glu Ser Val Asp Asn Ala Ser Met Pro Pro Val Lys Val Glu Phe Ser
                2675                2680                2685

Leu Thr Asp Tyr Gly Ser Lys Glu Lys Leu Val Asp Phe Leu Ser Arg
                2690                2695                2700

Gly Met Thr Gln Leu Gln Gly Thr Arg Ala Leu Gly Ser Ala Ile Glu
2705                2710                2715                2720

Tyr Thr Ile Glu Asn Val Phe Glu Ser Ala Pro Asn Pro Arg Asp Leu
                2725                2730                2735

Lys Ile Val Val Leu Met Leu Thr Gly Glu Val Pro Glu Gln Gln Leu
                2740                2745                2750

Glu Glu Ala Gln Arg Val Ile Leu Gln Ala Lys Cys Lys Gly Tyr Phe
```

```
                    2755                2760                2765
Phe Val Val Leu Gly Ile Gly Arg Lys Val Asn Ile Lys Glu Val Tyr
                    2770                2775                2780
Thr Phe Ala Ser Glu Pro Asn Asp Val Phe Phe Lys Leu Val Asp Lys
2785                2790                2795                2800
Ser Thr Glu Leu Asn Glu Glu Pro Leu Met Arg Phe Gly Arg Leu Leu
                    2805                2810                2815
Pro Ser Phe Val Ser Ser Glu Asn Ala Phe Tyr Leu Ser Pro Asp Ile
                    2820                2825                2830
Arg Lys Gln Cys Asp Trp Phe Gln Gly Asp Gln Pro Thr Lys Asn Leu
                    2835                2840                2845
Val Lys Phe Gly His Lys Gln Val Asn Val Pro Asn Asn Val Thr Ser
                    2850                2855                2860
Ser Pro Thr Ser Asn Pro Val Thr Thr Thr Lys Pro Val Thr Thr Thr
2865                2870                2875                2880
Lys Pro Val Thr Thr Thr Thr Lys Pro Val Thr Thr Thr Thr Lys Pro
                    2885                2890                2895
Val Thr Ile Ile Asn Gln Pro Ser Val Lys Pro Ala Ala Ala Lys Pro
                    2900                2905                2910
Ala Pro Ala Lys Pro Val Ala Ala Lys Pro Val Ala Thr Lys Met Ala
                    2915                2920                2925
Thr Val Arg Pro Pro Val Ala Val Lys Pro Ala Thr Ala Ala Lys Pro
                    2930                2935                2940
Val Ala Ala Lys Pro Ala Ala Val Arg Pro Pro Ala Ala Ala Ala Ala
2945                2950                2955                2960
Lys Pro Val Ala Thr Lys Pro Glu Val Pro Arg Pro Gln Ala Ala Lys
                    2965                2970                2975
Pro Ala Ala Thr Lys Pro Ala Thr Thr Lys Pro Met Val Lys Met Ser
                    2980                2985                2990
Arg Glu Val Gln Val Phe Glu Ile Thr Glu Asn Ser Ala Lys Leu His
                    2995                3000                3005
Trp Glu Arg Ala Glu Pro Pro Gly Pro Tyr Phe Tyr Asp Leu Thr Val
                    3010                3015                3020
Thr Ser Ala His Asp Gln Ser Leu Val Leu Lys Gln Asn Leu Thr Val
3025                3030                3035                3040
Thr Asp Arg Val Ile Gly Gly Leu Leu Ala Gly Gln Thr Tyr His Val
                    3045                3050                3055
Ala Val Val Cys Tyr Leu Arg Ser Gln Val Arg Ala Thr Tyr His Gly
                    3060                3065                3070
Ser Phe Ser Thr Lys Lys Ser Gln Pro Pro Pro Gln Pro Ala Arg
                    3075                3080                3085
Ser Ala Ser Ser Ser Thr Ile Asn Leu Met Val Ser Thr Glu Pro Leu
                    3090                3095                3100
Ala Leu Thr Glu Thr Asp Ile Cys Lys Leu Pro Lys Asp Glu Gly Thr
3105                3110                3115                3120
Cys Arg Asp Phe Ile Leu Lys Trp Tyr Tyr Asp Pro Asn Thr Lys Ser
                    3125                3130                3135
Cys Ala Arg Phe Trp Tyr Gly Gly Cys Gly Gly Asn Glu Asn Lys Phe
                    3140                3145                3150
Gly Ser Gln Lys Glu Cys Glu Lys Val Cys Ala Pro Val Leu Ala Lys
                    3155                3160                3165
Pro Gly Val Ile Ser Val Met Gly Thr
                    3170                3175
```

<210> SEQ ID NO 16
<211> LENGTH: 2615
<212> TYPE: PRT
<213> ORGANISM: Homo sapiens

<400> SEQUENCE: 16

Met Lys Ile Leu Leu Ile Ile Phe Val Leu Ile Ile Trp Thr Glu Thr
1               5                   10                  15

Leu Ala Asp Gln Ser Pro Gly Pro Gly Pro Val Tyr Ala Asp Val Val
            20                  25                  30

Phe Leu Val Asp Ser Ser Asp His Leu Gly Pro Lys Ser Phe Pro Phe
        35                  40                  45

Val Lys Thr Phe Ile Asn Lys Met Ile Asn Ser Leu Pro Ile Glu Ala
    50                  55                  60

Asn Lys Tyr Arg Val Ala Leu Ala Gln Tyr Ser Asp Glu Phe His Ser
65                  70                  75                  80

Glu Phe His Leu Ser Thr Phe Lys Gly Arg Ser Pro Met Leu Asn His
                85                  90                  95

Leu Lys Lys Asn Phe Gln Phe Ile Gly Gly Ser Leu Gln Ile Gly Lys
            100                 105                 110

Ala Leu Gln Glu Ala His Arg Thr Tyr Phe Ser Ala Pro Ile Asn Gly
        115                 120                 125

Arg Asp Arg Lys Gln Phe Pro Pro Ile Leu Val Val Leu Ala Ser Ala
    130                 135                 140

Glu Ser Glu Asp Glu Val Glu Glu Ala Ser Lys Ala Leu Gln Lys Asp
145                 150                 155                 160

Gly Val Lys Ile Ile Ser Val Gly Val Gln Lys Ala Ser Glu Glu Asn
                165                 170                 175

Leu Lys Ala Met Ala Thr Ser His Phe His Phe Asn Leu Arg Thr Ile
            180                 185                 190

Arg Asp Leu Ser Thr Phe Ser Gln Asn Met Thr Gln Ile Ile Lys Asp
        195                 200                 205

Val Thr Lys Tyr Lys Glu Gly Ala Val Asp Ala Asp Met Gln Val His
    210                 215                 220

Phe Pro Ile Ser Cys Gln Lys Asp Ser Leu Ala Asp Leu Val Phe Leu
225                 230                 235                 240

Val Asp Glu Ser Leu Gly Thr Gly Gly Asn Leu Arg His Leu Gln Thr
                245                 250                 255

Phe Leu Glu Asn Ile Thr Ser Ser Met Asp Val Lys Gly Asn Cys Met
            260                 265                 270

Arg Leu Gly Leu Met Ser Tyr Ser Asn Ser Ala Lys Thr Ile Ser Phe
        275                 280                 285

Leu Lys Ser Ser Thr Thr Gln Ser Glu Phe Gln Gln Gln Ile Lys Asn
    290                 295                 300

Leu Ser Ile Gln Val Gly Lys Ser Asn Thr Gly Ala Ala Ile Asp Gln
305                 310                 315                 320

Met Arg Arg Asp Gly Phe Ser Glu Ser Tyr Gly Ser Arg Arg Ala Gln
                325                 330                 335

Gly Val Pro Gln Ile Ala Val Leu Val Thr His Arg Pro Ser Asp Asp
            340                 345                 350

Glu Val His Asp Ala Ala Leu Asn Leu Arg Leu Glu Asp Val Asn Val
        355                 360                 365

Phe Ala Leu Ser Ile Gln Gly Ala Asn Asn Thr Gln Leu Glu Glu Ile

```
              370                 375                 380
Val Ser Tyr Pro Pro Glu Gln Thr Ile Ser Thr Leu Lys Ser Tyr Ala
385                 390                 395                 400

Asp Leu Glu Thr Tyr Ser Thr Lys Phe Leu Lys Lys Leu Gln Asn Glu
                405                 410                 415

Ile Trp Ser Gln Ile Ser Thr Tyr Ala Glu Gln Arg Asn Leu Asp Lys
                420                 425                 430

Thr Gly Cys Val Asp Thr Lys Glu Ala Asp Ile His Phe Leu Ile Asp
            435                 440                 445

Gly Ser Ser Ser Ile Gln Glu Lys Gln Phe Glu Gln Ile Lys Arg Phe
            450                 455                 460

Met Leu Glu Val Thr Glu Met Phe Ser Ile Gly Pro Asp Lys Val Arg
465                 470                 475                 480

Val Gly Val Val Gln Tyr Ser Asp Asp Thr Glu Val Glu Phe Tyr Ile
                485                 490                 495

Thr Asp Tyr Ser Asn Asp Ile Asp Leu Arg Lys Ala Ile Phe Asn Ile
                500                 505                 510

Lys Gln Leu Thr Gly Gly Thr Tyr Thr Gly Lys Ala Leu Asp Tyr Ile
            515                 520                 525

Leu Gln Ile Ile Lys Asn Gly Met Lys Asp Arg Met Ser Lys Val Pro
            530                 535                 540

Cys Tyr Leu Ile Val Leu Thr Asp Gly Met Ser Thr Asp Arg Val Val
545                 550                 555                 560

Glu Pro Ala Lys Arg Leu Arg Ala Glu Gln Ile Thr Val His Ala Val
                565                 570                 575

Gly Ile Gly Ala Ala Asn Lys Ile Glu Leu Gln Glu Ile Ala Gly Lys
                580                 585                 590

Glu Glu Arg Val Ser Phe Gly Gln Asn Phe Asp Ala Leu Lys Ser Ile
            595                 600                 605

Lys Asn Glu Val Arg Glu Ile Cys Ala Glu Lys Gly Cys Glu Asp
            610                 615                 620

Met Lys Ala Asp Ile Met Phe Leu Val Asp Ser Ser Trp Ser Ile Gly
625                 630                 635                 640

Asn Glu Asn Phe Arg Lys Met Lys Ile Phe Met Lys Asn Leu Leu Thr
                645                 650                 655

Lys Ile Gln Ile Gly Ala Asp Lys Thr Gln Ile Gly Val Val Gln Phe
                660                 665                 670

Ser Asp Lys Thr Lys Glu Glu Phe Gln Leu Asn Arg Tyr Phe Thr Gln
            675                 680                 685

Gln Glu Ile Ser Asp Ala Ile Asp Arg Met Ser Leu Ile Asn Glu Gly
            690                 695                 700

Thr Leu Thr Gly Lys Ala Leu Asn Phe Val Gly Gln Tyr Phe Thr His
705                 710                 715                 720

Ser Lys Gly Ala Arg Leu Gly Ala Lys Lys Phe Leu Ile Leu Ile Thr
                725                 730                 735

Asp Gly Val Ala Gln Asp Asp Val Arg Asp Pro Ala Arg Ile Leu Arg
                740                 745                 750

Gly Lys Asp Val Thr Ile Phe Ser Val Gly Val Tyr Asn Ala Asn Arg
            755                 760                 765

Ser Gln Leu Glu Glu Ile Ser Gly Asp Ser Ser Leu Val Phe His Val
        770                 775                 780

Glu Asn Phe Asp His Leu Lys Ala Leu Glu Arg Lys Leu Ile Phe Arg
785                 790                 795                 800
```

```
Val Cys Ala Leu His Asp Cys Lys Arg Ile Thr Leu Leu Asp Val Val
            805                 810                 815

Phe Val Leu Asp His Ser Gly Ser Ile Lys Lys Gln Tyr Gln Asp His
            820                 825                 830

Met Ile Asn Leu Thr Ile His Leu Val Lys Lys Ala Asp Val Gly Arg
            835                 840                 845

Asp Arg Val Gln Phe Gly Ala Leu Lys Tyr Ser Asp Gln Pro Asn Ile
            850                 855                 860

Leu Phe Tyr Leu Asn Thr Tyr Ser Asn Arg Ser Ala Ile Ile Glu Asn
865                 870                 875                 880

Leu Arg Lys Arg Arg Asp Thr Gly Gly Asn Thr Tyr Thr Ala Lys Ala
            885                 890                 895

Leu Lys His Ala Asn Ala Leu Phe Thr Glu Glu His Gly Ser Arg Ile
            900                 905                 910

Lys Gln Asn Val Lys Gln Met Leu Ile Val Ile Thr Asp Gly Glu Ser
            915                 920                 925

His Asp His Asp Gln Leu Asn Asp Thr Ala Leu Glu Leu Arg Asn Lys
            930                 935                 940

Gly Ile Thr Ile Phe Ala Val Gly Val Gly Lys Ala Asn Gln Lys Glu
945                 950                 955                 960

Leu Glu Gly Met Ala Gly Asn Lys Asn Asn Thr Ile Tyr Val Asp Asn
            965                 970                 975

Phe Asp Lys Leu Lys Asp Val Phe Thr Leu Val Gln Glu Arg Met Cys
            980                 985                 990

Thr Glu Ala Pro Glu Val Cys His Leu Gln Glu Ala Asp Val Ile Phe
            995                 1000                1005

Leu Cys Asp Gly Ser Asp Arg Val Ser Asn Ser Asp Phe Val Thr Met
            1010                1015                1020

Thr Thr Phe Leu Ser Asp Leu Ile Asp Asn Phe Asp Ile Gln Ser Gln
1025                1030                1035                1040

Arg Met Lys Ile Gly Met Ala Gln Phe Gly Ser Asn Tyr Gln Ser Ile
            1045                1050                1055

Ile Glu Leu Lys Asn Ser Leu Thr Lys Thr Gln Trp Lys Thr Gln Ile
            1060                1065                1070

Gln Asn Val Ser Lys Ser Gly Gly Phe Pro Arg Ile Asp Phe Ala Leu
            1075                1080                1085

Lys Lys Val Ser Asn Met Phe Asn Leu His Ala Gly Gly Arg Arg Asn
            1090                1095                1100

Ala Gly Val Pro Gln Thr Leu Val Val Ile Thr Ser Gly Asp Pro Arg
1105                1110                1115                1120

Tyr Asp Val Ala Asp Ala Val Lys Thr Leu Lys Asp Leu Gly Ile Cys
            1125                1130                1135

Val Leu Val Leu Gly Ile Gly Asp Val Tyr Lys Glu His Leu Leu Pro
            1140                1145                1150

Ile Thr Gly Asn Ser Glu Lys Ile Ile Thr Phe Gln Asp Phe Asp Lys
            1155                1160                1165

Leu Lys Asn Val Asp Val Lys Lys Arg Ile Ile Arg Glu Ile Cys Gln
            1170                1175                1180

Ser Cys Gly Lys Thr Asn Cys Phe Met Asp Ile Val Val Gly Phe Asp
1185                1190                1195                1200

Ile Ser Thr His Val Gln Gly Gln Pro Leu Phe Gln Gly His Pro Gln
            1205                1210                1215
```

-continued

Leu Glu Ser Tyr Leu Pro Gly Ile Leu Glu Asp Ile Ser Ser Ile Lys
            1220                1225                1230

Gly Val Ser Cys Gly Ala Gly Thr Glu Ala Gln Val Ser Leu Ala Phe
        1235                1240                1245

Lys Val Asn Ser Asp Gln Gly Phe Pro Ala Lys Phe Gln Ile Tyr Gln
        1250                1255                1260

Lys Ala Val Phe Asp Ser Leu Leu Gln Val Asn Val Ser Gly Pro Thr
1265                1270                1275                1280

His Leu Asn Ala Gln Phe Leu Arg Ser Leu Trp Asp Thr Phe Lys Asp
                1285                1290                1295

Lys Ser Ala Ser Arg Gly Gln Val Leu Leu Ile Phe Ser Asp Gly Leu
            1300                1305                1310

Gln Ser Glu Ser Asn Ile Met Leu Glu Asn Gln Ser Asp Arg Leu Arg
        1315                1320                1325

Glu Ala Gly Leu Asp Ala Leu Leu Val Val Ser Leu Asn Thr Thr Ala
        1330                1335                1340

His His Glu Phe Ser Ser Phe Glu Phe Gly Lys Arg Phe Asp Tyr Arg
1345                1350                1355                1360

Thr His Leu Thr Ile Gly Met Arg Glu Leu Gly Lys Lys Leu Ser Gln
                1365                1370                1375

Tyr Leu Gly Asn Ile Ala Glu Arg Thr Cys Cys Cys Thr Phe Cys Lys
            1380                1385                1390

Cys Pro Gly Ile Pro Gly Pro His Gly Thr Arg Gly Leu Gln Ala Met
        1395                1400                1405

Lys Gly Ser Gln Gly Leu Lys Gly Ser Arg Gly His Arg Gly Glu Asp
        1410                1415                1420

Gly Asn Pro Gly Val Arg Gly Asp Thr Gly Pro Gln Gly Asp Lys Gly
1425                1430                1435                1440

Ile Ala Gly Cys Pro Gly Ala Trp Gly Gln Lys Gly Leu Lys Gly Phe
                1445                1450                1455

Ser Gly Pro Lys Gly Gly His Gly Asp Asp Gly Ile Asp Gly Leu Asp
            1460                1465                1470

Gly Glu Glu Gly Cys His Gly Phe Pro Gly Ile Lys Gly Glu Lys Gly
        1475                1480                1485

Asp Pro Gly Ser Gln Gly Ser Pro Gly Ser Arg Gly Ala Pro Gly Gln
        1490                1495                1500

Tyr Gly Glu Lys Gly Phe Pro Gly Asp Pro Gly Asn Pro Gly Gln Asn
1505                1510                1515                1520

Asn Asn Ile Lys Gly Gln Lys Gly Ser Lys Gly Glu Gln Gly Arg Gln
                1525                1530                1535

Gly Arg Ser Gly Gln Lys Gly Val Gln Gly Ser Pro Ser Arg Gly
            1540                1545                1550

Ser Arg Gly Arg Glu Gly Gln Arg Gly Leu Arg Gly Val Ser Gly Glu
        1555                1560                1565

Pro Gly Asn Pro Gly Pro Thr Gly Thr Leu Gly Ala Glu Gly Leu Gln
        1570                1575                1580

Gly Pro Gln Gly Ser Gln Gly Asn Pro Gly Arg Lys Gly Glu Lys Gly
1585                1590                1595                1600

Ser Gln Gly Gln Lys Gly Pro Gln Gly Ser Pro Gly Leu Met Gly Ala
                1605                1610                1615

Lys Gly Ser Thr Gly Arg Pro Gly Leu Leu Gly Lys Lys Gly Glu Pro
            1620                1625                1630

Gly Leu Pro Gly Asp Leu Gly Pro Val Gly Gln Thr Gly Gln Arg Gly

```
                1635                1640                1645

Arg Gln Gly Asp Ser Gly Ile Pro Gly Tyr Gly Gln Met Gly Arg Lys
           1650                1655                1660

Gly Val Lys Gly Pro Arg Gly Phe Pro Gly Asp Ala Gly Gln Lys Gly
1665                1670                1675                1680

Asp Ile Gly Asn Pro Gly Ile Pro Gly Pro Gly Pro Lys Gly Phe
                1685                1690                1695

Arg Gly Leu Ala Leu Thr Val Gly Leu Lys Gly Glu Glu Gly Ser Arg
           1700                1705                1710

Gly Leu Pro Gly Pro Pro Gly Gln Arg Gly Ile Lys Gly Met Ala Gly
           1715                1720                1725

Gln Pro Val Tyr Ser Gln Cys Asp Leu Ile Arg Phe Leu Arg Glu His
           1730                1735                1740

Ser Pro Cys Trp Lys Glu Lys Cys Pro Ala Tyr Pro Thr Glu Leu Val
1745                1750                1755                1760

Phe Ala Leu Asp Asn Ser Tyr Asp Val Thr Glu Glu Ser Phe Asn Lys
                1765                1770                1775

Thr Arg Asp Ile Ile Thr Ser Ile Val Asn Asp Leu Asn Ile Arg Glu
           1780                1785                1790

Asn Asn Cys Pro Val Gly Ala Arg Val Ala Met Val Ser Tyr Asn Ser
           1795                1800                1805

Gly Thr Ser Tyr Leu Ile Arg Trp Ser Asp Tyr Asn Arg Lys Lys Gln
           1810                1815                1820

Leu Leu Gln Gln Leu Ser Gln Ile Lys Tyr Gln Asp Thr Thr Glu Pro
1825                1830                1835                1840

Arg Asp Val Gly Asn Ala Met Arg Phe Val Thr Arg Asn Val Phe Lys
                1845                1850                1855

Arg Thr Tyr Ala Gly Ala Asn Val Arg Arg Val Ala Val Phe Phe Ser
           1860                1865                1870

Asn Gly Gln Thr Ala Ser Arg Ser Ser Ile Ile Thr Ala Thr Met Glu
           1875                1880                1885

Phe Ser Ala Leu Asp Ile Ser Pro Thr Val Phe Ala Phe Asp Glu Arg
           1890                1895                1900

Val Phe Leu Glu Ala Phe Gly Phe Asp Asn Thr Gly Thr Phe Gln Val
1905                1910                1915                1920

Ile Pro Val Pro Pro Asn Gly Glu Asn Gln Thr Leu Glu Arg Leu Arg
                1925                1930                1935

Arg Cys Ala Leu Cys Tyr Asp Lys Cys Phe Pro Asn Ala Cys Ile Arg
           1940                1945                1950

Glu Ala Phe Leu Pro Glu Asp Ser Tyr Met Asp Val Val Phe Leu Ile
           1955                1960                1965

Asp Asn Ser Arg Asn Ile Ala Lys Asp Glu Phe Lys Ala Val Lys Ala
           1970                1975                1980

Leu Val Ser Ser Val Ile Asp Asn Phe Asn Ile Ala Ser Asp Pro Leu
1985                1990                1995                2000

Ile Ser Asp Ser Gly Asp Arg Ile Ala Leu Leu Ser Tyr Ser Pro Trp
                2005                2010                2015

Glu Ser Ser Arg Arg Lys Met Gly Thr Val Lys Thr Glu Phe Asp Phe
           2020                2025                2030

Ile Thr Tyr Asp Asn Gln Leu Leu Met Lys Asn His Ile Gln Thr Ser
           2035                2040                2045

Phe Gln Gln Leu Asn Gly Glu Ala Thr Ile Gly Arg Ala Leu Leu Trp
           2050                2055                2060
```

-continued

```
Thr Thr Glu Asn Leu Phe Pro Glu Thr Pro Tyr Leu Arg Lys His Lys
2065                2070                2075                2080

Val Ile Phe Val Val Ser Ala Gly Glu Asn Tyr Glu Arg Lys Glu Phe
            2085                2090                2095

Val Lys Met Met Ala Leu Arg Ala Lys Cys Gln Gly Tyr Val Ile Phe
        2100                2105                2110

Val Ile Ser Leu Gly Ser Thr Arg Lys Asp Asp Met Glu Glu Leu Ala
    2115                2120                2125

Ser Tyr Pro Leu Asp Gln His Leu Ile Gln Leu Gly Arg Ile His Lys
2130                2135                2140

Pro Asp Leu Asn Tyr Ile Ala Lys Phe Leu Lys Pro Phe Leu Tyr Ser
2145                2150                2155                2160

Val Arg Arg Gly Phe Asn Gln Tyr Pro Pro Met Leu Glu Asp Ala
            2165                2170                2175

Cys Arg Leu Ile Asn Leu Gly Gly Glu Asn Ile Gln Asn Asp Gly Phe
        2180                2185                2190

Gln Phe Val Thr Glu Leu Gln Glu Asp Phe Leu Gly Asn Gly Phe
    2195                2200                2205

Ile Gly Gln Glu Leu Asn Ser Gly Arg Glu Ser Pro Phe Val Lys Thr
    2210                2215                2220

Glu Asp Asn Gly Ser Asp Tyr Leu Val Tyr Leu Pro Ser Gln Met Phe
2225                2230                2235                2240

Glu Pro Gln Lys Leu Met Ile Asn Tyr Glu Lys Asp Gln Lys Ser Ala
            2245                2250                2255

Glu Ile Ala Ser Leu Thr Ser Gly His Glu Asn Tyr Gly Arg Lys Glu
        2260                2265                2270

Glu Pro Asp His Thr Tyr Glu Pro Gly Asp Val Ser Leu Gln Glu Tyr
    2275                2280                2285

Tyr Met Asp Val Ala Phe Leu Ile Asp Ala Ser Gln Arg Val Gly Ser
    2290                2295                2300

Asp Glu Phe Lys Glu Val Lys Ala Phe Ile Thr Ser Val Leu Asp Tyr
2305                2310                2315                2320

Phe His Ile Ala Pro Thr Pro Leu Thr Ser Thr Leu Gly Asp Arg Val
            2325                2330                2335

Ala Val Leu Ser Tyr Ser Pro Pro Gly Tyr Met Pro Asn Thr Glu Glu
        2340                2345                2350

Cys Pro Val Tyr Leu Glu Phe Asp Leu Val Thr Tyr Asn Ser Ile His
    2355                2360                2365

Gln Met Lys His His Leu Gln Asp Ser Gln Gln Leu Asn Gly Asp Val
    2370                2375                2380

Phe Ile Gly His Ala Leu Gln Trp Thr Ile Asp Asn Val Phe Val Gly
2385                2390                2395                2400

Thr Pro Asn Leu Arg Lys Asn Lys Val Ile Phe Val Ile Ser Ala Gly
            2405                2410                2415

Glu Thr Asn Ser Leu Asp Lys Asp Val Leu Arg Asn Val Ser Leu Arg
        2420                2425                2430

Ala Lys Cys Gln Gly Tyr Ser Ile Phe Val Phe Ser Phe Gly Pro Lys
    2435                2440                2445

His Asn Asp Lys Glu Leu Glu Glu Leu Ala Ser His Pro Leu Asp His
    2450                2455                2460

His Leu Val Gln Leu Gly Arg Thr His Lys Pro Asp Trp Asn Tyr Ile
2465                2470                2475                2480
```

```
Ile Lys Phe Val Lys Pro Phe Val His Leu Ile Arg Arg Ala Ile Asn
                2485                2490                2495

Lys Tyr Pro Thr Glu Asp Met Lys Ala Thr Cys Val Asn Met Thr Ser
            2500                2505                2510

Pro Asn Pro Glu Asn Gly Gly Thr Glu Asn Thr Val Leu Leu Leu Pro
            2515                2520                2525

Gly Ile Tyr Glu Ile Lys Thr Glu Asn Gly Asp Leu Phe Asp Glu Phe
            2530                2535                2540

Asp Ser Gln Ala Gln His Leu Leu Val Leu Gly Asn Asn His Ser Ser
2545                2550                2555                2560

Gly Ser Glu Thr Ala Thr Asp Leu Met Gln Lys Leu Tyr Leu Phe
                2565                2570                2575

Ser Thr Glu Lys Leu Ala Met Lys Asp Lys Glu Lys Ala His Leu Glu
            2580                2585                2590

Glu Ile Ser Ala Leu Val Val Asp Lys Gln Gln Glu Lys Glu Asp Lys
            2595                2600                2605

Glu Met Glu Ala Thr Asp Ile
    2610                2615

<210> SEQ ID NO 17
<211> LENGTH: 2263
<212> TYPE: PRT
<213> ORGANISM: Homo sapiens

<400> SEQUENCE: 17

Met Met Leu Leu Ile Leu Phe Leu Val Ile Cys Ser His Ile Ser
1               5                   10                  15

Val Asn Gln Asp Ser Gly Pro Glu Tyr Ala Asp Val Val Phe Leu Val
                20                  25                  30

Asp Ser Ser Asp Arg Leu Gly Ser Lys Ser Phe Pro Val Lys Met
            35                  40                  45

Phe Ile Thr Lys Met Ile Ser Ser Leu Pro Ile Glu Ala Asp Lys Tyr
    50                  55                  60

Arg Val Ala Leu Ala Gln Tyr Ser Asp Lys Leu His Ser Glu Phe His
65                  70                  75                  80

Leu Ser Thr Phe Lys Gly Arg Ser Pro Met Leu Asn His Leu Arg Lys
                85                  90                  95

Asn Phe Gly Phe Ile Gly Gly Ser Leu Gln Ile Gly Lys Ala Leu Gln
            100                 105                 110

Glu Ala His Arg Thr Tyr Phe Ser Ala Pro Ala Asn Gly Arg Asp Lys
        115                 120                 125

Lys Gln Phe Pro Pro Ile Leu Val Val Leu Ala Ser Ser Glu Ser Glu
    130                 135                 140

Asp Asn Val Glu Glu Ala Ser Lys Ala Leu Arg Lys Asp Gly Val Lys
145                 150                 155                 160

Ile Ile Ser Val Gly Val Gln Lys Ala Ser Glu Glu Asn Leu Lys Ala
                165                 170                 175

Met Ala Thr Ser Gln Phe His Phe Asn Leu Arg Thr Val Arg Asp Leu
            180                 185                 190

Ser Met Phe Ser Gln Asn Met Thr His Ile Ile Lys Asp Val Ile Lys
        195                 200                 205

Tyr Lys Glu Gly Ala Val Asp Asp Ile Phe Val Glu Ala Cys Gln Gly
    210                 215                 220

Pro Ser Met Ala Asp Val Val Phe Leu Leu Asp Met Ser Ile Asn Gly
225                 230                 235                 240
```

```
Ser Glu Glu Asn Phe Asp Tyr Leu Lys Gly Phe Leu Glu Glu Ser Val
            245                 250                 255

Ser Ala Leu Asp Ile Lys Glu Asn Cys Met Arg Val Gly Leu Val Ala
            260                 265                 270

Tyr Ser Asn Glu Thr Lys Val Ile Asn Ser Leu Ser Met Gly Ile Asn
            275                 280                 285

Lys Ser Glu Val Leu Gln His Ile Gln Asn Leu Ser Pro Arg Thr Gly
            290                 295                 300

Lys Ala Tyr Thr Gly Ala Ala Ile Lys Lys Leu Arg Lys Glu Val Phe
305                 310                 315                 320

Ser Ala Arg Asn Gly Ser Arg Lys Asn Gln Gly Val Pro Gln Ile Ala
            325                 330                 335

Val Leu Val Thr His Arg Asp Ser Glu Asp Asn Val Thr Lys Ala Ala
            340                 345                 350

Val Asn Leu Arg Arg Glu Gly Val Thr Ile Phe Thr Leu Gly Ile Glu
            355                 360                 365

Gly Ala Ser Asp Thr Gln Leu Glu Lys Ile Ala Ser His Pro Ala Glu
            370                 375                 380

Gln Tyr Val Ser Lys Leu Lys Thr Phe Ala Asp Leu Ala Ala His Asn
385                 390                 395                 400

Gln Thr Phe Leu Lys Lys Leu Arg Asn Gln Ile Thr His Thr Val Ser
            405                 410                 415

Val Phe Ser Glu Arg Thr Glu Thr Leu Lys Ser Gly Cys Val Asp Thr
            420                 425                 430

Glu Glu Ala Asp Ile Tyr Leu Leu Ile Asp Gly Ser Gly Ser Thr Gln
            435                 440                 445

Ala Thr Asp Phe His Glu Met Lys Thr Phe Leu Ser Glu Val Val Gly
            450                 455                 460

Met Phe Asn Ile Ala Pro His Lys Val Arg Val Gly Ala Val Gln Tyr
465                 470                 475                 480

Ala Asp Ser Trp Asp Leu Glu Phe Glu Ile Asn Lys Tyr Ser Asn Lys
            485                 490                 495

Gln Asp Leu Gly Lys Ala Ile Glu Asn Ile Arg Gln Met Gly Gly Asn
            500                 505                 510

Thr Asn Thr Gly Ala Ala Leu Asn Phe Thr Leu Ser Leu Leu Gln Lys
            515                 520                 525

Ala Lys Lys Gln Arg Gly Asn Lys Val Pro Cys His Leu Val Val Leu
530                 535                 540

Thr Asn Gly Met Ser Lys Asp Ser Ile Leu Glu Pro Ala Asn Arg Leu
545                 550                 555                 560

Arg Glu Glu His Ile Arg Val Tyr Ala Ile Gly Ile Lys Glu Ala Asn
            565                 570                 575

Gln Thr Gln Leu Arg Glu Ile Ala Gly Glu Lys Arg Val Tyr Tyr
            580                 585                 590

Val His Asp Phe Asp Ala Leu Lys Asp Ile Arg Asn Gln Val Val Gln
            595                 600                 605

Glu Ile Cys Thr Glu Ala Cys Lys Glu Met Lys Ala Asp Ile Met
            610                 615                 620

Phe Leu Val Asp Ser Ser Gly Ser Ile Gly Pro Glu Asn Phe Ser Lys
625                 630                 635                 640

Met Lys Thr Phe Met Lys Asn Leu Val Ser Lys Ser Gln Ile Gly Pro
            645                 650                 655
```

-continued

Asp Arg Val Gln Ile Gly Val Val Gln Phe Ser Asp Ile Asn Lys Glu
        660                 665                 670

Glu Phe Gln Leu Asn Arg Phe Met Ser Gln Ser Asp Ile Ser Asn Ala
        675                 680                 685

Ile Asp Gln Met Ala His Ile Gly Gln Thr Thr Leu Thr Gly Ser Ala
        690                 695                 700

Leu Ser Phe Val Ser Gln Tyr Phe Ser Pro Thr Lys Gly Ala Arg Pro
705                 710                 715                 720

Asn Ile Arg Lys Phe Leu Ile Leu Ile Thr Asp Gly Glu Ala Gln Asp
                    725                 730                 735

Ile Val Lys Glu Pro Ala Val Val Leu Arg Gln Glu Gly Val Ile Ile
        740                 745                 750

Tyr Ser Val Gly Val Phe Gly Ser Asn Val Thr Gln Leu Glu Glu Ile
        755                 760                 765

Ser Gly Arg Pro Glu Met Val Phe Tyr Val Glu Asn Phe Asp Ile Leu
        770                 775                 780

Gln Arg Ile Glu Asp Asp Leu Val Phe Gly Ile Cys Ser Pro Arg Glu
785                 790                 795                 800

Glu Cys Lys Arg Ile Glu Val Leu Asp Val Val Phe Val Ile Asp Ser
                    805                 810                 815

Ser Gly Ser Ile Asp Tyr Asp Glu Tyr Asn Ile Met Lys Asp Phe Met
        820                 825                 830

Ile Gly Leu Val Lys Lys Ala Asp Val Gly Lys Asn Gln Val Arg Phe
        835                 840                 845

Gly Ala Leu Lys Tyr Ala Asp Asp Pro Glu Val Leu Phe Tyr Leu Asp
850                 855                 860

Asp Phe Gly Thr Lys Leu Glu Val Ile Ser Val Leu Gln Asn Asp Gln
865                 870                 875                 880

Ala Met Gly Gly Ser Thr Tyr Thr Ala Glu Ala Leu Gly Phe Ser Asp
                    885                 890                 895

His Met Phe Thr Glu Ala Arg Gly Ser Arg Leu Asn Lys Gly Val Pro
        900                 905                 910

Gln Val Leu Ile Val Ile Thr Asp Gly Glu Ser His Asp Ala Asp Lys
        915                 920                 925

Leu Asn Ala Thr Ala Lys Ala Leu Arg Asp Lys Gly Ile Leu Val Leu
        930                 935                 940

Ala Val Gly Ile Asp Gly Ala Asn Pro Val Glu Leu Leu Ala Met Ala
945                 950                 955                 960

Gly Ser Ser Asp Lys Tyr Phe Phe Val Glu Thr Phe Gly Gly Leu Lys
                    965                 970                 975

Gly Ile Phe Ser Asp Val Thr Ala Ser Val Cys Asn Ser Ser Lys Val
                    980                 985                 990

Asp Cys Glu Ile Asp Lys Val Asp Leu Val Phe Leu Met Asp Gly Ser
        995                 1000                1005

Thr Ser Ile Gln Pro Asn Asp Phe Lys Lys Met Lys Glu Phe Leu Ala
        1010                1015                1020

Ser Val Val Gln Asp Phe Asp Val Ser Leu Asn Arg Val Arg Ile Gly
1025                1030                1035                1040

Ala Ala Gln Phe Ser Asp Thr Tyr His Pro Glu Phe Pro Leu Gly Thr
                    1045                1050                1055

Phe Ile Gly Glu Lys Glu Ile Ser Phe Gln Ile Glu Asn Ile Lys Gln
                    1060                1065                1070

Ile Phe Gly Asn Thr His Ile Gly Ala Ala Leu Arg Glu Val Glu His

-continued

```
            1075                1080                1085
Tyr Phe Arg Pro Asp Met Gly Ser Arg Ile Asn Thr Gly Thr Pro Gln
            1090                1095                1100
Val Leu Leu Val Leu Thr Asp Gly Gln Ser Gln Asp Glu Val Ala Gln
1105                1110                1115                1120
Ala Ala Glu Ala Leu Arg His Arg Gly Ile Asp Ile Tyr Ser Val Gly
            1125                1130                1135
Ile Gly Asp Val Asp Gln Gln Leu Ile Gln Ile Thr Gly Thr Ala
            1140                1145                1150
Glu Lys Lys Leu Thr Val His Asn Phe Asp Glu Leu Lys Lys Val Asn
            1155                1160                1165
Lys Arg Ile Val Arg Asn Ile Cys Thr Thr Ala Gly Glu Ser Asn Cys
            1170                1175                1180
Phe Val Asp Val Val Gly Phe Asp Val Ser Thr Gln Glu Lys Gly
1185                1190                1195                1200
Gln Thr Leu Leu Glu Gly Gln Pro Trp Met Glu Thr Tyr Leu Gln Asp
            1205                1210                1215
Ile Leu Arg Ala Ile Ser Ser Leu Asn Gly Val Ser Cys Glu Val Gly
            1220                1225                1230
Thr Glu Thr Gln Val Ser Val Ala Phe Gln Val Thr Asn Ala Met Glu
            1235                1240                1245
Lys Tyr Ser Pro Lys Phe Glu Ile Tyr Ser Glu Asn Ile Leu Asn Ser
            1250                1255                1260
Leu Lys Asp Ile Thr Val Lys Gly Pro Ser Leu Leu Asn Ala Asn Leu
1265                1270                1275                1280
Leu Asp Ser Leu Trp Asp Thr Phe Gln Asn Lys Ser Ala Ala Arg Gly
            1285                1290                1295
Lys Val Val Leu Leu Phe Ser Asp Gly Leu Asp Asp Val Glu Lys
            1300                1305                1310
Leu Glu Gln Lys Ser Asp Glu Leu Arg Lys Glu Gly Leu Asn Ala Leu
            1315                1320                1325
Ile Thr Val Ala Leu Asp Gly Pro Ala Asp Ser Ser Asp Leu Ala Asp
            1330                1335                1340
Leu Pro Tyr Ile Glu Phe Gly Lys Gly Phe Glu Tyr Arg Thr Gln Leu
1345                1350                1355                1360
Ser Ile Gly Met Arg Glu Leu Gly Ser Arg Leu Ser Lys Gln Leu Val
            1365                1370                1375
Asn Val Ala Glu Arg Thr Cys Cys Cys Leu Phe Cys Lys Cys Ile Gly
            1380                1385                1390
Gly Asp Gly Thr Met Gly Asp Pro Gly Pro Pro Gly Lys Arg Gly Pro
            1395                1400                1405
Pro Gly Phe Lys Gly Ser Glu Gly Tyr Leu Gly Glu Glu Gly Ile Ala
            1410                1415                1420
Gly Glu Arg Gly Ala Pro Gly Pro Val Gly Glu Gln Gly Thr Lys Gly
1425                1430                1435                1440
Cys Tyr Gly Thr Lys Gly Pro Lys Gly Asn Arg Gly Leu Asn Gly Gln
            1445                1450                1455
Glu Gly Glu Val Gly Glu Asn Gly Ile Asp Gly Leu Asn Gly Glu Gln
            1460                1465                1470
Gly Asp Asn Gly Leu Pro Gly Arg Lys Gly Lys Gly Asp Glu Gly
            1475                1480                1485
Ser Gln Gly Ser Pro Gly Lys Arg Gly Thr Pro Gly Asp Arg Gly Ala
            1490                1495                1500
```

-continued

```
Lys Gly Leu Arg Gly Asp Pro Gly Ala Pro Gly Val Asp Ser Ser Ile
1505                1510                1515                1520

Glu Gly Pro Thr Gly Leu Lys Gly Glu Arg Gly Arg Gln Gly Arg Arg
                1525                1530                1535

Gly Trp Pro Gly Pro Pro Gly Thr Pro Gly Ser Arg Arg Lys Thr Ala
                1540                1545                1550

Ala His Gly Arg Arg Gly His Thr Gly Pro Gln Gly Thr Ala Gly Ile
                1555                1560                1565

Pro Gly Pro Asp Gly Leu Glu Gly Ser Leu Gly Leu Lys Gly Pro Gln
                1570                1575                1580

Gly Pro Arg Gly Glu Ala Gly Val Lys Gly Glu Lys Gly Gly Val Gly
1585                1590                1595                1600

Ser Lys Gly Pro Gln Gly Pro Pro Gly Pro Gly Gly Glu Ala Gly Asn
                1605                1610                1615

Gln Gly Arg Leu Gly Ser Gln Gly Asn Lys Gly Glu Pro Gly Asp Leu
                1620                1625                1630

Gly Glu Lys Gly Ala Val Gly Phe Pro Gly Pro Arg Gly Leu Gln Gly
                1635                1640                1645

Asn Asp Gly Ser Pro Gly Tyr Gly Ser Val Gly Arg Lys Gly Ala Lys
                1650                1655                1660

Gly Gln Glu Gly Phe Pro Gly Glu Ser Gly Pro Lys Gly Glu Ile Gly
1665                1670                1675                1680

Asp Pro Gly Gly Pro Gly Glu Thr Gly Leu Lys Gly Ala Arg Gly Lys
                1685                1690                1695

Met Ile Ser Ala Gly Leu Pro Gly Glu Met Gly Ser Pro Gly Glu Pro
                1700                1705                1710

Gly Pro Pro Gly Arg Lys Gly Val Lys Gly Ala Lys Gly Leu Ala Ser
                1715                1720                1725

Phe Ser Thr Cys Glu Leu Ile Gln Tyr Val Arg Asp Arg Ser Pro Gly
                1730                1735                1740

Arg His Gly Lys Pro Glu Cys Pro Val His Pro Thr Glu Leu Val Phe
1745                1750                1755                1760

Ala Leu Asp His Ser Arg Asp Val Thr Glu Gln Glu Phe Glu Arg Met
                1765                1770                1775

Lys Glu Met Met Ala Phe Leu Val Arg Asp Ile Lys Val Arg Glu Asn
                1780                1785                1790

Ser Cys Pro Val Gly Ala His Ile Ala Ile Leu Ser Tyr Asn Ser His
                1795                1800                1805

Ala Arg His Leu Val Arg Phe Ser Asp Ala Tyr Lys Lys Ser Gln Leu
                1810                1815                1820

Leu Arg Glu Ile Glu Thr Ile Pro Tyr Glu Arg Ser Ser Ala Ser Arg
1825                1830                1835                1840

Glu Ile Gly Arg Ala Met Arg Phe Ile Ser Arg Asn Val Phe Lys Arg
                1845                1850                1855

Thr Leu Pro Gly Ala His Thr Arg Lys Ile Ala Thr Phe Phe Ser Ser
                1860                1865                1870

Gly Gln Ser Ala Asp Ala His Ser Ile Thr Thr Ala Ala Met Glu Phe
                1875                1880                1885

Gly Ala Leu Glu Ile Ile Pro Val Val Ile Thr Phe Ser Asn Val Pro
                1890                1895                1900

Ser Val Arg Arg Ala Phe Ala Ile Asp Asp Thr Gly Thr Phe Gln Val
1905                1910                1915                1920
```

-continued

```
Ile Val Val Pro Ser Gly Ala Asp Tyr Ile Pro Ala Leu Glu Arg Leu
                1925                1930                1935

Gln Arg Cys Thr Phe Cys Tyr Asp Val Cys Lys Pro Asp Ala Ser Cys
            1940                1945                1950

Asp Gln Ala Arg Pro Pro Val Gln Ser Tyr Met Asp Ala Ala Phe
        1955                1960                1965

Leu Leu Asp Ala Ser Arg Asn Met Gly Ser Ala Glu Phe Glu Asp Ile
    1970                1975                1980

Arg Ala Phe Leu Gly Ala Leu Leu Asp His Phe Glu Ile Thr Pro Glu
1985                1990                1995                2000

Pro Glu Thr Ser Val Thr Gly Asp Arg Val Ala Leu Leu Ser His Ala
                2005                2010                2015

Pro Pro Asp Phe Leu Pro Asn Thr Gln Lys Ser Pro Val Arg Ala Glu
                2020                2025                2030

Phe Asn Leu Thr Thr Tyr Arg Ser Lys Arg Leu Met Lys Arg His Val
            2035                2040                2045

His Glu Ser Val Lys Gln Leu Asn Gly Asp Ala Phe Ile Gly His Ala
        2050                2055                2060

Leu Gln Trp Thr Leu Asp Asn Val Phe Leu Ser Thr Pro Asn Leu Arg
2065                2070                2075                2080

Arg Asn Lys Val Ile Phe Val Ile Ser Ala Gly Glu Thr Ser His Leu
                2085                2090                2095

Asp Gly Glu Ile Leu Lys Lys Glu Ser Leu Arg Ala Lys Cys Gln Gly
            2100                2105                2110

Tyr Ala Leu Phe Val Phe Ser Leu Gly Pro Ile Trp Asp Asp Lys Glu
        2115                2120                2125

Leu Glu Asp Leu Ala Ser His Pro Leu Asp His His Leu Val Gln Leu
    2130                2135                2140

Gly Arg Ile His Lys Pro Asp His Ser Tyr Gly Val Lys Phe Val Lys
2145                2150                2155                2160

Ser Phe Ile Asn Ser Ile Arg Arg Ala Ile Asn Lys Tyr Pro Pro Ile
                2165                2170                2175

Asn Leu Lys Ile Lys Cys Asn Arg Leu Asn Ser Ile Asp Pro Lys Gln
                2180                2185                2190

Pro Pro Arg Pro Phe Arg Ser Phe Val Pro Gly Pro Leu Lys Ala Thr
            2195                2200                2205

Leu Lys Glu Asp Val Leu Gln Lys Ala Lys Phe Phe Gln Asp Lys Lys
        2210                2215                2220

Tyr Leu Ser Arg Val Ala Arg Ser Gly Arg Asp Asp Ala Ile Gln Asn
2225                2230                2235                2240

Phe Met Arg Ser Thr Ser His Thr Phe Lys Asn Gly Arg Met Ile Glu
                2245                2250                2255

Ser Ala Pro Lys Gln His Asp
            2260
```